United States Patent
Hahn

(10) Patent No.: US 7,700,350 B2
(45) Date of Patent: Apr. 20, 2010

(54) RECOMBINANT VECTOR CONTAINING INFECTIOUS HUMAN CYTOMEGALOVIRUS GENOME WITH PRESERVED WILD-TYPE CHARACTERISTICS OF CLINICAL ISOLATES

(75) Inventor: Gabriele Hahn, Munich (DE)

(73) Assignee: Vical Incorporated, San Diego, CA (US)

( * ) Notice: Subject to any disclaimer, the term of this patent is extended or adjusted under 35 U.S.C. 154(b) by 878 days.

(21) Appl. No.: 11/180,000

(22) Filed: Jul. 13, 2005

(65) Prior Publication Data
US 2006/0019369 A1    Jan. 26, 2006

Related U.S. Application Data

(63) Continuation of application No. 10/275,287, filed as application No. PCT/EP02/01867 on Feb. 21, 2002, now abandoned.

(30) Foreign Application Priority Data

Feb. 21, 2001  (EP)  .................................. 01104171
Jul. 2, 2001   (EP)  .................................. 01116044

(51) Int. Cl.
*C12N 15/00*   (2006.01)
*C12N 7/00*    (2006.01)
*C12N 7/01*    (2006.01)

(52) U.S. Cl. .................................. 435/320.1; 435/235.1

(58) Field of Classification Search ................ 435/320.1
See application file for complete search history.

(56) References Cited

FOREIGN PATENT DOCUMENTS

DE    197 33 364 A1    2/1999

OTHER PUBLICATIONS

Borst et al. Journal of Virology 1999 73 (10) pp. 8320-8329.*
Revello et al. J of General Virology 2001 vol. 82, pp. 1429-1438.*
Revello et al., "In vitro selection of human cytomegalovirus variants unable to transfer virus and virus products from infected cells to polymorphonuclear leukocytes and to grow in endothelial cells.", Jun. 2001, Journal of General Virology, vol. 82, No. 6, pp. 1429-1438, XP001121731.
Revello et al., "Diagnosis of human cytomegalovirus infection of the nervous system by pp65 detection in polymorphonuclear leukocytes of cerebrospinal fluid from AIDS patients.", 1994, Journal of Infectious Diseases, vol. 170, No. 5, p. 1275-1279, XP009002983.
Spaete et al., "Insertion and deletion mutagenesis of the human cytomegalievirus genome", Proceedings of the National Academy of Sciences of USA, National Academy of Science. Washington, US, vol. 84, pp. 7213-7217 XP002086760.
Borst, J., Virol. 1999 vol. 73, pp. 8320-8329.

* cited by examiner

*Primary Examiner*—Mary E Mosher
*Assistant Examiner*—Myron G Hill
(74) *Attorney, Agent, or Firm*—Sughrue Mion PLLC

(57) ABSTRACT

A recombinant vector containing infectious genome of human cytomegalovirus (HCMV) and being useful for the production of reconstituted HCMV virus retaining phenotypic characteristics of a clinical virus isolate including the ability to grow on endothelial cells and to induce microfusion is characterized in that it is obtainable by inserting DNA from a clinical isolate of HCMV virus into a bacterial cloning vehicle. Such vector can be used e.g., for production of reconstituted HCMV virus retaining the phenotypic characteristics of a parental clinical isolate and for studying genes and functions of genes of HCMV virus. A further aspect are mutant viruses and inter alia their use for studying aspects of infectivity of HCMV virus.

2 Claims, 70 Drawing Sheets

Figure 1A-F

Figure 6a

Figure 1:
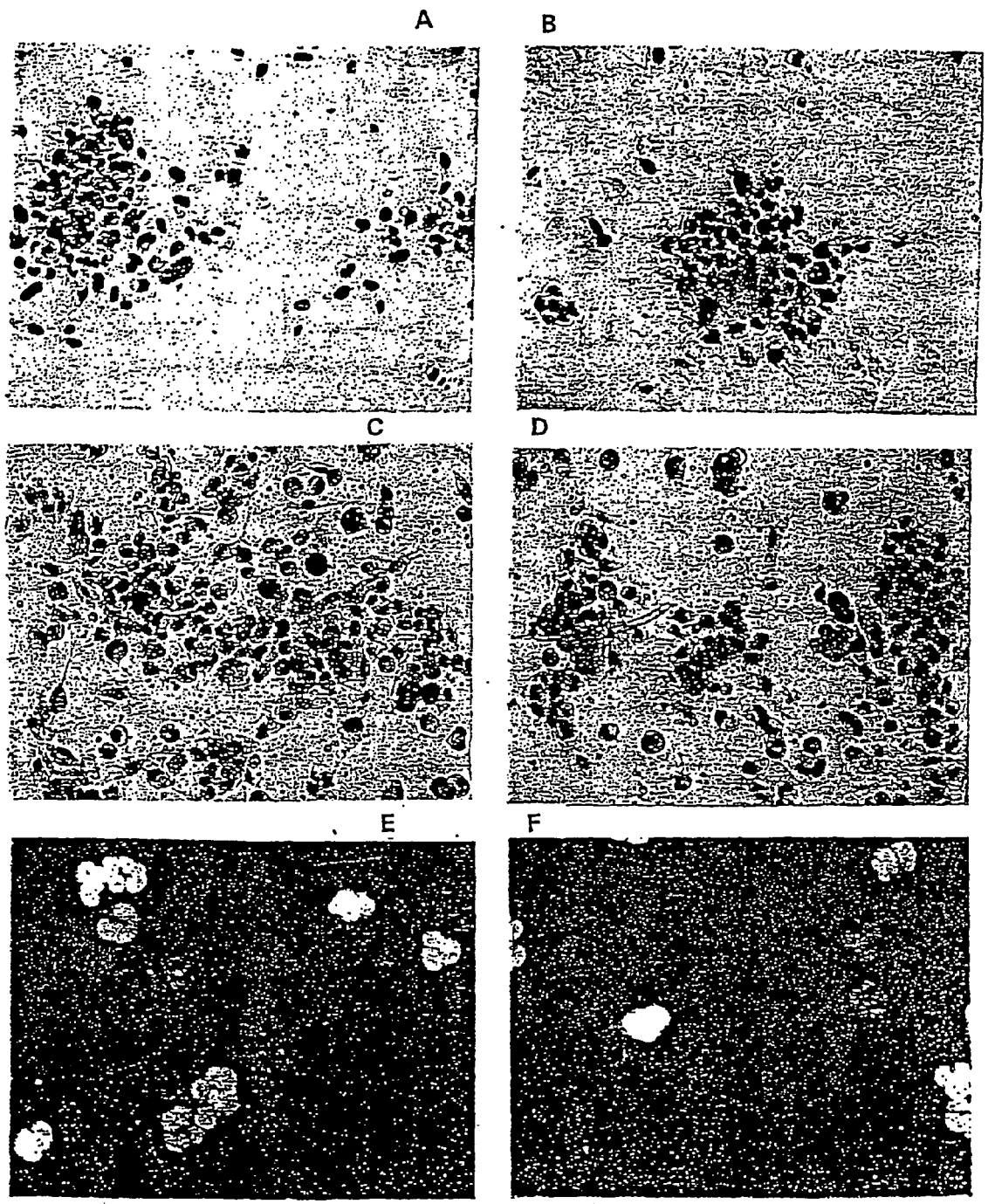

Comparison RACE clone1 - FIX genomic sequence upper line: RACE clone 1
lower line: FIX genomic sequence

```
   2   TGTGTCGGGTGTGGCTGTCTGTTTGTCTGTGCGCCGTGGTGCTGGGTCAGTGCCAGCGGG
       ||||||||||||||||||||||||||||||||||||||||||||||||||||||||||||
4803   TGTGTCGGGTGTGGCTGTCTGTTTGTCTGTGCGCCGTGGTGCTGGGTCAGTGCCAGCGGG

62   AGACCGCAGAAAAAAACGATTATTACCGAGTACCGCATTACTGGGACGCGTGCTCTCGCG
       ||||||||||||||||||||||||||||||||||||||||||||||||||||||||||||
4863   AGACCGCAGAAAAAAACGATTATTACCGAGTACCGCATTACTGGGACGCGTGCTCTCGCG

122   CGCTGCCTGACCAAACCCGTTACAAGTATGTGGAACAGCTCGTGGACCTCACGTTGAACT
       ||||||||||||||||||||||||||||||||||||||||||||||||||||||||||||
4923   CGCTGCCTGACCAAACCCGTTACAAGTATGTGGAACAGCTCGTGGACCTCACGTTGAACT

182   ACCACTACGATGCGAGCCACGGCTTGGACAACTTTGACGTGCTCAAG.............
       |||||||||||||||||||||||||||||||||||||||||||||||
4983   ACCACTACGATGCGAGCCACGGCTTGGACAACTTTGACGTGCTCAAGAGGTGAGGGTACG

229   ............................................................
5043   CGCTAAAGGTGTATGACAACGGGAAGGTAAGGGCGAACGGGTAACGGGTAGGTAACCGCA

229   ...............................AGAATCAACGTGACCGAGGTGTCGT
                                      |||||||||||||||||||||||||
5103   TGGGGTGTGAAATGACGTTCGGAACCTGTGCTTGCAGAATCAACGTGACCGAGGTGTCGT

254   TGCTCATCAGCGACTTTAGACGTCAGAACCGTCGCGGCGGCACCAACAAAAGGACCACGT
       ||||||||||||||||||||||||||||||||||||||||||||||||||||||||||||
5163   TGCTCATCAGCGACTTTAGACGTCAGAACCGTCGCGGCGGCACCAACAAAAGGACCACGT

314   TCAACGCCGCCGGTTCGCTGGCGCCTCACGCCCGGAGCCTCGAGTTCAGCGTGCGGCTCT
       ||||||||||||||||||||||||||||||||||||||||||||||||||||||||||||
5223   TCAACGCCGCCGGTTCGCTGGCGCCTCACGCCCGGAGCCTCGAGTTCAGCGTGCGGCTCT

374   TTGCCAAGTAGCCTGCGTCACGGGAAATAATATGCTACGGCTTCTGCTTCGTCACCACTT
       ||||||||||||||||||||||||||||||||||||||||||||||||||||||||||||
5283   TTGCCAACTAGCCTGCGTCACGGGAAATAATATGCTACGGCTTCTGCTTCGTCACCACTT

434   TCACTGCCTGCTTCTGTGCGCGGTTTGGGCAACGCCCTGTCTGGCGTCTCCGTGGTTCAC
       ||||||||||||||||||||||||||||||||||||||||||||||||||||||||||||
5343   TCACTGCCTGCTTCTGTGCGCGGTTTGGGCAACGCCCTGTCTGGCGTCTCCGTGGTTCAC

494   GCTAACGGCGAACCAGAATCCGTCCCCGCCATGGTCTAAACTGACGTATCCCAAACCGCA
       ||||||||||||||||||||||||||||||||||||||||||||||||||||||||||||
5403   GCTAACGGCGAACCAGAATCCGTCCCCGCCATGGTCTAAACTGACGTATCCCAAACCGCA

554   TGACGCGGCGACGTTTTACTGTCCTTTTCTCTATCCCTCGCCCCCACGGTCCCCCTCGCA
       ||||||||||||||||||||||||||||||||||||||||||||||||||||||||||||
5463   TGACGCGGCGACGTTTTACTGTCCTTTTCTCTATCCCTCGCCCCCACGGTCCCCCTCGCA

614   ATTCCCGGGGTTCCAGCGGGTATCAACGGGTCCCGAGTGTCGCAACGAGACCCTGTATCT
       ||||||||||||||||||||||||||||||||||||||||||||||||||||||||||||
5523   ATTCCCGGGGTTCCAGCGGGTATCAACGGGTCCCGAGTGTCGCAACGAGACCCTGTATCT

674   GCTGTACAACCGGGAAGGCCAGACCTTGGTGGAGAGAAGCTCCACCTGGGTGAAAAAGGT
       ||||||||||||||||||||||||||||||||||||||||||||||||||||||||||||
5583   GCTGTACAACCGGGAAGGCCAGACCTTGGTGGAGAGAAGCTCCACCTGGGTGAAAAAGGT

734   GATCTGGTATCTGAGCGGTCGCAATCAGACCATCCTCCAACGGATGCCCGAACGGCTTC
       |||||||||||||||||||||||||||||||||||||||||||||||||||||||||||
5643   GATCTGGTATCTGAGCGGTCGCAATCAGACCATCGTCCAACGGATGCCCGAACGGCTTC

794   GAAACCGAGCGACGGAAACGTGCAGATCAGCGTGGAAGACGCCAAGATTTTGGAGCGCA
       |||||||||||||||||||||||||||||||||||||||||||||||||||||||||||
5703   GAAACCGAGCGACGGAAACGTGCAGATCAGCGTGGAAGACGCCAAGATTTTGGAGCGCA

854   CATGGTGCCCAAGCAGACCAAGCTGCTACGTTTCGTCGTCAACGATGGCACACGTTATCA
       |||||||||||||||||||||||||||||||| ||||||||||||||||| |||||||
5763   CATGGTGCCCAAGCAGACCAAGCTGCTACGCTTCGTCGTCAACGATGGCACGCGTTATCA

914   GATGTGTGTGATGAAACTGGAGAGCTGGGCCCACGTCTTCCGGGACTACAGCGTGTCTTT
       ||||||||||||| |||||||||||||||||||||||||||||||||||||||||||||
5823   GATGTGTGTGATGAAGCTGGAGAGCTGGGCCCACGTCTTCCGGGACTACAGCGTGTCTTT

974   TCAGGTGCGATTGACGTTCACCGAGGCCAATAACCAGACTTACACCTTCTGCACCCATCC
       |||||||||||||||||||||||||||||||||||||||||||||||||||| |||||||
5883   TCAGGTGCGATTGACGTTCACCGAGGCCAATAACCAGACTTACACCTTCTGTACCCATCC

1034   CAATCTCATCGTTTGAGCCCGTCGCGCGCGCAGGGAATTTGAAAACCGCGTCATGAG
       |||||||||||||||||||||||||||||||||||||||||||||||||||||||||
5943   CAATCTCATCGTTTGAGCCCGTCGCGCGCGCAGGGAATTTTGAAAACCGCGCGTCATGAG

1094   TCCCAAAAACCTGACGCCGTTCTTGACGGCGTTGTGGCTGCTATTGGGTCACAGCCGCGT
       |||||||  ||||||||||||||||||||  ||||||||||||||||||||||||||||
6003   TCCCAAAGACCTGACGCCGTTCTTGACGACGTTGTGGCTGCTATTGGGTCACAGCCGCGT

1154   GCCGCGGGTACGCGCAGAAGAATGTTGCGAATTCATAAACGTCAACCACCCGCCGGAACG
       |||||||  |||||||||||||||||||||||||||||||||||||||||||||||||||
6063   GCCGCGGGTGCGCGCAGAAGAATGTTGCGAATTCATAAACGTCAACCACCCGCCGGAACG

1214   CTGTTACGATTTCAAAATGTGCAATCGCTTCACCGTCGCGTACGTATTTTCATGATTGTC
```

Figure 6a

```
         ||||||||||||||||||||||||||||||||||||||||||||||||| ||||||||
6123    CTGTTACGATTTCAAAATGTGCAATCGCTTCACCGTCGCGTACGTATTTTTATGATTGTC

1274    TGCGTTCTGTGGTGCGTCTGGATCTGTCTCTCGACGTTTCTGATAGCCATGTTCCATCGA
        ||||||||||||||||||||||||||| ||||||||||||||||||||||||||||||||
6183    TGCGTTCTGTGGTGCGTCTGGATTTGTCTCTCGACGTTTCTGATAGCCATGTTCCATCGA

1334    CGATCCTCGGGAATGCCAGAGTAGATTTTCATGAATCCACAGGCTGCGGTGTCCGGACGG
        ||||||||||||||||||||||||||||||||||||||||||||||||||||||||||||
6243    CGATCCTCGGGAATGCCAGAGTAGATTTTCATGAATCCACAGGCTGCGGTGTCCGGACGG

1394    CGAAGTCTGCTACAGTCCCGAGAAAACGGCTGAGATTCGCGGGATCGTCACCACCATGAC
        ||||||||||||||||||||||||||||||||||||||||||||||||||||||||||||
6303    CGAAGTCTGCTACAGTCCCGAGAAAACGGCTGAGATTCGCGGGATCGTCACCACCATGAC

1454    CCATTCATTGACACGCCAGGTCGTACACAACAAACTGACGAGCTGCAACTACAATCC...
        |||||||||||||||||||||||||||||||||||||||||||||||||||||||||
6363    CCATTCATTGACACGCCAGGTCGTACACAACAAACTGACGAGCTGCAACTACAATCCGTA

1511    ............................................................

6423    AGTCTCTTCCTCGAGGGCCTTACAGCCTATGGGAAAGTAAGACAGAGGGACAAAACATCA

1511    ........................................................GTTA
                                                                ||||
6483    TTAAAAAAAAAGTCTAATTTCACGTTTTGTACCCCCCCTTCCCCTCCGTGTTGTAGGTTA

1515    TACCTCGAAGCTGACGGGCGAATACGCTGCGGCAAAGTGAACGACAAGGCGCAGTACCTG
        ||||||||||||||||||||||||||||||||||||||||||||||||||||||||||||
6543    TACCTCGAAGCTGACGGGCGAATACGCTGCGGCAAAGTGAACGACAAGGCGCAGTACCTG

1575    CTGGGCGCCGCTGGCAGCGTTCCCTATCGATGGATCAACCTGGAATACGACAAGATAACC
        ||||||||||||||||||||||||||||||||||||||||||||||||||||||||||||
6603    CTGGGCGCCGCTGGCAGCGTTCCCTATCGATGGATCAACCTGGAATACGACAAGATAACC

1635    CGGATCGTGGGCCTGGATCAGTACCTGGAGAGCGTTAAGAAACACAAACGGCTGGATGTG
        |||||||||||||||||||||||||||||||||||||| |||||||||||||||||||||
6663    CGGATCGTGGGCCTGGATCAGTACCTGGAGAGCGTTAAAAAACACAAACGGCTGGATGTG

1695    TGCCGCGCTAAAATGGGCTATATGCTGCAGTGAATAATAAAATGTGTGTTTGTCCGAAAA
        |||||||||||||||||||||||||||||||||||||||||||||||||||||||||||
6723    TGCCGCGCTAAAATGGGCTATATGCTGCAGTGAATAATAAAATGTGTGTTTGTCCGAAAT
```

Figure 6b

Comparison RACE clone 3-10 - FIX genomic sequence upper line: RACE clone 3-10
lower line: FIX genomic sequence

```
   2  AATTCGGCTTTGTGTCGGGTAAGGCTGTCTGTTTGTCTGTGCGCCGTGGTGCTGGGTCAG
         ||   |     ||||||||||   ||||||||||||||||||||||||||||||||||
4793  AACATGCGGCTGTGTCGGGTGTGGCTGTCTGTTTGTCTGTGCGCCGTGGTGCTGGGTCAG

62  TGCCAGCGGGAGACCGCAGAAAAAAACGATTATTACCGAGTACCGCATTACTGGGACGCG
         ||||||||||||||||||||||||||||||||||||||||||||||||||||||||||
4853  TGCCAGCGGGAGACCGCAGAAAAAAACGATTATTACCGAGTACCGCATTACTGGGACGCG

122  TGCTCTCGCGCGCTGCCTGACCAAACCCGTTACAAGTATGTGGAACAGCTCGTGGACCTC
         ||||||||||||||||||||||||||||||||||||||||||||||||||||||||||
4913  TGCTCTCGCGCGCTGCCTGACCAAACCCGTTACAAGTATGTGGAACAGCTCGTGGACCTC

182  ACGTTGAACTACCACTACGATGCGAGCCACGGCTTGGACAACTTTGACGTGCTCAAGAGG
         ||||||||||||||||||||||||||||||||||||||||||||||||||||||||||
4973  ACGTTGAACTACCACTACGATGCGAGCCACGGCTTGGACAACTTTGACGTGCTCAAGAGG

242  TGAGGGTACGCGCTAAAGGTGTATGACAACGGGAAGGTAAGGGCGAACGGGTAACGGGTA
         ||||||||||||||||||||||||||||||||||||||||||||||||||||||||||
5033  TGAGGGTACGCGCTAAAGGTGTATGACAACGGGAAGGTAAGGGCGAACGGGTAACGGGTA

302  GGTAACCGCATGGGGTGTGAAATGACGTTCGGAACCTGTGCTTGCAGAATCAACGTGACC
         ||||||||||||||||||||||||||||||||||||||||||||||||||||||||||
5093  GGTAACCGCATGGGGTGTGAAATGACGTTCGGAACCTGTGCTTGCAGAATCAACGTGACC

362  GAGGTGTCGTTGCTCATCAGCGACTTTAGACGTCAGAACCGTCGCGGCGGCACCAACAAA
         ||||||||||||||||||||||||||||||||||||||||||||||||||||||||||
5153  GAGGTGTCGTTGCTCATCAGCGACTTTAGACGTCAGAACCGTCGCGGCGGCACCAACAAA

422  AGGACCACGTTCAACGCCGCCGGTTCGCTGGCGCCTCACGCCCGGAGCCTCGAGTTCAGC
         ||||||||||||||||||||||||||||||||||||||||||||||||||||||||||
5213  AGGACCACGTTCAACGCCGCCGGTTCGCTGGCGCCTCACGCCCGGAGCCTCGAGTTCAGC

482  GTGCGGCTCTTTGCCAACTAGCCTGCGTCACGGGAAATAATATGCTACGGCTTCTGCTTC
         ||||||||||||||||||||||||||||||||||||||||||||||||||||||||||
5273  GTGCGGCTCTTTGCCAACTAGCCTGCGTCACGGGAAATAATATGCTACGGCTTCTGCTTC

542  GTCA.CACTTTCACTGCCTGCTTCTGTGCGCGGTTTGGGCAACGCCCTGTCTGGCGTCTC
         ||||  |||||||||||||||||||||||||||||||||||||||||||||||||||||
5333  GTCACCACTTTCACTGCCTGCTTCTGTGCGCGGTTTGGGCAACGCCCTGTCTGGCGTCTC

601  CGTGGTTCACGCTAACGGCGAACCAGAATCCGTCCCCGCCATGGTCTAAACTGACGTATC
         ||||||||||||||||||||||||||||||||||||||||||||||||||||||||||
5393  CGTGGTTCACGCTAACGGCGAACCAGAATCCGTCCCCGCCATGGTCTAAACTGACGTATC

661  CCAAACCGCATGACGCGGCGACGTTTTACTGTCCTTTTCTCTATCCCTCGCCCCCACGGT
         ||||||||||||||||||||||||||||||||||||||||||||||||||||||||||
5453  CCAAACCGCATGACGCGGCGACGTTTTACTGTCCTTTTCTCTATCCCTCGCCCCCACGGT

721  CCCCCTCGCAATTCCCGGGGTTCCAGCGGGTATCAACGGGTCCCGAGTGTCGCAACGAGA
         ||||||||||||||||||||||||||||||||||||||||||||||||||||||||||
5513  CCCCCTCGCAATTCCCGGGGTTCCAGCGGGTATCAACGGGTCCCGAGTGTCGCAACGAGA

781  CCCTGTATCTGCTGTACAACCGGGAAGGCCAGACCTTGGTGGAGAGAAGCTCCACCTGGG
         ||||||||||||||||||||||||||||||||||||||||||||||||||||||||||
5573  CCCTGTATCTGCTGTACAACCGGGAAGGCCAGACCTTGGTGGAGAGAAGCTCCACCTGGG

841  TGAAAAAGGCGATCTGGTATCTGAGCGGTCGCAATCAGACCATCCTCCAACGGATGCCCC
         |||||||  |||||||||||||||||||||||||||||||||||||||||||||||||
5633  TGAAAAAGGTGATCTGGTATCTGAGCGGTCGCAATCAGACCATCCTCCAACGGATGCCCC

901  GAACGGCTTCGAAACCGAGCGACGGAAACGTGCAGATCAGCGTGGAAGACGCCAAGATTT
         ||||||||||||||||||||||||||||||||||||||||||||||||||||||||||
5693  GAACGGCTTCGAAACCGAGCGACGGAAACGTGCAGATCAGCGTGGAAGACGCCAAGATTT

961  TTGGAGCGCACATGGTGCCCAAGCAGACCAAGCTGCTACGTTTCGTCGTCAACGATGGCA
         |||||||||||||||||||||||||||||||||||  |||||||||||||||||||||
5753  TTGGAGCGCACATGGTGCCCAAGCAGACCAAGCTGCTACGCTTCGTCGTCAACGATGGCA

1021  CACGTTATCAGATGTGTGTGATGAAACTGGAGAGCTGGGCCCACGTCTTCCGGGACTACA
        |  ||||||||||||||||||||| ||||||||||||||||||||||||||||||||
5813  CGCGTTATCAGATGTGTGTGATGAAGCTGGAGAGCTGGGCCCACGTCTTCCGGGACTACA

1081  GCGTGTCTTTTCAGGTGCGATTGACGTTCACCGAGGCCAATAACCAGACTTACACCTTCT
         ||||||||||||||||||||||||||||||||||||||||||||||||||||||||||
5873  GCGTGTCTTTTCAGGTGCGATTGACGTTCACCGAGGCCAATAACCAGACTTACACCTTCT

1141  GCACCCATCCCAATCTCATTGTTTGAGCCCGTCGCGCGCGCAGGGAATTTTGAAAACCGC
        | |||||||||||||||| |||||||||||||||||||||||||||||||||||||||
5933  GTACCCATCCCAATCTCATCGTTTGAGCCCGTCGCGCGCGCAGGGAATTTTGAAAACCGC

1201  GCGTCATGAGTCCCAAAAACCTGACGCCGTTCTTGACGGCGTTGTGGCTGCTATTGGGTC
         ||||||||||||||||  |||||||||||||||||| |||||||||||||||||||||
5993  GCGTCATGAGTCCCAAAGACCTGACGCCGTTCTTGACGACGTTGTGGCTGCTATTGGGTC

1261  ACAGCCGCGTGCCGCGGGTACGCGCAGAAGAATGTTGCGAATTCATAAACGTCAACCACC
         ||||||||||||||||| |||||||||||||||||||||||||||||||||||||||
6053  ACAGCCGCGTGCCGCGGGTGCGCGCAGAAGAATGTTGCGAATTCATAAACGTCAACCACC
```

Figure 6b

```
1321  CGCCGGAACGCTGTTACGATTTCAAAATGTGCAATCGCTTCACCGTCGCGTACGTATTTT
      ||||||||||||||||||||||||||||||||||||||||||||||||||||||||||||
6113  CGCCGGAACGCTGTTACGATTTCAAAATGTGCAATCGCTTCACCGTCGCGTACGTATTTT

1381  CATGATTGTCTGCGTTCTGTGGTGCGTCTGGATCTGTCTCTCGACGTTTCTGATAGCCAT
      ||||||||||||||||||||||||||||||||| ||||||||||||||||||||||||||
6173  TATGATTGTCTGCGTTCTGTGGTGCGTCTGGATTTGTCTCTCGACGTTTCTGATAGCCAT

1441  GTTCCATCGACGATCCTCGGGAATGCCAGAGTAGATTTTCATGAATCCACAGGCTGCGGT
      ||||||||||||||||||||||||||||||||||||||||||||||||||||||||||||
6233  GTTCCATCGACGATCCTCGGGAATGCCAGAGTAGATTTTCATGAATCCACAGGCTGCGGT

1501  GTCCGGACGGCGAAGTCTGCTACAGTCCCGAGAAAACGGCTGAGATTCGCGGGATCGTCA
      ||||||||||||||||||||||||||||||||||||||||||||||||||||||||||||
6293  GTCCGGACGGCGAAGTCTGCTACAGTCCCGAGAAAACGGCTGAGATTCGCGGGATCGTCA

1561  CCACCATGACCCATTCATTGACACGCCAGGTCGTACACAACAAACTGACGAGCTGCAACT
      ||||||||||||||||||||||||||||||||||||||||||||||||||||||||||||
6353  CCACCATGACCCATTCATTGACACGCCAGGTCGTACACAACAAACTGACGAGCTGCAACT

1621  ACAATCC.....................................................
      |||||||
6413  ACAATCCGTAAGTCTCTTCCTCGAGGGCCTTACAGCCTATGGGAAAGTAAGACAGAGGGA

1628  ............................................................
6473  CAAAACATCATTAAAAAAAAAGTCTAATTTCACGTTTTGTACCCCCCCTTCCCCTCCGTG

1628  ......GTTATACCTCGAAGCTGACGGGCGAATACGCTGCGGCAAAGTGAACGACAAGGC
            ||||||||||||||||||||||||||||||||||||||||||||||||||||||
6533  TTGTAGGTTATACCTCGAAGCTGACGGGCGAATACGCTGCGGCAAAGTGAACGACAAGGC

1682  GCAGTACCTGCTGGGCGCCGCTGGCAGCGTTCCCTATCGATGGATCAACCTGGAATACGA
      |||||||||||| |||||||||||||||||||||||||||||||| ||||||||||||||
6593  GCAGTACCTGCTGGGCGCCGCTGGCAGCGTTCCCTATCGATGGATCAACCTGGAATACGA

1742  CAAGATAACCCGGATCGTGGGCCTGGATCAGTACCTGGAGAGCGTTAAGAAACACAAACG
      |||||||||||||||||||||||||||||||||||||||||||||| |||||||||||||
6653  CAAGATAACCCGGATCGTGGGCCTGGATCAGTACCTGGAGAGCGTTAAAAAAACACAAACG

1802  GCTGGATGTGTGCCGCGCTAAAATGGGCTATATGCTGCAGTGAATAATAAAATGTGTGTT
      ||||||||||||||||||||||||||||||||||||||||||||||||||||||||||||
6713  GCTGGATGTGTGCCGCGCTAAAATGGGCTATATGCTGCAGTGAATAATAAAATGTGTGTT

1862  TGTCCGGAAAAAAAAAAAAAAA
      |||||| || |          |
6773  TGTCCGAAATACGCGTTTTGA
```

Figure 6c

Comparison RACE clone1 - RACE clone 3-10 upper line: RACE clone1
lower line: RACE clone 3-10

```
   1   TTGTGTCGGGTGTGGCTGTCTGTTTGTCTGTGCGCCGTGGTGCTGGGTCAGTGCCAGCGG
       |||||||||||  |||||||||||||||||||||||||||||||||||||||||||||
  11   TTGTGTCGGGTAAGGCTGTCTGTTTGTCTGTGCGCCGTGGTGCTGGGTCAGTGCCAGCGG

61   GAGACCGCAGAAAAAAACGATTATTACCGAGTACCGCATTACTGGGACGCCGTGCTCTCGC
       ||||||||||||||||||||||||||||||||||||||||||||||| ||||||||||||
  71   GAGACCGCAGAAAAAAACGATTATTACCGAGTACCGCATTACTGGGACGCGTGCTCTCGC

121   GCGCTGCCTGACCAAACCCGTTACAAGTATGTGGAACAGCTCGTGGACCTCACGTTGAAC
       ||||||||||||||||||||||||||||||||||||||||||||||||||||||||||||
 131   GCGCTGCCTGACCAAACCCGTTACAAGTATGTGGAACAGCTCGTGGACCTCACGTTGAAC

181   TACCACTACGATGCGAGCCACGGCTTGGACAACTTTGACGTGCTCAAG............
       ||||||||||||||||||||||||||||||||||||||||||||||||
 191   TACCACTACGATGCGAGCCACGGCTTGGACAACTTTGACGTGCTCAAGAGGTGAGGGTAC

229   ............................................................

251   GCGCTAAAGGTGTATGACAACGGGAAGGTAAGGGCGAACGGGTAACGGGTAGGTAACCGC

229   .................................AGAATCAACGTGACCGAGGTGTCG
                                          ||||||||||||||||||||||||||
 311   ATGGGGTGTGAAATGACGTTCGGAACCTGTGCTTGCAGAATCAACGTGACCGAGGTGTCG

253   TTGCTCATCAGCGACTTTAGACGTCAGAACCGTCGCGGCGGCACCAACAAAAGGACCACG
       ||||||||||||||||||||||||||||||||||||||||||||||||||||||||||||
 371   TTGCTCATCAGCGACTTTAGACGTCAGAACCGTCGCGGCGGCACCAACAAAAGGACCACG

313   TTCAACGCCGCCGGTTCGCTGGCGCCTCACGCCCGGAGCCTCGAGTTCAGCGTGCGGCTC
       ||||||||||||||||||||||||||||||||||||||||||||||||||||||||||||
 431   TTCAACGCCGCCGGTTCGCTGGCGCCTCACGCCCGGAGCCTCGAGTTCAGCGTGCGGCTC

373   TTTGCCAACTAGCCTGCGTCACGGGAAATAATATGCTACGGCTTCTGCTTCGTCACCACT
       |||||||||||||||||||||||||||||||||||||||||||||||||||||||| |||
 491   TTTGCCAACTAGCCTGCGTCACGGGAAATAATATGCTACGGCTTCTGCTTCGTCA.CACT

433   TTCACTGCCTGCTTCTGTGCGCGGTTTGGGCAACGCCCTGTCTGGCGTCTCCGTGGTTCA
       ||||||||||||||||||||||||||||||||||||||||||||||||||||||||||||
 550   TTCACTGCCTGCTTCTGTGCGCGGTTTGGGCAACGCCCTGTCTGGCGTCTCCGTGGTTCA

493   CGCTAACGGCGAACCAGAATCCGTCCCCGCCATGGTCTAAACTGACGTATCCCAAACCGC
       ||||||||||||||||||||||||||||||||||||||||||||||||||||||||||||
 610   CGCTAACGGCGAACCAGAATCCGTCCCCGCCATGGTCTAAACTGACGTATCCCAAACCGC

553   ATGACGCGGCGACGTTTTACTGTCCTTTTCTCTATCCCTCGCCCCACGGTCCCCCTCGC
       ||||||||||||||||||||||||||||||||||||||||||||||||||||||||||
 670   ATGACGCGGCGACGTTTTACTGTCCTTTTCTCTATCCCTCGCCCCACGGTCCCCCTCGC

613   AATTCCCGGGGTTCCAGCGGGTATCAACGGGTCCCGAGTGTCGCAACGAGACCCTGTATC
       ||||||||||||||||||||||||||||||||||||||||||||||||||||||||||||
 730   AATTCCCGGGGTTCCAGCGGGTATCAACGGGTCCCGAGTGTCGCAACGAGACCCTGTATC

673   TGCTGTACAACCGGGAAGGCCAGACCTTGGTGGAGAGAAGCTCCACCTGGGTGAAAAAGG
       ||||||||||||||||||||||||||||||||||||||||||||||||||||||||||||
 790   TGCTGTACAACCGGGAAGGCCAGACCTTGGTGGAGAGAAGCTCCACCTGGGTGAAAAAGG

733   TGATCTGGTATCTGAGCGGTCGCAATCAGACCATCCTCCAACGGATGCCCCGAACGGCTT
       | ||||||||||||||||||||||||||||||||||||||||||||||||||||||||||
 850   CGATCTGGTATCTGAGCGGTCGCAATCAGACCATCCTCCAACGGATGCCCCGAACGGCTT

793   CGAAACCGAGCGACGGAAACGTGCAGATCAGCGTGGAAGACGCCAAGATTTTTGGAGCGC
       ||||||||||||||||||||||||||||||||||||||||||||||||||||||||||||
 910   CGAAACCGAGCGACGGAAACGTGCAGATCAGCGTGGAAGACGCCAAGATTTTTGGAGCGC

853   ACATGGTGCCCAAGCAGACCAAGCTGCTACGTTTCGTCGTCAACGATGGCACACGTTATC
       ||||||||||||||||||||||||||||||||||||||||||||||||||||||||||||
 970   ACATGGTGCCCAAGCAGACCAAGCTGCTACGTTTCGTCGTCAACGATGGCACACGTTATC

913   AGATGTGTGTGATGAAACTGGAGAGCTGGGCCCACGTCTTCCGGGACTACAGCGTGTCTT
       ||||||||||||||||||||||||||||||||||||||||||||||||||||||||||||
1030   AGATGTGTGTGATGAAACTGGAGAGCTGGGCCCACGTCTTCCGGGACTACAGCGTGTCTT

973   TTCAGGTGCGATTGACGTTCACCGAGGCCAATAACCAGACTTACACCTTCTGCACCCATC
       ||||||||||||||||||||||||||||||||||||||||||||||||||||||||||||
1090   TTCAGGTGCGATTGACGTTCACCGAGGCCAATAACCAGACTTACACCTTCTGCACCCATC

1033   CCAATCTCATCGTTTGAGCCCGTCGCGCGCGCAGGGAATTTTGAAAACCGCGCGTCATGA
       |||||||||  |||||||||||||||||||||||||||||||||||||||||||||||||
1150   CCAATCTCATTGTTTGAGCCCGTCGCGCGCGCAGGGAATTTTGAAAACCGCGCGTCATGA

1093   GTCCCAAAAACCTGACGCCGTTCTTGACGGCGTTGTGGCTGCTATTGGGTCACAGCCGCG
       ||||||||||||||||||||||||||||||||||||||||||||||||||||||||||||
1210   GTCCCAAAAACCTGACGCCGTTCTTGACGGCGTTGTGGCTGCTATTGGGTCACAGCCGCG

1153   TGCCGCGGGTACGCGCAGAAGAATGTTGCGAATTCATAAACGTCAACCACCCGCCGGAAC
       ||||||||||||||||||||||||||||||||||||||||||||||||||||||||||||
1270   TGCCGCGGGTACGCGCAGAAGAATGTTGCGAATTCATAAACGTCAACCACCCGCCGGAAC

1213   GCTGTTACGATTTCAAAATGTGCAATCGCTTCACCGTCGCGTACGTATTTTCATGATTGT
```

Figure 6c

```
1330  GCTGTTACGATTTCAAAATGTGCAATCGCTTCACCGTCGCGTACGTATTTTCATGATTGT
      ||||||||||||||||||||||||||||||||||||||||||||||||||||||||||||
1273  CTGCGTTCTGTGGTGCGTCTGGATCTGTCTCTCGACGTTTCTGATAGCCATGTTCCATCG
      ||||||||||||||||||||||||||||||||||||||||||||||||||||||||||||
1390  CTGCGTTCTGTGGTGCGTCTGGATCTGTCTCTCGACGTTTCTGATAGCCATGTTCCATCG

1333  ACGATCCTCGGGAATGCCAGAGTAGATTTTCATGAATCCACAGGCTGCGGTGTCCGGACG
      ||||||||||||||||||||||||||||||||||||||||||||||||||||||||||||
1450  ACGATCCTCGGGAATGCCAGAGTAGATTTTCATGAATCCACAGGCTGCGGTGTCCGGACG

1393  GCGAAGTCTGCTACAGTCCCGAGAAAACGGCTGAGATTCGCGGGATCGTCACCACCATGA
      ||||||||||||||||||||||||||||||||||||||||||||||||||||||||||||
1510  GCGAAGTCTGCTACAGTCCCGAGAAAACGGCTGAGATTCGCGGGATCGTCACCACCATGA

1453  CCCATTCATTGACACGCCAGGTCGTACACAACAAACTGACGAGCTGCAACTACAATCCGT
      ||||||||||||||||||||||||||||||||||||||||||||||||||||||||||||
1570  CCCATTCATTGACACGCCAGGTCGTACACAACAAACTGACGAGCTGCAACTACAATCCGT

1513  TATACCTCGAAGCTGACGGGCGAATACGCTGCGGCAAAGTGAACGACAAGGCGCAGTACC
      ||||||||||||||||||||||||||||||||||||||||||||||||||||||||||||
1630  TATACCTCGAAGCTGACGGGCGAATACGCTGCGGCAAAGTGAACGACAAGGCGCAGTACC

1573  TGCTGGGCGCCGCTGGCAGCGTTCCCTATCGATGGATCAACCTGGAATACGACAAGATAA
      ||||||||||||||||||||||||||||||||||||||||||||||||||||||||||||
1690  TGCTGGGCGCCGCTGGCAGCGTTCCCTATCGATGGATCAACCTGGAATACGACAAGATAA

1633  CCCGGATCGTGGGCCTGGATCAGTACCTGGAGAGCGTTAAGAAACACAAACGGCTGGATG
      ||||||||||||||||||||||||||||||||||||||||||||||||||||||||||||
1750  CCCGGATCGTGGGCCTGGATCAGTACCTGGAGAGCGTTAAGAAACACAAACGGCTGGATG

1693  TGTGCCGCGCTAAAATGGGCTATATGCTGCAGTGAATAATAAAATGTGTGTTTGTCCGAA
      |||||||||||||||||||||||||||||||||||||||||||||||||||||||||| |
1810  TGTGCCGCGCTAAAATGGGCTATATGCTGCAGTGAATAATAAAATGTGTGTTTGTCCGGA

1753  AAAAAAAAAAAAAAAAAAAAAAAAA
      |||||||||||||  |||||||||
1870  AAAAAAAAAAAAAAAGAAAAAAAAG
```

Figure 6D:
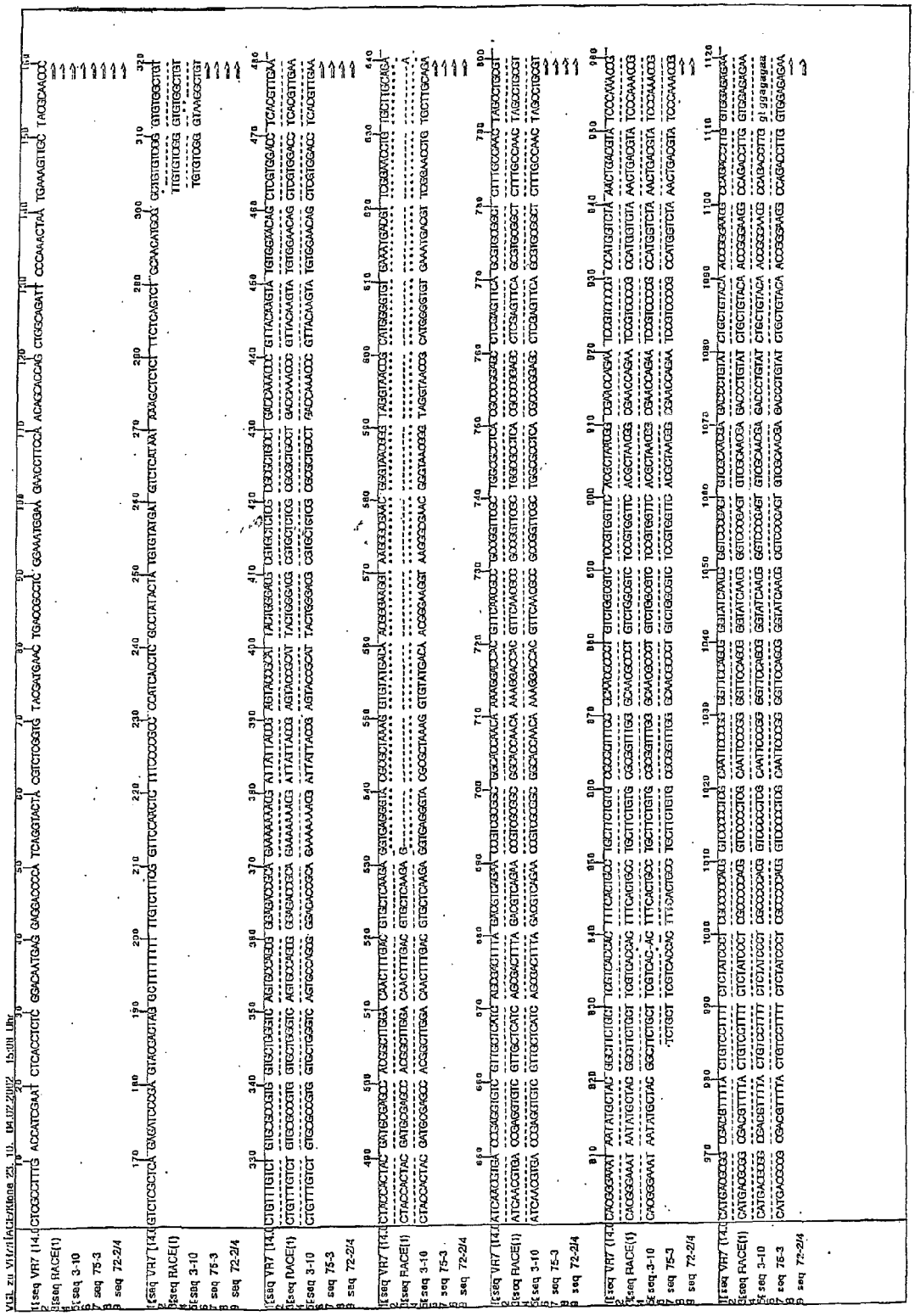
Figure 6D:
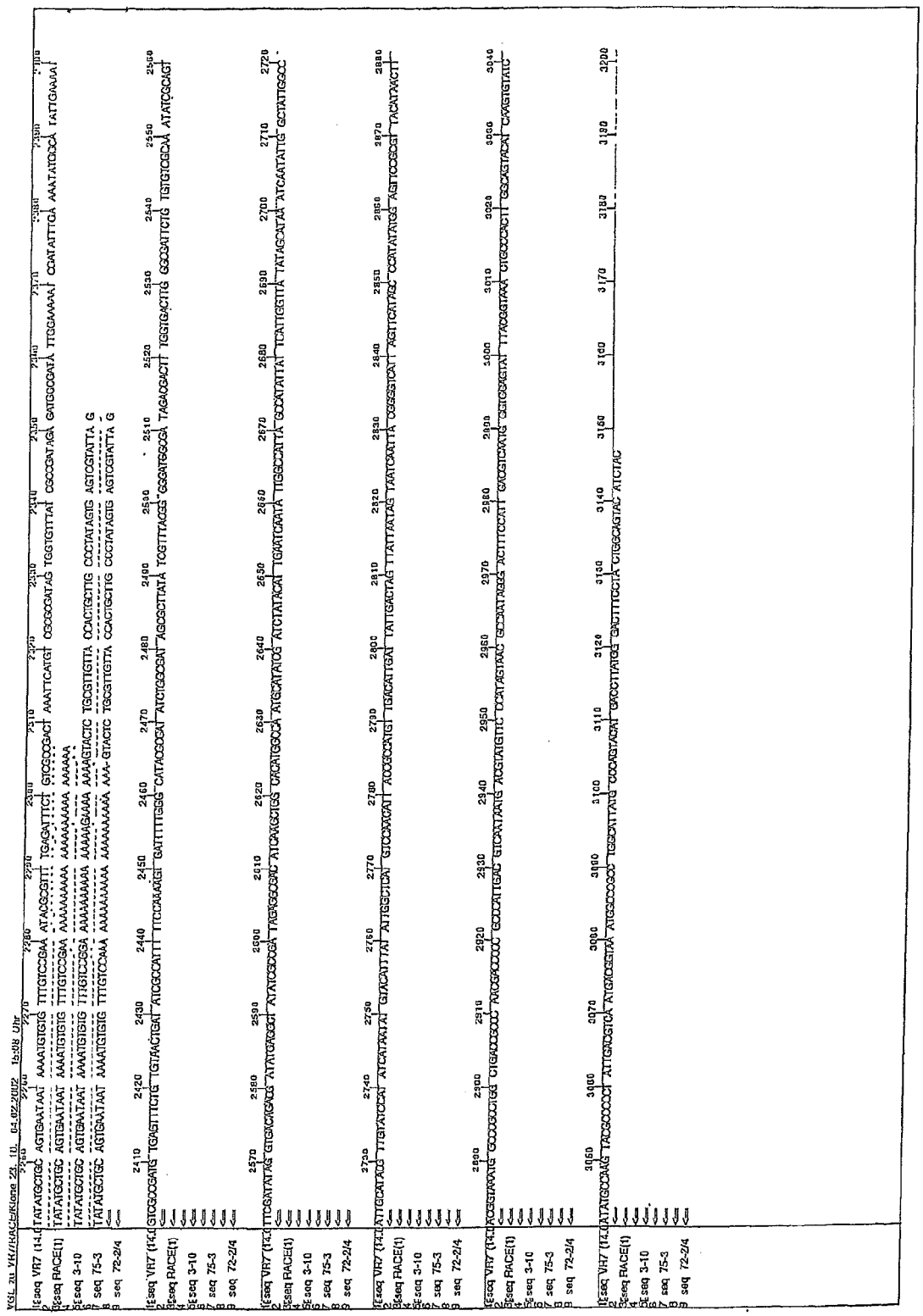
Figure 6E:
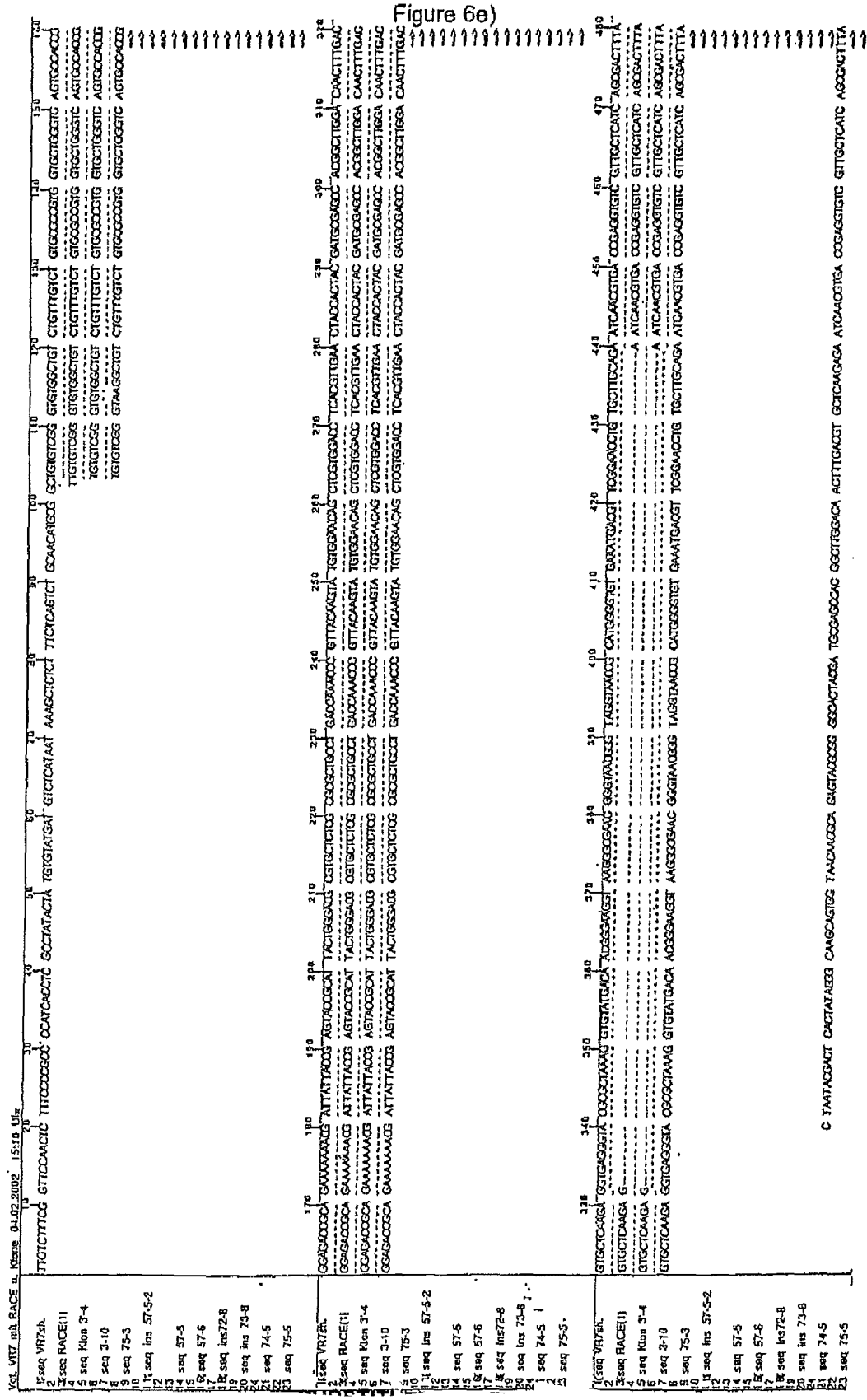

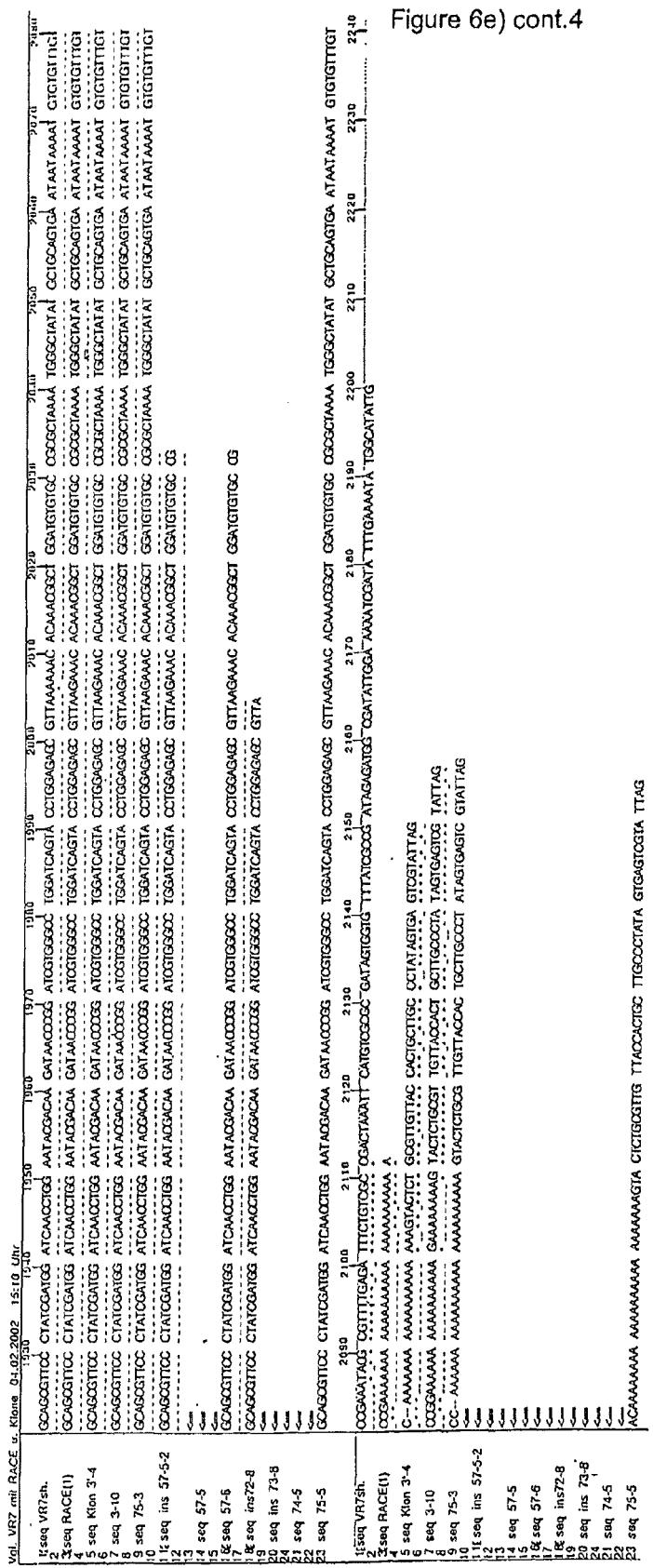
Figure 6e) cont.4

Figure 6e) cont.5

Figure 7a

Fast alignment of DNA sequences FIX7 and HCU33331 (Toledo)

Upper line: SEQ VR7 (14.8.), from 1 to 7644
Lower line: HCU33331, from 7829 to 15478

FIX7:HCU33331 identity= 84%

```
   1  ACTGTGGCTAGAAACTGGTTACCTGTGAAGATGGCTGACTATCCTGTTGTGTCCTGGAAA
      ||||||||| ||||||||||||||||||||||||| |||||||||| ||||||||||||
7829  ACTGTGGCTGGAAACTGGTTACCTGTGAAGATGGCTAACTATCCTGTTCTGTCCTGGAAA

61  AGCTTTCAGCGTCGTAGGTGGACTTTGCAGTATGCGGGTTAGTGAAGTTATGTCATTTAT
      | ||||  ||||||||||||||||||||||||||||||||||||||||||||||||||||
7889  AACTTTTGGCGTCGTAGGTGGACTTTGCAGTATGCGGGTTAGTGAAGTTATGTCATTTAT

121  TTACGTTTACGATCTCGTATTACAAACCGCGGAGAGGATGATACCGTTCGGCCCCATGAG
      ||||||||||||||||||||||||||||||||||||||||||||||||||||||||||||
7949  TTACGTTTACGATCTCGTATTACAAACCGCGGAGAGGATGATACCGTTCGGCCCCATGAG

181  TTATTTTTATTCTTCCGGTAGGAGGCATGAAGCCTCTGGTGATGCTTATTTTGCTGAGTA
      |||||||||||||||||||||||||||||||||||||| |||||| ||  ||  |  | |
8009  TTATTTTTATTCTTCCGGTAGGAGGCATGAAGCCTCTGATAATGCTCATCTGCTTTGCTG

241  TGCTATTGGCATGCATAGGGAAAACTGAAATATGCAAACCCGAAGAAGTGCAATTAGGAA
      || ||||        | ||   ||| || ||  |  | |||||||| | || ||  | |
8069  TGATATTATTGCAGCTTGGAGTGACTAAAGTGTGTCAGCATAATGAAGTGCAACTGGGCA

301  ATCAGTGTTGTCCCCCATGTAAACAAGGATATCGTGTTACAGGACAATGTACGCAATATA
      ||  ||| || ||  |    ||     ||| |  | |||| | |||  |  | || ||||
8129  ATGAGTGCTGCCCTCCGTGTGGTTCGGGACAAAAGAGTTACTAAAGTATGCACGGATTATA

361  CGAGTACAACATGTACACTTTGCCCTAACGGTACGTATGTATCAGGGCTTTACAATTGTA
      | |||  ||| ||||| |||||| ||||||| |||||||||||||||||||| ||||||
8189  CCAGTGTAACGTGTACCCCTTGCCCCAACGGGACGTATGTATCGGGACTTTACAACTGTA

421  CCAATTGCACTGAGTGTAATGACACTGAGGTTACAATTCGTAACTGCACTTCCACTAATA
      || |||||||| | ||||| | ||| ||| | ||||||||||||||||||||| ||||
8249  CCGATTGCACTCAATGTAACGTCACTCAGGTCATGATTCGTAACTGCACTTCCACCAATA

481  ACAGCGTATGCGCATCTAAGAATTATACGTCGTTGTCCGTTCCAGGCGTCCAACATCATA
      | ||||||||||| |||||| ||||||| |||| |  ||| ||||||||||||||||| |
8309  ATACCGTATGCGCACCTAAGAACCATACGTACTTTTCCACTCCAGGCGTCCAACATCACA

541  AGCAACGA...CAAAATCATACCGCACATGTAACCGTCAAACAAGGGAAAAGTGGTCGTC
      | ||||||   | |||||||||| |||| ||||||||||||||||||||||| |||||||
8369  AACAACGACAGCAAAATCATACCGCACATATAACCGTCAAACAAGGGAAAAGCGGTCGTC

598  ATACTCTAGCCTGGTTGTCCCTCTTCATGTTTCTCGTGGGTATCATACTTTTAATTCTCT
      ||||||||||||||||||| | || || ||  ||| |||||||||||||||||||||||
8429  ATACTCTAGCCTGGTTGTCTCTCTTTATCTTCTTGTGGGTATCATACTTTTAATTCTCT

658  ATCTTATAGCCGCCTATCGGAGTGAGAGATGCCAACAGTGTTGCTCAATCGGCAAAATTT
      ||||||||||||||||||||||||||||||||||||||||||||||||||||||||||||
8489  ATCTTATAGCCGCCTATCGGAGTGAGAGATGCCAACAGTGTTGCTCAATCGGCAAAATTT

718  TCTACCGCACCCTGTAAGCTTCCTGTTGTTGTTTTTACATCACGGTGCGATGAAGTCACA
      ||||||||||||||||||||||||||||||||||||||||||||||| ||||||||||||
8549  TCTACCGCACCCTGTAAGCTTCCTGTTGTTGTTTTTACATCACGGTACGATGAAGTCACA

778  CAGATAATTACAGATGAGCTGTTCATATTTTTATTATTTTTCCAATTCCTGCACTAAA
      ||||||||||||||||||||| ||||||||||||||||||||||||||||||||||||
8609  CAGATAATTACAGATGAGCTGTTCATATTTTTATTATTTTTCCAATTCCTGCACTAAA

838  AAAAGAAGCACTTTACGGAACCGTGTCTGAATATCTGTGGGAATTTAGGTACTTTTTGC
      ||||||||||||||||||||||||||||| ||||||||||||||||||||||||||||
8669  AAAAGAAGCACTTTACGGAACCGTGTCTGAGTATCTGTGGGAATTTAGGTACTTTTTGC

898  CGACGTCAGGAAAAATAAGCTGTCGCCTACATAAGAGCCCGGTGCTATCGTGCTGTCACT
      |||||||||||||||||||  |||||||||||||||||||||||||||||||||||||||
8729  CGACGTCAGGAAAAATAAG.TGTCGCCTACATAAGAGCCCGGTGCTATCGTGCTGTCACT

958  CTTTCTTGTTGCCTTCGATGTACGGCGTCCTGGCTCATTACTACTCCTTCATCAGTAGCC
      |||||||||||||||||||||||||||||||||||||||||||||||||||||||||||
8788  CTTTCTTGTTGCCTTCGATGTACGGCGTCCTGGCTCATTACTACTCCTTCATCAGTAGCC

1018  CCAGCGTTATGGTTAATTTTAAACATCATAACGCCGTGCAGCTGTTGTGTGCACGGACCC
      ||||||||||||||||||||   ||||||||||||||||||||||||| ||||||||||
8848  CCAGCGTTATGGTTAATTTTAAGCATCATAACGCCGTGCAGCTGTTATGTGCACGGACCC

1078  GAGACGGCACTGCCGGATGGGAACGTTTAACCCATCATGCGTCGTATCACGCGAACTATG
      |||||  ||||||||||||||||||||||||||||||||| |||||||||||||||||| |
8908  GAGAC.GCACTGCCGGATGGGAACGTTTAACCCATCATGCGTCGTATCACGCGAACTACG
```

Figure 7a cont.

```
1138  GGGCATACGCCGTGTTGATGGCTACATCGCAAAGAAAGTCCCTAGTGTTACATCGATACA
      ||||||||||||||||||||||||||||||||||||||||||||||||||||||||||||
8967  GGGCATACGCCGTGTTGATGGCTACATCGCAAAGAAAGTCCCTAGTGTTACATCGATACA

1198  GTGCCGTGACAGCCGTGGCCCTGCAGCTCATGCCTGTTGAGATGCTCCGTAAGCTAGATC
      |||||||||||||||||||||||||||||||||||||||||||| |||| |||||||||||
9027  GTGCCGTGACAGCCGTGGCCCTGCAGCTCATGCCTGTTGAGATCGTCCGCAAGCTAGATC

1258  AGTCGGACTGGGTACGGGGTGCCTGGATCGTGTCAGAGACTTTTCCAACCAGCGACCCCA
      |||||||||||| |||||||||||||||||||||||||||||||||||| ||||||||||
9087  AGTCGGACTGGGTGCGGGGTGCCTGGATCGTGTCAGAGACTTTTCCAACTAGCGACCCCA

1318  AAGGATTTTGGAGCGACGATGACTCCTCGATGGGTGGAAGTGATGATTGATGATGAGAAC
      ||||| ||||||||||||||||| ||||||||||||||||||||||||||||||||||||
9147  AAGGAGTTTGGAGCGACGATGACTGCTCGATGGGTGGAAGTGATGATTGATGATGAGAAC

1378  CTGACAAGAAAGACGAGAGAGAAATTCAGAGCTGTCATTGTAGAATTAGTCTAGATTCCT
      ||||||||||||||||||||||||| |||||||||||||||||||||||||||||||||||
9207  CTGACAAGAAAGACGAGAGAGAAATTTAGAGCTGTCATTGTAGAATTAGTCTAGATTCCT

1438  GATAATAAACGGTATCGATTTTGAAACCTAATTGACGTGTGATCGATTTTTAAACCTGTG
      |||||||||| |||||||||||||||||||||||||||||||||||||||||||||| ||
9267  GATAATAAACAGTATCGATTTTGAAACCTAATTGACGTGTGATCGATTTTTAAACCTCTG

1498  TGTTGTGTGATTGATTGGTATGTGGGGGATCCGATTTCAAAGGGGGTACTTATCGGGA
      ||||||||||||||||||||||||||||||||||||||||||||||||||||||||||
9327  TGTTGTGTGATTGATTGGTATGTGGGGGATCCGATTTCAAAGGGGGTACTTATCGGGA

1558  ATTGATGTGTCATGGACGCAGTTTTGAGTGATTTTCCGGGAATACCGGATATTACGAATT
      |||||||||||||||||||||||||||||||| ||||||||||||||||||||||||||
9387  ATTGATGTGTCATGGACGCAGTTTTGAGCGATTTCCGGGAATACCGGATATTACGAATT

1618  GATGTAAGTTACGTCAGTAATTAAGTCAGGATGCGGTTTATTTTCGGTTTGCTGATTGGT
      ||  ||| ||||    |||| ||  |  ||||| ||  ||||| |||   |  ||||  |
9447  ACTGGTAGTGACGTAGATAATAAAATTATAATGCGATTAATTTTTGGTGCGTTGATTATT

1678  CTTGTAATCGTGTATACGTATTATTATGAAGTACAAAGTACGGAACTACGTTGCCCATGC
      ||  ||      ||| |||| ||||||| | ||  |  ||| |||  ||||| ||  |||
9507  TTTTTAGCA...TATGTGTATCATTATGAGGTGAATGGAACAGAATTACGCTGCAGATGT

1738  ACTAATGGTTTACACGATCCTTTATATGGCATATT......TTATGCTGGTCGTGACCCT
      |  ||  |   |    |||  |  |||||  ||||      || |  |  |||  | ||
9564  CTTCATAGAAAATGGCCGCCTAATAAAAATTATATTGGGTAATTATTGGCTTCATCGCGAT

1792  CCACGTCCTCCCGGTTGTGAAAAAGATCAATATTATTTAAAACCTCCCAAAGGTAAA..G
      ||  |    |||||  |  ||   ||||| || || ||  |  | |    |||||    |
9624  CCCAGAGGGCCCGGATGCGATAAAAATGAACATTTATTGTATCCAGACGGAAGGAAACCG

1850  CTGTATGCTTAGGTCCACATCATCATTTATCAATATGGCTCAATGGTCAAAATAGTAGTT
      |      ||  ||      ||  |   ||||  || || |  || || ||||| | | |
9684  CCTGGACCTGGAGTATGTTTATCGCCCGATCACCTCTTCTCAAAATGGTTAGACAAACAC

1910  TATGGCACAAAGTGCTGGTGACGGGAAAAAACGGTAATGGACCACACGTAACTAAGAAAG
      |  |  | |   | || || |   |   |   ||  || | |       |  || |  |
9744  AACGATAATAGGTGGTATAATGTTAACATAACGAAATCACCAGGACCGAGACGAATAAAT

1970  GTGACTTTCCTAGAGGTCGAAAAAATATAATGATTTAGCTTAATATGGATATATACGATA
      .| || || ||| || || | | |  |  | |      ||  ||||            |  | |||    |
9804  ATAACCTTGATAGGTGTTAGAGGATAATATTTA............ATGTATGTTTTC

2030  GCTGATAAATTTTCCACGAAAAAGGATAACGCAATATGTTTTTGATATGGTGCTAACATG
      ||  |  |||      |   |||  ||    || || ||| |||| ||||||||||||||
9849  AAACAGACAAGTTCGTTAAAACAAAATATTACAGTATGTGTTTAATATGGTGCTAACATG

2090  GTTACATCATTCGATTATAAACTCGCATATCAAACTTTTATCGGTACCACACCTGTCATT
      |||  |  ||| || || ||  |||||||||||| ||||||||||| || ||||||||||
9909  GTTGCACCATCCGGTTTCAAACTCGCATATCAATCTGTTATCGGTACGACACCTGTCATT

2150  GACCGCATATATGTTATTTACCGTGTGTTTCCCG...GTCCATCTTTTAGAATTGGAAGA
      |  |||||||||||| |||| ||||||| || |    ||||| |||||||||| |||||
9969  AATCGCATATATGTTACTTACCATATGTCCCCTAGCCGTCCATGTTTTAGAACTAGAAGA

2207  TTACGACAGGCGTTGTCGTTGTAACAACCAAATTCTGTTGAATACCCTGCCGGTCGGAAC
      ||||||||||| || |||||| ||||||||||||||||||||||||||||||||||||||
10029 TTACGACAGGCGCTGCCGTTGCAACAACCAAATTCTGTTGAATACCCTGCCGGTCGGAAC

2267  TCAACTGCTTAAGCCAATCGCAGCGAGCGAAAGCTGCAATCGTCAGGAAGTGCTGGCTAT
      || ||||||||||||||||||||||||||||||||||||||||||||||||||||||||
10089 CGAATTGCTTAAGCCAATCGCAGCGAGCGAAAGCTGCAATCGTCAGGAAGTGCTGGCTAT

2327  TTTAAAGGACAAAGGAACCAAGTGTCTCAATCCTAACGCGCAAGCCGTGCGTCGTCACAT
      ||||||||||| |||||||||||||||||||||||||||||||| |||||||||||||||
10149 TTTAAAGGACAAGGGAACCAAGTGTCTCAATCCTAACGCGCAAGCCGTGCGTCGTCACAT

2387  CAACCGGCTATTTTTCGGTTAATCTTAGACGAGGAACAACGCATTTACGACGTAGTGTC
      ||||||||||||||||||||||||||||||||||||||||||||||||||||||||||||
10209 CAACCGGCTATTTTTCGGTTAATCTTAGACGAGGAACAACGCATTTACGACGTAGTGTC

2447  TACCAATATTGAGTTCGGTGCCTGGCCAGTCCGTACGGCCTACAAAGCCTTTCTCTGGAA
      ||||||||| |||||||||||||||||||||||||||||||||||||||||||| |||||
10269 TACCAATATTGAGTTCGGTGCCTGGCCAGTCCCTACGGCCTACAAAGCCTTTCTTTGGAA

2507  ATACGCCAAGAAACTTAATTACCACTACTTTAGACTGCGTTGGTGATCATGTCCCTATTT
```

Figure 7a cont.

```
       ||||||||||||  |||  ||  ||||||  ||||  ||||||||  ||||||||||||||||||)
10329  ATACGCCAAGAGACTGAACTACCACCACTTCAGACTGCGCTGGTGATCATGTCCCTATTT

2567  TACCGTGCGGTAGCCCTGGGCACGCTGAGCGCTCTGGTGTGGTATAGCACTAGTATCCTG
       |||||||||||||| ||||||||||| ||||||| |||||||||| ||||||| |||||
10389  TACCGTGCGGTAGCTCTGGGCACGCTAAGCGCTTTGGTGTGGTACAGCACTAGCATCCTC

2627  GCAGAGATTAACGAAGAATCCTGCTCCTCATCTTCTGTGGACCACGAAGACTGCGAGGAA
       |||||||||||||| |  |||||||||||||||||||  |||  ||||||||||||||||
10449  GCAGAGATTAACGAAAATTCCTGCTCCTCATCTTCTGCGGATCACGAAGACTGCGAGGAA

2687  CCGGACGAGATCGTTCGCGAAGAGCAAGACTATCGGGCTCTGCTGGCCTTTTCCCTAGTG
       ||||||||||||||||||||||||||||||||||||||||||||||| ||||||||||||
10509  CCGGACGAGATCGTTCGCGAAGAGCAAGACTATCGGGCTCTGCTGGCCTTTTCCCTAGTG

2747  ATTTGCGGTACGCTCCTCGTCACTTGTGTGATCTGAGACGTCATGCTGGTAGCGTTTATG
       |||||||||||||||||||||||||||||||||||||||||||||||||||||||||||
10569  ATTTGCGGTACGCTCCTCGTCACTTGTGTGATCTGAGACGTCATGCTGGTAGCGTTTATG

2807  AGTCGGGCGGTGGCCGGCACGCCGCATTTCCTAACCCGCGCAGCATGTTGCGCTTGCTGT
       |||||||||||||||  |||||||||||||||||||||||||||||||||||||||||||
10629  AGTCGGGCGGTGGCCGACACGCCGCATTTCCTAACCCGCGCAGCATGTTGCGCTTGCTGT

2867  TCACGCTCGTCCTACTGGCCCTCCACGGGCCGTCTGTCAACGCTAGCCGCGACTATGTGC
       ||||||||||||||  ||||||||||||| |||||| |||||||||||||||||||||
10689  TCACGCTCGTCCTGCTGGCCCTCCACGGGCAGTCTGTCGGCGCTAGCCGCGACTATGTGC

2927  ATGTTCGGCTACTGAGCTACCGAGGCGACCCCCTGGTCTTCAAGCACACTTTTTCGGGTG
       ||||||||||||||||||||||||||||||||||||||||||||||||||||| ||||||
10749  ATGTTCGGCTACTGAGCTACCGAGGCGACCCCCTGGTCTTCAAGCACACTTTCTCGGGTG

2987  TGCGTCGACCCTTCACCGAGCTAGGCTGGGCTGTGTGTCGCGACTGGGACAGTATGCATT
       ||||||||||||||||||||||||||||||| ||||||||||||||||||||||||||||
10809  TGCGTCGACCCTTCACCGAGCTAGGCTGGGCTGCGTGTCGCGACTGGGACAGTATGCATT

3047  GCACGCCTTTCTGGTCTACCGATCTGGAGCAGATGACCGACTCGGTGCGACGTTACAGCA
       ||||  ||||||||||||||||||||||||||||||||||||||||  ||||||||||||
10869  GCACACCCTTCTGGTCTACCGATCTGGAGCAGATGACCGACTCGGTGCGGCGTTACAGCA

3107  CGGTGAGCCCCGGCAAGGAAGTGACGCTTCAGCTTCACGGGAACCAAACCGTACAGCCGT
       ||||||||||||||||||||||||||||||||||||||||||||||||||||||||||||
10929  CGGTGAGCCCCGGCAAGGAAGTGACGCTTCAGCTTCACGGGAACCAAACCGTACAGCCGT

3167  CGTTTCTAAGCTTTACGTGCCGCCTGCAGCTAGAACCCGTGGTGGAAAATGTTGGCCTCT
       ||||||||||||||||||||||||||||||||||||||||| |||||||||||||||||
10989  CGTTTCTAAGCTTTACGTGCCGCCTGCAGCTAGAACCCGTGGTGGAAAATGTTGGCCTCT

3227  ACGTGGCCTACGTGGTCAACGACGGTGAACGCCCACAGCAGTTTTTTACACCGCAAGTAG
       ||||||||||||||||||||||||||  |||||||||||  |||||||||||||  ||||
11049  ACGTGGCCTACGTGGTCAACGACGGCGAACGCCCACAACAGTTTTTTACACCGCAGGTAG

3287  ACGTGGTACGCTTTGCTCTATATCTAGAAACGCTCTCCCGGATCGTGGAACCGTTAGAAT
       |||||||||||||||||||||||||||||| |||||||||||||||||||||||||||
11109  ACGTGGTACGCTTTGCTCTATATCTAGAAACACTCTCCCGGATCGTGGAACCGTTAGAAT

3347  CAGGTCGCCTGGCAGTGGAATTTGATACGCCTGACCTAGCTCTGGCGCCCGATTTAGTAA
       |||||||||||||||||||||||||||||||| |||||||||||||||||||||||||||
11169  CAGGTCGCCTGGCAGTGGAATTTGATACGCCTGACCTAGCTCTGGCGCCCGATTTAGTAA

3407  GCAGCCTCTTCGTGGCCGGACACGGCGAGACCGACTTTTACATGAACTGGACGCTGCGTC
       ||||||||||||||||||||||||||||||||||||||||||||||||||||||||||||
11229  GCAGCCTCTTCGTGGCCGGACACGGCGAGACCGACTTTTACATGAACTGGACGCTGCGTC

3467  GCAGTCAGACCCACTACCTGGAGGAGATGGCCTTACAGGTGGAGATTCTAAAGCCCCGCG
       |||||||||||||||||||||||||||||||||||||||||||||||||||| |||||||
11289  GCAGTCAGACCCACTACCTGGAGGAGATGGCCTTACAGGTGGAGATTCTAAAACCCCGCG

3527  GCGTACGTCACCGCGCTATTATCCACCATCCTAAGCTACAGCCGGGCGTTGGCCTGTGGA
       ||||||||||||||||||||||||||||||| ||||||||||| ||||||||||||||||
11349  GCGTACGTCACCGCGCTATTATCCACCATCCGAAGCTACAGCCGGGCGTTGGCCTGTGGA

3587  TAGATTTCTGCGTGTACCGCTACAACGCGCGCCTGACCCGCGGCTACGTACGATACACCC
       ||||||||||||||||||||||||||||||||||||||||||||||||| ||||||||||
11409  TAGATTTCTGCGTGTACCGCTACAACGCGCGCCTGACCCGCGGCTACGTACGATACACCC

3647  TGTCACCGAAAGCGCGCTTGCCCGCAAAAGCAGAGGGTTGGCTGGTGTCACTAGACAGAT
       ||||||||||||||||||||||||||||||||||||||||||||||||||||||||||||
11469  TGTCACCGAAAGCGCGCTTGCCCGCAAAAGCAGAGGGTTGGCTGGTGTCACTAGACAGAT

3707  TCATCGTGCAGTACCTCAACACATTGCTGATTACAATGATGGCGGCGATATGGGCTCGCG
       |||||||||||||||||||||||||||||||||||||||||||||||||||||||||||
11529  TCATCGTGCAGTACCTCAACACATTGCTGATTACAATGATGGCGGCGATATGGGCTCGCG

3767  TTTTGATAACCTACCTGGTGTCGCGGCGTCGGTAGAGGCTTGCGGAAACCACGTCCTCGT
       |||||||||||||||||||||||||||||||||||||||||||||||||| |||||||||
11589  TTTTGATAACCTACCTGGTGTCGCGGCGTCGGTAGAGGCTTGCGGAAACCACGTCCTCGT

3827  CACACGTCGTTCGCGGACATAGCAAGAAATTCACGTCGCCACGCTCTCGAGAATGCCGGCC
       ||||||||||||||||||||||||||||||| ||||||||||| ||||||||||||||||
11649  CACACGTCGTTCGCGGACATAGCAAGAAATCCACGTCGCCACATCTCGAGAATGCCGGCC

3887  CCGCGGGGTCCCCTTCGCGCAACATTCCTGGCCCTGGTCGCGTTCGGATTGCTGTTTCAG
       |||||||||||||||||||||||||||||||||||||||||||||||| ||||||  ||||
```

Figure 7a cont.

```
11709 TTGCGGGGTCCCCTTCGCGCAACATTCCTGGCCCTGGTCGCGTTCGGGTTGCTGCTTCAG

3947 ATAGACCTCAGCGACGCTACAAATGTGACCAACAGCACAAACGTCCCTACTAGCACCAGC
      |||||||||||||||||| ||||||||| ||||||||| |||||||||||||||||
11769 ATAGACCTCAGCGACGCTACGAATGTGACCAGCAGCACAAAAGTCCCTACTAGCACCAGC

4007 AGCAGAAATAGCGTCGACAACGCCACGAGTAGCGGACCCACGACCGGGATCAACATGACC
      | ||||||| |||||||||||||||||||||| |||||||||||||||||
11829 AACAGAAATAACGTCGACAACGCCACGAGTAGCGGACCCACAACCGGGATCAACATGACC

4067 ACCACCCACGAGTCTTCCGTTCACAACGTGCGCAATGACAAAATCATGAAAGTGCTGGCT
      |||||||||||||||||||||||||||||||||||||||| || | ||||||||||||||||
11889 ACCACCCACGAGTCTTCCGTTCACAAGGTGCGCAATAACGAGATCATGAAAGTGCTGGCT

4127 ATCCTCTTCTACATCGTGACAGGCACCTCCATTTTCAGCTTCATAGCGGTACTCATCGCG
      ||||||||||||||||||||||||||||||||||||||||||||||||||| ||||||
11949 ATCCTCTTCTACATCGTGACAGGCACCTCCATTTTCAGCTTCATAGCGGTACTGATCGCG

4187 GTAGTTTACTCCTCGTGTTGCAAGCACCCGGGCCGCTTTCGTTTCGCCGACGAAGAAGCC
      ||||||||||||||||||||||||||||||||||||||||||||||||||||||||||| |||
12009 GTAGTTTACTCCTCGTGTTGCAAGCACCCGGGCCGCTTTCGTTTCGCCGACGAAGAGGCC

4247 GTCAATCTGTTGGACGACACGGACGACAGTGGCGGCAGCAGCCCGTTGGCAGCGGTTCC
      ||||| ||||||||||||||||||||||||||||||||||||||| ||||||||||||||
12069 GTCAACCTGTTGGACGACACGGACGACAGTGGCGGCAGCAGCCCGTTTGGCAGCGGTTCC

4307 CGACGAGGTTCTCAGATCCCCGCCGGATTTTGTTCCTCGAGCCCTTATCAGCGGTTGGAA
      ||||||||||||||||||||||||||||||||||||||||||||||||||||||||||||
12129 CGACGAGGTTCTCAGATCCCCGCCGGATTTTGTTCCTCGAGCCCTTATCAGCGGTTGGAA

4367 ACTCGGGACTGGGACGAGGAGGAGGAGGCGTCCGCGGCCCGCGAGCGCATGAAACATGAT
      ||||||||||||||||||||||||||||| |||||||||||||||||||||||||||||
12189 ACTCGGGACTGGGACGAGGAGGAGGAGGCGTCCGCGGCCCGCGAGCGCATGAAACATGAT

4427 CCTGAGAACGTCATCTATTTCAGAAAGGATGGCAACTTGGACACGTCGTTCGTGAATCCC
      ||||||||||||||||||||||||||||||||||||||||||||||||||||||||||||
12249 CCTGAGAACGTCATCTATTTCAGAAAGGATGGCAACTTGGACACGTCGTTCGTGAATCCC

4487 AATTATGGGAGAGGCTCGCCTTTGACCATCGAATCTCACCTCTCGGACAATGAGGAGGAC
      ||||||||||||||||||||||||||||||||||||||||||||||||||||||||||||
12309 AATTATGGGAGAGGCTCGCCTTTGACCATCGAATCTCACCTCTCGGACAATGAGGAGGAC

4547 CCCATCAGGTACTACGTCTCGGTGTACGATGAACTGACCGCCTCGGAAATGGAAGAACCT
      |||||||||||||| |||||||||||||||||||||||||||||||||||||||||||||
12369 CCCATCAGGTACTACGTTTCGGTGTACGATGAACTGACCGCCTCGGAAATGGAAGAACCT

4607 TCCAACAGCACCAGCTGGCAGATTCCCAAACTAATGAAAGTTGCTACGCAACCCGTCTCG
      ||  ||||||||||||||||||||||||||||||||||||||||| | ||||||||||||
12429 TCGAACAGCACCAGCTGGCAGATTCCCAAACTAATGAAAGTTGCCATGCAACCCGTCTCG

4667 CTCAGAGATCCCGAGTACGACTAGGCTTTTTTTTTTGTCTTTCGGTTCCAACTCTTTCCC
      ||||||||||||||||||||||||||||||||||||||||||||||||||||||||||||
12489 CTCAGAGATCCCGAGTACGACTAGGCTTTTTTTTTTGTCTTTCGGTTCCAACTCTTTCCC

4727 CGCCCCATCACCTCGCCTATACTATGTGTATGATGTCTCATAATAAAGCTCTCTTTCTCA
      |||||||||||||||| |||||||||||||||||||||||||||||||| ||||||||||
12549 CGCCCCATCACCTCGCCTGTACTATGTGTATGATGTCTCATAATAAAGCTTTCTTTCTCA

4787 GTCTGCAACATGCGGCTGTGTCGGGTGTGGCTGTCTGTTTGTCTGTGCGCCGTGGTGCTG
      |||||||||||| ||||||||||||||||||||||||||||||||||||||||||||
12609 GTCTGCAACATGCAGCTGTGTCGGGTGTGGCTGTCTGTTTGTCTGTGCGCCGTGGTGCTG

4847 GGTCAGTGCCAGCGGGGAGACCGCAGAAAAAAACGATTATTACCGAGTACCGCATTACTGG
      |||||||||||||||| |||||  ||||||||||||||||||||||||||||||||||||
12669 GGTCAGTGCCAGCGGGAAACCGCGGAAAAAAACGATTATTACCGAGTACCGCATTACTGG

4907 GACGCGTGCTCTCGCGCGCTGCCTGACCAAACCCGTTACAAGTATGTGGAACAGCTCGTG
      |||||||||||||||||||| |||||||||||||||||||||||||||||||||||||||
12729 GACGCGTGCTCTCGCGCGCTGCCCGACCAAACCCGTTACAAGTATGTGGAACAGCTCGTG

4967 GACGTCACGTTGAACTACCACTACGATGCGAGCCACGGCTTGGACAACTTTGACGTGCTC
      |||||||||||||||||||||||||||||||||||||||||||||||||||||||||||
12789 GACCTCACGTTGAACTACCACTACGATGCGAGCCACGGCTTGGACAACTTTGACGTGCTC

5027 AAGAGGTGAGGGTACGCGCTAAAGGTGTATGACAACGGGAAGGTAAGGGCGAACGGGTAA
      |||||||||||||||||||||||| ||||||||| ||||||||||||||||||||||||
12849 AAGAGGTGAGGGTACGCGCTAAAGGTGCATGACAACGGGAAGGTAAGGGCGAACGGGTAA

5087 CGGGTAGGTAACCGCATGGGGTGTGAAATGACGTTCGGAACCTGTGCTTGCAGAATCAAC
      ||| || ||||||||||||| ||||||||||||| |||||||||||||||||||||||
12909 CGGCTAAGTAACCGCATGGGGTATGAAATGACGTTTGGAACCTGTGCTTGCAGAATCAAC

5147 GTGACCGAGGTGTCGTTGCTCATCAGCGACTTTAGACGTCAGAACCGTCGCGGCGGCACC
      |||||||||||||||||||||||||||||||||||||||||||||||||||||||||||
12969 GTGACCGAGGTGTCGTTGCTCATCAGCGACTTTAGACGTCAGAACCGTCGCGGCGGCACC

5207 AACAAAAGGACCACGTTCAACGCCGCCGGTTCGCTGGCGCCTCACGCCCGGAGCCTCGAG
      ||||||||||||||||||||||||||||||||||||||||||| |||||||||||||||
13029 AACAAAAGGACCACGTTCAACGCCGCCGGTTCGCTGGCGCCCACACGCCCGGAGCCTCGAG

5267 TTCAGCGTGCGGCTCTTTGCCAACTAGCCTGCGTCACGGGAAATAATATGCTACGGCTTC
      ||||||||||||||||||||||||| ||||||||||||||||||||||||| ||||||
13089 TTCAGCGTGCGGCTCTTTGCCAACTAGCCTGCGTCACGGGAAATAATATGCTGCGGCTTC
```

Figure 7a cont.

```
5327  TGCTTCGTCACCACTTTCACTGCCTGCTTCTGTGCGCGGTTTGGGCAACGCCCTGTCTGG
      ||||||||||||||||||||||||||||||||||||||||||||||||||||||||||||
13149 TGCTTCGTCACCACTTTCACTGCCTGCTTCTGTGCGCGGTTTGGGCAACGCCCTGTCTGG

5387  CGTCTCCGTGGTTCACGCTAACGGCGAACCAGAATCCGTCCCCGCCATGGTCTAAACTGA
      |||||||||||  ||||||||||| ||||||||||||||||||||||||||||||||||
13209 CGTCTCCGTGGTCGACGCTAACGGCAAACCAGAATCCGTCCCCGCCATGGTCTAAACTGA

5447  CGTATCCCAAACCGCATGACGCGGCGACGTTTTACTGTCCTTTTCTCTATCCCTCGCCCC
      ||||| ||||||||||||||||||||||||||||||||||||||||||||||||||||||
13269 CGTATTCCAAACCGCATGACGCGGCGACGTTTTACTGTCCTTTTCTCTATCCCTCGCCCC

5507  CACGGTCCCCCTCGCAATTCCCGGGGTTCCAGCGGGTATCAACGGGTCCCGAGTGTCGCA
      ||||||||||| ||||||| |||||||||||||| ||||||||||||||||||||||||
13329 CACGGTCCCCCTTGCAATTCTCGGGGTTCCAGCAGGTATCAACGGGTCCCGAGTGTCGCA

5567  ACGAGACCCTGTATCTGCTGTACAACGGGAAGGCCAGACCTTGGTGGAGAGAAGCTCCA
      |||||||||||||||||||||||||||||||||||||||||||||||||||||||||||
13389 ACGAGACCCTGTATCTGCTGTACAACGGGAAGGCCAGACCTTGGTGGAGAGAAGCTCCA

5627  CCTGGGTGAAAAAGGTGATCTGGTATCTGAGCGGTCGCAATCAGACCATCCTCCAACGGA
      |||||||||||||||||||||||||||||||||||||||||| |||||||||||||||||
13449 CCTGGGTGAAAAAGGTGATCTGGTATCTGAGCGGTCGCAACCAGACCATCCTCCAACGGA

5687  TGCCCCGAACGGCTTCGAAACCGAGCGACGGAAACGTGCAGATCAGCGTGGAAGACGCCA
      ||||||  ||||||||||||||||||||||||||||||||||||||||||||||||||||
13509 TGCCCCAAACGGCTTCGAAACCGAGCGACGGAAACGTGCAGATCAGCGTGGAAGACGCCA

5747  AGATTTTTGGAGCGCACATGGTGCCCAAGCAGACCAAGCTGCTACGCTTCGTCGTCAACG
      ||||||||||||||||||||||||||||||||||||||||||||||||||||||||||||
13569 AGATTTTTGGAGCGCACATGGTGCCCAAGCAGACCAAGCTGCTACGCTTCGTCGTCAACG

5807  ATGGCACGCGTTATCAGATGTGTGTGATGAAGCTGGAGAGCTGGGCCCACGTCTTCCGGG
      ||||||||||||||||||||||||||||||||||||||||||||||||||||||||||||
13629 ATGGCACGCGTTATCAGATGTGTGTGATGAAGCTGGAGAGCTGGGCCCACGTCTTCCGGG

5867  ACTACAGCGTGTCTTTTCAGGTGCGATTGACGTTCACCGAGGCCAATAACCAGACTTACA
      ||||||||||||||||||||||||||||||||||||||||||||||||||||||||||||
13689 ACTACAGCGTGTCTTTTCAGGTGCGATTGACGTTCACCGAGGCCAATAACCAGACTTACA

5927  CCTTCTGTACCCATCCCAATCTCATCGTTTGAGCCCGTCGCGCGCGCAGGGAATTTTGAA
      |||||||||||||||||||||||||||| ||||||||||||||||||||||||||||||
13749 CCTTCTGTACCCATCCCAATCTCATCATTTGAGCCCGTCGCGCGCGCAGGGAATTTTGAA

5987  AACCGCGCGTCATGAGTCCCAAAGACCTGACGCCGTTCTTGACGACGTTGTGGCTGCTAT
      ||||||||||||||||||||||||||||||||||||||||||||||||||||||||||||
13809 AACCGCGCGTCATGAGTCCCAAAGACCTGACGCCGTTCTTGACGACGTTGTGGCTGCTAT

6047  TGGGTCACAGCCGCGTGCCGCGGGTGCGCGGCAGAAGAATGTTGCGAATTCATAAACGTCA
      ||||||||||||||||||||||||||||||||||||||||||||||||||||||||||||
13869 TGGGTCACAGCCGCGTGCCGCGGGTGCGCGGCAGAAGAATGTTGCGAATTCATAAACGTCA

6107  ACCACCCGCCGGAACGCTGTTACGATTTCAAAATGTGCAATCGCTTCACCGTCGCGTACG
      ||||||||||||||||||||||||||||||||||||||||||||||||||||||||||||
13929 ACCACCCGCCGGAACGCTGTTACGATTTCAAAATGTGCAATCGCTTCACCGTCGCGTACG

6167  TATTTTTATGATTGTCTGCGTTCTGTGGTGCGTCTGGATTTGTCTCTCGACGTTTCTGAT
      ||||||  ||||||||||||||||||||||||||||||||||||||||||||||||||||
13989 TATTTTTCATGATTGTCTGCGTTCTGTGGTGCGTCTGGATTTGTCTCTCGACGTTTCTGAT

6227  AGCCATGTTCCATCGACGATCCTCGGGAATGCCAGAGTAGATTTTCATGAATCCACAGGC
      ||||||||||||||||||||||||||||||||||||||||||||||||||||||||||||
14049 AGCCATGTTCCATCGACGATCCTCGGGAATGCCAGAGTAGATTTTCATGAATCCACAGGC

6287  TGCGGTGTCCGGACGGCGAAGTCTGCTACAGTCCCGAGAAAACGGCTGAGATTCGCGGGA
      ||||||||||||||||||||||||||||||||||||||||||||||||||||||||||||
14109 TGCGGTGTCCGGACGGCGAAGTCTGCTACAGTCCCGAGAAAACGGCTGAGATTCGCGGGA

6347  TCGTCACCACCATGACCCATTCATTGACACGCCAGGTCGTACACAACAAACTGACGAGCT
      ||||||||||||||||||||||||||||||||||||||||||||||||||||||||||||
14169 TCGTCACCACCATGACCCATTCATTGACACGCCAGGTCGTACACAACAAACTGACGAGCT

6407  GCAACTACAATCCGTAAGTCTCTTCCTCGAGGGCCTTACAGCCTATGGGAAAGTAAGAC.
      ||||||||||||||||||||||||||||||||||||||||||||||||||||| ||||||
14229 GCAACTACAATCCGTAAGTCTCTTCCTCGAGGGCCTTACAGCCTATGGGAGAGTAAGACA

6466  .AGAGGGACAAAACATCATT.AAAAAAAAAGTCTAATTTCACGTTTTGTACCCCCCCTTC
       ||||||||||||||||||  |||||||||||||||||||||||||||||||  ||||||||
14289 GAGAGGGACAAAACATCATTAAAAAAAAAAGTCTAATTTCACGTTTTGTA.CCCCCTTC

6524  CCCTCCGTGTTGTAGGTTATA..CCTCGAAGCTGACGGGCGAATACGCTGCGGCAAAGTG
      ||||||||||||||  ||  ||  |  ||||||  |||  | |  ||||
14348 CCCTCCGTGTTGTAGCCCATCGGCCGCGGCGATCTCCTAGTAACACTCGTCCGACACTTC

6582  AACGACAAGGCGCAGTACCTGCTGGGCGCCGCTGGCAGCGTTCCCTATCGATGGATCAAC
      || |     ||   || |||  ||   |   |   |  |  |   |||    |||
14408 CACCATCTCCAGCTCGGCCGGCGGTTCGGCATCCTCTACCAGCGGCGTCGTCTCATCTTT

6642  CTGGAATACGACAAGATAACCCGGATCGTGGGCCTGGATCAGTACCTGGAGAGCGTTAAA
      ||  |  |   |      ||  ||  ||      |  || | ||||
14468 GCCGCAGCAGCGGACGCACACCCTTCTCCAGGCAGAACGCCACCAGCTGCCGCCGAACGTA
```

Figure 7a cont.

```
6702  AAACACAAACGGCTGGATGTGTGCCGCGCTAAAATGGGCTATATGCTGCAGTGAATAATA
      ||| || ||| |||     | ||.|     ||           |
14528 CCACAGGTACACGTGCAGACCTGCGAACAGGACTACGGAGGTCATGACCACCACGACGCA

6762  AAATGTGTGTTTGTCCGAAATACGCGTTTTGAGATTTCTGTCGCCGACTAAATTCATGTC
      | |     |   ||   | || | || ||         | || | |           |
14588 CACGGGAATCCAGGGATCGAGATTGTTGCTGGAAACTCGCTATCGCCACCGACGTGCCCGC

6822  GCGCGATAGTGGTGTTTATCGCCGATAGAGATGGCGATATTGGAAAAATCGATATTTGAA
      | |              |||||   |  |  | ||| |                    |
14648 GTCTGTCTCACCGCGCTCGCCCGATGTCGCGCGGCTTGTTATACGCTAGCCCGTCGCCG

6882  AATATGGCATATTGAAAATGTCGCCGATGTGAGTTTCTGTGTAACTGATATCGCCATTTT
      | ||           |  || | || || ||  || ||| |  | ||    |   |||
14708 CCTCGGGGCACGGTGCCCTCCTACCCACGTAACTTCCTCCGTGACTTAAAGTCGCGTGTG

6942  TCCAAAAGTGATTTTTGGGCATACGCGATATCTGGCGATAGCGCTT....ATATCGTTTA
      |       | |||  | |           ||||||| ||    || ||
14768 GTAGATCTCCTGCTCCGTGGACGAACCGTCCGGCAGGATAGCGGTTAAGGATTCGGTGCT

6998  CGGGGGATGGCGATAGACGACTTTGGTGACTTGGGCGATTCTGTGTGTCGCAAATATCGC
      ||  || || |         || |  ||   |        |  |           |  |
14828 AAGGCCGTGTCGCCAACGTCGAATGCTACGTTGCAACAGCTTCGACGGACGGCCATCCCC

7058  AGTTTCGATATAGGTGACAGACGATATGAGGCTATATCGCCGATAGAGGCGACATCAAGC
      | ||          |    | ||  | ||        || | || |    |||| |
14888 TCTCTCATCGCAATAATAAAACACCAGCAG.........CGCGCACGACGCGATCACGG

7118  TGGCACATGGCCAATGCATATCGATCTATACATTGAATCAATATTGGCCATTAGCCATAT
      || |||    |                | ||                        |||||
14938 TGACACCCATGATTAGACCCACGCAGATAGCCAGCCCCGCTAGCGTATCTAGCGCCATCG

7178  TATTCA......TTGGTTATATAGCATAAATCAATATTGGCTATTGGCCATTGCATACGT
      |||    |||  |    |||  |        |  | ||      |    || |
14998 CGTTCGCTCCCGTTGTCTCCTGAGCGAAGCAACTTCTCGGTCCCCGTTTTCAACAGTTTT

7232  TGTATCCATATCA....TAATATGTACATTTATATTGGCTCATGTCCAACATTACCGCC
      ||| ||| | ||     ||  ||                | | ||     |    |  |
15058 TGTTTCCTTCTCCGCGACTAGATGTTAACGCCCGGGGTCTTTCCGGCCGTGCTCTACCTC

7287  ATGTTGACATTGATTATTGACTAGTTATTAATAGTAATCAATTACGGGGTCATTAGTTCA
      ||     | |      | ||  |    | ||    | || ||||
15118 CTGGCGCTTGTCGTCTGGGTTGAGATGTTCTGCCTCGTCGCCGTAGCCGTCGTCGAGCGC

7347  TAGCCCATATATGGAGTTCCGCGTTACATAACTTACGGTAAATGGCCCGCCTGGCTGACC
      ||  |  |   |  |  | ||     ||       |||   | | |  | | |  |  |
15178 GAGATCGCCTGGGCGCTGCTGCTGCGGATGCTGGTCGTTGGCCTGATGGTGGAAGTCGGC

7407  GCCCAACGACCCCCGCCCATTGACGTCAATAATGACGTATGTTCCCATAGTAACGCCAAT
      |||      |  |||  |    |    |     | ||  |               ||  |
15238 GCCGCCGCCGCTTGGACCTTCGTGCGTTGTCTTGCCTATCAGCGCTCCTTCCCCGTGCTT

7467  AGGGACTTTCCATTGACGTCAATGGGTGGAGTATTTACGGTAAACTGCCCACTTGGCAGT
      | || ||| || |  |  | ||            | | |     ||       |  ||
15298 ACGGCCTTCCCCTGAAACCCACGTTAACCGACCGTCCCAAAAACGCCGGTGTTAACACAG

7527  ACATCAAGTGTATCATATGCCAAGTACGCCC...CCTATTGACGTCAATGACGGTAAATG
      | ||    | ||  ||       | |  || |      ||| || || |  |||  |  |
15358 GAAAAAAGAAACCACGCAGGAACCGCGCAGGAACCACGCGGAACATGGGACACTATCTG

7584  GCCCGCCTGGCATTATGCCCAGTACATGACCTTATGGGACTTTCCTACTGGCAGTACATC
      |  ||||      | ||       || ||   ||   ||    |    |     || |||
15418 GAAATCCTGTTCAACGTCATCGTCTTCACTCTGCTGCTTCGCCGTCATGGTCAGTATCGTC

7644  T
15478 G
```

Figure 7b

Fast alignment of DNA sequences TB40E4 and HCU33331 (Toledo)

Upper line: TB40E4 from 1 to 6137
Lower line: HCU33331 from 9315 to 15450

TB40E4:HCU33331 identity= 82%

```
   1    TTTAAACCTGTGTGTTGTGTGATTGATTGGTACGTGGGGGGATCCGATTTCAAAGGGAGG
        |||||||| ||||||||||||||||||||||| |||||||||||||||||||||||| ||
 9315   TTTAAACCTCTGTGTTGTGTGATTGATTGGTATGTGGGGGATCCGATTTCAAAGGGGGG

61    TAGTTATCGGGAGTTGATGTGTCATGGACGTAGTTTTGAGTGATTTTCCGGGAATACCGG
        || |||||||||| ||||||||||||||||| |||||||||| |||||||||||||||||
 9375   TACTTATCGGGAATTGATGTGTCATGGACGCAGTTTTGAGCGATTTTCCGGGAATACCGG

121    ATATTACGAATTACTGATAGTGACGTAGATAATAAAATTATAATGCGATTTATTTTTAGT
        |||||||||||||||| ||||||||||||||||||||||||||||||||||| |||| ||
 9435   ATATTACGAATTACTGGTAGTGACGTAGATAATAAAATTATAATGCGATTAATTTTTGGT

181    CTGTTTGGTCTTTTGATCGC......GTTGTGCTATAAGGTGGAAAGTGTGGAACTACGT
        |||   | ||||  |  ||          ||  |||||||| |  ||||| | |   |||  ||| ||||
 9495   GCGTTGATTATTTTTTTAGCATATGTGTATCATTATGAGGTGAATGAACAGAATTACGC

235    TGTCGGTGTAGCAATGGTTCAAATCATCCCGTATTCGGCGTTTTTTGGGTCGGCTATAAA
        || | |||    ||| |  ·|||   ||          || | ||    |||
 9555   TGCAGATGTCTTCATAG...AAAATGGCCGCCTAATAAAATTATATTGGGTAATTATTGG

295    CCTCCAGATCCTACATGCGACAAAACGCAACAGTTTTTATTACCTGCCCGACAAACACCT
        | ||         | | ||         |                 |||      |   ||
 9612   CTTCATCGCGATCCCAGAGGGCCCGGATGCGATAAAAATGAACATTTATTGTATCCAGAC

355    GTATGTTTGTCTCCTGATCATTATCTATCGAAATGGGTTGATGGCAAACGAAGTAACTGG
        | | |   | ||||  ||    |||    || |     ||| |     || |||
 9672   GGAAGGAAACCGCCTGGACCTGGAGTATGTTTATCGCCCGATCACCTCTTCTCAAAATGG

415    TGGCATAAAGTGTTTATAAAGAAAAACTCTGATAATGGACCACATATAGAAGACAAAAGT
        |   | |||.          || |            ||| || |   |||||         ||    ||
 9732   TTAGACAAACACAACGATAATAGGTGGTATAATGTTA....ACATAACGAAATCACCAGG

475    GACACCAATAGACACCCGCCTTGGCGACTATAATTTTTATAAATTGTAAAACGAGTTGG
        |   |   |        |   |              |    |     ||||   | |||     |||
 9788   ACCGAGACGAATAAATATAACCTTGATAGGTGTTAGAGGATAATATTTAATGTATGTTTT

535    CAATATCACGTATATAGCGAAA.AAGGTAATACAATGTGTTTCGACATGGTTTTGACAT
        |||    ||     ||| ||   |||| ||  || || ||||   ||||
 9848   CAAACAGACAAGTTCGTTAAAACAAAATATTACAGTATGTGTTTAATATGGTGCTAACAT

594    GGTTACACCATCCGATTCCAAATTCGCACATCAAAGTCTTATCGGTACGATACCTGTATT
        |||| |||||||| || |||| ||||| ||||| |||||  | |||||||||||| ||||||   |
 9908   GGTTGCACCATCCGGTTTCAAACTCGCATATCAATCTGTTATCGGTACGACACCTGTCAT

654    TGACCGCATATGTGTTATTTTCCACGTGTCCCGTATTCGTCTATCTCTTAGAATTGGAAG
        | | ||||| || ||| ||| || ||| ||||||||  ||| ||  | || |||| | ||||
 9968   TAATCGCATATATGTTACTTACCATATGTCCCCTAGCCGTCCATGTTTTAGAACTAGAAG

714    ATTACGACAAGCGCTGTCGTTGCAACAACCAAATTCTGTTGAATACCCTGCCAGTCGGAA
        |||||||||  |||||| |||||||||||||||||||||||||||||||||||||  ||||||||
10028   ATTACGACAGGCGCTGCCGTTGCAACAACCAAATTCTGTTGAATACCCTGCCGGTCGGAA

774    CTCAACTGCTTAAGCCAATCGCAGCGAGCGAAAGCTGCAATCGTCAGGAAGTGCTGGCTA
        |  || |||||||||||||||||||||||||||||||||||||||||||||||||||||||
10088   CCGAATTGCTTAAGCCAATCGCAGCGAGCGAAAGCTGCAATCGTCAGGAAGTGCTGGCTA

834    TTTTAAAGGACAAGGGCACCAAGTGTCTCAATCCTAACGCGCAAGCTGTGCGTCGTCACA
        ||||||||||||||| ||||||||||||||||||||||||||||||||| ||||||||||||
10148   TTTTAAAGGACAAGGGAACCAAGTGTCTCAATCCTAACGCGCAAGCCGTGCGTCGTCACA

894    TCAACCGGCTATTTTTCGGTTAATCTTAGACGAAGAACAACGCATTTACGACGTAGTGT
        ||||||||||||||||||||||||||||||||| ||||||||||||||||||||||||||||
10208   TCAACCGGCTATTTTTCGGTTAATCTTAGACGAGGAACAACGCATTTACGACGTAGTGT

954    CTACCAATATTGAGTTTGGTGCCTGGCCAGCCCCTACGGCCTACAAAGCCTTTCTCTGGA
        ||||||||||||||| |||||||||||||||| ||||||||||||||||||||||||| ||||
10268   CTACCAATATTGAGTTCGGTGCCTGGCCAGTCCCTACGGCCTACAAAGCCTTTCTTTGGA

1014    AATACGCCAAGAAATTGAACTACCACCACTTCAGACTGCGCTGGTGATCATGTCCCTATT
        ||||||||||| | ||||||||||||||||||||||||||||||||||||||||||||||
10328   AATACGCCAAGAGACTGAACTACCACCACTTCAGACTGCGGTGGTGATCATGTCCCTATT

1074    TTACCGTGCGGTAGCTCTGGGCACACTAAGCGCTCTGGTGTGGTACAGCACTAGTATCCT
        ||||||||||||||||||||||||||| |||||||| |||||||||||||||||| |||||
10388   TTACCGTGCGGTAGCTCTGGGCACGCTAAGCGCTTTGGTGTGGTACAGCACTAGCATCCT

1134    CGCAGAGATTAACGAAAATTCCTGCTCCTCATCTTCTGTGGACCACGAAGAGTGTGAGGA
```

Figure 7b cont.

```
10448 CGCAGAGATTAACGAAAATTCCTGCTCCTCATCTTCTGCGGATCACGAAGACTGCGAGGA

1194 ACCGGACGAGATCGTTCGCGAAGAGCAAGACTATCGGGCTCTGCTGGCCTTTTCCCTAGT
10508 ACCGGACGAGATCGTTCGCGAAGAGCAAGACTATCGGGCTCTGCTGGCCTTTTCCCTAGT

1254 GATTTGCGGTACGCTCCTCGTCACTTGTGTGATCTGAGACGTCATGCTGGTAGTGTTTAT
10568 GATTTGCGGTACGCTCCTCGTCACTTGTGTGATCTGAGACGTCATGCTGGTAGCGTTTAT

1314 GAGTCGGGCGGTGGCCGGCACGCCGCATTTCCTAACCCGCGCAGCATGTTGCGCTTGCTG
10628 GAGTCGGGCGGTGGCCGACACGCCGCATTTCCTAACCCGCGCAGCATGTTGCGCTTGCTG

1374 TTCACGCTCGTCCTGCTGGCCCTCCACGGGCCGTCTGTCAATGCTAGCCGCGACTATGTG
10688 TTCACGCTCGTCCTGCTGGCCCTCCACGGGCAGTCTGTCGGCGCTAGCCGCGACTATGTG

1434 CATGTTCGGCTATTGAGCTACCGAGGCGACCCCCTGGTCTTCAAGCACACTTTTTCGGGT
10748 CATGTTCGGCTACTGAGCTACCGAGGCGACCCCCTGGTCTTCAAGCACACTTTCTCGGGT

1494 GTGCGTCGACCCTTCACCGAGCTAGGCTGGGCTGCGTGTCGCGACTGGGACAGTATGCAT
10808 GTGCGTCGACCCTTCACCGAGCTAGGCTGGGCTGCGTGTCGCGACTGGGACAGTATGCAT

1554 TGCACGCCCTTCTGGTCTACCGATCCGGAGCAGATGACCGACTCGGTGCGGCGTTACAGC
10868 TGCACACCCTTCTGGTCTACCGATCGGAGCAGATGACCGACTCGGTGCGGCGTTACAGC

1614 ACAGTGAGCCCCGGCAAGGAAGTGACGCTTCAGCTTCACGGGAACCAAACCGTACAGCCG
10928 ACGGTGAGCCCCGGCAAGGAAGTGACGCTTCAGCTTCACGGGAACCAAACCGTACAGCCG

1674 TCGTTTCTAAGCTTTACGTGCCGCCTGCAGCTAGAACCCGTGGTGGAAAATGTTGGCCTC
10988 TCGTTTCTAAGCTTTACGTGCCGCCTGCAGCTAGAACCCGTGGTGGAAAATGTTGGCCTC

1734 TACGTGGCCTACGTGGTCAACGACGGTGAACGCCCACAGCAGTTTTTTACACCGCAGGTA
11048 TACGTGGCCTACGTGGTCAACGACGGCGAACGCCCACAACAGTTTTTTACACCGCAGGTA

1794 GACGTGGTACGCTTTGCTCTATATCTAGAGACGCTCTCCCGGATCGTGGAACCGTTAGAA
11108 GACGTGGTACGCTTTGCTCTATATCTAGAAACAGTCTCCCGGATCGTGGAACCGTTAGAA

1854 TCAGGTCGCCTGGCAGTGGAATTTGATACGCCTGACCTAGCTCTGGCGCCCGATTTAGTA
11168 TCAGGTCGCCTGGCAGTGGAATTTGATACGCCTGACCTAGCTCTGGCGCCCGATTTAGTA

1914 AGCAGCCTCTTCGTGGCCGGACACGGCGAGACCGACTTTTACATGAACTGGACGCTGCGT
11228 AGCAGCCTCTTCGTGGCCGGACACGGCGAGACCGACTTTTACATGAACTGGACGCTGCGT

1974 CGCAGTCAGACCCACTACCTGGAGGAGATGGCCTTACAGGTGGAGATTCTAAAGCCCCGC
11288 CGCAGTCAGACCCACTACCTGGAGGAGATGGCCTTACAGGTGGAGATTCTAAAACCCCGC

2034 GGCGTACGTCACCGCGCTATTATCCACCATCCGAAGCTACAGCCGGGCGTTGGCCTGTGG
11348 GGCGTACGTCACCGCGCTATTATCCACCATCCGAAGCTACAGCCGGGCGTTGGCCTGTGG

2094 ATAGATTTCTGCGTGTACCGCTACAACGCGCGCCTGACCCGCGGCTACGTACGATACACC
11408 ATAGATTTCTGCGTGTACCGCTACAACGCGCGCCTGACCCGCGGCTACGTACGATACACC

2154 CTGTCACCGAAAGCGCGCTTGCCCGCAAAAGCAGAGGGTTGGCTGGTGTCACTAGACAGA
11468 CTGTCACCGAAAGCGCGCTTGCCCGCAAAAGCAGAGGGTTGGCTGGTGTCACTAGACAGA

2214 TTCATCGTGCAGTACCTCAACACATTGCTGATTACAATGATGGCGGCGATATGGGCTCGC
11528 TTCATCGTGCAGTACCTCAACACATTGCTGATTACAATGATGGCGGCGATATGGGCTCGC

2274 GTTTTGATAACCTACCTGGTGTCGCGGCGTCGGTAGAGGCTTGCGGAAACCACGTCCTCG
11588 GTTTTGATAACCTACCTGGTGTCGCGGCGTCGGTAGAGGCTTGCGGAAACCACGTCCTCG

2334 TCACACGTCGTTCGGGACATAGCAAGAAATCCACGTCGCCACGTCTCGAGAATGCCGGC
11648 TCACACGTCGTTCGGGACATAGCAAGAAATCCACGTCGCCACATCTCGAGAATGCCGGC

2394 CCCGCGGGGTCCCCTTCGCGCAACATTCCTGGCCCTGGTCGCGTTCGGGTTGCTGCTTCA
11708 CTTGCGGGGTCCCCTTCGCGCAACATTCCTGGCCCTGGTCGCGTTCGGGTTGCTGCTTCA

2454 GATAGACCTCAGCGACGCTACGAATGTGACCAGCAGCACAAAAGTCCCTACTAGCACCAG
11768 GATAGACCTCAGCGACGCTACGAATGTGACCAGCAGCACAAAAGTCCCTACTAGCACCAG

2514 CAGCAGAAATAGCGTCGACAATGCCACGAGTAGCGGACCCACGACCGGGATCAACATGAC
```

Figure 7b cont.

```
11828 CAACAGAAATAACGTCGACAACGCCACGAGTAGCGGACCCACAACCGGGATCAACATGAC

2574 CACCACCCACGAGTCTTCCGTTCACAGCGTGCGCAATGACGAAATCATGAAAGTGCTGGC
      ||||||||||||||||||||||||| ||||||||| |||| |||||||||||||||||
11888 CACCACCCACGAGTCTTCCGTTCACAACGTGCGCAATAACGAGATCATGAAAGTGCTGGC

2634 TATCCTCTTCTACATCGTGACAGGCACCTCCATTTTCAGCTTCATAGCGGTACTGATCGC
      ||||||||||||||||||||||||||||||||||||||||||||||||||||||||||||
11948 TATCCTCTTCTACATCGTGACAGGCACCTCCATTTTCAGCTTCATAGCGGTACTGATCGC

2694 GGTAGTTTACTCCTCGTGTTGCAAGCACCCGGGCCGCTTTCGTTTCGCCGACGAAGAAGC
      |||||||||||||||||||||||||||||||||||||||||||||||||||||||| ||
12008 GGTAGTTTACTCCTCGTGTTGCAAGCACCCGGGCCGCTTTCGTTTCGCCGACGAAGAGGC

2754 CGTCAACCTGTTGGACGACACGGACGACAGTGGCGGTGGCAGCCCGTTTGGCAGCGGTTC
      |||||||||||||||||||||||||||||||||| ||||||||||||||||||||||||
12068 CGTCAACCTGTTGGACGACACGGACGACAGTGGCGGCAGCAGCCCGTTTGGCAGCGGTTC

2814 CCGACGAGGTTCTCAGATCCCCGCCGGATTTTGTTCCTCGAGCCCTTATCAGCGGTTGGA
      ||||||||||||||||||||||||||||||||||||||||||||||||||||||||||||
12128 CCGACGAGGTTCTCAGATCCCCGCCGGATTTTGTTCCTCGAGCCCTTATCAGCGGTTGGA

2874 AACTCGGGACTGGGACGAGGAGGAGGAGGCGTCCGCGGCCCGCGAGCGCATGAAACATGA
      ||||||||||||||||||||||||||||||||||||||||||||||||||||||||||
12188 AACTCGGGACTGGGACGAGGAGGAGGAGGCGTCCGCGGCCCGCGAGCGCATGAAACATGA

2934 TCCTGAGAACGTCATCTATTTCAGAAAGGATGGCAACTTGGACACGTCGTTCGTGAATCC
      ||||||||||||||||||||||||||||||||||||||||||||||||||||||||||||
12248 TCCTGAGAACGTCATCTATTTCAGAAAGGATGGCAACTTGGACACGTCGTTCGTGAATCC

2994 CAATTATGGGAGAGGCTCGCCTTTGACCATCGAATCTCACCTCTCGGACAATGAGGAAGA
      |||||||||||||||||||||||||||||||||||||||||||||||||||||||| ||
12308 CAATTATGGGAGAGGCTCGCCTTTGACCATCGAATCTCACCTCTCGGACAATGAGGAGGA

3054 CCCCATCAGGTACTACGTCTCGGTGTACGATGAACTGACCGCCTCGGAAATGGAAGAACC
      |||||||||||||| ||||||||||||||||||||||||||||||||||||||||||||
12368 CCCCATCAGGTACTACGTTTCGGTGTACGATGAACTGACCGCCTCGGAAATGGAAGAACC

3114 TTCGAACAGCACCAGCTGGCAGATTCCCAAACTAATGAAAGTTGCCATGCAACCCGTCTC
      ||||||||||||||||||||||||||||||||||||||||||||||||||||||||||||
12428 TTCGAACAGCACCAGCTGGCAGATTCCCAAACTAATGAAAGTTGCCATGCAACCCGTCTC

3174 GCTCAGAGATCCCGAGTACGACTAGGCTTTTTTTTTTTATCTTTCGGTTCCAACTCTTT
      ||||||||||||||||||||||||||||  ||||||||| |||||||||||||||||||
12488 GCTCAGAGATCCCGAGTACGACTAGGC..TTTTTTTTTGTCTTTCGGTTCCAACTCTTT

3234 CCCCGCCCCATCACCTCGCCTATACTATGTGTATGATGTCTCATAATAAAGCTTTCTTTC
      |||||||||||||||||||||||| |||||||||||||||||||||||||||||||||||
12546 CCCCGCCCCATCACCTCGCCTGTACTATGTGTATGATGTCTCATAATAAAGCTTTCTTTC

3294 TCAGTCTGCAACATGCGGCTGTGTCGGGTGTGGCTGTCTGTTTGTCTGTGCGCCGTGGTG
      ||||||||||||||| ||||||||||||||||||||||||| ||||||||||||||||||
12606 TCAGTCTGCAACATGCAGCTGTGTCGGGTGTGGCTGTCTGTTGTCTGTGCGCCGTGGTG

3354 CTGGGTCAGTGCCAGCGGGAGACCGCAGAAAAAAACGATTATTACCGAGTACCGCATTAC
      ||||||||||||||||||| |||||| |||||||||||||||||||||||||||||||
12666 CTGGGTCAGTGCCAGCGGGAAACCGCGGAAAAAAAACGATTATTACCGAGTACCGCATTAC

3414 TGGGACGCGTGCTCTCGCGCGCTGCCCGACCAAACCCGTTACAAGTATGTGGAACAGCTC
      |||||||| |||||||||||||||||||||||||||||||||||||||||||||||||||
12726 TGGGACGCGTGCTCTCGCGCGCTGCCCGACCAAACCCGTTACAAGTATGTGGAACAGCTC

3474 GTGGACCTCACGTTGAACTACCACTACGATGCGAGCCACGGCTTGGACAACTTTGACGTG
      ||||||||||||||||||||||||||||||||||||||||||||||||||||||||||||
12786 GTGGACCTCACGTTGAACTACCACTACGATGCGAGCCACGGCTTGGACAACTTTGACGTG

3534 CTCAAGAGGTGAGGATACGCGCTAAAGGTGTATGACAACGGGAAGGTAAGGGCGAACGGG
      |||||||||||| |||||||||||||||| ||||||||||||||||||||||||||||||
12846 CTCAAGAGGTGAGGGTACGCGCTAAAGGTGCATGACAACGGGAAGGTAAGGGCGAACGGG

3594 TAACGGGCAGGTAACCGCATGGGGTGTGAAATGACGTTCGGAACCTGTGCTTGCAGAATC
      ||||||  ||||||||||||||| ||||||||||||| |||||||||||||||||||||
12906 TAACGGGCTAAGTAACCGCATGGGGTATGAAATGACGTTTGGAACCTGTGCTTGCAGAATC

3654 AACGTGACCGAGGTGTCGTTGCTCATCAGCGACTTTAGACGTCAGAACCGTCGCGGCGGC
      |||||||| ||||||||||||||||||||||||||||||||||||||||||||||||||
12966 AACGTGACCGAGGTGTCGTTGCTCATCAGCGACTTTAGACGTCAGAACCGTCGCGGCGGC

3714 ACCAACAAAAGGACCACGTTCAACGCCGCCGGTTCGCTGGCGCCGCACGCCCGGAGCCTC
      ||||||||||||||||||||||||||||||||||||||||||| |||||||||||||||
13026 ACCAACAAAAGGACCACGTTCAACGCCGCCGGTTCGCTGGCGCCACACGCCCGGAGCCTC

3774 GAGTTCAGCGTGCGGCTCTTTGCCAACTAGCCTGCGTCACGGGAAATAATATGCTACGGC
      ||||||||||||||||||||||||||||||||||||||||||||||||||||||| |||
13086 GAGTTCAGCGTGCGGCTCTTTGCCAACTAGCCTGCGTCACGGGAAATAATATGCTGCGGC

3834 TTCTGCTTCGTCACCACTTTCACTGCCTGCTTCTGTGCGCGGTTTGGGCAACGCCCTGTC
      ||||||||||||||||||||||||||||||||||||||||||||||||||||||||||||
13146 TTCTGCTTCGTCACCACTTTCACTGCCTGCTTCTGTGCGCGGTTTGGGCAACGCCCTGTC

3894 TGGCGTCTCCGTGGTCAACGCTAACGGCGAACCAGAATCCGTCCCCGCTATGGTCTAAAC
      ||||||||||||||| ||||||||||||  |||||||||||||||||||||||||||||
13206 TGGCGTCTCCGTGGTCGACGCTAACGGCAAACCAGAATCCGTCCCCGCCATGGTCTAAAC
```

Figure 7b cont.

```
3954  TGACGTATTCCAAACCGCATGACGCGGCGACGTTTTACTGTCCTTTTATCTATCCCTCGC
      ||||||||||||||||||||||||||||||||||||||||||||||| |||||||||||
13266 TGACGTATTCCAAACCGCATGACGCGGCGACGTTTTACTGTCCTTTTCTCTATCCCTCGC

4014  CCCCACGGTCCCCCTTGCAATTCTCGGGGTTCCAGCGGGTATTAACGGGTCCCGAGTGTC
      |||||||||||||||||||||||||||||||||||||||| ||||| ||||||||||||
13326 CCCCACGGTCCCCCTTGCAATTCTCGGGGTTCCAGCAGGTATCAACGGGTCCCGAGTGTC

4074  GCAACGAGACCCTGTATCTGCTGTACAACCGGGAAGGCCAGACCTTGGTGGAGAGAAGCT
      ||||||||||||||||||||||||||||||||||||||||||||||||||||||||||||
13386 GCAACGAGACCCTGTATCTGCTGTACAACCGGGAAGGCCAGACCTTGGTGGAGAGAAGCT

4134  CCACCTGGGTGAAAAAGGTGATCTGGTACCTGAGCGGTCGCAACCAGACCATCCTCCAAC
      ||||||||||||||||||||||||||||| ||||||||||||||||||||||||||||||
13446 CCACCTGGGTGAAAAAGGTGATCTGGTATCTGAGCGGTCGCAACCAGACCATCCTCCAAC

4194  GGATGCCCCGAACGGCTTCAAAACCGAGCGACGGAAACGTGCAGATCAGCGTGGAAGACG
      |||||||| |||||||||| ||||||||||||||||||||||||||||||||||||||||
13506 GGATGCCCCAAACGGCTTCGAAACCGAGCGACGGAAACGTGCAGATCAGCGTGGAAGACG

4254  CCAAGATTTTTGGAGCGCACATGGTGCCCAAGCAGACCAAGCTGCTACGCTTCGTCGTCA
      ||||||||||||||||||||||||||||||||||||||||||||||||||||||||||||
13566 CCAAGATTTTTGGAGCGCACATGGTGCCCAAGCAGACCAAGCTGCTACGCTTCGTCGTCA

4314  ACGATGGCACACGTTATCAGATGTGTGTGATGAAGCTGGAGAGCTGGGCTCACGTCTTCC
      |||||||||| |||||||||||||||||||||||||||||||||| |||||||||||||
13626 ACGATGGCACGCGTTATCAGATGTGTGTGATGAAGCTGGAGAGCTGGGCCCACGTCTTCC

4374  GGGACTACAGCGTGTCTTTTCAGGTGCGATTGACGTTCACCGAGGCCAATAACCAGACTT
      ||||||||||||||||||||||||||||||||||||||||||||||||||||||||||||
13686 GGGACTACAGCGTGTCTTTTCAGGTGCGATTGACGTTCACCGAGGCCAATAACCAGACTT

4434  ACACCTTCTGCACCCATCCCAATCTCATGTTTGAGCCCGTCGCGCGCGCAGGGAATTTT
      |||||||| |||||||||||||||||| |||||||||||||||||||||||||||||||
13746 ACACCTTCTGTACCCATCCCAATCTCATCATTTGAGCCCGTCGCGCGCGCAGGGAATTTT

4494  GAAAACCGCGCGTCATGAGTCCCAAAAACCTGACGCCGTTCTTGACGGCGTTGTGGCTGT
      ||||||||||||||||||||||||||||| ||||||||||||||||| |||||||||||
13806 GAAAACCGCGCGTCATGAGTCCCAAAGACCTGACGCCGTTCTTGACGACGTTGTGGCTGC

4554  TATTGGATCACAGCCGCGTGCCGCGGGTACGCGCAGAAGAATGTTGCGAATTCATAAACG
      ||||||  ||||||||||||||||||||| ||||||||||||||||||||||||||||||
13866 TATTGGGTCACAGCCGCGTGCCGCGGGTGCGCGCAGAAGAATGTTGCGAATTCATAAACG

4614  TCAACCACCCGCCGGAACGCTGTTACGATTTCAAAATGTGCAATCGCTTCACCGTCGCGT
      ||||||||||||||||||||||||||||||||||||||||||||||||||||||||||||
13926 TCAACCACCCGCCGGAACGCTGTTACGATTTCAAAATGTGCAATCGCTTCACCGTCGCGT

4674  ACGTATTTTCATGATTGTCTGCGTTCTGTGGTGCGTCTGGATCTGTCTCTCGACGTTTCT
      ||||||||||||||||||||||||||||||||||||||||||| ||||||||||||||||
13986 ACGTATTTTCATGATTGTCTGCGTTCTGTGGTGCGTCTGGATTTGTCTCTCGACGTTTCT

4734  GATAGCCATGTTCCATCGACGATCCTCGGGAATGCCAGAGTAGATTTTCATGAATACACA
      |||||||||||||||||||||||||||||||||||||||||||||||||||||||| |||
14046 GATAGCCATGTTCCATCGACGATCCTCGGGAATGCCAGAGTAGATTTTCATGAATCCACA

4794  GGCTGCGGTGTCCGGACGGCGAAGTCTGCTACAGTCCCGAGAAAACGGCTGAGATTCGCG
      ||||||||||||||||||||||||||||||||||||||||||||||||||||||||||||
14106 GGCTGCGGTGTCCGGACGGCGAAGTCTGCTACAGTCCCGAGAAAACGGCTGAGATTCGCG

4854  GGATCGTCACCACCATGACCCATTCATTGACACGCCAGGTCGTACACAACAAACTGACGA
      ||||||||||||||||||||||||||||||||||||||||||||||||||||||||||||
14166 GGATCGTCACCACCATGACCCATTCATTGACACGCCAGGTCGTACACAACAAACTGACGA

4914  GCTGCAACTACAATCCGTAAGTCTCTTCCTCGAGGGCCTTACAGCCTATGGGAGAGTAAG
      ||||||||||||||||||||||||||||||||||||||||||||||||||||||||||||
14226 GCTGCAACTACAATCCGTAAGTCTCTTCCTCGAGGGCCTTACAGCCTATGGGAGAGTAAG

4974  ACAGAGAGGGACAAAACATCATTAAAAAAAAAAGTCTAATTTCACGTTTTGTACCCCCCT
      |||||||||||||||||||||||||||||||||||||||||||||||||||||||||||
14286 ACAGAGAGGGACAAAACATCATTAAAAAAAAAAGTCTAATTTCACGTTTTGTACCCCCCT

5034  .....TCCGTGTTGTAGGTTATACCTCGAAGCTGACGGGCGAATACGCTGCGGCAAAGTG
           |||||||||||  ||  ||  |      ||  ||        ||
14346 TCCCCTCCGTGTTGTAGCCCATCGGCCGCGGCGATCTCCTAGTAACACTG.......GTC

5089  AACGACAAGGCGCAGTACCTGCTGGGCGCCGCTGGCAGCGTTCCCTA.........TCGA
             ||   ||  || ||| |||       |  ||| |||       |||
14399 CGACACTTCCACCATCCAGCTCGGCCGGCGGTTCGGCATCCTCTACCAGCGGCGTCGT

5140  TGGATCAACCTGGAATACGACAAGATAACCCGGATCGTGGGCCTGGATCAGTACCTGGAG
      |||   ||  |  |  |  | ||  ||  ||       ||  |||  |
14459 CTCATCTTTGCCGCAGCAGCGGACGCACACCTTCTCCAGGCAGAACGCCACCAGCTGCCG

5200  AGCGTTAAGAAACACAAACGGCTGGATGTGTGCCGCGCTAAAATGGGCTATATGCTGCAG
            |||        ||| ||   |||  |||  |       |     ||    ||
14519 CCGAACGTACCACAGGTACACGTGCAGACCTGCGAACAGGACTACGGAGGTCATGACCAC

5260  TGAATAATAAAATGTGTGTTTGTCCGAAATACGCGTTTTGAGATTTCTGTCGCCGACTAA
        ||||       |     ||   ||  |  ||  |   |||          |||  |
14579 CACGACGCACACGGGAATCCAGGGATCGAGATTGTTGCTGGAACTCGCTATCGCCACCGA
```

Figure 7b cont.

```
5320  ATTCATGTCGCGCGATAGTGGTGTTTATCGCCGATAGAGATGGCGATATTGGAAAAATCA
       |   ||  |              |||||  |    |   | ||  |
14639 CGTGCCCGCGTCTGTCTCACCGCCGCTCGCCCGATGTCGCGCGGCTTGTTATACGCTAGC

5380  ATATTTGAAAATATGGCATATTGAAAATGTCGCCGATGTGAGTTTCTGTGTAACTGATAT
       |     |  |       |    .  |   || | || || ||  || ||| | |
14699 CCGTCGCCGCCTCGGGGCACGGTGCCCTCCTACCCACGTAACTTCCTCCGTGACTTAAAG

5440  CGCCATTTTTCCAAAAGTGATTTTTGGGCATACGCGATATCTGGCGATAGCGCTTATATC
       |||      |         ||||    ||               ||||||| |||
14759 TCGCGTGTGGTAGATCTCCTGCTCCGTGGACGAACCGTCCGGCAGGATAGCGGTTAAGGA

5500  GTTTACGGGGGATGGCGATAGACGACTTTGGCGACTTGGGCGATTCGGTGTGTCGCAAAT
       |    || | |                 ||        ||    |    |   | ||
14819 TTC....GGTGCTAAGGCCGTGTCGCCAACGTCGAATGCTACGTTGCAACAGCTTCGACG

5560  ATCGCAGTTTCGATATAGGTGACAGACGATATGAGGCCATATCGCCGATAGAGGCGACAT
       ||    |  | ||        |   ||| | |||.      ||  || ||||
14875 GACGGCCATCCCCTCTCTCATCGCAATAATAAAACACCAGCAGCGCGCACGACGCGATCA

5620  CGAGTTGGCACATGGCCAATGGATATCGATATATACATT..GCATCAATATTGGCCATTA
       ||   | ||||                 |     |||     |||      |||
14935 CGGTGACACCCATGATTAGACCCACGCAGATAGCCAGCCCCGCTAGCGTATCTAGCGCCA

5678  GCCATATTAGTCATTGGTTATATAGCGTAAATCAATATTGGCTAATGGCCATTGCATACG
       ||   | ||    ||  ||  || ||| |            ||   || | |
14995 TCCCGTTCGCTCCCGTTGTCTCCTGAGCGAAGCAACTTCTCGGTCCCGTTTTCAACAGT

5738  TTGCATCTATATCATAATGTGTACAT.TTATATTGGCTCATGTCCAATATGACCGCCATG
       ||   ||  |    |     | ||| |||        ||                 |
15055 TTTTGTTTCCTTCTCCGCGACTAGATGTTAACGCCCGCGGTCTTTCCGGCCGTGCTCTAC

5797  TTGACATTGATTATTGACTAGTTATTAATAGTAATCAATTACGGGGTCATTAGTTCATAG
       |     ||| | ||| ||      || |  |       || ||             ||
15115 CTCCTGGCGCTTGTCGTCTGGGTTGAGATGTTCTGCCTCGTCGCCGTAGCCGTCGTCGAG

5857  CCCATATATGGAGTTCCGCGTTACATAACTTACGGTAAATGGCCCGCCTGGCTGACCGCC
       ||        ||  ||  |        | |||       |||              |
15175 CGCGA.....GATCGCCTGGGCGCTGCTGCTGCGGATGCTGGTCGTTGGCCTGATGGTGG

5917  CAACGACCCCCGCCCATTGACGTCAATAATGACGTGGGTTCCCATAGTAACGCCAATAGG
       |  | ||||   |            |     ||| |   ||| | ||| |  |
15230 AAGTCGGCGCCGCCGCCGCTTGGACCTTCGTGCGTTGTCTTGCCTATCAGCGCTCCTTCC

5977  GACTTTCCATTGACGTCAATGGGAGGAGTATTTACGGTAAACTGCCCACTTGGCAGTACA
        |    |   | ||||  ||             |||   |    |||   ||  ||
15290 CCGTGCTTACGGCCTTCCCCTGAAACCCACGTTAACCGACGTCCCAAAAACGCCGGTGT

6037  TCAAGTGTATCATATGCCAAGTACGCCCCCTATTGACGTCAATGACGGTAAATGGCCCGC
       | |           |   ||  ||||           |      ||  |||     |
15350 TAACACAGGAAAAAAGAAACCACGCAGGAACCGCGCAGGAACCACGCGGAACATGGGAC

6097  CTGGCATTATGCCCAGTACATGACCTTACGGGACTTTCCTA
           |                      ||     ||
15410 ACTATCTGGAAATCCTGTTCAACGTCATCGTCTTCACTCTG
```

Figure 7c

Fast alignment of DNA sequences PAN1 and HCU33331 (Toledo)

Upper line: Seqpan1, from 1008 to 16569
Lower line: HCU33331, from 28 to 15576

PAN1:HCU33331 identity= 88%

```
1008  CGCTGTAGGGATAAATAGTGCGATGGCGTTTGTGGGAGAACGCAGTAGCGATGGGTTGCG
      ||||||||||||||||||||||||||||||||||||||||||||||||||||||||||||
  28  CGCTGTAGGGATAAATAGTGCGATGGCGTTTGTGGGAGAACGCAGTAGCGATGGGTTGCG

1068  ACGTGCACGATCCTTCGTGGCAATGCCAATGGGGCGTTCCCACGATTATTGTGGCCTGGA
      ||||||||||||||||||||||||||||||||||||||||||||||||| ||||||||||
  88  ACGTGCACGATCCTTCGTGGCAATGCCAATGGGGCGTTCCCACGATTATCGTGGCCTGGA

1128  TAGCATGCGCGGCCCTGGGAATTTGGTGTTTGGCGGGATGGTCGTCGGAATTTGTCTTCTG
      || |||||||||  | ||||||||||||||||||||||| |||| || | |||||| |
 148  TAACATGCGCGGCTTTAGGAATTTGGTGTTTGGCGGGATCGTCGGCGGATGTCTCTTCGG

1188  GAGCCGGCATTGCAGCCGTGGTCGGCTGTTCTGTTTTCATGATTTTCCTTTGCGCGTACC
      || |||||| |||||||    ||||||||||||||||||||||||||| |||||||| |
 208  GACCCGGCATCGCAGCCGTAGTCGGCTGTTCTGTTTTCATGATTTTCCTCTGCGCGTATC

1248  TCATCCGTTACCGGGAATTCTTTAAAGACTCCGTAATCGACCTCCTCACCTGCCGATGGG
      |||||||||||||||||||| || |||||||||||||||||||||| |||||||||||||
 268  TCATCCGTTACCGGGAATTGTTCAAAGACTCGGTAATCGACCTCCTTACCTGCCGATGGG

1308  TTCGCTACTGCAGCTGCAGCTGCAAGTGCAGCTGCAAATGCATCTGGGGCGCCTGCAGCC
      |||||||||||||||||||||| ||||||||||||||||||||||||||||||||  |||
 328  TTCGCTACTGCAGCTGCAGCTGTAAGTGCAGCTGCAAATGCATCTGGGGCCCCTGTAGCC

1368  GCTGCTGTTCAGCGTGTTACAAAGAGACGATGATTTACGACATGGTCCAATACGGTCATC
      |||||||||||||||||||||| ||||||||||||||||||||||||||||||||||||
 388  GCTGCTGTTCAGCGTGTTACAAGGAGACGATGATTTACGACATGGTCCAATACGGTCATC

1428  GACGGCGTCCCGGACACGGCGACGATCCCGACAGGGTGATCTGCGAGATAGTGGAAAGTC
      |||||||||||||||||||||||||||||||||||||||||||||||||||||| || ||
 448  GACGGCGTCCCGGACACGGCGACGATCCCGACAGGGTGATCTGCGAGATAGTCGAGAGTC

1488  CCCCGGTTTCGGCGCCGACGGTGTCCGTCCCCCCGCCGTCGGAGGAGTCCCACCAGCCCG
      ||||||||||||||||||||||||||||||||||||||||||||||||||||||||||||
 508  CCCCGGTTTCGGCGCCGACGGTGTCCGTCCCCCCGCCGTCGGAGGAGTCCCACCAGCCCG

1548  TCATCCCACCGCAGCCGCCAGCACCGACATCGGAACCCAAACCGAAGAAAGGTAGGGCGA
      ||||||||||||||||||||||||||||||||||||||||||||||||||||||||||||
 568  TCATCCCACCGCAGCCGCCAGCACCGACATCGGAACCCAAACCGAAGAAAGGTAGGGCGA

1608  AAGATAAACCGAAGGGTAGACCGAAGGACAAACCTCCGTGTGAACCGACGGTGAGTCCAC
      |||||||| |||||||||||||||| |||||||||||||||  ||||||||||||| |||
 628  AAGATAAACCGAAGGGTAGACCGAAAGACAAACCTCCGTGCGAACCGACGGTGAGTTCAC

1668  AACCACCGTCGCAGCCGACGGCGATGCCCGGCGGTCCGCCCGACACGCCTCGCCCCGCCA
      ||||||||||||||||||||||||||  |||||||||||||||| ||||||| ||||||
 688  AACCACCGTCGCAGCCGACGGCAATGCCCGGCGGTCCGCCCGACGCGCCTCCCCCGCCA

1728  TGCCGCAGATGCCACCCGGCGTAGCCGAGGCGGTACAAGCTGCCGTGCAGGCGGCCGTGG
      ||||||||||||||||||||||| |||||||||||||||||||||||||||||||||||
 748  TGCCGCAGATGCCACCCGGCGTGGCCGAGGCGGTACAAGCTGCCGTGCAGGCGGCCGTGG

1788  CCGCGACTCTACAACAACAACAGCAGCAGCATCAGACCGGAACGTAACCCGCCCCCGGTG
      ||||| ||||      |||||||||||||||||||||||||||||||||||||||||||
 808  CCGCGGCTCT...ACAACAACAGCAGCAGCATCAGACCGGAACGTAACCCGCCCCCGGTG

1848  TGATGAGGAATTTTCCGACTTGGCCCACATGTCCTTCCTCAGTGTTTGGACAATAAACAC
      ||| |||||||||||||||||||| ||||||||||||| ||||||||||||||||||||
 865  CGATAAGGAATTTTCCGACTTGGCGCACATCTCCTTCCTCAATGTTTGGACAATAAACAC

1908  ATTCCTTGCCAAAAAATGACGTTTCCAGAAATCCAAGGCATAAATGTCCGTACACCGGCC
      ||||||||||||||||||||||| ||||||||||||||||||||||||||||||||||||
 925  ATTCCTTGCCAAAAAATGACGTTTCCAGAAATCCAAGGCATAAATGTCCGTACACCGGCC

1968  CTTCCCGACACGGAGTTTGAGATTCCAAGCAGGAGAGAAGATCATGGTGTGGATATGGCT
      ||||||  |||||||||||||||||||||||||||||||||||||||||||||||||||
 985  CTTCCCAACACGGAGTTTGAGATTCCAAGCAGGAGAGAAGATCATGGTGTGGATATGGCT

2028  CGGCGTCGGGCTCCTCGGCGGTACCGGACTGGCTTCCCTGGTCCTGGCCATTTCCTTATT
      |||| ||||||||||||||||||||||||||||||||||||||||||||||||||||||
1045  CGGCATCGGGCTCCTCGGCGGTACCGGACTGGCTTCCCTGGTCCTGGCCATTTCCTTATT

2088  TACCCAGCGCCGAGGCCGCAAGCGATCCGACGAGACTTCGTCGCGAGGCCGGCTCCCGGG
      ||||||||||||||||||||||||||||||||||||||||||||||||||||||||||||
1105  TACCCAGCGCCGAGGCCGCAAGCGATCCGACGAGACTTCGTCGCGAGGCCGGCTCCCGGG

2148  TGCTGCTTCTGATAAGCGTGGTGCCTGCGCGTGCTGCTATCGAAATCCGAAAGAAGACGT
      ||||||||||||||||||||||||||||||||||||||||||||||||||||||||||||
```

Figure 7c cont.

```
1165 TGCTGCTTCTGATAAGCGTGGTGCCTGCGCGTGCTGCTATCGAAATCCGAAAGAAGACGT

2208 CGTCGAGCCGCTGGATCTGGAACTGGGGCTCATGCGGGTGGCCACCCACCCGCCGACGCC
     ||||||||||||||||||||||||||||||||||||||||||||| |||||||||||||||
1225 CGTCGAGCCGCTGGATCTGGAACTGGGGCTCATGCGGGTGGACACCCACCCGCCGACGCC

2268 GCAGGTGCCGCGGTGTACGTCGCTCTACATAGGAGAGGATGGTCTGCCGATAGATAAACC
     ||||||||||||||||||||||||||||||||||||||||||||||||||||||||||||
1285 GCAGGTGCCGCGGTGTACGTCGCTCTACATAGGAGAGGATGGTCTGCCGATAGATAAACC

2328 CGAGTTTCCTCCGGCGCGGTTCGAAATCCCCGACGTATCCACGCCGGGAACGCCGACCAG
     ||||||||||||||||||||||| |||||||||||||||||||||||||||||||||||
1345 CGAGTTTCCTCCGGCGCGGTTCGAGATCCCCGACGTATCCACGCCGGGAACGCCGACCAG

2388 CATCGGCCGATCTCCGTCGCATTGCTCCTCGTTGAGCTCTTTGTCGTCTTCGACCAGCGT
     ||||||||||||||||||||||||||||||||| ||||||||||||| ||||||||||
1405 CATCGGCCGATCTCCGTCGCATTGCTCCTCGTCGAGCTCTTTGTCGTCCTCGACCAGCGT

2448 CGACACGGTGCTGCATCAGCCGCCGCCATCCTGGAAGCCACCTCCGCCGCCCGAGCGCAA
     |||||||||||| |||||||||||||||||||||||||||||||||||||| ||||||
1465 CGACACGGTGCTGTATCAGCCGCCGCCATCCTGGAAGCCACCTCCGCCGCCCGGGCGCAA

2508 GAAGCGGCCGCCTACGCCGCCGGTCCGGGCCCCCACCACGCGGCTGTCGTCGCACAGGCC
     |||||||||||||||||||||||||||||||||||||||||||||||||||||||| ||
1525 GAAGCGGCCGCCTACGCCGCCGGTCCGGGCCCCCACCACGCGGCTGTCGTCGCACAGACC

2568 CCCGACGCCGATACCCGCGCCGCGCGTAAGAACCTGAGCACGCCGCCCATCAAGAAACACC
     ||||||||||||||| |||||||||||||||||||||||||||||||| ||||||||| ||
1585 CCCGACGCCGATACCCGGCGCCGCGTAAGAACCTGAGCACGCCGCCCACCAAGAAAACGCC

2628 GCCGCCCACGAAACCCAAGCCGGTCGGCTGGACACCGCCGGTGACACCCAGGCCCTTCCC
     ||||||||||||||||||||||||||||||||||||||||||||||||||||||||||||
1645 GCCGCCCACGAAACCCAAGCCGGTCGGCTGGACACCGCCGGTGACACCCAGGCCCTTCCC

2688 GAAAACGCCGACGCCACAAAAGCGCCGCGGAATCCGAGACTACCACGCACCGTCGGTCT
     |||||||||||||||||||||||||||||||||||||||||||| ||||||||||||||
1705 GAAAACGCCGACGCCACAAAAGCGCCGCGGAATCCGAGACTACCGCGCACCGTCGGTCT

2748 GGAGAATCTCTCGAAAGTGGGACTCTCGTGTCCCTGTCCCCGACCCCGCACGCCGACGGA
     ||||||||||||||| |||||||||||||||||||||||||| ||||||||||||||||
1765 GGAGAATCTCTCGAAGGTGGGACTCTCGTGTCCCTGTCCCCGACCCCGCACGCCGACGGA

2808 GCCGACCACGCTGCCTATCGTGTCGGTTTCCGAGTTAGCCCCGCCTCCTCGATGGTCGGA
     |||||||||||||||||||||||||||||||| |||||||||||||||||||||||||
1825 GCCGACCACGCTGCCTATCGTGTCGGTTTCCGAGCTAGCCCCGCCTCCTCGATGGTCGGA

2868 CATCGAGGAACTCTTGGAAAAGGCGGTGCAGAGCGTCATGAAGGACGCTGAGTCTATGCA
     |||||||||||||||||| ||||||||||||||||||||||||||||| ||||| |||||
1885 CATCGAGGAACTCTTGGAACAGGCGGTGCAGAGCGTCATGAAGGACGCCGAGTCGATGCA

2928 GATGACCTGAGACCGAAGGAGCGAGCGCGTCCGTTGTACAGTTGTATAGCAGCACACGCC
     |||||||||||||||||| |||||||||||||||||||||||||||||||||||||||||
1945 GATGACCTGAGACCGAAAGAGCGAGCGCGTCCGTTGTACAGTTGTATAGCAGCACACGCC

2988 TTCCCTCTTTTTCACCGCAGCTAAGAGAGAGAAAGAGAGTATGTCAGTCAAGGGCGTGGA
     ||||||||||||||||||||||||||||||||||||||||||||||||||||||||||||
2005 TTCCCTCTTTTTCACCGCAGCTAAGAGAGAGAAAGAGAGTATGTCAGTCAAGGGCGTGGA

3048 GATGCCAGAAATGACGTGGGACTTGGACGTTGGAAATAAATGGCGGCGTCGAAAGGCCCT
     ||||||||||||||||||||||||||||||| |||||||||||||||||||||||||||
2065 GATGCCAGAAATGACGTGGGACTTGGACGTTAGAAATAAATGGCGCGCGTCGAAAGCCCT

3108 GAGTCGCATTCACCGGTTCTGGGAATGTCGGCTACGGGTGTGGTGGCTGAGTGACGCCGG
     ||||||||||||||||||||||||||||||||||||||||||||||||||||||||||||
2125 GAGTCGCATTCACCGGTTCTGGGAATGTCGGCTACGGGTGTGGTGGCTGAGTGACGCCGG

3168 CGTAAGAGAAACCGACCCACCGCGTCCCCGACGCCGCCCGACTTGGATGACCGCGGTGTT
     ||||||||||| ||||||||||||||||||||||||||||||||||||||||| ||||||
2185 CGTAAGAGAAACCGACCCACCGCGTCCCCGACGCCGCCCGACTTGGATGACCGCGGTGTT

3228 TCACGTTATCTGTGCCGTTTTGCTTACGCTTATGATTATGGCCATCGGCGCGCTCATCGC
     |||||||||||||||||||||||||||||||||||||||||||||||||||||||||||
2245 TCACGTTATCTGTGCCGTTTTGCTTACGCTTATGATTATGGCCATCGGCGCGCTCATCGC

3288 GTACTAAGATATTATCACCAGGACAGTTGGCGAGACATGCTCCACGATCTATTTTGCGG
     |||||||||||| |||||||||||||||||||||||||||||||||||||||||||||
2305 GTACTTAAGATATTACCACCAGGACAGTTGGCGAGACATGTCCACGATCTATTTTGCGG

3348 CTGTCATTATCCCGAGAAGTGCCGTCGGCACCACGAGCGGCAGAGAAGGAGACGGCGAGC
     |||||||||||||||||||||||||||||||||||||||||||||||||||||||| |||
2365 CTGTCATTATCCCGAGAAGTGCCGTCGGCACCACGAGCGGCAGAGAAGGAGACGGCAAGC

3408 CATGGATGTGCCCGACCCGGAACTCGGCGACCCGGCCCGCGGCCGTTGAACGAAGCTAT
     ||||||||||||||||||||||||||||||||||||||||||||||||||||| ||||||
2425 CATGGATGTGCCCGACCCGGAACTCGGCGACCCGGCCCGCGGCCGTTGAACGGAGCTAT

3468 GTACTACGGCAGCGGCTGTCGCTTCGACACGGTGGAAATGGTGGACGAGACGAGACCCGC
     |||||||||||||||||||||||||||||||||||||||||||||||||||||||||||
2485 GTACTACGGCAGCGGCTGTCGCTTCGACACGGTGGAAATGGTGGACGAGACGAGACCCGC

3528 GCCGCCGGCGCTGTCGTCGCCCGAAACCGGCGACGATAGCAACGACGACGCGGTTGCCGG
     |||||||||||| |||||||||||||||||||||||||||||||||||||||||||||||
2545 GCCGCCGGCGCTGTCATCGCCCGAAACCGGCGACGATAGCAACGACGACGCGGTTGCCGG
```

Figure 7c cont.

```
3588 CGGAGGTGCTGGCGGGGTAACATCACCCGCGACTCGTACGACGTCGCCGAACGCGCTGCT
     ||||||||||||||||||C||||||||||||||||||||||||||||||||| |||||
2605 CGGAGGTGCTGGCGGGGTAACATCACCCGCGACTCGTACGACGTCGCCGAACGCACTGCT

3648 GCCGGAATGGATGGATGCGGTGCATGTGGCGGTCCAAGCCGCCGTTCAAGCGACCGTGCA
     ||| |||||||||||||||||||||||||||||||||||||||||||||||||||||||
2665 GCCAGAATGGATGGATGCGGTGCATGTGGCGGTCCAAGCCGCCGTTCAAGCGACCGTGCA

3708 AGTAAGTGGCCCGCGGGAGAACGCCGTATCTCCCGCTACGTAAGAGGGTTGAGGGGGCCG
     ||||||||||||||||||||||||||||||||||||||||||||||||||||| |||||
2725 AGTAAGTGGCCCGCGGGAGAACGCCGTATCTCCCGCTACGTAAGAGGGTTGAGGGGGCCG

3768 TTCCCGCGCGAGTGCTGTACAAAAGAGAGAGACTGGGACGTAGATCCGGACAGAGGACGG
     ||||||||||||||||||||||||||||||||||||||||||||||||||||||||||||
2785 TTCCCGCGCGAGTGCTGTACAAAAGAGAGAGACTGGGACGTAGATCCGGACAGAGGACGG

3828 TCACCATGGACGATCTGCCGCTGAATGTCGGGTTACCCATCATCGGCGTGATGCTCGTGC
     ||||||||||||||||||||||||||||||||||||||||||||||||||||||||||||
2845 TCACCATGGACGATCTGCCGCTGAATGTCGGGTTACCCATCATCGGCGTGATGCTCGTGC

3888 TGATCGTGGCCATCCTCTGCTATCTGGCTTACCACTGGCACGACACCTTCAAACTAGTGC
     ||||||||||||||||||||||||||||||||||||||||||||||||||||||| ||||
2905 TGATCGTGGCCATCCTCTGCTATCTGGCTTACCACTGGCACGACACCTTCAAACTGGTGC

3948 GCATGTTTCTGAGCTACCGCTGGCTGATCCGCTGTTGCGAGCTGTACGGGGAGTACGAGC
     ||||||||||||||||||||||||||||||||||||||||||||||||||| |||||||
2965 GCATGTTTCTGAGCTACCGCTGGCTGATCCGCTGTTGCGAGCTGTACGGGAGTACGAGC

4008 GCCGGTTCGCGGACCTGTCGTCTCTGGGCCTCGGCGCCGTACGGCGGGAGTCGGACAGAC
     ||||||||||||||||||||||||||||||||||||||||||||||||||||||||||||
3025 GCCGGTTCGCGGACCTGTCGTCTCTGGGCCTCGGCGCCGTACGGCGGGAGTCGGACAGAC

4068 GATACCGTTTCTCCGAACGGCCCGACGAGATCTTGGTCCGTTGGGAGGAAGTGTCTTCCC
     ||||||||||||||||||||||||||||||||||||||||||||||||||||||||||||
3085 GATACCGTTTCTCCGAACGGCCCGACGAGATCTTGGTCCGTTGGGAGGAAGTGTCTTCCC

4128 AGTGCAGCTACGCGTCGTCGCGGATAACAGACCGCCGCGCGGGTTCATCGTCTTCGTCGT
     |||||||||||||||||||||||||||||||||||||| | ||||||||||||||||||
3145 AGTGCAGCTACGCGTCGTCGCGGATAACAGACCGCCGTGTGGGTTCATCGTCTTCGTCGT

4188 CGGTCCACGTCGCTAGCCAGAGAAACAGCGTGCCTCCGCCGGACATGGCGGTGACGGCGC
     ||||||||||||||||||||||||||||||||||||||||||||||||||||||||||||
3205 CGGTCCACGTCGCTAGCCAGAGAAACAGCGTGCCTCCGCCGGACATGGCGGTGACGGCGC

4248 CGCTGACCGACGTCGATCTGTTGAAACCCGTGACGGGATCCGCGACGCAGTTCACCACCG
     ||||||||||||||||||||||||||||||||||||||||||||||||||||||||||||
3265 CGCTGACCGACGTCGATCTGTTGAAACCCGTGACGGGATCCGCGACGCAGTTCACCACCG

4308 TAGCCATGGTACATTATCATCAAGAGTACACGTGAATGAGAAAAAGAAAAAAGAGGGGAG
     ||||||||||||||||||||||||||||||||||||||||||||||||||||||||||||
3325 TAGCCATGGTACATTATCATCAAGAGTACACGTGAATGAGAAAAAGAAAAAAGAGGGGAG

4368 CGGATCGCGATAATGTCGCTTTGACATTCTCTGCTCGATCTACTCAGCGTCTGCACGAAA
     ||||||||||||||||||||||||||||||||||||||||||||||||||||||||||||
3385 CGGATCGCGATAATGTCGCTTTGACATTCTCTGCTCGATCTACTCAGCGTCTGCACGAAA

4428 CGGCGTCCGCACGGAGGCGAGCCCAAGCGTATCTGCAGCAAGCGGTTCTTTCTCTCGGTG
     |||| ||||||||||||||||||||||||||||||||||||||||||||||| ||||||
3445 CGGCATCCGCACGGAGGCGAGCCCAAGCGTATCTGCAGCAAGCGGTTCTTTCCCTCGGTG

4488 ATGGTGGCAGCATCGGTGGCGGGAGCTTGTTCGGACGATGGACGGTGAGGAGTCCCTGGC
     ||||||||||||||||||||||||||||||||||||||||||||||||||||||||||||
3505 ATGGTGGCAGCATCGGTGGCGGGAGCTTGTTCGGACGATGGACGGTGAGGAGTCCCTGGC

4548 GATCAGGCGGCTCCCGGGTGTGGAGTTCAACGGGTGGTAATGGTGGCGGTGATCGGTGTT
     ||||||||||||||||||||||||||||||||||||||||||||||||||||||||||||
3565 GATCAGGCGGCTCCCGGGTGTGGAGTTCAACGGGTGGTAATGGTGGCGGTGATCGGTGTT

4608 AGAAAACGGTGGCCCTGGCAAACATATATCTACTGTAAATCCTCTGCTCTGTTAATAAAA
     |||||||||||||||||||||||||||||||||||||||| |||||||||||||||||||
3625 AGAAAACGGTGGCCCTGGCAAACATATATCTACTGTAAACCCTCTGCTCTGTTAATAAAA

4668 AGCACACTTTTCACATGAGTTCGTAATTTTATTGTGTAGTGGAAATTTTTACGTCATTGG
     ||||||||||||||||||||||||||||||||||||||||||||||||||||||||||||
3685 AGCACACTTTTCACATGAGTTCGTAATTTTATTGTGTAGTGGAAATTTTTACGTCATTGG

4728 GAAACCCCAGAATGAAAGAGTATAATGTGCACATCACCGGGAGTTCCCGTGTCAGTACGAA
     |||||||||||||||||||||||||||||||-||||||||| |||||||||||||||||
3745 GAAACCCCAGAATGAAAGAGTATAATGTGCATATCACCGGGGGTTCCCGTGTCAGTACGAA

4788 TGTACACAACGCGGGTTACATTACGATAAACTTTCCGGTAAAACAATGCCGATACAGCGT
     ||||||||||||||||||||||||||||||||||||||||||| |||||||||||||||
3805 TGTACACAACGCGGGTTACATTACGATAAACTTTCCGGTAAAACGATGCCGATACAGCGT

4848 GTATAACGCTGATTGTTACGACAAAGGGGTTCGTATATCAATTATATAGTAACGGACATG
     ||||||||||||||||||||||||| ||| ||||||| |||||||||||||||| ||||
3865 GTATAACGCTGATTGTTACGACAAACGAGTTGGTATATCCATTATATAGTAACGAACATG

4908 CTGTGGATACTAGCTTTACTTGCGCTTACCGCGACAGCGAGTGAGACTACTACAGGCACC
     ||||||||| ||| |||| |||| || |||| | ||||||||| || |||||||||| |||
3925 CTGTGGATATTAGTTTTATTTGCACTCGCCGCATCGGCGAGTGAAACCACTACAGGTACC
```

Figure 7c cont.

```
4960  AGTTGTAATTCCAGTACTTCCACCAATAGCAGCAACAGTACTGTAGCACCAACCACGCCA
      || |||||||||||  || ||              || ||   | | | |||| |
3985  AGCTCTAATTCCAGTCAATCTAC..............TAGTGCTACCGCCAACACGACC

5028  TCAGTAGCATGCGTTCAAGCTTTTGGCGGCAGTAATTGGACATTTCCACAGCTCGCGCTG
      |    ||||  | | || | |   |||||||| ||||||  |||||||||||||||||
4030  GTATCGACATGTATTAATGCCTCTAACGGCAGTAGCTGGACAGTACCACAGCTCGCGCTG

5088  CTTGCCGCTAGCGGCTGGACATTATCTGGACTCCTTCTCTTATTTACCTGCTGCTTTTGC
      ||||||||||||||||||||||||||||||||||||||||||||||||||||||||||||
4090  CTTGCCGCTAGCGGCTGGACATTATCTGGACTCCTTCTCTTATTTACCTGCTGCTTTTGC

5148  TGCTTTTGGCTAGTACGTAAAATCTGCAGCTGCTGCGGCAACTCCTCCGAGTCAGAGAGC
      ||||||||||||||||||||||||||||||||||||||||||||||||||||||||||||
4150  TGCTTTTGGCTAGTACGTAAAATCTGCAGCTGCTGCGGCAACTCCTCCGAGTCAGAGAGC

5208  AAAACAACCCACGCGTACACCAATGCCGCATTCACTTCTTCCGACGCGGACGCTACCCATG
      |||||||||||||||||||||||||||||||||||||||||||||| ||| ||||||||
4210  AAAACAACCCACGCGTACACCAATGCCGCATTCACTTCTTCCGACGCGAACGTTACCCATG

5268  GGCACTACAGGGTCGTACACTGCGGCCACAGGACGGCTCATTTCCACCTCCGCCTCGGTGA
      ||||||||||||||||||||| ||||| |||||||||||||||||||||||||||||||
4270  GGCACTACAGGGTCGTACACTCCCCCACAGGACGGCTCATTTCCACCTCCGCCTCGGTGA

5328  CACAGGGTAAACCGAAACCAACGTTGAATCTGACGCGGTTTCGGAAAGCCTGAGACGTCA
      |  |||  ||||||||||| |||||||| || |||||||||||| ||||||||||||||
4330  CGTAGGCTAAACCGAAACCCACGTTGAACCTAACGCGGTTTCGGAAGGCCTGAGACGTCA

5388  CTTTCACAATGACGTTCGTAGACACGTTGATCATAAAACACCGTAGAGGCTAAGGCTTCG
      ||||||||||||||| |||  ||||||||||||||||||||||||||||||||||||||
4390  CTTTCACAATGACGTCCGTATACACGTTCATCATAAAACACCGTAGAGGCTAAGGCTTCG

5448  GTAGGGAGACACCTCAACTGTTGCTGATGAGCACCCGCGCTCTCATCTCTTCAGACTTGT
      ||||||||  ||||||||||| |||||||||||||||| ||||||||||||||||||||
4450  GTAGGGAGAGACCTCAACTGTTCCTGATGAGCACCCGTGCTCTCATCTCTTCAGACTTGT

5508  CATGACCCCCGGCTCAGACTAACGCCACTACCACCGTGCACCCGGCACGACGCAAAAAACGG
      |||||||||||||||||||||||| ||||||||||||||||||||||||||||||||||
4510  CATGACCCCCGGCTCAGACTAACGCGACTACCACCGTGCACCCGGCACGACGCAAAAAACGG

5568  CAGCGGCGGTAGTGCCCTGCCGACCCTCGTCGTTTTCGGCTTCATCGTTACGCTACTTTT
      |||||||||||||||||||||||||||||||||| ||||| || |||||||||||||||
4570  CAGCGGCGGTAGTGCCGTGCCGACCCTCGTCGTTTTCGGCTTTATCGTTACGCTACTTTT

5628  CTTTCTCTTTATGCTCTACTTTTGGAACAACGACGTGTTCCGTAAGCTGCTCCGCTGCGC
      |||||||||||||||||||||||||||||||||||||||||||||||||||  |||||
4630  CTTTCTCTTTATGCTCTACTTTTGGAACAACGACGTGTTCCGTAAGCTGCTCCG.TGCGC

5688  TTGGATCCAGCGCTGCTGCGACCGCTTCGACGCGTGGCAAGACGAGGTCATCTACCGTCG
      |||||||||||||| || |||||||||||||||||||||||||||||||||||||||||
4689  TTGGATCCAGCGCTGTTGCGACCGCTTCGACGCGTGGCAAGACGAGGTCATCTACCGTCG

5748  TCCATCACGTCGTTCCCAAAGCGACGACGAGAGTCGTACTAACAGCGTGTCATCGTACGT
      |||||||||||||||||   |||||||||||||||||||||||||||||||||||||||
4749  TCCATCACGTCGTTCCCAGAGCGACGACGAGAGTCGTACTAACAGCGTGTCATCGTACGT

5808  TCTTTTATCACCCGCGTCCGATGGCAGTTTTGACAACCCGGCACTGACAGAAGCCGTCGA
      |||||||||||||||||||||||||| |||||||||||||||||||||||| |||||||
4809  TCTTTTATCACCCGCGTCCGATGGCGGTTTTGACAACCCGGCACTGACAGAGGCCGTCGA

5868  CAGCGTGGACGACTGGGCGACCACCTCGGTTTTTTACGCCACGTCCGACGAAACGGCGGA
      |||||||||||||||||||||| |||||||||| ||||||||||||||||||||||||
4869  CAGCGTGGACGACTGGGCGACCACCTCGGTTTTCTACGCCACGTCCGACGAAACGGCGGA

5928  CACCGAGCGCCGAGATTCGCAGCAACTGCTCATCGAGCTTCCGCCGGAGCCGCTCCCGCC
      |  ||||||||||||  ||||||||||||||||||||||||||||||||||||||||||
4929  CGCCGAGCGCCGAGACTCGCAGCAACTGCTCATCGAGCTTCCGCCGGAGCCGCTCCCGCC

5988  CGATGTGGTAGCGGCCATGCAGAAAGCGGTGAAACGCGCTGTACAGAACGCGCTGCGCCA
      ||| |||||  ||||||||||||||||| |||||||||||||||||||||| || || ||
4989  CGACGTGGTGGCGGCCATGCAGAAAGCAGTGAAACGCGCTGTACAGAACGCACTACGACA

6048  CAGCCACGACTCTTGGCAGCCTTCATCAGACCCTGTGACG.CAGATGAACGTTCCTTCTTA
      ||||||||||||||||||||||||||||||||||||||| |||||||||||||||||||
5049  CAGCCACGACTCTTGGCAGCCTTCATCAGACCCTGTGACGCCAGATGAACGTTCCTTCTTA

6107  AACATCCGAGGTAGCAATGAGACAGGTCGCGTACCGCCGGCGACGCGAGAGTTCCTGCGC
      ||||||||||||||||||||||||||||||||||||||||||||||||||||||||||
5109  AACATCCGAGGTAGCAATGAGACAGGTCGCGTACCGCCGGCGACGCGAGAGTTCCTGCGC

6167  GGTGCTGGTCCACCACGTCGGCCGCGACGGCGACGGCGAGGAGGAGGCAGCAAAAAAGAC
      ||||||||||||||||||||||||||||||||||||||  |||||||||||||||||||
5169  GGTGCTGGTCCACCACGTCGGCCGCGACGGCGACGGCGAGGGGGAGGCAGCAAAAAAGAC

6227  CTGCAAAAAAACCGGACGCTCAGTTGCGGGCATCCCGGGCGAGAAGCTGCGTCGCACGGT
      ||||||||||||||||||||||||||||||||||||||||||||||||||||||||||
5229  CTGCAAAAAAACCGGACGCTCAGTTGCGGGCATCCCGGGCGAGAAGCTGCGTCGCACGGT

6287  GGTCACCACCACGCCGGCCCGACGTTTGAGCGGCCGACACACGGAGCAGGAGCAGGCGGG
      ||||||||||||||||||||||||||||||||||||||||||||||||||||||||||
5289  GGTCACCACCACGCCGGCCCGACGTTTGAGCGGCCGACACACGGAGCAGGAGCAGGCGGG

6347  CA.GCGTCTCTGTGAAAAAGGGAAGAAAAGAATCATCATGTGCCGCGGGGAGTCGCTCCG
```

Figure 7c cont.

```
5349  CATGCGTCTCTGTGAAAAAGGGAAGAAAAGAATCATCATGTGCCGCCGGGAGTCGCTCCG

6406  AACTCTGCCGTGGCTGTTCTGGGCGCTGTTGAGCTGCCCGCGACTCCTCGAATATTCTTC
5409  AACTCTGCCGTGGCTGTTCTGGGTGCTGTTGAGCTGCCCGCGACTCCTCGAATATTCTTC

6466  CTCTTCGTTCCCCTTCGCCACCGCTGACATCGCCGAAAAGATGTGGGCCGAGAACTATGA
5469  CTCTTCGTTCCCCTTCGCCACCGCTGACATTGCCGAAAAGATGTGGGCCGAGAATTATGA

6526  GACCACGTCGCCGGCGCCGGTGTTGGTCGCCGAGGGAGAGCAAGTTACCATCCCCTGCAC
5529  GACCACGTCGCCGGCGCCGGTGTTGGTCGCCGAGGGAGAGCAAGTTACCATCCCCTGCAC

6586  GGTCATGACACACTCCTGGCCCATGGTTTCCATTCGCGCACGTTTCTGTCGTTCCCACGA
5589  GGTCATGACACACTCCTGGCCCATGGTCTCCATTCGCGCACGTTTCTGTCGTTCCCACGA

6646  CGGTAGCGACGAGCTCATCCTGGACGCCGTCAAAGGCCATCGGCTGATGAACGGACTCCA
5649  CGGCAGCGACGAGCTCATCCTGGACGCCGTCAAAGGCCATCGGCTGATGAACGGACTCCA

6706  GTACCGCCTGCCGTACGCCACTTGGAATTTCTCGCAGTTGCATCTCGGCCAAATATTCTC
5709  GTACCGCCTGCCGTACGCCACTTGGAATTTCTCGCAATTGCATCTCGGCCAAATATTCTC

6766  GCTTACTTTTAACGTATCGATGGACACGGCCGGCATGTACGAGTGCGTGCTGCGCAATTA
5769  GCTTACTTTTAACGTATCGATGGACACAGCCGGCATGTACGAATGCGTGCTACGCAACTA

6826  CAGCCACGGCCTCATCATGCAACGCTTTGTAATTCTCACGCAGCTGGAGACGCTCAGCCG
5829  CAGCCACGGCCTCATCATGCAACGCTTCGTAATTCTCACGCAGCTGGAGACGCTCAGCCG

6886  GCCCGATGAACCTTGTTGCACACCGGCGGTTAGGTCGCTACTCGTTGGGAGACCAGATCTG
5889  GCCCGACGAACCCTTGCTGCACACCGGCGTTAGGTCGCTACTCGCTGGGAGACCAGATCTG

6946  GTCGCCGACGCCCTGGCGTCTACGGAATCACGACTGCGGAACGTACCGCGGCTTTCAACG
5949  GTCGCCGACGCCCTGGCGTCTACGGAATCACGACTGCGGAACGTACCGCGGCTTTCAACG

7006  CAACTACTTCTATATCGGCCGCGCCGACGCCGAGGATTGCTGGAAACCCGCATGTCCGGA
6009  CAACTACTTCTATATCGGCCGCGCCGACGCCGAGGATTGCTGGAAACCCGCATGTCCGGA

7066  CGAGGAACCCGACCGCTGTTGGACAGTGATACAGCGTTACCGGCTCCCCGGCGACTGCTA
6069  CGAGGAACCCGACCGCTGTTGGACAGTGATACAGCGTTACCGGCTCCCCGGCGACTGCTA

7126  CCGTTCGCAGCCACACCCGCCGAAATTTTTACCGGTGACGCCAGCACCGCCGGCCGACAT
6129  CCGTTCGCAGCCACACCCGCCGAAATTTTTACCGGTGACGCCAGCACCGCCGGCCGACAT

7186  AGACACCGGGATGTCTCCCTGGGCCACTCGGGGAATCGCGGCGTTTTAGGATTTTGGAG
6189  AGACACCGGGATGTCTCCCTGGGCCACTCGGGGAATCGCGGCGTTTTGGGGTTTTGGAG

7246  TATTTTTACCGTATGTTTCCTATGCTACCTGTGTTACCTGCAGTGTTGTGGACGCTGGTG
6249  TATTTTTACCGTATGTTTCCTATGCTACCTGTGTTATCTGCAGTGTTGTGGACGCTGGTG

7306  TCCCACGCCGGGAAGGGGACGACGAGGCGGTGAGGGCTATCGACGCCTACCGACTTACGA
6309  TCCCACGCCGGGAAGGGGACGACGAGGCGGTGAGGGCTATCGACGCCTACCGACTTACGA

7366  TAGTTACCCCGGTGTTAGAAAGATGAAGAGGTGAGAACACGCATAAAATAAAAAAATGAG
6369  TAGTTACCCCGGTGTTAGAAAGATGAAGAGGTGAGAACACGTATAAAATAAAAAAATAAT

7426  ATATTAAAAAATGTAGTGTGTGAAGTGTGAATAGTATGATTAAAAATATGCGGATTGAATG
6429  ATGTTAAAAAATGCAGTGTGTGAAGTGTGAATAGTGTGATTAAAAATATGCGGATTGAATG

7486  GGCGTGTTTGTTATTCGGATACTTTGTGTCATCCGTTGGGAGCGAACGGTCATTATCCTA
6489  GGTGTGGTGGTTATTCGGATACTTTGTGTCATCCGTTGGGAGCGAACGGTCATTATCCTA

7546  TCGTTACCACCTGGAATCTAATTCATCTACCAACGTGGTTTGCAACGGAAACATTTCCGT
6549  TCGTTACCACTTGGAATCTAATTCATCTACCAACGTGGTTTGCAACGGAAACATTTCCGT

7606  GTTTGTAAACGGCACCCTGGGTGTTCGGTATGACGTTACAATAGGAATCGGTAGTCCATA
6609  GTTTGTAAACGGCACCCTAGGTGTGCGGTATAACATTACGGTAGGAATC...AGTTCGTC

7666  TCCACTAGTAGGACACCTCACAATCATAAGTCTTGAATCTTGGTTTAAACCTTGGATTTT
6666  TTTATTAATAGGACACCTTACTATACAAGTATTGGAATCATGGTTCACACCCTGGGTCCA

7726  AAACACAACTTACAATAAAATATCCATTAAATACAACTGAAACGTTTTATAATGTAGACGC
```

Figure 7c cont.

```
6726  AAATAAAAGTTACAACAAACAACCCCTAGGTGACACTGAAACGCTTTATAATATAGATAG

7786  GGAAAATTTACGTCGCGTATCCCAATATTTCTACAAACTAGGGTGGGTAAAAACGAGTTT
      |||||  | |  |||||||||| ||||||||  ||| |  | ||     |    |
6786  CGAAAACATTCATCGCGTATCTCAATATTTTCACACAAGATGGATAAAATCTCTGCAAGA

7846  ACAAGAAAATCACACCTGTAACCTCACAAACAATATACCTACCTATGAATATCAGGTAAA
      |  |||| |  |  |   |   |    ||  |   ||| ||| ||  |  | |||| ||
6846  GAATCACACTTGCGACCTCACAAACAGTACACCTACCTATACATATCAAGTAAACGTGAA

7906  CGTAAACAACACGGATTACCTAACACTAATATCCTCGGGATGGCAAGACCATCTAAACTA
      |  |  ||     |||||||   | | | |   ||||||||||||||||| |  || ||
6906  CAACACGAATTACCTAACACTAACATCCTCGGGATGGCAAGACCGTCTAAATTACACCGT

7966  CA..................CCACCATAAATAGTACACACTTTAACCTCACAAAATCG.
      ||                   ||| ||| | ||||                 ||| |||
6966  CATAAATAGTACACACTTTAACCTCACAGAATCGAACATAACCAGCATTCAAAAATATCT

8006  .AACATAACCAGCATTCAAAAATATCTCAACACTACCTGCATAGAAAGACTCCGTA.ACT
       |||| ||| |||| ||| | |  |||  | |||  ||||              || ||
7026  CAACACTACCTGCATAGAAAGACTCCGTAACTACACCTTG.......GAGTCCGTATACA

8064  ACACCTTGGAGCCCGTATACACCACAACTATGCCTCAAAACGTAA...........CAA
      |||   | ||| | ||||| | ||||||| || ||||  | ||            |||
7079  CCACAACTGTGCCTCAAAACATAACAACATCTCAACACGCAACAACCACTATGCACACAA

8112  CACCTCAACACATAACAACCACTCTGTACACAAACACCTCCAAATGCAATAACAATTCAAG
      ||||| | | | |||  |||  | ||||||      |  |||  ||||| || ||  |
7139  TACCTCCAAATACAATAACAATTCAAAATACAACTCAAAGCCATACTGTACAGACGCCGT

8172  ATACAACTCAAAGCCATACTGTACAGACGCCGTCTTTTAACGACACACATAACGTGACGG
      |  |  | ||||  |  ||| |  ||  || |||  | |||||||||||||| || ||
7199  CTTTTAACGACACACATAACGTGACGAAACACACGTTAAACATAAGCTACGTTTTATCAC

8232  AACACACGTTAAACATAAGCTACGTTTTATCACAAAAAACGAATAACAACAACATCACCGT
      || | ||| |||| | ||| ||  ||       ||  |     ||   |||  |||  ||
7259  AAAAAACGAATAACACAA.............CATCACCGTGGATATATGCCATACCTAT

8292  GGGTATATGCCATACCTATGGGCGCCACAGCCACAATAGGCGCCAGTTTATATATCGGGA
      |||          ||   ||  |    |       |||  ||| |||||||||||| |
7305  GGGCGCTACAGCCACAATAGGCGCCGGTTTATATATCGGGAAACACTTTACGCCGGTTAA

8352  AACACTTTACGCC....GGTTAGGTCCGTATACGAAGTATGGCGCGGTCAGTAAAGATGA
      | |||||||||||    ||  ||||  ||| |  |  | ||      |   | |   |
7365  GTTCGTATACGAGGTATGGCGCGGTCAGTAAAGACGATTCGGATTCAACACATATACTCC

8408  TTCTGATTCAACACATATACCCCCCACGATCCTCGAACACCTTACAGCATATGAGCAAAA
       |||  |    |  ||| ||     | |||  || |||  | ||||| ||||| ||
7425  CCACGATCCTCGAACACCTTACAGCATATGAGCAAAAAACAAGAAAGTATAGCCACAATG

8468  AACAAGAAAGTATAACCACAATCACATTTGGGCGAATAACACGCTGTCATCCACTAACGT
      |   |  |  |  ||   |   |  ||||| | ||  ||||  |  | ||
7485  ACATTTGGGCGAATAACATGCTGTCATC..........CACTAGCGTCTATTAATCTAA

8528  CTATTAATCTAATGTTTAACGGGAGCTGTACTGTCGCCGTTAAAATGTCCATGGGAGTCA
       ||||   |   ||  ||||||||||||||||||| ||||||||| |  ||||| |  ||
7534  TGTTTAACGGGAGCTGTACTGTCACCGTTAAAATATCCATGGGAATCAACGGGTCAACCA

8588  ATGTAC.....................CTGGGTAACCGCTGTCAGCCTTGGTGACAGG
      | || |                       ||||||||||||||||||||| |||||||
7594  ACGTCCATCAGCTTGTGATTGTGCTCCATCTGGGTAACCGCTGTCAGCCTTGGCGACAGG

8625  TGTAATCACAGCTGCCACATAACTCACGAAGCCTCCAATCACAGCAGCACACACAATCCT
      |||||||||||| |||||||||||||||||||||||||||||||||||||||||   ||
7654  TGTAATCACAGCTGTCACATAACTCACGAAGCCTCCAATCACAGCAGCACACATAGTGCT

8685  AACGCCATTGGCGTGTATAAAAGTTCGGAAAACTCGACGGTTGTACGGCACGACAAATCG
      ||||||||||||||||||||||||||||||||| ||||||||||||||||||||||||||
7714  AACGCCATTGGCGTGTATAAAAGTTCGGAAAACTTGACGGTTGTACGGCACGACAAATCG

8745  ATGTAGTGGTATGTGTTTCCAGCGGGGACCGTGTGCGGTCTCTTAGGTTCGCTATACTGT
      |||||||||||| ||||||||||| ||||||||||||||||||||||||||||||||||||
7774  ATGTAGTGGTATGTTTTTCCAGCAGAGACCGTGTGCGGTCTCTTAGGTTCGCTATACTGT

8805  GGCTGGAAACTGGTTACCTGTGAAGATGGCTGACTATCCTGTTCTGTCCTGGAAAAACTT
      ||||||||||||||||||||||||||||||| ||||||||||||||||||||||||||
7834  GGCTGGAAACTGGTTACCTGTGAAGATGGCTAACTATCCTGTTCTGTCCTGGAAAAACTT

8865  TCAGCGTCGTAGGTGGACTTTGCAGTATGCGGATTAGTGAAGTTATGTCATTTATTTACG
      |  ||||||||||||||||||||||||||||  ||||||||||||||||||||||||||||
7894  TTGGCGTCGTAGGTGGACTTTGCAGTATGCGGGTTAGTGAAGTTATGTCATTTATTTACG

8925  TTTACGATCTCGTATTACAAACCGCGGAGAGGATGATACCGTTCGGCCCCATGAGTTATT
      ||||||||||||||||||||||||||||||||||||||||||||||||||||||||||||
7954  TTTACGATCTCGTATTACAAACCGCGGAGAGGATGATACCGTTCGGCCCCATGAGTTATT

8985  TTTATTCTTCCGGTAGGAGGCATGAAGCCTCTGGTGATGCTCATCTGCTTCGGTGTGTTT
      ||||||||||||||||||||||||||||||||| |  |||||||||||| |  |||| |
8014  TTTATTCTTCCGGTAGGAGGCATGAAGCCTCTGATAATGCTCATCTGCTTTGCTGTGATA

9043  TTACTACAGCTTGGGGGAAGCAAAATGTGTAAGCCCGATGAGGTGAAGCTGGGTAACCAA
      ||| | ||||||||||| |||| ||| ||||||| ||||  |||  ||| | ||  ||
8074  TTATTGCAGCTTGGAGTGACTAAAGTGTGTCAGCATAATGAAGTGCAACTGGGCAATGAG
```

Figure 7c cont.

```
9105 TGCTGCCCGCCATGCGGATCAGGACAAAAAGTTACAAAAGTGTGTACAGAGAATAGTGGC
     |||||||| || || || || ||||||| |||||| |||||| || || || ||    |
8134 TGCTGCCCTCCGTGTGGTTCGGGACAAAGAGTTACTAAAGTATGCACGGATTATACCAGT

9165 ATAACGTGTACACTGTGCCCAAACGGCACTTATCTCACAGGGCTTTACAACTGTACTAAT
     |||||||||| |  ||||| ||||||||| ||| |  | || ||||||||||||||  ||
8194 GTAACGTGTACCCCTTGCCCCAACGGCACGTATGTATCGGGACTTTACAACTGTACCGAT

9225 TGTACTCAATGTAACGACACTCAGATCACGGTTCGTAACTGCACTTCCACTAATAACACC
     || |||||||||||||  |||||||| |||||  | |||||||||||||||||  ||| ||
8254 TGCACTCAATGTAACGTCACTCAGGTCATGATTCGTAACTGCACTTCCACCAATAATACC

9285 ATATGCGCATCTAAGAATCATACATTGTTTTCCACTCCAGGTGTCCAACATCACAAGCAA
     |||||||| |||||||| ||||| ||||| | |||||||||||||| ||||||||||||| |||
8314 GTATGCGCACCTAAGAACCATACGTACTTTTCCACTCCAGGCGTCCAACATCACAAACAA

9345 CGACAGCAAAATCATACCGCACATGTAACCGTCAAACAAGGGAAAAGTGGTCGTCATACT
     ||||||||||||||||||||||||| | |||||||||||||||||||||| ||||||||||||
8374 CGACAGCAAAATCATACCGCACATATAACCGTCAAACAAGGAAAAAGCGGTCGTCATACT

9405 CTAGCCTGGTTGTCCCTGTTCATCTTTCTCGTGGGTATCATACTTTTAATTCTCTATCTT
     ||||||||||||| ||||| |||||||| |||||||||||||||||||||||||||||||||
8434 CTAGCCTGGTTGTCTCTCTTTATCTTTCTTGTGGGTATCATACTTTTAATTCTCTATCTT

9465 ATAGCCGCCTATCGGAGTGAGAGATGCCAACAGTGTTGCTCAATCGGCAAAATTTCTAC
     ||||||||||||||||||||||||||||||||||||||||||||||||||||||||||||
8494 ATAGCCGCCTATCGGAGTGAGAGATGCCAACAGTGTTGCTCAATCGGCAAAATTTCTAC

9525 CGCACCCTGTAAGCTTCCTGTTGTTGTTTTACATCACGGTACGATGAAGTCACACAGAT
     |||||||||||||||||||||||||||||||||||||||||||||||||||||||||||
8554 CGCACCCTGTAAGCTTCCTGTTGTTGTTTTACATCACGGTACGATGAAGTCACACAGAT

9585 AATTACAGATGAGCTGTTCATATTTTTTATTATTTTTTCCAATTCCTGCACTAAAAAAG
     |||||||||||||||||||||||||||||||||||||||||||||||||||||||||||
8614 AATTACAGATGAGCTGTTCATATTTTTTATTATTTTTTCCAATTCCTGCACTAAAAAAG

9645 AAGCACTTTACGGAACCGTGTCTGAATATCTGTGGGGAATTTAGGTACTTTTTGCCGACG
     ||||||||||||||||||||||||| |||||||||||||||||||||||||||||||||||
8674 AAGCACTTTACGGAACCGTGTCTGAGTATCTGTGGGGAATTTAGGTACTTTTTGCCGACG

9705 TCAGGAAAAATAAGCTGTCGCCTACATAAGAGCCCGGTTCTATCGTGCTGTCACTCTTTC
     ||||||||||||| || ||||||||||||||||| ||| |||||||||||||||||||||
8734 TCAGGAAAAATAAG.TGTCGCCTACATAAGAGCCCGGTGCTATCGTGCTGTCACTCTTTC

9765 TTGTTGCCTTCGATGTACGGCGTCCTGGCTCATTACTACTCCTTCATCAGTAGCCCCAGC
     ||||||||||||||||||||||||||||||||||||||||||||||||||||||||||||
8793 TTGTTGCCTTCGATGTACGGCGTCCTGGCTCATTACTACTCCTTCATCAGTAGCCCCAGC

9825 GTTATGGTTAATTTTAAGCATCATAACGCTGTACAGCTGTTGTGTGCACGGACCCGAGAC
     ||||||||||||||||||||||||| || ||||||| |||||||||||||||||||||||
8853 GTTATGGTTAATTTTAAGCATCATAACGCCGTGCAGCTGTTATGTGCACGGACCCGAGAC

9885 GGCACTGCCGGATGGGAACGTTTAACCCATCATGCGTCGTATCACGCGAATTATGGGGCA
     ||||||||||||||||||||||||||||||||||||||||||||||||||| || ||||||
8913 .GCACTGCCGGATGGGAACGTTTAACCCATCATGCGTCGTATCACGCGAACTACGGGGCA

9945 TACGCCGTGTTGATGGCTACATCGCAAAGAAAGTCCCTAGTGTTACATCGATATAGTGCC
     ||||||||||||||||||||||||||||||||||||||||||||||||||||||| |||||
8972 TACGCCGTGTTGATGGCTACATCGCAAAGAAAGTCCCTAGTGTTACATCGATACAGTGCC

10005 GTGACAGCCGTGGCCCTGCAGCTCATGCCTGTTGAGATGCTGCGCAAGCTAGACCAGTCG
      ||||||||||||||||||||||||||||||||| | ||||||||| ||||||
9032  GTGACAGCCGTGGCCCTGCAGCTCATGCCTGTTGAGATCGTCCGCAAGCTAGATCAGTCG

10065 GACTGGGTGCGGGGTGCCTGGATCGTGTCAGAGACTTTTCCAACTAGCGACCCCAAAGGA
      ||||||||||||||||||||||||||||||||||||||||||||||||||||||||||||
9092  GACTGGGTGCGGGGTGCCTGGATCGTGTCAGAGACTTTTCCAACTAGCGACCCCAAAGGA

10125 TTTTGGAGCGACGATGACTCCTCGATGGGTGGAAGTGAAGATTGATGATGAGAACCTGAC
      |||||||||||||||||||||||||||||||||| |||||||| ||||||||||||||||
9152  GTTTGGAGCGACGATGACTCCTCGATGGGTGGAAGTGATGATTGATGATGAGAACCTGAC

10185 AAGAAAGACGATAGAGAAATTCAGAGCTGTCATTGTAGAATTAGTCTAGATTCCTGATAA
      |||||||||| ||||||| |||||||||||||||||||||||||||||||||||||||||
9212  AAGAAAGACGAGAGAGAAATTTAGAGCTGTCATTGTAGAATTAGTCTAGATTCCTGATAA

10245 TAAACGGTATCGATTTTGAAACCTAATTGACGTGTGATCGATTTTTAAACCTGTGTGTTG
      ||||| |||||||||||||||||||||||||||||||||||||||| ||||||
9272  TAAACAGTATCGATTTTGAAACCTAATTGACGTGTGATCGATTTTTAAACCTCTGTGTTG

10305 TGTGATTGATTGGTACGTGGGGGGATCCGATTTCAAAGGGAGGTAGTTATCGGGAATTGA
      ||||||||||||| ||||||||||||||||||||||||||||||| ||| ||||||||||
9332  TGTGATTGATTGGTATGTGGGGGGATCCGATTTCAAAGGGGGGTACTTATCGGGAATTGA

10365 TGTGTCATGGACGCAGTTTTGAGTGATTTTCCGGGAATACCGGATATTACGAATTACTGT
      |||||||||||||||||||| ||| ||||||||||||||||||||||||||||||||| |
9392  TGTGTCATGGACGCAGTTTTGAGCGATTTTCCGGGAATACCGGATATTACGAATTACTGG

10425 AAGTGACGTCAGAAATTAAATTATAATGCGTTTAATTTTTGGTTTATTGATCATTTTTAT
      ||||||||  ||| ||||||||||||||  ||||||||||| ||||| ||||| ||||| |
9452  TAGTGACGTAGATAATAAAATTATAATGCGATTAATTTTTGGTGCGTTGATTATTTTTTT
```

Figure 7c cont.

```
10485 TGTTACAGATACATGTAACGGCGGTTTTGGCACTGAAGGTAATCGTCGTTGTGCATGCAT
      |    |    |   | |  | |  ||| || |||     |  | |||       |||
9512  AGCATATGTGTATCATTATGAGGTGAATGGAACAGAATTACGCTGCAGATGTCTT..CAT

10545 AGGGTATCATCGACTTTTAGGACAATTGCCTCGTGGAACTTTCTGGTTAGGACATTTACC
      ||  || || || ||    || |        || | ||  ||| |    |      ||
9570  AGAAAATGGCCGCCTAATA....AAATTATATTGGGTAATTATTGGCTTCATCGCGATCC

10605 ACCAGGCTCACATTGCCCAAAGGGACAAGTCATGAT...........AAAGATAGGCCA
      ||| |    |||  ||   ||    ||       |            || ||  |
9626  CAGAGGGCCCGGATGCGATAAAAATGAACATTTATTGTATCCAGACGGAAGGAAACCGCC

10653 AGGACCGATCGTCTGTTTATCCGATTATCATCCTTTATCTAAGTGGATGTATGGAAATCA
      |||||    || |||||||||  |||| |  || || || || |||  |     |  |
9686  TGGACCTGGAGTATGTTTATCGCCCGATCACCTGTTCTGAAAATGGTTAGACAAACAC..

10713 TAAATCTGGTTCGGAAACATGGCTTCAGATAAAAATGGAAGGTCCAAGAAATGCTACAGT
                                  || ||  ||||  | ||        |||
9744  .............................AACGATAATAGGTGGTATAATGTTAACATA

10773 AGTACAAAGATCGAATACTCGTCCATAAAGATAACGAATGTTCATAAGAATTGTACTTTT
      |  |     | |        |||||| |||||
9774  ACGAAATCACCAGGACCGAGACGAATAAATATAACCTT.....................

10833 ATATGTATGTAAGTTTATGGATCTTTATGTTTGTCATCATATACATTAGTAGTAACATAC

9812  ............................................................

10893 TCAACACACTATGCGTGTACAATTTGTTTTATAGATCCGTAGTGTACAATAAATATTACG
      |||. || |  |    ||||   |||
9812  .............................GATAGGTGTTAGAGGATAATATTTAAT

10953 ATAAATTTTTAACGTCGGATACATTTACGATACTAAACGTACTGTATTGCATTTTTTGCA
      ||  |||| ||    |       |   |  ||  || |||| |||| || ||  ||  |
9839  GTATGTTTTCAAACAGACAAGTTCGTTAAAACAAAATATTACAGTATGTGTTTAATATGG

11013 CGATGTTGACATCACATTGCTGGGCTACAAGATGGCATAACAAA...TTATTGGTACGAT
       | |     |  |  || | |||||| |||||| |||  |||     ||||  ||||||
9899  TGCTAACATGGTTGCACCATCCGGTTTCAAACTCGCATATCAATCTGTTATCGGTACGAC

11070 ACCTGTCATTGACTATATATATGTTACTGACCGTATGTCCCCTAGCCGTCCATCTTTTAG
      |||||| ||| |    ||||||||||| ||||| ||||||||||||||||||| ||||||
9959  ACCTGTCATTAATCGCATATATGTTACTTACCATATGTCCCCTAGCCGTCCATGTTTTAG

11130 AATTGGAAGATTACGACAGACGCTGTCGTTGTAACAATCAAATTCTGTTGAATACTCTGC
      || | |||||||||||||| |||||| ||||| |||||||| ||||||||||||||||||
10019 AACTAGAAGATTACGACAGGCGCTGCCGTTGCAACAACCAAATTCTGTTGAATACCCTGC

11190 CAATCGGAACTGAATTGCTTAAGCCAATCGCGGCGAGCGAAAGCTGCAATCGTCAGGAAG
      |  ||||||  ||||||||||||||||||||||||||||| |||||||||||||||||||
10079 CGGTCGGAACCGAATTGCTTAAGCCAATCGCAGCGAGCGAAAGCTGCAATCGTCAGGAAG

11250 TGCTGGCTATTTTAAAGGACAAGGGCACCAAGTGTCTCAATCCTAACGCGCAAGCCGTGC
      |||||||||||||||||||||||||||| |||||||||||||||||||||||||||||||
10139 TGCTGGCTATTTTAAAGGACAAGGGAACCAAGTGTCTCAATCCTAACGCGCAAGCCGTGC

11310 GTCGTCACATCAACCGGCTATTTTTTCGGTTAATATTAGACGAGGAACAACGCATTTACG
      |||||||||||||||||||||||||||||||||||| |||||||||||||||||||||||
10199 GTCGTCACATCAACCGGCTATTTTTTCGGTTAATCTTAGACGAGGAACAACGCATTTACG

11370 ACGTAGTGTCTACCAATATTGAGTTCGGTGCCTGGCCAGTCCCTACGGCCTACAAAGCCT
      ||||||||||||||||||||||||||||||||||||||||||||||||||||||||||||
10259 ACGTAGTGTCTACCAATATTGAGTTCGGTGCCTGGCCAGTCCCTACGGCCTACAAAGCCT

11430 TTCTCTGGAAATACGCCAAGAAACTGAACTACCACCACTTCAGATTGCGCTGGTGATCAT
      |||| ||||||||||||||||| |||||||||||||||||||||| ||||||||||||||
10319 TTCTTTGGAAATACGCCAAGAGACTGAACTACCACCACTTCAGACTGCGCTGGTGATCAT

11490 GTCCCTATTTTACCGTGCGGTAGCCCTGGGCACACTGAGCGCTCTGGTGTGGTACAGCAC
      ||||||||||||||||||||||||| || ||||||||| ||||||| |||||||||||||
10379 GTCCCTATTTTACCGTGCGGTAGCTCTGGGCACGCTAAGCGCTTTGGTGTGGTACAGCAC

11550 TAGTATCCTGGCAGAAATTAACGAAGAATCCTGCTCGTCATCTTCTGTGGACCACGAAGA
      |||  |||||  |||||||||||||| | |||||||||||||||||||  ||||||||||
10439 TAGCATCCTCGCAGAGATTAACGAAAATTCCTGCTCCTCATCTTCTGCGGATCACGAAGA

11610 CTGCGAGGAACCGGACGAGATCGTTCGCGAAGAGCAAGACTATCGGGCTCTGCTGGCCTT
      ||||||||||||||||||||||||||||||||||||||||||| ||||||||||||||||
10499 CTGCGAGGAACCGGACGAGATCGTTCGCGAAGAGCAAGACTATCGGGCTCTGCTGGCCTT

11670 TTCCCTAGTGATTTGCGGTACGCTCCTCGTCACTTGTGTGATCTGAGACGTCATGCTGGT
      ||||||||||||||||||||||||||||||||||||||||||||||||||||||||||||
10559 TTCCCTAGTGATTTGCGGTACGCTCCTCGTCACTTGTGTGATCTGAGACGTCATGCTGGT

11730 AGCGTTTATGAGTCGGGCGGTGGCCGACACGCCGCATTTCCTAACCCGCGCAGCATGTTG
      ||||||||||||||||||||||||||||||||||||||||||||||||||||||||||||
10619 AGCGTTTATGAGTCGGGCGGTGGCCGACACGCCGCATTTCCTAACCCGCGCAGCATGTTG

11790 CGCTTGCTGTTCACGCTCGTCCTGCTGGCCCTCCACGGGCAGTCTGTCGGCGCTAGCCGC
      ||||||||||||||||||||||||||||||||||||||||||||||||||||||||||||
10679 CGCTTGCTGTTCACGCTCGTCCTGCTGGCCCTCCACGGGCAGTCTGTCGGCGCTAGCCGC

11850 GACTATGTGCATGTTCGGCTACTGAGCTACCGAGGCGACCCCCTGGTCTTCAAGCACACT
```

Figure 7c cont.

```
10739 GACTATGTGCATGTTCGGCTACTGAGCTACCGAGGCGACCCCCTGGTCTTCAAGCACACT

11910 TTCTCGGGTGTGCGTCGACCCTTCACCGAGCTAGGCTGGGCTGCGTGTCGCGACTGGGAC
10799 TTCTCGGGTGTGCGTCGACCCTTCACCGAGCTAGGCTGGGCTGCGTGTCGCGACTGGGAC

11970 AGTATGCATTGCACACCCTTCTGGTCTACCGATCTGGAGCAGATGACCGACTCGGTGCGG
10859 AGTATGCATTGCACACCCTTCTGGTCTACCGATCTGGAGCAGATGACCGACTCGGTGCGG

12030 CGTTACAGCACGGTGAGCCCCGGTAAGGAAGTGACGCTTCAGCTTCACGGGAACCAAACC
10919 CGTTACAGCACGGTGAGCCCCGGCAAGGAAGTGACGCTTCAGCTTCACGGGAACCAAACC

12090 GTACAGCCGTCGTTTCTAAGCTTTACGTGCCGCCTGCAGCTAGAACCCGTGGTGGAAAAT
10979 GTACAGCCGTCGTTTCTAAGCTTTACGTGCCGCCTGCAGCTAGAACCCGTGGTGGAAAAT

12150 GTTGGCCTCTACGTGGCCTACGTGGTCAACGACGGTGAACGCCCACAGCAGTTTTTTACA
11039 GTTGGCCTCTACGTGGCCTACGTGGTCAACGACGGCGAACGCCCACAACAGTTTTTTACA

12210 CCGCAGGTAGACGTGGTACGCTTTGCTCTATATCTAGAAACGCTCTCCCGGATCGTGGAA
11099 CCGCAGGTAGACGTGGTACGCTTTGCTCTATATCTAGAAACACTCTCCCGGATCGTGGAA

12270 CCGTTAGAATCAGGTCGCCTGGCAGTGGAATTTGATACGCCTGACCTAGCTCTGGCGCCC
11159 CCGTTAGAATCAGGTCGCCTGGCAGTGGAATTTGATACGCCTGACCTAGCTCTGGCGCCC

12330 GATTTAGTAAGCAGCCTCTTCGTGGCCGGACACGGCGAGACCGACTTTTACATGAACTGG
11219 GATTTAGTAAGCAGCCTCTTCGTGGCCGGACACGGCGAGACCGACTTTTACATGAACTGG

12390 ACGCTGCGTCGCAGTCAGACCCACTACCTGGAGGAGATGGCCTTACAGGTGGAGATTCTA
11279 ACGCTGCGTCGCAGTCAGACCCACTACCTGGAGGAGATGGCCTTACAGGTGGAGATTCTA

12450 AAGCCACGCGGCGTACGTCACCGCGCTATTATCCACCATCCGAAGCTACAGCCGGGCGTT
11339 AAACCCCGCGGCGTACGTCACCGCGCTATTATCCACCATCCGAAGCTACAGCCGGGCGTT

12510 GGCCTGTGGATAGATTTCTGCGTGTACCGCTACAACGCGGCCCTGACCCGCGGCTACGTA
11399 GGCCGTGTGGATAGATTTCTGCGTGTACCGCTACAACGCGGCCCTGACCCGCGGCTACGTA

12570 CGATACACCCTGTCACCGAAAGCGCGCTTGCCCGCAAAAGCAGAGGGTTGGCTGGTGTCA
11459 CGATACACCCTGTCACCGAAAGCGCGCTTGCCCGCAAAAGCAGAGGGTTGGCTGGTGTCA

12630 CTAGACAGATTCATCGTGCAGTACCTCAACACATTGCTGATTACAATGATGGCGGCGATA
11519 CTAGACAGATTCATCGTGCAGTACCTCAACACATTGCTGATTACAATGATGGCGGCGATA

12690 TGGGCTCGCGTTTTGATAACCTACCTGGTGTCGCGGCGTCGGTAGAGGCTTGCGGAAACC
11579 TGGGCTCGCGTTTTGATAACCTACCTGGTGTCGCGGCGTCGGTAGAGGCTTGCGGAAACC

12750 ACGTCCTCGTCACACGTCGTTCGCGGACATAGCAAGAAATCCACGTCGCCACGTCTCGAG
11639 ACGTCCTCGTCACACGTCGTTCGCGGACATAGCAAGAAATCCACGTCGCCACATCTCGAG

12810 AATGCCGGCCCCGCGGGGTCTCCTTCGCGCAACATTCCTGGCCCTGGTCGCCGTTCGGGTT
11699 AATGCCGGCCTTGCGGGGTCCCCTTCGCGCAACATTCCTGGCCCTGGTCGCCGTTCGGGTT

12870 GCTGCTTTACATGGACTTCAGCGACGCTACAAATATGACCAGCAGCACAAACGTCCCTAC
11759 GCTGCTTCAGATAGACCTCAGCGACGCTACGAATGTGACCAGCAGCACAAAAGTCCCTAC

12930 TAGCACCAGCAGCAGAAATACCGTCGAGAGCACCACGAGTAGCGAACCTACAACCGAAAC
11819 TAGCACCAGCAACAGAAATAACGTCGACAACGCCACGAGTAGCGGACCCACAACCGGGAT

12990 CAACATGACCACCGCCCGCGAATCTTCCGTTCACGACGCGCGCAATGATGAAATCATGAA
11879 CAACATGACCACCACCCACGAGTCTTCCGTTCACAACGTGCGCAATAACGAGATCATGAA

13050 AGTGCTGGCTATCCTCTTCTACATCGTGACAGGCACCTCCATTTTCAGCTTCATAGCGGT
11939 AGTGCTGGCTATCCTCTTCTACATCGTGACAGGCACCTCCATTTTCAGCTTCATAGCGGT

13110 ACTGATCGCGGTAGTTTACTCCTCGTGTTGCAAGCACCCGGGCCGCTTTCGTTTCGCCGA
11999 ACTGATCGCGGTAGTTTACTCCTCGTGTTGCAAGCACCCGGGCCGCTTTCGTTTCGCCGA

13170 CGAAGAGGCCGTCAACCTGTTGGACGACACGGACGACAGTGGCGGTAGCAGCCCGTTTGG
12059 CGAAGAGGCCGTCAACCTGTTGGACGACACGGACGACAGTGGCGGCAGCAGCCCGTTTGG

13230 CAGCGGTTCCCGACGAGGTTCTCAGATCCCCGCCGGATTTTGTTCCTCGAGCCCTTATCA
```

Figure 7c cont.

```
12119 CAGCGGTTCCCGACGAGGTTCTCAGATCCCGCCGGATTTTGTTCCTCGAGCCCTTATCA

13290 GCGGTTGGAAACTCGGGACTGGGACGAGGAGGAGGAGGCGTCCGCGGCCCGCGAGCGCAT
      ||||||||||||||||||||||||||||||||||||||||||||||||||||||||||||
12179 GCGGTTGGAAACTCGGGACTGGGACGAGGAGGAGGAGGCGTCCGCGGCCCGCGAGCGCAT

13350 GAAACATGATCCTGAGAACGTCATCTATTTCAGAAAGGATGGCAACTTGGACACGTCGTT
      ||||||||||||||||||||||||||||||||||||||||||||||||||||||||||||
12239 GAAACATGATCCTGAGAACGTCATCTATTTCAGAAAGGATGGCAACTTGGACACGTCGTT

13410 CGTGAATCCCAATTATGGGAGAGGCTCACCTTTGACCATCGAATCTCACCTCTCGGACAA
      ||||||||||||||||||||||||||||||| ||||||||||||||||||||||||||||
12299 CGTGAATCCCAATTATGGGAGAGGCTCGCCTTTGACCATCGAATCTCACCTCTCGGACAA

13470 TGAGGAGGACCCCATCAGGTACTACGTTTCGGTGTACGATGAACTGACCGCCTCGGAAAT
      ||||||||||||||||||||||||||||||||||||||||||||||||||||||||||||
12359 TGAGGAGGACCCCATCAGGTACTACGTTTCGGTGTACGATGAACTGACCGCCTCGGAAAT

13530 GGAAGAACCTTCGAACAGCACCAGCTGGCAGATTCCCAAACTAATGAAAGTTGCCATGCA
      ||||||||||||||||||||||||||||||||||||||||||||||||||||||||||||
12419 GGAAGAACCTTCGAACAGCACCAGCTGGCAGATTCCCAAACTAATGAAAGTTGCCATGCA

13590 ACCCGTCTCGCTCAGAGATCCCGAGTACGACTAGGCTTTTTTTTTTGTCTTTCAGTTCCA
      ||||||||||||||||||||||||||||||||||||||||||||||||||||| ||||||
12479 ACCCGTCTCGCTCAGAGATCCCGAGTACGACTAGGCTTTTTTTTTTGTCTTTCGGTTCCA

13650 ACTCTTTCCCCGCCCCATCACCTCGCCTATACTATGTGTATGATGTCTCATAATAAAGCT
      |||||||||||||||||||||||||||| |||||||||||||||||||||||||||||||
12539 ACTCTTTCCCCGCCCCATCACCTCGCCTGTACTATGTGTATGATGTCTCATAATAAAGCT

13710 TTCTTTCTCAGTCTGCAACATGCGGCTGTGTCGGGTGTGGCTGTCTGTTTGTCTGTGCGC
      |||||||||||||||||||||||||||| ||||||||||||||||||| |||||||||||
12599 TTCTTTCTCAGTCTGCAACATGCAGCTGTGTCGGGTGTGGCTGTCTGTTTGTCTGTGCGC

13770 CGTGGTGCTGGGTCAGTGCCAGCGGGAAACGGCGGAAAAAAACGATTATTACCGAGTACC
      ||||||||||||||||||||||||||||||||||||||||||||||||||||||||||||
12659 CGTGGTGCTGGGTCAGTGCCAGCGGGAAACGGCGGAAAAAAACGATTATTACCGAGTACC

13830 GCATTACTGGGACGCGTGCTCTCGCGCGCTGCCCGACCAAACCCGTTACAAGTATGTGGA
      ||||||||||||||||||||||||||||||||||||||||||||||||||||||||||||
12719 GCATTACTGGGACGCGTGCTCTCGCGCGCTGCCCGACCAAACCCGTTACAAGTATGTGGA

13890 ACAGCTCGTGGACCTCACGTTGAACTACCACTACGATGCGAGCCACGGCTTGGACAACTT
      ||||||||||||||||||||||||||||||||||||||||||||||||||||||||||||
12779 ACAGCTCGTGGACCTCACGTTGAACTACCACTACGATGCGAGCCACGGCTTGGACAACTT

13950 TGACGTGCTCAAGAGGTGAGGATACGCGCTAAAGGTGCATGACAACGGGAAGGTAAGGGC
      |||||||||||||||||||||| |||||||||||||||||||||||||||||||||||||
12839 TGACGTGCTCAAGAGGTGAGGGTACGCGCTAAAGGTGCATGACAACGGGAAGGTAAGGGC

14010 GAACGGGTAACGGGTAAGTAACCGCATGGGGTATGAAATGACGTTTGGAACCTGTGCTTG
      |||||||||||| |||||||||||||||||||||||||||||||| ||||||||||||||
12899 GAACGGGTAACGGCTAAGTAACCGCATGGGGTATGAAATGACGTTTGGAACCTGTGCTTG

14070 CAGAATCAACGTGACCGAGGTGTCGTTGCTCATCAGCGACTTTAGACGTCAGAACCGTCG
      |||||||||||||||||||||||||||||||||||||||||||||||||||||||||||| 
12959 CAGAATCAACGTGACCGAGGTGTCGTTGCTCATCAGCGACTTTAGACGTCAGAACCGTCG

14130 CGGCGGCACCAACAAAAGGACCACGTTCAACGCCGCCGGTTCGCTGGCGCCGCACGCCCG
      |||||||||||||||||||||||||||||||||||||||||||||||||||| |||||||
13019 CGGCGGCACCAACAAAAGGACCACGTTCAACGCCGCCGGTTCGCTGGCGCCACACGCCCG

14190 GAGCGTCGAGTTCAGCGTGCGGCTCTTTGCCAACTAGCCTGCGTCACGGGAAATAATATG
      ||||||||||||||||||||||||||||||||||||||||||||||||||||||||||||
13079 GAGCCTCGAGTTCAGCGTGCGGCTCTTTGCCAACTAGCCTGCGTCACGGGAAATAATATG

14250 CTGCGGCTTCTGCTTCGTCACCACTTTCACTGCCTGCTTCTGTGCGCGGTTGGGCAACG
      ||||||||||||||||||||||||||||||||||||||||||||||||||||||||||
13139 CTGCGGCTTCTGCTTCGTCACCACTTTCACTGCCTGCTTCTGTGCGCGGTTTGGGCAACG

14310 CCCTGTCTGGCGTCTCCGTGGTCGACGCTAACGGCAAACCAGAATCCGTCCCCGCCATGG
      ||||||||||||||||||||||||||||||||||||||||||||||||||||||||||||
13199 CCCTGTCTGGCGTCTCCGTGGTCGACGCTAACGGCAAACCAGAATCCGTCCCCGCCATGG

14370 TCTAAACTGACGTATTCCAAACCGCATGACGCGGCGACGTTTTACTGTCCTTTTTCTAT
      ||||||||||||||||||||||||||||||||||||||||||||||||||||| |||||
13259 TCTAAACTGACGTATTCCAAACCGCATGACGCGGCGACGTTTTACTGTCCTTTTCTCTAT

14430 CCCTCGCCCCCACGGTCCCCCTTGCAATTCTCGGGGTTCCAGCAGGTATCAACGGGTCCC
      ||||||||||||||||||||||||||||||||||||||||||||||||||||||||||||
13319 CCCTCGCCCCCACGGTCCCCCTTGCAATTCTCGGGGTTCCAGCAGGTATCAACGGGTCCC

14490 GAGTGTCGGCAACGAGACCCTGTATCTGCTGTACAACCGGAAGGCCAGACCTTGGTAGAG
      |||||||||||||||||||||||||||||||||||||||||||||||||||||||||| ||
13379 GAGTGTCGCAACGAGACCCTGTATCTGCTGTACAACCGGAAGGCCAGACCTTGGTGGAG

14550 AGAAGCTCCACCTGGGTGAAAAAGGTGATCTGGTACCTGAGCGGTCGCAACCAGACCATC
      ||||||||||||||||||||||||||||||||| |||||||||||||||||||||||||
13439 AGAAGCTCCACCTGGGTGAAAAAGGTGATCTGGTATCTGAGCGGTCGCAACCAGACCATC

14610 CTTCAACGGATGCCCCGAACGGCTTCGAAACCGAGCGACGGAAACGTGCAGATCAGCGTG
      || ||||||||||||| |||||||||||||||||||||||||||||||||||||||||||
13499 CTCCAACGGATGCCCCAAACGGCTTCGAAACCGAGCGACGGAAACGTGCAGATCAGCGTG
```

Figure 7c cont.

```
14670 GAAGACGCCAAGATTTTTGGAGCGCACATGGTGCCCAAGCAGACCAAGCTGCTACGCTTC
      ||||||||||||||||||||||||||||||||||||||||||||||||||||||||||||
13559 GAAGACGCCAAGATTTTTGGAGCGCACATGGTGCCCAAGCAGACCAAGCTGCTACGCTTC

14730 GTCGTCAACGATGGCACACGTTATCAGATGTGTGTGATGAAGCTGGAGAGCTGAGCTCAC
      |||||||||||||||| |||||||||||||||||||||||||||||||||||  || |||
13619 GTCGTCAACGATGGCACGCGTTATCAGATGTGTGTGATGAAGCTGGAGAGCTGGGCCCAC

14790 GTCTTCCGGGACTACAGCGTGTCTTTTCAGGTGCGATTGACGTTCACCGAGGCCAATAAC
      ||||||||||||||||||||||||||||||||||||||||||||||||||||||||||||
13679 GTCTTCCGGGACTACAGCGTGTCTTTTCAGGTGCGATTGACGTTCACCGAGGCCAATAAC

14850 CAGACTTACACCTTCTGCACCCATCCCAATCTCATCGTTTGAGCCCGTCGCGCGCGCAGG
      |||||||||||||||| ||||||||||||||||||| |||||||||||||||||||||||
13739 CAGACTTACACCTTCTGTACCCATCCCAATCTCATCATTTGAGCCCGTCGCGCGCGCAGG

14910 GAATTTTGAAAACCGCGCGTCATGAGTCCCAAAGACCTGACGCCGTTCTTGACGGCGTTG
      ||||||||||||||||||||||||||||||||||||||||||||||||||||||| ||||
13799 GAATTTTGAAAACCGCGCGTCATGAGTCCCAAAGACCTGACGCCGTTCTTGACGACGTTG

14970 TGGCTGCTATTGGGTCACAGCCGCGTGCCGCGGGTGCGCGCAGAAGAATGTTGCGAATTC
      ||||||||||||||||||||| ||||||||||||||||||||||||||||||||||||| 
13859 TGGCTGCTATTGGGTCACAGCCGCGTGCCGCGGGTGCGCGCAGAAGAATGTTGCGAATTC·

15030 ATAAACGTCAACCACCCGCCGGAACGCTGTTACGATTTCAAAATGTGCAACCGCTTCACC
      ||||||||||||||||||||||||||||||||||||||||||||||||||| ||||||||
13919 ATAAACGTCAACCACCCGCCGGAACGCTGTTACGATTTCAAAATGTGCAATCGCTTCACC

15090 GTCGCGTACGTATTTTCATGATTGTCTGCGTTCTGTGGTGCGTCTGGATCTGTCTCTCGA
      ||||||||||||||||||||||||||||||||||||||||||||| |||||||||||||
13979 GTCGCGTACGTATTTTCATGATTGTCTGCGTTCTGTGGTGCGTCTGGATTTGTCTCTCGA

15150 CGTTTCTGATAGCCATGTTCCATCGACGATCCTCGGGAATGCCAGAGTAGATTTTCATGA
      ||||||||||||||||||||||||||||||||||||||||||||||||||||||||||||
14039 CGTTTCTGATAGCCATGTTCCATCGACGATCCTCGGGAATGCCAGAGTAGATTTTCATGA

15210 ATCCACAGGCTGCGGTGTCCGGACGGGCGAAGTCTGCTACAGTCCCGAGAAAACGGCTGAG
      ||||||||| ||||||||||||||||||||||||||||||||||||||||||||||||||
14099 ATCCACAGGCTGCGGTGTCCGGACGGCGAAGTCTGCTACAGTCCCGAGAAAACGGCTGAG

15270 ATTCGCGGGATCGTCACCACCATGACCCATTCATTGACGCGCCAGGTCGTACACAACAAA
      |||||||||||||||||||||||||||||||||||||| ||||||||||||||||||||
14159 ATTCGCGGGATCGTCACCACCATGACCCATTCATTGACACGCCAGGTCGTACACAACAAA

15330 CTGACGAGCTGCAACTACAATCCGTAAGTCTCTTCCTCGAGGGCCTTACAGCTTATGGGA
      ||||||||||||||||||||||||||||||||||||||||||||||| |||| |||||||
14219 CTGACGAGCTGCAACTACAATCCGTAAGTCTCTTCCTCGAGGGCCTTACAGCCTATGGGA

15390 AAGTAAGACAGAGAGGGACAAAACATCATTAAAAAAAAAAAGTCTAATTTCACGTTTTGT
      | ||||||||||||||||||||||||||||  |||||||||||||||||||||||||||
14279 GAGTAAGACAGAGAGGGACAAAACATCATT.AAAAAAAAAGTCTAATTTCACGTTTTGT

15450 ACCCCCCCTTCCCCTCCGTGTTGTAGGTTATA,.CCTCGAAGCTGACGGGCGAATACGCT
      | ||||||||||||||||||||||   ||   ||  ||  |        ||  |
14338 A.CCCCCCTTCCCCTCCGTGTTGTAGCCCATCGGCCGCGGCGATCTCCTAGTAACACTCG

15508 GCGGCAAAGTGAACGACAAGGCGCAGTACCTGCTGGGCGCCGCTGGCAGCGTTCCCTATC
       |  |  |  ||   ||      || ||| |  |  ||| ||   |  |  |     ||
14397 TCCGACACTTCCACCATCTCCAGCTCGGCCGGCGGTTCGGCATCCTCTACCAGCGGCGTC

15568 GATGGATCAATCTGGAATACGACAAGATAACCCGGATCGTGGGCCTGGATCAGTACCTGG
       |  |||  | |  |   |  |     |   |   |    ||  |  ||   |   |||
14457 GTCTCATCTTTGCCGCAGCAGCGGACGCACACCTTCTCCAGGCAGAACGCCACCAGCTGC

15628 AGAGCGTTAAGAAACACAAACGGCTGGATGTGTGCCGCGCTAAAATGGGCTATATGCTGC
       |      |||  ||  |||   |||  |  |  ||  |    ||    | |  |
14517 CGCCGAACGTACCACAGGTACACGTGCAGACCTGCGAACAGGACTACGGAGGTCATGACC

15688 AGTGAATAATAAAATGTGTGTTTGTCCGAAATACGCGTTTCGAGATTTCTGTCGCCGACT
      |     |    |  |  |       |     | || |  |   |       ||   |||
14577 ACCACGACGCACACGGGAATCCAGGGATCGAGATTGTTGCTGGAACTCGCTATCGCCACC

15748 AAATTCATGTCGCGCGATAGTGGTGTTTATCGCCGATAGAGATGGCGATATTGGAAGAAT
      ||  ||   ||  |            |||||    |   |  |||  |||  ||
14637 GACGTGCCCGCGTCTGTCTCACCGCCGCTCGCCCGATGTCGCGCGGCTTGTTATACGCTA

15808 CGATATTTGAAAATATGGCATATTGAAAATGTCGCCGATGTGAGTTTCTGTGTAACTGAT
      |  .   | ||           |    ||| || || || ||  || ||| |
14697 GCCCGTCGCCGCCTCGGGGCACGGTGCCCTCCTACCCACGTAACTTCCTGCGTGACTTAA

15868 ATCGCCATTTTTAAAAAAGTGATTTTTGGGCATATGCGATATCTGGCGATAACGCTTATA
      |    | |||             ||  |     |  |   |     |||| || |||
14757 AGTCGCGTGTGGTAGATCTCCTGCTCCGTGGACGAACCGTCCGGCAGGATAGCGGTTAAG

15928 ...TCGTTTACGGGGGATGGCGATAGACGACTTTGGCGACTTGGGCGATTCTGTGTGTCG
         ||| |  ||     |     |||   || || || ||    |    ||  |
14817 GATTCGGTGCTAAGGCCGTGTCGCCAACGTCGAATGCTACGTTGCAACAGCTTCGACGGA

15985 CAAATATCGCAGTTTCGATATAGGTGACAGACGATATGAGGCCATATCGCCGATAGAGGC
      |   |||·| |    |  | |       |||   ||||   ||  ||    || ||  ||
14877 CGGCCATCCCCTCTCTCATGCAATA.......ATAAAACACCAGCAGCGCGCACGACGC
```

Figure 7c cont.

```
16045 GACATCAAGTTGGCACATGG.....CCAATGCATATCGATATATACATTGAATCAATATT
      ||   |    | ||||   || | ||| ||  |    |    |
14930 GATCACGGTGACACCCATGATTAGACCCACGCAGATAGCCAGCCCCGCTAGCGTATCTAG

16100 GGCCATTAGCCACATTAGTCATTGGTTATATAGTATAAATCAATATTGGCTAATGGCCAT
      |||||    |  |   |||  |  ||   |     | ||   |
14990 CGCCATCCCGTTCGCTCCCG.TTGTCTCCTGAGCGAAGCAACTTCTCGGTCCCCGTTTTC

16160 TGCATACGTTGTATCTATATCATAATATGTACATTTATA....................
      ||   |||| || | ||      |   |||
15049 AACAGTTTTTGTTTCCTTCTCCGCGACTAGATGTTAACGCCCGCGGTCTTTCCGGCCGTG

16199 ............................................
15109 CTCTACCTCCTGGCGCTTGTCGTCTGGGTTGAGATGTTCTGCCTCGTCGCCGTAGCCGTC

16199 .........................................TTGGCTCATATCCA
                                               |||||
15169 GTCGAGCGCGAGATCGCCTGGGCGCTGCTGCTGCGGATGCTGGTCGTTGGCCTGATGGTG

16213 ATATAACCGCCATGTTGACATTGATTATTGATTAGTTATTAATAGTAATCAATTACGGGG
      |     |        |||   ||  | ||||    ||               |
15229 GAAGTCGGCGGCGCCGCCGCTTGGACGTTCGTGCGTTGTCTTGCCTATCAGCGCTCCT..

16273 TCATTAGTTCATAGCCCATATATGGAGTTCCGCGTTACATAACTTACGGTAAATGGCCCG
      ||     | ||  |  || | ||||| || | |||| |   |||  |
15287 TCCCCGTGCTTACGGCCTTCCCCTGAAACCCACGTTAACCGACCGTCCCAAAAACGCCGG

16333 CCTGGCTGACCGCCCAACGACCCCCGCCCATTGACGT..............CAATA
      |    |   ||      || || ||                            ||
15347 TGTTAACACAGGAAAAAAAGAAACCACGCAGGAACCGCGCAGGAACCACGCGGAACATGG

16375 ATGACGTGAGTTCCCATAGTAACACCAATAGGGACTTTCCATTGACGTCAATGGGAGGAG
      ||              ||| |  |  ||| | |||     |    |
15407 GACACTATCTGGAAATCCTGTTCAACGTCATCGTCTTCACTCTGCTGCTCGGCGTCATGG

16435 TATTTACGGTAAACTGCCCACTTGGCAGTACATCAAGTGTATCATATGCCAAGTACGCCC
      |  ||  ||   ||              ||||  |||  |  | |     |       |
15467 TCAGTATCGTCGCTTG..........GTACTTCACGTGAACCACCGTCGTCCCGGTTTA

16495 CCTATTGACGTCAATGACGGTAAATGGCCCGCCTGGCATTATGCCCAGTACATGACCTTA
      |    | || | | | || |           || || ||        |||
15518 AAAACCATCATCGACGGCCGTTATAAAGCCACCCGGACACGCGCCG.............

16555 CGGGACTTTCCTACT
      ||| |||| ||||||
15562 CGGCACTTGCCTACG
```

Figure 7d

Fast alignment of DNA sequences TB40E1 and FIX7

Upper line: TB40E1, from 1 to 6141
Lower line: FIX7 from 1486 to 7633

```
   1   TTTAAACCTGTGTGTTGTGTGATTGATTGGTACGTGGGGGGATCCGATTTCAAAGGGAGG
       |||||||||||||||||||||||||||||||  |||||||||||||||||||||||  ||
1486   TTTAAACCTGTGTGTTGTGTGATTGATTGGTATGTGGGGGGATCCGATTTCAAAGGGGGG

61   TAGTTATCGGGAGTTGATGTGTCATGGACGTAGTTTTGAGTGATTTTCCGGGAATACCGG
       ||  ||||||||| |||||||||||||||| ||||||||||||||||||||||||||||
1546   TACTTATCGGGAATTGATGTGTCATGGACGCAGTTTTGAGTGATTTTCCGGGAATACCGG

121   ATATTACGAATTACTAATAGTGACGTAGATAATAAAATTATAATGCGATTTATTTTTAGT
       ||||||||||||| |  |||| ||||     |||| |||||| |||  | |||||| ||
1606   ATATTACGAATTGATGTAAGTTACGTCAGTAATTAAGTCAGGATGCGGTTTATTTTCGGT

181   ...CTGTTTGGTCTTTTGATCG......CGTTGTGCTATAAGGTGGAAAGTGTGGAACTA
          ||| |||||||| | ||||      |||   ||| |||||  |||  |  |||||||
1666   TTGCTGATTGGTCTTGTAATCGTGTATACGTATTATTATGAAGTACAAAGTACGGAACTA

232   CGTTGTCGGTGTAGCAATGGTTCAAATCATCCCGTATTCGGCGTTTTTTGGGTCGGCTAT
       |||||  || |  ||||||| |  ||||  |||  ||| |||  ||| ||  |    |
1726   CGTTCCCCATGCACTAATGGTTTACACGATCCTTTATATGGCATATTTTATGCTGGTCGT

292   AAACCTCCAGATCCTACA...TGCGACAAAACGCAACACTTTTATTACCTCCCCGACAA
       | |||||  |||| |    |||| || || || |  | | || ||||||||    |
1786   GACCCTCCACGTCCTCCCGGTTGTGAAAAAGATCAATATTATTTAAAACCTCCCAAAGGT

349   ACACCTGTATGTTTGTCTCCTGATCATTATCTATCGAAATGGGTTGATGGCAAACGAAGT
       |  ||||| ||  || | ||||| | ||||| |||| |||| | |||| ||||  |||
1846   AAAGCTGTATGCTTAGGTCCACATCATCATTTATCAATATGGCTCAATGGTCAAAATAGT

409   AACTGGTGGCATAAAGTGTTTATAAAGAAAAACTCTGATAATGACCACATATAGAAGAC
       | |  ||||| ||||||| | ||| |  |  |||      |  ||  ||||||||||
1906   AGTTTATGGCACAAAGTGCTGGTGACGGGAAAAAACGGTAATGGACCACACGTAACTAAG

469   AAAAGTGACACCAATAGACACCCGCCTTGGCGACTATAATTTTTTATAAATTGTAAAACG
       ||| |||||    ||||   |         | |||||   |||||   ||| ||| |
1966   AAAGGTGACTTTCCTAGAGGTCGAAAAAATATA..ATGATTTAGCTTAATATGGATATAT

529   AGTTGGCAATATCACGTATATAGCGAAAAAGGTAATACAATGTGTTTTCGACATGGTTTT
       |     ||  |  | |      ||||| ||| |||||||||| ||||||  ||||| |
2024   ACGATAGCTGATAAATTTTCCACGAAAAAGGATAACGCAATATGTTTTTGATATGGTGCT

589   GACATGGTTACACCCATCCGATTCCAAATTCGCACATCAAAGTCTTATCGGTACGATACCT
       | ||||||||| |||| || ||  |||| || | |||| | ||| ||||||| | |||||
2084   AACATGGTTACATCATTGGATTATAAACTCGCATATCAAACTTTATCGGTACCACACCT

649   GTATTTGACCGCATATGTGTTATTTTCCACGTGTCCCCTATTCGTCTATCTCTTAGAATT
       ||  |||||||||||||||| |||  ||||||| |||   |||  ||| ||||||||||
2144   GTCATTGACCGCATATATGTTATTTACCGTGTGTTTCCCG...GTCCATCTTTTAGAATT

709   GGAAGATTACGACAAGCGCTGTCGTTGCAACAACCAAATTCTGTTGAATACCCTGCCAGT
       |||||||||||||  ||||||||||| |||||||||||||||||||||||||||| |||
2201   GGAAGATTACGACAGGCGTTGTCGTTGTAACAACCAAATTCTGTTGAATACCCTGCCGGT

769   CGGAACTCAACTGCTTAAGCCAATCGCAGCGAGCGAAAGCTGCAATCGTCAGGAAGTGCT
       |||||||||||||||||||||||||||||||||||||||||||||||||||||||||||
2261   CGGAACTCAACTGCTTAAGCCAATCGCAGCGAGCGAAAGCTGCAATCGTCAGGAAGTGCT

829   GGCTATTTTAAAGGACAAGGGCACCAAGTGTCTCAATCCTAACGCGCAAGCTGTGCGTCG
       |||||||||||||||||||||| ||  |||||||||||||||||||||||| ||||||||
2321   GGCTATTTTAAAGGACAAAGGAACCAAGTGTCTCAATCCTAACGCGCAAGCCGTGCGTCG

889   TCACATCAACCGGCTATTTTTTCGGTTAATCTTAGACGAAGAACAACGCATTTACGACGT
       ||||||||||||||||||||||||||||||||||||| |||||||||||||||||||||
2381   TCACATCAACCGGCTATTTTTTCGGTTAATCTTAGACGAGGAACAACGCATTTACGACGT

949   AGTGTCTACCAATATTGAGTTTGGTGCCTGGCCAGCCCCTACGGCCTACAAAGCCTTTCT
       |||||||| |||||||||||| ||||||||||||| |||||||||||||||||||||||
2441   AGTGTCTACCAATATTGAGTTCGGTGCCTGGCCAGTCCCTACGGCCTACAAAGCCTTTCT

1009   CTGGAAATACGCCAAGAAATTGAACTACCACCACTTCAGACTGCGCTGGTGATCATGTCC
       ||||||||||||||||||| || | || |||||| ||||| |||| |||||||||||||
2501   CTGGAAATACGCCAAGAAACTTAATTACCACTACTTTAGACTGCGTTGGTGATCATGTCC

1069   CTATTTTACCGTGCGGTAGCTCTGGGCACACTAAGCGCTCTGGTGTGTACAGCACTAGT
       |||||||||||||||||| |||||||  ||||||||||||||||||||||| |||||||
2561   CTATTTTACCGTGCGGTAGCCCTGGGCACGCTGAGCGCTCTGGTGTGTATAGCACTAGT

1129   ATCCTCGCAGAGATTAACGAAAATTCCTGCTCCTCATCTTCTGTGGACCACGAAGAGTGT
       |||||  ||||||||||||| |||||||||||||||||||||||||||||||||||| |
2621   ATCCTGGCAGAGATTAACGAAGAATCCTGCTCCTCATCTTCTGTGGACCACGAAGACTGC

1189   GAGGAACCGGACGAGATCGTTCGCGAAGAGCAAGACTATCGGGCTCTGCTGGCCTTTCC
       ||||||||||||||||||||||||||||||||||||||||||||||||||||||||||
2681   GAGGAACCGGACGAGATCGTTCGCGAAGAGCAAGACTATCGGGCTCTGCTGGCCTTTCC

1249   CTAGTGATTTGCGGTACGCTCCTCGTCACTTGTGTGATCTGAGACGTCATGCTGGTAGTG
       |||||||||||||||||||||||||||||||||||||||||||||||||||||||||| |
```

Figure 7d cont.

```
2741 CTAGTGATTTGCGGTACGCTCCTCGTCACTTGTGTGATCTGAGACGTCATGCTGGTAGCG

1309 TTTATGAGTCGGGCGGTGGCCGGCACGCCGCATTTCCTAACCCGCGCAGCATGTTGCGCT
     ||||||||||||||||||||||||||||||||||||||||||||||||||||||||||||
2801 TTTATGAGTCGGGCGGTGGCCGGCACGCCGCATTTCCTAACCCGCGCAGCATGTTGCGCT

1369 TGCTGTTCACGCTCGTCCTGCTGGCCCTCCACGGGCCGTCTGTCAATGCTAGCCGCGACT
     ||||||||||||||||| |||||||||||||||||||||||| |||||||||||||||||
2861 TGCTGTTCACGCTCGTCCTACTGGCCCTCCACGGGCCGTCTGTCAACGCTAGCCGCGACT

1429 ATGTGCATGTTCGGCTATTGAGCTACCGAGGCGACCCCCTGGTCTTCAAGCACACTTTTT
     ||||||||||||||||| |||||||||||||||||||||||||||||||||||||||||
2921 ATGTGCATGTTCGGCTACTGAGCTACCGAGGCGACCCCCTGGTCTTCAAGCACACTTTTT

1489 CGGGTGTGCGTCGACCCTTCACCGAGCTAGGCTGGGCTGCGTGTCGCGACTGGGACAGTA
     ||||||||||||||||||||||||||||||||||||||| ||||||||||||||||||||
2981 CGGGTGTGCGTCGACCCTTCACCGAGCTAGGCTGGGCTGTGTGTCGCGACTGGGACAGTA

1549 TGCATTGCACGCCCTTCTGGTCTACCGATCCGGAGCAGATGACCGACTCGGTGCGGCGTT
     |||||||||||| ||||||||||||||||| |||||||||||||||||||||||| ||||
3041 TGCATTGCACGCCTTTCTGGTCTACCGATCTGGAGCAGATGACCGACTCGGTGCGACGTT

1609 ACAGCACAGTGAGCCCCGGCAAGGAAGTGACGCTTCAGCTTCACGGGAACCAAACCGTAC
     ||||||| ||||||||||||||||||||||||||||||||||||||||||||||||||||
3101 ACAGCACGGTGAGCCCCGGCAAGGAAGTGACGCTTCAGCTTCACGGGAACCAAACCGTAC

1669 AGCCGTCGTTTCTAAGCTTTACGTGCCGCCTGCAGCTAGAACCCGTGGTGGAAAATGTTG
     ||||||||||||||||||||||||||||||||||||||| ||||||||||||||||||||
3161 AGCCGTCGTTTCTAAGCTTTACGTGCCGCCTGCAGCTAGAACCCGTGGTGGAAAATGTTG

1729 GCCTCTACGTGGCCTACGTGGTCAACGACGGTGAACGCCCACAGCAGTTTTTTACACCGC
     ||||||||||||||||||||||||||||||||||||||||||||||||||||||||||||
3221 GCCTCTACGTGGCCTACGTGGTCAACGACGGTGAACGCCCACAGCAGTTTTTTACACCGC

1789 AGGTAGACGTGGTACGCTTTGCTCTATATCTAGAGACGCTCTCCCGGATCGTGGAACCGT
     | ||||||||||||||||||||||||||||||||| ||||||||| |||||||||||||
3281 AAGTAGACGTGGTACGCTTTGCTCTATATCTAGAAACGCTCTCCCGGATCGTGGAACCGT

1849 TAGAATCAGGTCGCCTGGCAGTGGAATTTGATACGCCTGACCTAGCTCTGGCGCCCGATT
     ||||||||||||||||||||||||||||||||||||||||||||||||||||||||||||
3341 TAGAATCAGGTCGCCTGGCAGTGGAATTTGATACGCCTGACCTAGCTCTGGCGCCCGATT

1909 TAGTAAGCAGCCTCTTCGTGGCCGGACACGGCGAGACCGACTTTTACATGAACTGGACGC
     ||||||||||||||||||||||||||||||||||||||||||||||||||||||||||||
3401 TAGTAAGCAGCCTCTTCGTGGCCGGACACGGCGAGACCGACTTTTACATGAACTGGACGC

1969 TGCGTCGCAGTCAGACCCACTACCTGGAGGAGATGGCCTTACAGGTGGAGATTCTAAAGC
     ||||||||||||||||||||||||||||||||||||||||||| ||||||||||||||||
3461 TGCGTCGCAGTCAGACCCACTACCTGGAGGAGATGGCCTTACAGGTGGAGATTCTAAAGC

2029 CCCGCGGCGTACGTCACCGCGCTATTATCCACCATCCGAAGCTACAGCCGGGCGTTGGCC
     |||||||||||||||||||||||||||||||||||||| |||||||||||||||||||||
3521 CCCGCGGCGTACGTCACCGCGCTATTATCCACCATCCTAAGCTACAGCCGGGCGTTGGCC

2089 TGTGGATAGATTTCTGCGTGTACCGCTACAACGCGCGCCTGACCCGCGGCTACGTACGAT
     ||||||||||||||||||||||||||||||||||||||||||||||||||||||||||||
3581 TGTGGATAGATTTCTGCGTGTACCGCTACAACGCGCGCCTGACCCGCGGCTACGTACGAT

2149 ACACCCTGTCACCGAAAGCGCGCTTGCCCGCAAAAGCAGAGGGTTGGCTGGTGTCACTAG
     ||||||||||||||||||||||||||||||||||||||||||||||||||||||||||||
3641 ACACCCTGTCACCGAAAGCGCGCTTGCCCGCAAAAGCAGAGGGTTGGCTGGTGTCACTAG

2209 ACAGATTCATCGTGCAGTACCTCAACACATTGCTGATTACAATGATGGCGGCGATATGGG
     ||||||||||||||||||||||||||||||||||||||||||||||||||||||||||||
3701 ACAGATTCATCGTGCAGTACCTCAACACATTGCTGATTACAATGATGGCGGCGATATGGG

2269 CTCGCGTTTTGATAACCTACCTGGTGTCGCGGCGTCGGTAGAGGCTTGCGGAAACCACGT
     ||||||||||||||||||||||||||||||||||||||||||||||||||||||||||||
3761 CTCGCGTTTTGATAACCTACCTGGTGTCGCGGCGTCGGTAGAGGCTTGCGGAAACCACGT

2329 CCTCGTCACACGTCGTTCGCGGACATAGCAAGAAATCCACGTCGCCACGTCTCGAGAATG
     |||||||||||||||||||||||||||||||||| |||||||||||||||||||||||||
3821 CCTCGTCACACGTCGTTCGCGGACATAGCAAGAAATTCACGTCGCCACGTCTCGAGAATG

2389 CCGGCCCCGCGGGGTCCCCTTCGCGCAACATTCCTGGCCCTGGTCGCGTTCGGGTTGCTG
     |||||||||||||||||||||||||||||||||||||||||||||||||||||| ||||||
3881 CCGGCCCCGCGGGGTCCCCTTCGCGCAACATTCCTGGCCCTGGTCGCGTTCGGATTGCTG

2449 CTTCAGATAGACCTCAGCGACGCTACGAATGTGACCAGCAGCACAAAAGTCCCTACTAGC
     |||||||||||||||||||||||||| ||||||||| ||||||| |||||||||||||||
3941 TTTCAGATAGACCTCAGCGACGCTACAAATGTGACCAACAGCACAAAAGTCCCTACTAGC

2509 ACCAGCAGCAGAAATAGCGTCGACAATGCCACGAGTAGCGGACCCACGACCGGGATCAAC
     |||||||||||||||||||||||| ||||||||||||||||||||||||||||||||||||
4001 ACCAGCAGCAGAAATAGCGTCGACAACGCCACGAGTAGCGGACCCACGACCGGGATCAAC

2569 ATGACCACCACCCACGAGTCTTCCGTTCACAGCGTGCGCAATGACGAAATCATGAAAGTG
     |||||||||||||||||||||||||||||||| ||||||||||||||||||||||||||
4061 ATGACCACCACCCACGAGTCTTCCGTTCACAACGTGCGCAATGACAAAATCATGAAAGTG

2629 CTGGCTATCCTCTTCTACATCGTGACAGGCACCTCCATTTTCAGCTTCATAGCGGTACTG
     ||||||||||||||||||||||||||||||||||||||||||||||||||||||||||||
4121 CTGGCTATCCTCTTCTACATCGTGACAGGCACCTCCATTTTCAGCTTCATAGCGGTACTG

2689 ATCGCGGTAGTTTACTCCTCGTGTTGCAAGCACCCGGGCCGCTTTCGTTTCGCCGACGAA
     ||||||||||||||||||||||||||||||||||||||||||||||||||||||||||||
4181 ATCGCGGTAGTTTACTCCTCGTGTTGCAAGCACCCGGGCCGCTTTCGTTTCGCCGACGAA

2749 GAAGCCGTCAACCTGTTGGACGACACGGACGACAGTGGCGGTGGCAGCCCGTTTGGCAGC
```

Figure 7d cont.

```
4241 GAAGCCGTCAATCTGTTGGACGACACGGACGACAGTGGCGGCAGCAGCCCGTTTGGCAGC

2809 GGTTCCCGACGAGGTTCTCAGATCCCCGCCGGATTTTGTTCCTCGAGCCCTTATCAGCGG
4301 GGTTCCCGACGAGGTTCTCAGATCCCCGCCGGATTTTGTTCCTCGAGCCCTTATCAGCGG

2869 TTGGAAACTCGGGACTGGGACGAGGAGGAGGAGGCGTCCGCGGCCCGCGAGCGCATGAAA
4361 TTGGAAACTCGGGACTGGGACGAGGAGGAGGAGGCGTCCGCGGCCCGCGAGCGCATGAAA

2929 CATGATCCTGAGAACGTCATCTATTTCAGAAAGGATGGCAACTTGGACACGTCGTTCGTG
4421 CATGATCCTGAGAACGTCATCTATTTCAGAAAGGATGGCAACTTGGACACGTCGTTCGTG

2989 AATCCCAATTATGGGAGAGGCTCGCCTTTGACCATCGAATCTCACCTCTCGGACAATGAG
4481 AATCCCAATTATGGGAGAGGCTCGCCTTTGACCATCGAATCTCACCTCTCGGACAATGAG

3049 GAAGACCCCATCAGGTACTACGTCTCGGTGTACGATGAACTGACCGCCTCGGAAATGGAA
4541 GAGGACCCCATCAGGTACTACGTCTCGGTGTACGATGAACTGACCGCCTCGGAAATGGAA

3109 GAACCTTCGAACAGCACCAGCTGGCAGATTCCCAAACTAATGAAAGTTGCCATGCAACCC
4601 GAACCTTCCAACAGCACCAGCTGGCAGATTCCCAAACTAATGAAAGTTGCTACGCAACCC

3169 GTCTCGCTCAGAGATCCCGAGTACGACTAGGCTTTTTTTTTTTATCTTCGGTTCCAAC
4661 GTCTCGCTCAGAGATCCCGAGTACGACTAGGC..TTTTTTTTTGTCTTTCGGTTCCAAC

3229 TCTTTCCCCGCCCCATCACCTCGCCTATACTATGTGTATGATGTCTCATAATAAAGCTTT
4719 TCTTTCCCCGCCCCATCACCTCGCCTATACTATGTGTATGATGTCTCATAATAAAGCTCT

3289 CTTTCTCAGTCTGCAACATGCGGCTGTGTCGGGTGTGGCTGTCTGTTTGTCTGTGCGCCG
4779 CTTTCTCAGTCTGCAACATGCGGCTGTGTCGGGTGTGGCTGTCTGTTTGTCTGTGCGCCG

3349 TGGTGCTGGGTCAGTGCCAGCGGGAGACCGCAGAAAAAAACGATTATTACCGAGTACCGC
4839 TGGTGCTGGGTCAGTGCCAGCGGGAGACCGCAGAAAAAAACGATTATTACCGAGTACCGC

3409 ATTACTGGGACGCGTGCTCTCGCGCGCTGCCCGACCAAACCCGTTACAAGTATGTGGAAC
4899 ATTACTGGGACGCGTGCTCTCGCGCGCTGCCTGACCAAACCCGTTACAAGTATGTGGAAC

3469 AGCTCGTGGACCTCACGTTGAACTACCACTACGATGCGAGCCACGGCTTGGACAACTTTG
4959 AGCTCGTGGACCTCACGTTGAACTACCACTACGATGCGAGCCACGGCTTGGACAACTTTG

3529 ACGTGCTCAAGAGGTGAGGATACGCGCTAAAGGTGTATGACAACGGGAAGGTAAGGGCGA
5019 ACGTGCTCAAGAGGTGAGGGTACGCGCTAAAGGTGTATGACAACGGGAAGGTAAGGGCGA

3589 ACGGGTAACGGGCAGGTAACCGCATGGGGTGTGAAATGACGTTCGGAACCTGTGCTTGCA
5079 ACGGGTAACGGGTAGGTAACCGCATGGGGTGTGAAATGACGTTCGGAACCTGTGCTTGCA

3649 GAATCAACGTGACCGAGGTGTCGTTGCTCATCAGCGACTTTAGACGTCAGAACCGTCGCG
5139 GAATCAACGTGACCGAGGTGTCGTTGCTCATCAGCGACTTTAGACGTCAGAACCGTCGCG

3709 GCGGCACCAACAAAAGGACCACGTTCAACGCCGCCGGTTCGCTGGCGCCGCACGCCCGGA
5199 GCGGCACCAACAAAAGGACCACGTTCAACGCCGCCGGTTCGCTGGCGCCCTCACGCCCGGA

3769 GCCTCGAGTTCAGCGTGCGGCTCTTTGCCAACTAGCCTGCGTCACGGGAAATAATATGCT
5259 GCCTCGAGTTCAGCGTGCGGCTCTTTGCCAACTAGCCTGCGTCACGGGAAATAATATGCT

3829 ACGGCTTCTGCTTCGTCACCACTTTCACTGCCTGCTTCTGTGCGCGGTTTGGGCAACGCC
5319 ACGGCTTCTGCTTCGTCACCACTTTCACTGCCTGCTTCTGTGCGCGGTTTGGGCAACGCC

3889 CTGTCTGGCGTCTCCGTGGTCAACGCTAACGGCGAACCAGAATCCGTCCCCGCTATGGTC
5379 CTGTCTGGCGTCTCCGTGGTTCACGCTAACGGCGAACCAGAATCCGTCCCGGCCATGGTC

3949 TAAACTGACGTATTCCAAACCGCATGACGCGGCGACGTTTACTGTCCTTTTATCTATCC
5439 TAAACTGACGTATCCCAAACCGCATGACGCGGCGACGTTTTACTGTCCTTTTCTCTATCC

4009 CTCGCCCCCACGGTCCCCCTTGCAATTCTCGGGGTTCCAGCGGGTATTAACGGGTCCCGA
5499 CTCGCCCCCACGGTCCCCCTCGCAATTCCGGGGTTCCAGCGGGTATCAACGGGTCCCGA

4069 GTGTCGCAACGAGACCCTGTATCTGCTGTACAACCGGGAAGGCCAGACCTTGGTGGAGAG
5559 GTGTCGCAACGAGACCCTGTATCTGCTGTACAACCGGGAAGGCCAGACCTTGGTGGAGAG

4129 AAGCTCCACCTGGGTGAAAAAGGTGATCTGGTACCTGAGCGGTCGCAACCAGACCATCCT
5619 AAGCTCCACCTGGGTGAAAAAGGTGATCTGGTATCTGAGCGGTCGCAATCAGACCATCCT

4189 CCAACGGATGCCCCGAACGGCTTCAAAACCGAGCGACGGAAACGTGCAGATCAGCGTGGA
5679 CCAACGGATGCCCCGAACGGCTTCGAAACCGAGCGACGGAAACGTGCAGATCAGCGTGGA
```

Figure 7d cont.

```
4249  AGACGCCAAGATTTTTGGAGCGCACATGGTGCCCAAGCAGACCAAGCTGCTACGCTTCGT
      ||||||||||||||||||||||||||||||||||||||||||||||||||||||||||||
5739  AGACGCCAAGATTTTTGGAGCGCACATGGTGCCCAAGCAGACCAAGCTGCTACGCTTCGT

4309  CGTCAACGATGGCACACGTTATCAGATGTGTGTGATGAAGCTGGAGAGCTGGGCTCACGT
      |||||||||||||| |||||||||||||||||||||||||||||||||||||||| ||||
5799  CGTCAACGATGGCACGCGTTATCAGATGTGTGTGATGAAGCTGGAGAGCTGGGCCCACGT

4369  CTTCCGGGACTACAGCGTGTCTTTTCAGGTGCGATTGACGTTCACCGAGGCCAATAACCA
      ||||||||||||||||||||||||||||||||||||||||||||||||||||||||||||
5859  CTTCCGGGACTACAGCGTGTCTTTTCAGGTGCGATTGACGTTCACCGAGGCCAATAACCA

4429  GACTTACACCTTCTGCACCCATCCCAATCTCATCGTTTGAGCCCGTCGCGCGCGCAGGGA
      |||||||||||||||| |||||||||||||||||||||||||||||||||||||||||||
5919  GACTTACACCTTCTGTACCCATCCCAATCTCATCGTTTGAGCCCGTCGCGCGCGCAGGGA

4489  ATTTTGAAAACCGCGCGTCATGAGTCCCAAAAACCTGACGCCGTTCTTGACGGCGTTGTG
      |||||||||||||||||||||||||||||||| |||||||||||||||||| ||||||||
5979  ATTTTGAAAACCGCGCGTCATGAGTCCCAAAGACCTGACGCCGTTCTTGACGACGTTGTG

4549  GCTGTTATTGGATCACAGCCGCGTGCCGCGGGTACGCGCAGAAGAATGTTGCGAATTCAT
      |||| |||||| |||||||||||||||||||||| |||||||||||||||||||||||||
6039  GCTGCTATTGGGTCACAGCCGCGTGCCGCGGGTGCGCGCAGAAGAATGTTGCGAATTCAT

4609  AAACGTCAACCACCCGCCGGAACGCTGTTACGATTTCAAAATGTGCAATCGCTTCACCGT
      ||||||||||||||||||||||||||||||||||||||||||||||||||||||||||||
6099  AAACGTCAACCACCCGCCGGAACGCTGTTACGATTTCAAAATGTGCAATCGCTTCACCGT

4669  CGCGTACGTATTTTCATGATTGTCTGCGTTCTGTGGTGCGTCTGGATCTGTCTCTCGACG
      |||||||||||||| |||||||||||||||||||||||||||||||| ||||||||||||
6159  CGCGTACGTATTTTTATGATTGTCTGCGTTCTGTGGTGCGTCTGGATTTGTCTCTCGAAG

4729  TTTCTGATAGCCATGTTCCATCGACGATCCTCGGGAATGCCAGAGTAGATTTTCATGAAT
      ||||||||||||||||||||||||||||||||||||||||||||||||||||||||||||
6219  TTTCTGATAGCCATGTTCCATCGACGATCCTCGGGAATGCCAGAGTAGATTTTCATGAAT

4789  CCACAGGCTGCGGTGTCCGGACGGCGAAGTCTGCTACAGTCCCGAGAAAAACGGCTGAGA
      |||||||||||||||||||||||||||||||||||||||||||| |||||||||||||||
6279  CCACAGGCTGCGGTGTCCGGACGGCGAAGTCTGCTACAGTCCCGAG.AAAAACGGCTGAGA

4849  TTCGCGGGATCGTCACCACCATGACCCATTCATTGACACGCCAGGTCGTACACAACAAAC
      ||||||||||||||||||||||||||||||||||||||||||||||||||||||||||||
6338  TTCGCGGGATCGTCACCACCATGACCCATTCATTGACACGCCAGGTCGTACACAACAAAC

4909  TGACGAGCTGCAACTACAATCCGTAAGTCTCTTCCTCGAGGGCCTTACAGCCTATGGGAG
      |||||||||||||||||||||||||||||||||||||||||||||||||||||||||||
6398  TGACGAGCTGCAACTACAATCCGTAAGTCTCTTCCTCGAGGGCCTTACAGCCTATGGGAA

4969  AGTAAGACAGAGAGGGACAAAACATCATTAAAAAAAAAAGTCTAATTTCACGTTTTGTAC
      |||||||   |||||||||||||||||| ||||||||||||||||||||||||||||||
6458  AGTAAGAC..AGAGGGACAAAACATCATT.AAAAAAAAGTCTAATTTCACGTTTTGTAC

5029  CC......CCCTTCCGTGTTGTAGGTTATACCTCGAAGCTGACGGGCGAATACGCTGCGG
      ||      ||| |||||||||||||||||||||||||||||||||||||||||||||||
6515  CCCCCCCTTCCCCTCCGTGTTGTAGGTTATACCTCGAAGCTGACGGGCGAATACGCTGCGG

5083  CAAAGTGAACGACAAGGCGCAGTACCTGCTGGGCGCCGCTGGCAGCGTTCCCTATCGATG
      ||||||||||||||||||||||||||||||||||||||||||||||||||||||||||||
6575  CAAAGTGAACGACAAGGCGCAGTACCTGCTGGGCGCCGCTGGCAGCGTTCCCTATCGATG

5143  GATCAACCTGGAATACGACAAGATAACCCGGATCGTGGGCCTGGATCAGTACCTGGAGAG
      ||||||||||||||||||||||||||||||||||||||||||||||||||||||||||||
6635  GATCAACCTGGAATACGACAAGATAACCCGGATCGTGGGCCTGGATCAGTACCTGGAGAG

5203  CGTTAAGAAACACAAACGGCTGGATGTGTGCCGCGCTAAAATGGGCTATATGCTGCAGTG
      ||||||    |||||||||||||||||||||||||||||||||||||||||||||||||
6695  CGTTAAAAAACACAAACGGCTGGATGTGTGCCGCGCTAAAATGGGCTATATGCTGCAGTG

5263  AATAATAAAATGTGTGTTTGTCCGAAATACGCGTTTTGAGATTTCTGTCGCCGACTAAAT
      ||||||||||||||||||||||||||||||||||||||||||||||||||||||||||||
6755  AATAATAAAATGTGTGTTTGTCCGAAATACGCGTTTTGAGATTTCTGTCGCCGACTAAAT

5323  TCATGTCGCGCGATAGTGGTGTTTATCGCCGATAGAGATGGCGATATTGGAAAAATCAAT
      |||||||||||||||||||||||||||||||||||||||||||||||||||||||||| ||
6815  TCATGTCGCGCGATAGTGGTGTTTATCGCCGATAGAGATGGCGATATTGGAAAAATCGAT

5383  ATTTGAAAATATGGCATATTGAAAATGTCGCCGATGTGAGTTTCTGTGTAACTGATATCG
      ||||||||||||||||||||||||||||||||||||||||||||||||||||||||||||
6875  ATTTGAAAATATGGCATATTGAAAATGTCGCCGATGTGAGTTTCTGTGTAACTGATATCG

5443  CCATTTTTCCAAAAGTGATTTTTGGGCATACGCGATATCTGGCGATAGCGCTTATATCGT
      ||||||||||||||||||||||||||||||||||||||||||||||||||||||||||||
6935  CCATTTTTCCAAAAGTGATTTTTGGGCATACGCGATATCTGGCGATAGCGCTTATATCGT

5503  TTACGGGGATGGCGATAGACGACTTTGGCGACTTGGGCGATTCGGTGTGTCGCAAATAT
      ||||||||||||||||||||||||||||||||   ||||||||||| |||||||||||||
6995  TTACGGGGATGGCGATAGACGACTTTGGTGACTTGGGCGATTCTGTGTGTCGCAAATAT

5563  CGCAGTTTCGATATAGGTGACAGACGATATGAGGCCATATCGCCGATAGAGGCGACATCG
      |||||||||||||||||||||||||||||||||||| |||||||||||||||||||||| 
7055  CGCAGTTTCGATATAGGTGACAGACGATATGAGGCTATATCGCCGATAGAGGCGACATCA

5623  AGTTGGCACATGGCCAATGGATATCGATATATACATTGCATCAATATTGGCCATTAGCCA
      || |||||||||||||||||| |||||||  |||||||| ||||||||||||||||||||
7115  AGCTGGCACATGGCCAATGCATATCGATCTATACATTGAATCAATATTGGCCATTAGCCA

5683  TATTAGTCATTGGTTATATAGCGTAAATCAATATTGGCTAATGCCATTGCATACGTTGC
      |||| |||||||||||||||||||| ||||||||||||| |||||||||||||||||| 
7175  TATTATTCATTGGTTATATAGCATAAATCAATATTGGCTATTGGCCATTGCATACGTTGT
```

Figure 7d cont.

```
5743  ATCTATATCATAATGTGTACATTTATATTGGCTCATGTCCAATATGACCGCCATGTTGAC
      ||| |||||||||| ||||||||||||||||||||||||| || |||||||||||||||
7235  ATCCATATCATAATATGTACATTTATATTGGCTCATGTCCAACATTACCGCCATGTTGAC

5803  ATTGATTATTGACTAGTTATTAATAGTAATCAATTACGGGGTCATTAGTTCATAGCCCAT
      ||||||||||||||||||||||||||||||||||||||||| |||||||||||||||||
7295  ATTGATTATTGACTAGTTATTAATAGTAATCAATTACGGGTCATTAGTTCATAGCCCAT

5863  ATATGGAGTTCCGCGTTACATAACTTACGGTAAATGGCCCGCCTGGCTGACCGCCCAACG
      |||||||||||||||||||||||||||||||||||||||||||||||||||| ||||||
7355  ATATGGAGTTCCGCGTTACATAACTTACGGTAAATGGCCCGCCTGGCTGACCGCCCAACG

5923  ACCCCCGCCCATTGACGTCAATAATGACGTGGGTTCCCATAGTAACGCCAATAGGGACTT
      |||||||||||||||||||||||||||||||  |||||||||||||||||||||||||
7415  ACCCCCGCCCATTGACGTCAATAATGACGTATGTTCCCATAGTAACGCCAATAGGGACTT

5983  TCCATTGACGTCAATGGGAGGAGTATTTACGGTAAACTGCCCACTTGGCAGTACATCAAG
      ||||||||||||||||||  ||||||||||||||||||||||| ||||||||||||||
7475  TCCATTGACGTCAATGGGTGGAGTATTTACGGTAAACTGCCCACTTGGCAGTACATCAAG

6043  TGTATCATATGCCAAGTACGCCCCCTATTGACGTCAATGACGGTAAATGGCCCGCCTGGC
      ||||||||||||||||||||||||||||||||||||||||||||||||||||||||||
7535  TGTATCATATGCCAAGTACGCCCCCTATTGACGTCAATGACGGTAAATGGCCCGCCTGGC

6103  ATTATGCCCAGTACATGACCTTACGGGACTTTCCTACTT
      ||||||||||||||||||||| |||||||||||||||
7595  ATTATGCCCAGTACATGACCTTATGGGACTTTCCTACTG
```

Figure 7e

Fast alignment of DNA sequences TB40E1 and TB40E4

Upper line: TB40E1, from 1 to 6139
Lower line: TB40E4, from 1 to 6138

```
   1    TTTAAACCTGTGTGTTGTGTGATTGATTGGTACGTGGGGGGATCCGATTTCAAAGGGAGG
        ||||||||||||||||||||||||||||||||||||||||||||||||||||||||||||
   1    TTTAAACCTGTGTGTTGTGTGATTGATTGGTACGTGGGGGGATCCGATTTCAAAGGGAGG

61    TAGTTATCGGGAGTTGATGTGTCATGGACGTAGTTTTGAGTGATTTTCCGGGAATACCGG
        ||||||||||||||||||||||||||||||||||||||||||||||||||||||||||||
  61    TAGTTATCGGGAGTTGATGTGTCATGGACGTAGTTTTGAGTGATTTTCCGGGAATACCGG

121    ATATTACGAATTACTAATAGTGACGTAGATAATAAAATTATAATGCGATTTATTTTTAGT
        ||||||||||||||  ||||||||||||||||||||||||||||||||||||||||||||
 121    ATATTACGAATTACTGATAGTGACGTAGATAATAAAATTATAATGCGATTTATTTTTAGT

181    CTGTTTGGTCTTTTGATCGCGTTGTGCTATAAGGTGGAAAGTGTGGAACTACGTTGTCGG
        ||||||||||||||||||||||||||||||||||||||||||||||||||||||||||||
 181    CTGTTTGGTCTTTTGATCGCGTTGTGCTATAAGGTGGAAAGTGTGGAACTACGTTGTCGG

241    TGTAGCAATGGTTCAAATCATCCCGTATTCGGCGTTTTTGGGTCGGCTATAAACCTCCA
        ||||||||||||||||||||||||||||||||||||||||||||||||||||||||||||
 241    TGTAGCAATGGTTCAAATCATCCCGTATTCGGCGTTTTTGGGTCGGCTATAAACCTCCA

301    GATCCTACATGCGACAAAACGCAACACTTTTATTACCTCCCCGACAAACACCTGTATGT
        ||||||||||||||||||||||||||||||||||||||||||||||||||||||||||||
 301    GATCCTACATGCGACAAAACGCAACACTTTTATTACCTCCCCGACAAACACCTGTATGT

361    TTGTCTCCTGATCATTATCTATCGAAATGGGTTGATGGCAAACGAAGTAACTGGTGGCAT
        ||||||||||||||||||||||||||||||||||||||||||||||||||||||||||||
 361    TTGTCTCCTGATCATTATCTATCGAAATGGGTTGATGGCAAACGAAGTAACTGGTGGCAT

421    AAAGTGTTTATAAAGAAAAACTCTGATAATGGACCACATATAGAAGACAAAAGTGACACC
        ||||||||||||||||||||||||||||||||||||||||||||||||||||||||||||
 421    AAAGTGTTTATAAAGAAAAACTCTGATAATGGACCACATATAGAAGACAAAAGTGACACC

481    AATAGACACCCGCCTTGGCGACTATAATTTTTTATAAATTGTAAAACGAGTTGGCAATAT
        ||||||||||||||||||||||||||||||||||||||||||||||||||||||||||||
 481    AATAGACACCCGCCTTGGCGACTATAATTTTTTATAAATTGTAAAACGAGTTGGCAATAT

541    CACGTATATAGCGAAAAAGGTAATACAATGTGTTTTCGACATGGTTTTGACATGGTTACA
        ||||||||||||||||||||||||||||||||||||||||||||||||||||||||||||
 541    CACGTATATAGCGAAAAAGGTAATACAATGTGTTTTCGACATGGTTTTGACATGGTTACA

601    CCATCCGATTCCAAATTCGCACATCAAAGTCTTATCGGTACGATACCTGTATTTGACCGC
        ||||||||||||||||||||||||||||||||||||||||||||||||||||||||||||
 601    CCATCCGATTCCAAATTCGCACATCAAAGTCTTATCGGTACGATACCTGTATTTGACCGC

661    ATATGTGTTATTTTCCACGTGTCCCCTATTCGTCTATCTCTTAGAATTGGAAGATTACGA
        ||||||||||||||||||||||||||||||||||||||||||||||||||||||||||||
 661    ATATGTGTTATTTTCCACGTGTCCCCTATTCGTCTATCTCTTAGAATTGGAAGATTACGA

721    CAAGCGCTGTCGTTGCAACAACCAAATTCTGTTGAATACCCTGCCAGTCGGAACTCAACT
        ||||||||||||||||||||||||||||||||||||||||||||||||||||||||||||
 721    CAAGCGCTGTCGTTGCAACAACCAAATTCTGTTGAATACCCTGCCAGTCGGAACTCAACT

781    GCTTAAGCCAATCGCAGCGAGCGAAAGCTGCAATCGTCAGGAAGTGCTGGCTATTTTAAA
        ||||||||||||||||||||||||||||||||||||||||||||||||||||||||||||
 781    GCTTAAGCCAATCGCAGCGAGCGAAAGCTGCAATCGTCAGGAAGTGCTGGCTATTTTAAA

841    GGACAAGGGCACCAAGTGTCTCAATCCTAACGCGCAAGCTGTGCGTCGTCACATCAACCG
        ||||||||||||||||||||||||||||||||||||||||||||||||||||||||||||
 841    GGACAAGGGCACCAAGTGTCTCAATCCTAACGCGCAAGCTGTGCGTCGTCACATCAACCG

901    GCTATTTTTTCGGTTAATCTTAGACGAAGAACAACGCATTTACGACGTAGTGTCTACCAA
        ||||||||||||||||||||||||||||||||||||||||||||||||||||||||||||
 901    GCTATTTTTTCGGTTAATCTTAGACGAAGAACAACGCATTTACGACGTAGTGTCTACCAA

961    TATTGAGTTTGGTGCCTGGCCAGCCCCTACGGCCTACAAAGCCTTTCTCTGGAAATACGC
        ||||||||||||||||||||||||||||||||||||||||||||||||||||||||||||
 961    TATTGAGTTTGGTGCCTGGCCAGCCCCTACGGCCTACAAAGCCTTTCTCTGGAAATACGC

1021    CAAGAAATTGAACTACCACCACTTCAGACTGCGCTGGTGATCATGTCCCTATTTTACCGT
        ||||||||||||||||||||||||||||||||||||||||||||||||||||||||||||
1021    CAAGAAATTGAACTACCACCACTTCAGACTGCGCTGGTGATCATGTCCCTATTTTACCGT

1081    GCGGTAGCTCTGGGCACACTAAGCGCTCTGGTGTGGTACAGCACTAGTATCCTCGCAGAG
        ||||||||||||||||||||||||||||||||||||||||||||||||||||||||||||
1081    GCGGTAGCTCTGGGCACACTAAGCGCTCTGGTGTGGTACAGCACTAGTATCCTCGCAGAG

1141    ATTAACGAAAATTCCTGCTCCTCATCTTCTGTGGACCACGAAGAGTGTGAGGAACCGGAC
        ||||||||||||||||||||||||||||||||||||||||||||||||||||||||||||
1141    ATTAACGAAAATTCCTGCTCCTCATCTTCTGTGGACCACGAAGAGTGTGAGGAACCGGAC

1201    GAGATCGTTCGCGAAGAGCAAGACTATCGGGCTCTGCTGGCCTTTTCCCTAGTGATTTGC
        ||||||||||||||||||||||||||||||||||||||||||||||||||||||||||||
1201    GAGATCGTTCGCGAAGAGCAAGACTATCGGGCTCTGCTGGCCTTTTCCCTAGTGATTTGC

1261    GGTACGCTCCTCGTCACTTGTGTGATCTGAGACGTCATGCTGGTAGTGTTTATGAGTCGG
        ||||||||||||||||||||||||||||||||||||||||||||||||||||||||||||
1261    GGTACGCTCCTCGTCACTTGTGTGATCTGAGACGTCATGCTGGTAGTGTTTATGAGTCGG

1321    GCGGTGGCCGGCACGCCGCATTTCCTAACCCGCGCAGCATGTGCGCTTGCTGTTCACGC
        ||||||||||||||||||||||||||||||||||||||||||||||||||||||||||||
```

Figure 7e cont.

```
1321  GCGGTGGCCGGCACGCCGCATTTCCTAACCCGCGCAGCATGTTGCGCTTGCTGTTCACGC
1381  TCGTCCTGCTGGCCCTCCACGGGCCGTCTGTCAATGCTAGCCGCGACTATGTGCATGTTC
      ||||||||||||||||||||||||||||||||||||||||||||||||||||||||||||
1381  TCGTCCTGCTGGCCCTCCACGGGCCGTCTGTCAATGCTAGCCGCGACTATGTGCATGTTC

1441  GGCTATTGAGCTACCGAGGCGACCCCCTGGTCTTCAAGCACACTTTTTCGGGTGTGCGTC
      ||||||||||||||||||||||||||||||||||||||||||||||||||||||||||||
1441  GGCTATTGAGCTACCGAGGCGACCCCCTGGTCTTCAAGCACACTTTTTCGGGTGTGCGTC

1501  GACCCTTCACCGAGCTAGGCTGGGCTGCGTGTCGCGACTGGGACAGTATGCATTGCACGC
      ||||||||||||||||||||||||||||||||||||||||||||||||||||||||||||
1501  GACCCTTCACCGAGCTAGGCTGGGCTGCGTGTCGCGACTGGGACAGTATGCATTGCACGC

1561  CCTTCTGGTCTACCGATCCGGAGCAGATGACCGACTCGGTGCGGCGTTACAGCACAGTGA
      ||||||||||||||||||||||||||||||||||||||||||||||||||||||||||||
1561  CCTTCTGGTCTACCGATCCGGAGCAGATGACCGACTCGGTGCGGCGTTACAGCACAGTGA

1621  GCCCCGGCAAGGAAGTGACGCTTCAGCTTCACGGGAACCAAACCGTACAGCCGTCGTTTC
      ||||||||||||||||||||||||||||||||||||||||||||||||||||||||||||
1621  GCCCCGGCAAGGAAGTGACGCTTCAGCTTCACGGGAACCAAACCGTACAGCCGTCGTTTC

1681  TAAGCTTTACGTGCCGCCTGCAGCTAGAACCCGTGGTGGAAAATGTTGGCCTCTACGTGG
      ||||||||||||||||||||||||||||||||||||||||||||||||||||||||||||
1681  TAAGCTTTACGTGCCGCCTGCAGCTAGAACCCGTGGTGGAAAATGTTGGCCTCTACGTGG

1741  CCTACGTGGTCAACGACGGTGAACGCCCACAGCAGTTTTTTACACCGCAGGTAGACGTGG
      ||||||||||||||||||||||||||||||||||||||||||||||||||||||||||||
1741  CCTACGTGGTCAACGACGGTGAACGCCCACAGCAGTTTTTTACACCGCAGGTAGACGTGG

1801  TACGCTTTGCTCTATATCTAGAGACGCTCTCCCGGATCGTGGAACCGTTAGAATCAGGTC
      ||||||||||||||||||||||||||||||||||||||||||||||||||||||||||||
1801  TACGCTTTGCTCTATATCTAGAGACGCTCTCCCGGATCGTGGAACCGTTAGAATCAGGTC

1861  GCCTGGCAGTGGAATTTGATACGCCTGACCTAGCTCTGGCGCCCGATTTAGTAAGCAGCC
      ||||||||||||||||||||||||||||||||||||||||||||||||||||||||||||
1861  GCCTGGCAGTGGAATTTGATACGCCTGACCTAGCTCTGGCGCCCGATTTAGTAAGCAGCC

1921  TCTTCGTGGCCGGACACGGCGAGACCGACTTTTACATGAACTGGACGCTGCGTCGCAGTC
      ||||||||||||||||||||||||||||||||||||||||||||||||||||||||||||
1921  TCTTCGTGGCCGGACACGGCGAGACCGACTTTTACATGAACTGGACGCTGCGTCGCAGTC

1981  AGACCCACTACCTGGAGGAGATGGCCTTACAGGTGGAGATTCTAAAGCCCCGCGGCGTAC
      ||||||||||||||||||||||||||||||||||||||||||||||||||||||||||||
1981  AGACCCACTACCTGGAGGAGATGGCCTTACAGGTGGAGATTCTAAAGCCCCGCGGCGTAC

2041  GTCACCGCGCTATTATCCACCATCCGAAGCTACAGCCGGGCGTTGGCCTGTGGATAGATT
      ||||||||||||||||||||||||||||||||||||||||||||||||||||||||||||
2041  GTCACCGCGCTATTATCCACCATCCGAAGCTACAGCCGGGCGTTGGCCTGTGGATAGATT

2101  TCTGCGTGTACCGCTACAACGCGCGCCTGACCCGCGGCTACGTACGATACACCCTGTCAC
      ||||||||||||||||||||||||||||||||||||||||||||||||||||||||||||
2101  TCTGCGTGTACCGCTACAACGCGCGCCTGACCCGCGGCTACGTACGATACACCCTGTCAC

2161  CGAAAGCGCGCTTGCCCGCAAAAGCAGAGGGTTGGCTGGTGTCACTAGACAGATTCATCG
      ||||||||||||||||||||||||||||||||||||||||||||||||||||||||||||
2161  CGAAAGCGCGCTTGCCCGCAAAAGCAGAGGGTTGGCTGGTGTCACTAGACAGATTCATCG

2221  TGCAGTACCTCAACACATTGCTGATTACAATGATGGCGGCGATATGGGCTCGCGTTTTGA
      ||||||||||||||||||||||||||||||||||||||||||||||||||||||||||||
2221  TGCAGTACCTCAACACATTGCTGATTACAATGATGGCGGCGATATGGGCTCGCGTTTTGA

2281  TAACCTACCTGGTGTCGCGGCGTCGGTAGAGGCTTGCGGAAACCACGTCCTCGTCACACG
      ||||||||||||||||||||||||||||||||||||||||||||||||||||||||||||
2281  TAACCTACCTGGTGTCGCGGCGTCGGTAGAGGCTTGCGGAAACCACGTCCTCGTCACACG

2341  TCGTTCGCGGACATAGCAAGAAATCCACGTCGCCACGTCTCGAGAATGCCGGCCCCGCGG
      ||||||||||||||||||||||||||||||||||||||||||||||||||||||||||||
2341  TCGTTCGCGGACATAGCAAGAAATCCACGTCGCCACGTCTCGAGAATGCCGGCCCCGCGG

2401  GGTCCCCTTCGCGCAACATTCCTGGCCCTGGTCGCGTTCGGGTTGCTGCTTCAGATAGAC
      ||||||||||||||||||||||||||||||||||||||||||||||||||||||||||||
2401  GGTCCCCTTCGCGCAACATTCCTGGCCCTGGTCGCGTTCGGGTTGCTGCTTCAGATAGAC

2461  CTCAGCGACGCTACGAATGTGACCAGCAGCACAAAAGTCCCTACTAGCACCAGCAGCAGA
      ||||||||||||||||||||||||||||||||||||||||||||||||||||||||||||
2461  CTCAGCGACGCTACGAATGTGACCAGCAGCACAAAAGTCCCTACTAGCACCAGCAGCAGA

2521  AATAGCGTCGACAATGCCACGAGTAGCGGACCCACGACCGGGATCAACATGACCACCACC
      ||||||||||||||||||||||||||||||||||||||||||||||||||||||||||||
2521  AATAGCGTCGACAATGCCACGAGTAGCGGACCCACGACCGGGATCAACATGACCACCACC

2581  CACGAGTCTTCCGTTCACAGCGTGCGCAATGACGAAATCATGAAAGTGCTGGCTATCCTC
      ||||||||||||||||||||||||||||||||||||||||||||||||||||||||||||
2581  CACGAGTCTTCCGTTCACAGCGTGCGCAATGACGAAATCATGAAAGTGCTGGCTATCCTC

2641  TTCTACATCGTGACAGGCACCTCCATTTTCAGCTTCATAGCGGTACTGATCGCGGTAGTT
      ||||||||||||||||||||||||||||||||||||||||||||||||||||||||||||
2641  TTCTACATCGTGACAGGCACCTCCATTTTCAGCTTCATAGCGGTACTGATCGCGGTAGTT

2701  TACTCCTCGTGTTGCAAGCACCCGGGCCGCTTTCGTTTCGCCGACGAAGAAGCCGTCAAC
      ||||||||||||||||||||||||||||||||||||||||||||||||||||||||||||
2701  TACTCCTCGTGTTGCAAGCACCCGGGCCGCTTTCGTTTCGCCGACGAAGAAGCCGTCAAC

2761  CTGTTGGACGACACGGACGACAGTGGCGGTGGCAGCCCGTTTGGCAGCGGTTCCCGACGA
      ||||||||||||||||||||||||||||||||||||||||||||||||||||||||||||
2761  CTGTTGGACGACACGGACGACAGTGGCGGTGGCAGCCCGTTTGGCAGCGGTTCCCGACGA

2821  GGTTCTCAGATCCCCGCCGGATTTTGTTCCTCGAGCCCTTATCAGCGGTTGGAAACTCGG
      ||||||||||||||||||||||||||||||||||||||||||||||||||||||||||||
```

Figure 7e cont.

```
2821  GGTTCTCAGATCCCCGCCGGATTTTGTTCCTCGAGCCCTTATCAGCGGTTGGAAACTCGG

2881  GACTGGGACGAGGAGGAGGAGGCGTCCGCGGCCCGCGAGCGCATGAAACATGATCCTGAG
      ||||||||||||||||||||||||||||||||||||||||||||||||||||||||||||
2881  GACTGGGACGAGGAGGAGGAGGCGTCCGCGGCCCGCGAGCGCATGAAACATGATCCTGAG

2941  AACGTCATCTATTTCAGAAAGGATGGCAACTTGGACACGTCGTTCGTGAATCCCAATTAT
      ||||||||||||||||||||||||||||||||||||||||||||||||||||||||||||
2941  AACGTCATCTATTTCAGAAAGGATGGCAACTTGGACACGTCGTTCGTGAATCCCAATTAT

3001  GGGAGAGGCTCGCCTTTGACCATCGAATCTCACCTCTCGGACAATGAGGAAGACCCCATC
      ||||||||||||||||||||||||||||||||||||||||||||||||||||||||||||
3001  GGGAGAGGCTCGCCTTTGACCATCGAATCTCACCTCTCGGACAATGAGGAAGACCCCATC

3061  AGGTACTACGTCTCGGTGTACGATGAACTGACCGCCTCGGAAATGGAAGAACCTTCGAAC
      ||||||||||||||||||||||||||||||||||||||||||||||||||||||||||||
3061  AGGTACTACGTCTCGGTGTACGATGAACTGACCGCCTCGGAAATGGAAGAACCTTCGAAC

3121  AGCACCAGCTGGCAGATTCCCAAACTAATGAAAGTTGCCATGCAACCCGTCTCGCTCAGA
      ||||||||||||||||||||||||||||||||||||||||||||||||||||||||||||
3121  AGCACCAGCTGGCAGATTCCCAAACTAATGAAAGTTGCCATGCAACCCGTCTCGCTCAGA

3181  GATCCCGAGTACGACTAGGCTTTTTTTTTTTATCTTTCGGTTCCAACTCTTTCCCCGCC
      ||||||||||||||||||||||||||||||||||||||||||||||||||||||||||||
3181  GATCCCGAGTACGACTAGGCTTTTTTTTTTTATCTTTCGGTTCCAACTCTTTCCCCGCC

3241  CCATCACCTCGCCTATACTATGTGTATGATGTCTCATAATAAAGCTTTCTTTCTCAGTCT
      ||||||||||||||||||||||||||||||||||||||||||||||||||||||||||||
3241  CCATCACCTCGCCTATACTATGTGTATGATGTCTCATAATAAAGCTTTCTTTCTCAGTCT

3301  GCAACATGCGGCTGTGTCGGGTGTGGCTGTCTGTTTGTCTGTGCGCCGTGGTGCTGGGTC
      ||||||||||||||||||||||||||||||||||||||||||||||||||||||||||||
3301  GCAACATGCGGCTGTGTCGGGTGTGGCTGTCTGTTTGTCTGTGCGCCGTGGTGCTGGGTC

3361  AGTGCCAGCGGGAGACCGCAGAAAAAAACGATTATTACCGAGTACCGCATTACTGGGACG
      ||||||||||||||||||||||||||||||||||||||||||||||||||||||||||||
3361  AGTGCCAGCGGGAGACCGCAGAAAAAAACGATTATTACCGAGTACCGCATTACTGGGACG

3421  CGTGCTCTCGCGCGCTGCCCGACCAAACCCGTTACAAGTATGTGGAACAGCTCGTGGACC
      ||||||||||||||||||||||||||||||||||||||||||||||||||||||||||||
3421  CGTGCTCTCGCGCGCTGCCCGACCAAACCCGTTACAAGTATGTGGAACAGCTCGTGGACC

3481  TCACGTTGAACTACCACTACGATGCGAGCCACGGCTTGGACAACTTTGACGTGCTCAAGA
      ||||||||||||||||||||||||||||||||||||||||||||||||||||||||||||
3481  TCACGTTGAACTACCACTACGATGCGAGCCACGGCTTGGACAACTTTGACGTGCTCAAGA

3541  GGTGAGGATACGCGCTAAAGGTGTATGACAACGGGAAGGTAAGGGCGAACGGGTAACGGG
      ||||||||||||||||||||||||||||||||||||||||||||||||||||||||||||
3541  GGTGAGGATACGCGCTAAAGGTGTATGACAACGGGAAGGTAAGGGCGAACGGGTAACGGG

3601  CAGGTAACCGCATGGGGTGTGAAATGACGTTCGGAACCTGTGCTTGCAGAATCAACGTGA
      ||||||||||||||||||||||||||||||||||||||||||||||||||||||||||||
3601  CAGGTAACCGCATGGGGTGTGAAATGACGTTCGGAACCTGTGCTTGCAGAATCAACGTGA

3661  CCGAGGTGTCGTTGCTCATCAGCGACTTTAGACGTCAGAACCGTCGCGGCGGCACCAACA
      ||||||||||||||||||||||||||||||||||||||||||||||||||||||||||||
3661  CCGAGGTGTCGTTGCTCATCAGCGACTTTAGACGTCAGAACCGTCGCGGCGGCACCAACA

3721  AAAGGACCACGTTCAACGCCGCCGGTTCGCTGGCGCCGCACGCCCGGAGCCTCGAGTTCA
      ||||||||||||||||||||||||||||||||||||||||||||||||||||||||||||
3721  AAAGGACCACGTTCAACGCCGCCGGTTCGCTGGCGCCGCACGCCCGGAGCCTCGAGTTCA

3781  GCGTGCGGCTCTTTGCCAACTAGCCTGCGTCACGGGAAATAATATGCTACGGCTTCTGCT
      ||||||||||||||||||||||||||||||||||||||||||||||||||||||||||||
3781  GCGTGCGGCTCTTTGCCAACTAGCCTGCGTCACGGGAAATAATATGCTACGGCTTCTGCT

3841  TCGTCACCACTTTCACTGCCTGCTTCTGTGCGCGGTTTGGGCAACGCCCTGTCTGGCGTC
      ||||||||||||||||||||||||||||||||||||||||||||||||||||||||||||
3841  TCGTCACCACTTTCACTGCCTGCTTCTGTGCGCGGTTTGGGCAACGCCCTGTCTGGCGTC

3901  TCCGTGGTCAACGCTAACGGCGAACCAGAATCCGTCCCGCTATGGTCTAAACTGACGTA
      ||||||||||||||||||||||||||||||||||||||||||||||||||||||||||||
3901  TCCGTGGTCAACGCTAACGGCGAACCAGAATCCGTCCCGCTATGGTCTAAACTGACGTA

3961  TTCCAAACCGCATGACGCGGCGACGTTTTACTGTCCTTTTATCTATCCCTCGCCCCCACG
      ||||||||||||||||||||||||||||||||||||||||||||||||||||||||||||
3961  TTCCAAACCGCATGACGCGGCGACGTTTTACTGTCCTTTTATCTATCCCTCGCCCCCACG

4021  GTCCCCCTTGCAATTCTCGGGGTTCCAGCGGGTATTAACGGGTCCCGAGTGTCGCAACGA
      ||||||||||||||||||||||||||||||||||||||||||||||||||||||||||||
4021  GTCCCCCTTGCAATTCTCGGGGTTCCAGCGGGTATTAACGGGTCCCGAGTGTCGCAACGA

4081  GACCCTGTATCTGCTGTACAACCGGGAAGGCCAGACCTTGGTGGAGAGAAGCTCCACCTG
      ||||||||||||||||||||||||||||||||||||||||||||||||||||||||||||
4081  GACCCTGTATCTGCTGTACAACCGGGAAGGCCAGACCTTGGTGGAGAGAAGCTCCACCTG

4141  GGTGAAAAAGGTGATCTGGTACCTGAGCGGTCGCAACCAGACCATCCTCCAACGGATGCC
      ||||||||||||||||||||||||||||||||||||||||||||||||||||||||||||
4141  GGTGAAAAAGGTGATCTGGTACCTGAGCGGTCGCAACCAGACCATCCTCCAACGGATGCC

4201  CCGAACGGCTTCAAAACCGAGCGACGGAAACGTGCAGATCAGCGTGGAAGACGCCAAGAT
      ||||||||||||||||||||||||||||||||||||||||||||||||||||||||||||
4201  CCGAACGGCTTCAAAACCGAGCGACGGAAACGTGCAGATCAGCGTGGAAGACGCCAAGAT

4261  TTTTGGAGCGCACATGGTGCCCAAGCAGACCAAGCTGCTACGCTTCGTCGTCAACGATGG
      ||||||||||||||||||||||||||||||||||||||||||||||||||||||||||||
4261  TTTTGGAGCGCACATGGTGCCCAAGCAGACCAAGCTGCTACGCTTCGTCGTCAACGATGG

4321  CACACGTTATCAGATGTGTGTGATGAAGCTGGAGAGCTGGGCTCACGTCTTCCGGGACTA
      ||||||||||||||||||||||||||||||||||||||||||||||||||||||||||||
```

Figure 7e cont.

```
4321 CACACGTTATCAGATGTGTGTGATGAAGCTGGAGAGCTGGGCTCACGTCTTCCGGGACTA

4381 CAGCGTGTCTTTTCAGGTGCGATTGACGTTCACCGAGGCCAATAACCAGACTTACACCTT
     ||||||||||||||||||||||||||||||||||||||||||||||||||||||||||||
4381 CAGCGTGTCTTTTCAGGTGCGATTGACGTTCACCGAGGCCAATAACCAGACTTACACCTT

4441 CTGCACCCATCCCAATCTCATCGTTTGAGCCCGTCGCGCGCGCAGGGAATTTTGAAAACC
     ||||||||||||||||||||||||||||||||||||||||||||||||||||||||||||
4441 CTGCACCCATCCCAATCTCATCGTTTGAGCCCGTCGCGCGCGCAGGGAATTTTGAAAACC

4501 GCGCGTCATGAGTCCCAAAAACCTGACGCCGTTCTTGACGGCGTTGTGGCTGTTATTGGA
     ||||||||||||||||||||||||||||||||||||||||||||||||||||||||||||
4501 GCGCGTCATGAGTCCCAAAAACCTGACGCCGTTCTTGACGGCGTTGTGGCTGTTATTGGA

4561 TCACAGCCGCGTGCCGCGGGTACGCGCAGAAGAATGTTGCGAATTCATAAACGTCAACCA
     ||||||||||||||||||||||||||||||||||||||||||||||||||||||||||||
4561 TCACAGCCGCGTGCCGCGGGTACGCGCAGAAGAATGTTGCGAATTCATAAACGTCAACCA

4621 CCCGCCGGAACGCTGTTACGATTTCAAAATGTGCAATCGCTTCACCGTCGCGTACGTATT
     ||||||||||||||||||||||||||||||||||||||||||||||||||||||||||||
4621 CCCGCCGGAACGCTGTTACGATTTCAAAATGTGCAATCGCTTCACCGTCGCGTACGTATT

4681 TTCATGATTGTCTGCGTTCTGTGGTGCGTCTGGATCTGTCTCTCGACGTTTCTGATAGCC
     ||||||||||||||||||||||||||||||||||||||||||||||||||||||||||||
4681 TTCATGATTGTCTGCGTTCTGTGGTGCGTCTGGATCTGTCTCTCGACGTTTCTGATAGCC

4741 ATGTTCCATCGACGATCCTCGGGAATGCCAGAGTAGATTTTCATGAATCCACAGGCTGCG
     ||||||||||||||||||||||||||||||||||||||||||||||||||||||||||||
4741 ATGTTCCATCGACGATCCTCGGGAATGCCAGAGTAGATTTTCATGAATACACAGGCTGCG

4801 GTGTCCGGACGGCGAAGTCTGCTACAGTCCCGAGAAAAACGGCTGAGATTCGCGGGATCG
     ||||||||||||||||||||||||||||||| ||||||||||||||||||||||||||||
4801 GTGTCCGGACGGCGAAGTCTGCTACAGTCCCGAG.AAAACGGCTGAGATTCGCGGGATCG

4861 TCACCACCATGACCCATTCATTGACACGCCAGGTCGTACACAACAAACTGACGAGCTGCA
     ||||||||||||||||||||||||||||||||||||||||||||||||||||||||||||
4860 TCACCACCATGACCCATTCATTGACACGCCAGGTCGTACACAACAAACTGACGAGCTGCA

4921 ACTACAATCCGTAAGTCTCTTCCTCGAGGGCCTTACAGCCTATGGGAGAGTAAGACAGAG
     ||||||||||||||||||||||||||||||||||||||||||||||||||||||||||||
4920 ACTACAATCCGTAAGTCTCTTCCTCGAGGGCCTTACAGCCTATGGGAGAGTAAGACAGAG

4981 AGGGACAAAACATCATTAAAAAAAAAGTCTAATTTCACGTTTTGTACCCCCCTTCCGTG
     |||||||||||||||||||||||||||||||||||||||||||||||||||||||||||
4980 AGGGACAAAACATCATTAAAAAAAAAAGTCTAATTTCACGTTTTGTACCCCCCTTCCGTG

5041 TTGTAGGTTATACCTCGAAGCTGACGGGCGAATACGCTGCGGCAAAGTGAACGACAAGGC
     ||||||||||||||||||||||||||||||||||||||||||||||||||||||||||||
5040 TTGTAGGTTATACCTCGAAGCTGACGGGCGAATACGCTGCGGCAAAGTGAACGACAAGGC

5101 GCAGTACCTGCTGGGCGCCGCTGGCAGCGTTCCCTATCGATGGATCAACCTGGAATACGA
     ||||||||||||||||||||||||||||||||||||||||||||||||||||||||||||
5100 GCAGTACCTGCTGGGCGCCGCTGGCAGCGTTCCCTATCGATGGATCAACCTGGAATACGA

5161 CAAGATAACCCGGATCGTGGGCCTGGATCAGTACCTGGAGAGCGTTAAGAAACACAAACG
     ||||||||||||||||||||||||||||||||||||||||||||||||||||||||||||
5160 CAAGATAACCCGGATCGTGGGCCTGGATCAGTACCTGGAGAGCGTTAAGAAACACAAACG

5221 GCTGGATGTGTGCCGCGCTAAAATGGGCTATATGCTGCAGTGAATAATAAAATGTGTGTT
     ||||||||||||||||||||||||||||||||||||||||||||||||||||||||||||
5220 GCTGGATGTGTGCCGCGCTAAAATGGGCTATATGCTGCAGTGAATAATAAAATGTGTGTT

5281 TGTCCGAAATACGCGTTTTGAGATTTCTGTCGCCGACTAAATTCATGTCGCGCGATAGTG
     ||||||||||||||||||||||||||||||||||||||||||||||||||||||||||||
5280 TGTCCGAAATACGCGTTTTGAGATTTCTGTCGCCGACTAAATTCATGTCGCGCGATAGTG

5341 GTGTTTATCGCCGATAGAGATGGCGATATTGGAAAAATCAATATTTGAAAATATGGCATA
     ||||||||||||||||||||||||||||||||||||||||||||||||||||||||||||
5340 GTGTTTATCGCCGATAGAGATGGCGATATTGGAAAAATCAATATTTGAAAATATGGCATA

5401 TTGAAAATGTCGCCGATGTGAGTTTCTGTGTAACTGATATCGCCATTTTTCCAAAAGTGA
     ||||||||||||||||||||||||||||||||||||||||||||||||||||||||||||
5400 TTGAAAATGTCGCCGATGTGAGTTTCTGTGTAACTGATATCGCCATTTTTCCAAAAGTGA

5461 TTTTTGGGCATACGCGATATCTGGCGATAGCGCTTATATCGTTTACGGGGGATGGCGATA
     ||||||||||||||||||||||||||||||||||||||||||||||||||||||||||||
5460 TTTTTGGGCATACGCGATATCTGGCGATAGCGCTTATATCGTTTACGGGGGATGGCGATA

5521 GACGACTTTGGCGACTTGGGCGATTCGGTGTGTCGCAAATATCGCAGTTTCGATATAGGT
     ||||||||||||||||||||||||||||||||||||||||||||||||||||||||||||
5520 GACGACTTTGGCGACTTGGGCGATTCGGTGTGTCGCAAATATCGCAGTTTCGATATAGGT

5581 GACAGACGATATGAGGCCATATCGCCGATAGAGGCGACATCGAGTTGGCACATGGCCAAT
     ||||||||||||||||||||||||||||||||||||||||||||||||||||||||||||
5580 GACAGACGATATGAGGCCATATCGCCGATAGAGGCGACATCGAGTTGGCACATGGCCAAT

5641 GGATATCGATATATACATTGCATCAATATTGGCCATTAGCCATATTAGTCATTGGTTATA
     ||||||||||||||||||||||||||||||||||||||||||||||||||||||||||||
5640 GGATATCGATATATACATTGCATCAATATTGGCCATTAGCCATATTAGTCATTGGTTATA

5701 TAGCGTAAATCAATATTGGCTAATGGCCATTGCATACGTTGCATCTATATCATAATGTGT
     ||||||||||||||||||||||||||||||||||||||||||||||||||||||||||||
5700 TAGCGTAAATCAATATTGGCTAATGGCCATTGCATACGTTGCATCTATATCATAATGTGT

5761 ACATTTATATTGGCTCATGTCCAATATGACCGCCATGTTGACATTGATTATTGACTAGTT
     ||||||||||||||||||||||||||||||||||||||||||||||||||||||||||||
5760 ACATTTATATTGGCTCATGTCCAATATGACCGCCATGTTGACATTGATTATTGACTAGTT

5821 ATTAATAGTAATCAATTACGGGGTCATTAGTTCATAGCCCATATATGGAGTTCCGCGTTA
     ||||||||||||||||||||||||||||||||||||||||||||||||||||||||||||
```

Figure 7e cont.

```
5920  ATTAATAGTAATCAATTACGGGGTCATTAGTTCATAGCCCATATATGGAGTTCCGCGTTA

5881  CATAACTTACGGTAAATGGCCCGCGTGGCTGACCGCCCAACGACCCCCGCCCATTGACGT
      ||||||||||||||||||||||||||||||||||||||||||||||||||||||||||||
5880  CATAACTTACGGTAAATGGCCCGCCTGGCTGACCGCCCAACGACCCCCGCCCATTGACGT

5941  CAATAATGACGTGGGTTCCCATAGTAACGCCAATAGGGACTTTCCATTGACGTCAATGGG
      ||||||||||||||||||||||||||||||||||||||||||||||||||||||||||||
5940  CAATAATGACGTGGGTTCCCATAGTAACGCCAATAGGGACTTTCCATTGACGTCAATGGG

6001  AGGAGTATTTACGGTAAACTGCCCACTTGGCAGTACATCAAGTGTATCATATGCCAAGTA
      ||||||||||||||||||||||||||||||||||||||||||||||||||||||||||||
6000  AGGAGTATTTACGGTAAACTGCCCACTTGGCAGTACATCAAGTGTATCATATGCCAAGTA

6061  CGCCCCCTATTGACGTCAATGACGGTAAATGGCCCGCCTGGCATTATGCCCAGTACATGA
      ||||||||||||||||||||||||||||||||||||||||||||||||||||||||||||
6060  CGCCCCCTATTGACGTCAATGACGGTAAATGGCCCGCCTGGCATTATGCCCAGTACATGA

6121  CCTTACGGGACTTTCCTAC
      |||||||||||||||||||
6120  CCTTACGGGACTTTCCTAC
```

Figure 7f

Fast alignment of DNA sequences TB40E4 and FIX7

Upper line: TB40E4 from 9 to 6138
Lower line: FIX7 from 1498 to 7631

```
9     TGTGTGTTGTGTGATTGATTGGTACGTGGGGGGATCCGATTTCAAAGGGAGGTAGTTATC
      |||  ||  ||||||| |  ||    ||||| |  || || |||   |
1498  TGTTGTGTGATTGATTGGTATGTG...GGGGGATCCGATTTCAAAGGGGGGTACTTATCG

69    GGGAGTTGATGTGTCATGGACGTAGTTTTGAGTGATTTT.......CCGGGAATACCGG
      || | |              |   |||      |||           |||| || ||
1555  GGAATTGATGTGTCATGGACGCAGTTTTGAGTGATTTTCCGGGAATACCGGATATTACGA

121   ATATTACGAATTACTGATAGTGACGTAGATAATAAAATTATAATGCGATTTATTTTTAGT
      ||    |||| |   |||  ||  || |       | ||     | |  |   |
1615  ATTGATGTAAGTTACGTCAGTAATTAAGTCAGGATGCGGTTTATTTTCGGTTTGCTGATT

181   CTGTTTGGTCTTTTGATCGCGTTGTGCTATAAGGTGGAAAGTGTGGAACTACGTTGTCGG
               |||   |  |||   | ||| || ||||| |||||||||||| |
1675  GGTCTTGTAATCGTGTATACGTATTATTATGAAGTACAAAGTACGGAACTACGTTGCCCA

241   TGTAGCAATGGTTCAAATCATCCCGTATTCGGCGTTTTTGGGTCGGCTATAAACCTCCA
      ||  ||||||||| |  ||||  | |||  ||   |  |  ||   | |  |||||||
1735  TGCACTAATGGTTTACACGATCCTTTATATGGCATATTTTATGCTGGTCGTGACCCTCCA

301   GATCCTACA...TGCGACAAAACGCAACAGTTTTTATTACCTCCCCGACAAACACCTGTA
      |||| |     || || |||   ||| | ||||    |  |    ||| | |||| |||
1795  CGTCCTCCCGGTTGTGAAAAAGATCAATATTATTTAAAACCTCCCAAAGGTAAAGCTGTA

358   TGTTTGTCTCCTGATCATTATCTATCGAAATGGGTTGATGGCAAACGAAGTAACTGGTGG
      || ||   |||  ||||| || ||| |  |||| | ||||  ||   | |    |   ||
1855  TGCTTAGGTCCACATCATCATTTATCAATATGGCTCAATGGTCAAAATAGTAGTTTATGG

418   CATAAAGTGTTTATAAAGAAAAACTCTGATAATGGACCACATATAGAAGACAAAAGTGAC
      || ||||||  |  |  |||      |||     | |||| ||||||| | |||| |||
1915  CACAAAGTGCTGGTGACGGGAAAAAACGGTAATGGACCACACGTAACTAAGAAGGTGAC

478   ACCAATAGACACCCGCCTTGGCGACTATAATTTTTATAAATTGTAAAACGAGTTGGCAA
      ||||         |     | ||| |       |||  |||  || | | |
1975  TTTCCTAGAGGTCGAAAAAATATA..ATGATTTAGCTTAATATGGATATATACGATAGCT

538   TATCACGTATATAGCGAAAAAGGTAATACAATGTGTTTTCGACATGGTTTTGACATGGTT
      ||   |   |    ||||   ||  |   |||| |||||  |||| | ||| ||||||||
2033  GATAAATTTTCCACGAAAAAAGGATAACGCAATATGTTTTGATATGGTGCTAACATGGTT

598   ACACCATCCGATTCCAAATTCGCACATCAAAGTCTTATCGGTACGATACCTGTATTTGAC
      ||| || ||||| ||||||| |||||| |||| ||||||||||  |  | ||| | ||||
2093  ACATCATTCGATTATAAACTCGCATATCAAACTTTTATCGGTACCACACCTGTCATTGAC

658   CGCATATGTGTTATTTTCCACGTGTCCCCTATTCGTCTATCTCTTAGAATTGGAAGATTA
      ||||||| ||||||||| |||| |||||    ||   || |  || ||||||||||||||
2153  CGCATATATGTTATTTACCGTGTGTTTCCCG..GTCCATCTTTTAGAATTGGAAGATTA

718   CGACAAGCGCTGTCGTTGCAACAACCAAATTCTGTTGAATACCCTGCCAGTCGGAACTCA
      ||||  |||| ||||||| |||||||||||||||||||||||||||||| |||||||||
2210  CGACAGGCGTTGTCGTTGTAACAACCAAATTCTGTTGAATACCCTGCCGGTCGGAACTCA

778   ACTGCTTAAGCCAATCGCAGCGAGCGAAAGCTGCAATCGTCAGGAAGTGCTGGCTATTTT
      |||||||||||||||||||||||||||||||||||||||||||||||||| |||||||||
2270  ACTGCTTAAGCCAATCGCAGCGAGCGAAAGCTGCAATCGTCAGGAAGTGCTGGCTATTTT

838   AAAGGACAAGGGCACCCAAGTGTCTCAATCCTAACGCGCAAGCTGTGCGTCGTCACATCAA
      |||||||| || ||||||||||||||||  |||||||||||| ||| |||||||||||||
2330  AAAGGACAAAGGAACCAAGTGTCTCAATCCTAACGCGCAAGCCGTGCGTCGTCACATCAA

898   CCGGCTATTTTTCGGTTAATCTTAGACGAAGAACAACGCATTTACGACGTAGTGTCTAC
      |||||||||||||||| ||||||||||| |||||||||||||||||||||||||||||
2390  CCGGCTATTTTTCGGTTAATCTTAGACGAGGAACAACGCATTTACGACGTAGTGTCTAC

958   CAATATTGAGTTTGGTGCCTGGCCAGCCCCTACGGCCTACAAAGCCTTTCTCTGGAAATA
      |||||||||  || |||||||||||||| |||||||||||||||||||||||||||||
2450  CAATATTGAGTTCGGTGCCTGGCCAGTCCCTACGGCCTACAAAGCCTTTCTCTGGAAATA

1018  CGCCAAGAAATTGAACTACCACCACTTCAGACTGCGCTGGTGATCATGTCCCTATTTTAC
      ||||||||||  || |||| || || |||||||||| |||||||||||| |||||||||
2510  CGCCAAGAAACTTAATTACCACTACTTTAGACTGCGTTGGTGATCATGTCCCTATTTTAC

1078  CGTGCGGTAGCTCTGGGCACACTAAGCGCTCTGGTGTGTGGTACAGCACTAGTATCCTGCA
      |||||||||||| |||||||||| |||| |||||||| |||||||||||||||||||| |
2570  CGTGCGGTAGCCCTGGGCACGCTGAGCGCTCTGGTGTGGTATAGCACTAGTATCCTGGCA

1138  GAGATTAACGAAAATTCCTGCTCCTCATCTTCTGTGGACCACGAAGAGTGTGAGGAACCG
      |||||||||| | ||||||||||||||||||||||||||||||||| || ||||||||||
2630  GAGATTAACGAAGAATCCTGCTCCTCATCTTCTGTGGACCACGAAGACTGCGAGGAACCG
```

Figure 7f cont.

```
1198  GACGAGATCGTTCGCGAAGAGCAAGACTATCGGGCTCTGCTGGCCTTTTCCCTAGTGATT
      ||||||||||||||||||||||||||||||||||||||||||||||||||||||||||||
2690  GACGAGATCGTTCGCGAAGAGCAAGACTATCGGGCTCTGCTGGCCTTTTCCCTAGTGATT

1258  TGCGGTACGCTCCTCGTCACTTGTGTGATCTGAGACGTCATGCTGGTAGTGTTTATGAGT
      ||||||||||||||||||||||||||||||||||||||||||||||||||  ||||||||
2750  TGCGGTACGCTCCTCGTCACTTGTGTGATCTGAGACGTCATGCTGGTAGCGTTTATGAGT

1318  CGGGCGGTGGCCGGCACGCCGCATTTCCTAACCCGCGCAGCATGTTGCGCTTGCTGTTCA
      ||||||||||||||||||||||||||||||||||||||||||||||||||||||||||||
2810  CGGGCGGTGGCCGGCACGCCGCATTTCCTAACCCGCGCAGCATGTTGCGCTTGCTGTTCA

1378  CGCTCGTCCTGCTGGCCCTCCACGGGCCGTCTGTCAATGCTAGCCGCGACTATGTGCATG
      ||||||||||  |||||||||||||||||||||||||||  |||||||||||||||||||
2870  CGCTCGTCCTACTGGCCCTCCACGGGCCGTCTGTCAACGCTAGCCGCGACTATGTGCATG

1438  TTCGGCTATTGAGCTACCGAGGCGACCCCCTGGTCTTCAAGCACACTTTTCGGGTGTGC
      |||||||| |||||||||||||||||||||||||||||||||||||||||||||||||||
2930  TTCGGCTACTGAGCTACCGAGGCGACCCCCTGGTCTTCAAGCACACTTTTCGGGTGTGC

1498  GTCGACCCTTCACCGAGCTAGGCTGGGCTGCGTGTCGGACTGGGACAGTATGCATTGCA
      ||||||||||||||||||||||||||||||||||||  ||||||||||||||||||||||
2990  GTCGACCCTTCACCGAGCTAGGCTGGGCTGTGTGTCGCGACTGGGACAGTATGCATTGCA

1558  CGCCCTTCTGGTCTACCGATCCGGAGCAGATGACCGACTCGGTGCGGCGTTACAGCACAG
      ||||  |||||||||||||||  |||||||||||||||||||||||||||||||||||| |
3050  CGCCTTTCTGGTCTACCGATCTGGAGCAGATGACCGACTCGGTGCGACGTTACAGCACGG

1618  TGAGCCCCGGCAAGGAAGTGACGCTTCAGCTTCACGGGAACCAAACCGTACAGCCGTCGT
      ||||||||||||||||||||||||||||||||||||||||||||||||||||||||||||
3110  TGAGCCCCGGCAAGGAAGTGACGCTTCAGCTTCACGGGAACCAAACCGTACAGCCGTCGT

1678  TTCTAAGCTTTACGTGCCGCCTGCAGCTAGAACCCGTGGTGGAAAATGTTGGCCTCTACG
      ||||||||||||||||||||||||||||||||||||||||||||||||||||||||||||
3170  TTCTAAGCTTTACGTGCCGCCTGCAGCTAGAACCCGTGGTGGAAAATGTTGGCCTCTACG

1738  TGGCCTACGTGGTCAACGACGGTGAACGCCCACAGCAGTTTTTTACACCGCAGGTAGACG
      |||||||||||||||||||||||||||||||||||||||||||||||||||||  ||||||
3230  TGGCCTACGTGGTCAACGACGGTGAACGCCCACAGCAGTTTTTTACACCGCAAGTAGACG

1798  TGGTACGCTTTGCTCTATATCTAGAGACGCTCTCCCGGATCGTGGAACCGTTAGAATCAG
      |||||||||||||||||||||||||  ||||||||||||||||||||||||||||||||||
3290  TGGTACGCTTTGCTCTATATCTAGAAACGCTCTCCCGGATCGTGGAACCGTTAGAATCAG

1858  GTCGCCTGGCAGTGGAATTTGATACGCCTGACCTAGCTCTGGCGCCCGATTTAGTAAGCA
      ||||||||||||||||||||||||||||||||||||||||||||||||||||||||||||
3350  GTCGCCTGGCAGTGGAATTTGATACGCCTGACCTAGCTCTGGCGCCCGATTTAGTAAGCA

1918  GCCTCTTCGTGGCCGGACACGGCGAGACCGACTTTTACATGAACTGGACGCTGCGTCGCA
      ||||||||||||||||||||||||||||||||||||||||||||||||||||||||||||
3410  GCCTCTTCGTGGCCGGACACGGCGAGACCGACTTTTACATGAACTGGACGCTGCGTCGCA

1978  GTCAGACCCACTACCTGGAGGAGATGGCCTTACAGGTGGAGATTCTAAAGCCCGCGGCG
      ||||||||||||||||||||||||||||||||||||||||||||||||||||||||||||
3470  GTCAGACCCACTACCTGGAGGAGATGGCCTTACAGGTGGAGATTCTAAAGCCCCGCGGCG

2038  TACGTCACCGCGCTATTATCCACCATCCGAAGCTACAGCCGGGCGTTGGCCTGTGGATAG
      |||||||||||||||||||||||||||||  |||||||||||||||||||||||||||||
3530  TACGTCACCGCGCTATTATCCACCATCCTAAGCTACAGCCGGGCGTTGGCCTGTGGATAG

2098  ATTTCTGCGTGTACCGCTACAACGCGCGCCTGACCCGCGGCTACGTACGATACACCCTGT
      ||||||||||||||||||||||||||||||||||||||||||||||||||||||||||||
3590  ATTTCTGCGTGTACCGCTACAACGCGCGCCTGACCCGCGGCTACGTACGATACACCCTGT

2158  CACCGAAAGCGCGCTTGCCCGGCAAAAGCAGAGGGTTGGCTGGTGTCACTAGACAGATTCA
      ||||||||||||||||||||||||||||||||||||||||||||||||||||||||||||
3650  CACCGAAAGCGCGCTTGCCCGGCAAAAGCAGAGGGTTGGCTGGTGTCACTAGACAGATTCA

2218  TCGTGCAGTACCTCAACACATTGCTGATTACAATGATGGCGGCGATATGGGCTCGCGTTT
      ||||||||||||||||||||||||||||||||||||||||||||||||||||||||||||
3710  TCGTGCAGTACCTCAACACATTGCTGATTACAATGATGGCGGCGATATGGGCTCGCGTTT

2278  TGATAACCTACCTGGTGTCGCGGCGTCGGTAGAGGCTTGCGGAAACCACGTCCTCGTCAC
      ||||||||||||||||||||||||||||||||||||||||||||||||||||||||||||
3770  TGATAACCTACCTGGTGTCGCGGCGTCGGTAGAGGCTTGCGGAAACCACGTCCTCGTCAC

2338  ACGTCGTTCGCGGACATAGCAAGAAATCCACGTCGCCACGTCTCGAGAATGCCGGCCCCG
      ||||||||||||||||||||||||   |||||||||||||||||||||||||||||||||
3830  ACGTCGTTCGCGGACATAGCAAGAAATTCACGTCGCCACGTCTCGAGAATGCCGGCCCCG

2398  CGGGGTCCCCTTCGCGCAACATTCCTGGCCCTGGTCGCGTTCGGGTTGCTGCTTCAGATA
      ||||||||||||||||||||||||||||||||||||||||||  ||||| ||||||||||
3890  CGGGGTCCCCTTCGCGCAACATTCCTGGCCCTGGTCGCGTTCGGATTGCTGTTTCAGATA

2458  GACCTCAGCGACGCTACGAATGTGACCAGCAGCACAAAAGTCCCTACTAGCACCAGCAGC
      |||||||||||||||||||||||||||||||||||||  |||||||||||||||||||||
3950  GACCTCAGCGACGCTACGAAATGTGACCAACAGCACAAACGTCCCTACTAGCACCAGCAGC

2518  AGAAATAGCGTCGACAATGCCACGAGTAGCGGACCCACGACCGGGATCAACATGACCACC
      ||||||||||||||||   ||||||||||||||||||||||||||||||||||||||||||
4010  AGAAATAGCGTCGACAACGCCACGAGTAGCGGACCCACGACCGGGATCAACATGACCACC

2578  ACCCACGAGTCTTCCGTTCACAGCGTGCGCAATGACGAAATCATGAAAGTGCTGGCTATC
```

Figure 7f cont.

```
4070 ACCCACGAGTCTTCCGTTCACAACGTGCGCAATGACAAAATCATGAAAGTGCTGGCTATC

2638 CTCTTCTACATCGTGACAGGCACCTCCATTTTCAGCTTCATAGCGGTACTGATCGCGGTA
4130 CTCTTCTACATCGTGACAGGCACCTCCATTTTCAGCTTCATAGCGGTACTCATCGCGGTA

2698 GTTTACTCCTCGTGTTGCAAGCACCCGGGCCGCTTTCGTTTCGCCGACGAAGAAGCCGTC
4190 GTTTACTCCTCGTGTTGCAAGCACCCGGGCCGCTTTCGTTTCGCCGACGAAGAAGCCGTC

2758 AACCTGTTGGACGACACGGACGACAGTGGCGGTGGCAGCCCGTTTGGCAGCGGTTCCCGA
4250 AATCTGTTGGACGACACGGACGACAGTGGCGGCAGCAGCCCGTTTGGCAGCGGTTCCCGA

2818 CGAGGTTCTCAGATCCCCGCCGGATTTTGTTCCTCGAGCCCTTATCAGCGGTTGGAAACT
4310 CGAGGTTCTCAGATCCCCGCCGGATTTTGTTCCTCGAGCCCTTATCAGCGGTTGGAAACT

2878 CGGGACTGGGACGAGGAGGAGGAGGCGTCCGCGGCCCGCGAGCGCATGAAACATGATCCT
4370 CGGGACTGGGACGAGGAGGAGGAGGCGTCCGCGGCCCGCGAGCGCATGAAACATGATCCT

2938 GAGAACGTCATCTATTTCAGAAAGGATGGCAACTTGGACACGTCGTTCGTGAATCCCAAT
4430 GAGAACGTCATCTATTTCAGAAAGGATGGCAACTTGGACACGTCGTTCGTGAATCCCAAT

2998 TATGGGAGAGGCTCGCCTTTGACCATCGAATCTCACCTCTCGGACAATGAGGAAGACCCC
4490 TATGGGAGAGGCTCGCCTTTGACCATCGAATCTCACCTCTCGGACAATGAGGAGGACCCC

3058 ATCAGGTACTACGTCTCGGTGTACGATGAACTGACCGCCTCGGAAATGGAAGAACCTTCG
4550 ATCAGGTACTACGTCTCGGTGTACGATGAACTGACCGCCTCGGAAATGGAAGAACCTTCC

3118 AACAGCACCAGCTGGCAGATTCCCAAACTAATGAAAGTTGCCATGCAACCCGTCTCGCTC
4610 AACAGCACCAGCTGGCAGATTCCCAAACTAATGAAAGTTGCTACGCAACCCGTCTCGCTC

3178 AGAGATCCCGAGTACGACTAGGCTTTTTTTTTTTTATCTTTCGGTTCCAACTCTTTCCCC
4670 AGAGATCCCGAGTACGACTAGGC..TTTTTTTTTGTCTTTCGGTTCCAACTCTTTCCCC

3238 GCCCCATCACCTCGCCTATACTATGTGTATGATGTCTCATAATAAAGCTTTCTTTCTCAG
4728 GCCCCATCACCTCGCCTATACTATGTGTATGATGTCTCATAATAAAGCTCTCTTTCTCAG

3298 TCTGCAACATGCGGCTGTGTCGGGTGTGGCTGTCTGTTTGTCTGTGCGCCGTGGTGCTGG
4788 TCTGCAACATGCGGCTGTGTCGGGTGTGGCTGTCTGTTTGTCTGTGCGCCGTGGTGCTGG

3358 GTCAGTGCCAGCGGGAGACCGCAGAAAAAAACGATTATTACCGAGTACCGCATTACTGGG
4848 GTCAGTGCCAGCGGGAGACCGCAGAAAAAAACGATTATTACCGAGTACCGCATTACTGGG

3418 ACGCGTGCTCTCGCGCGCTGCCCGACCAAACCCGTTACAAGTATGTGGAACAGCTCGTGG
4908 ACGCGTGCTCTCGCGCGCTGCCTGACCAAACCCGTTACAAGTATGTGGAACAGCTCGTGG

3478 ACCTCACGTTGAACTACCACTACGATGCGAGCCACGGCTTGGACAACTTTGACGTGCTCA
4968 ACCTCACGTTGAACTACCACTACGATGCGAGCCACGGCTTGGACAACTTTGACGTGCTCA

3538 AGAGGTGAGGATACGCGCTAAAGGTGTATGACAACGGGAAGGTAAGGGCGAACGGGTAAC
5028 AGAGGTGAGGGTACGCGCTAAAGGTGTATGACAACGGGAAGGTAAGGGCGAACGGGTAAC

3598 GGGCAGGTAACCGCATGGGGTGTGAAATGACGTTCGGAACCTGTGCTTGCAGAATCAACG
5088 GGGTAGGTAACCGCATGGGGTGTGAAATGACGTTCGGAACCTGTGCTTGCAGAATCAACG

3658 TGACCGAGGTGTCGTTGCTCATCAGCGACTTTAGACGTCAGAACCGTCGCGGCGGCACCA
5148 TGACCGAGGTGTCGTTGCTCATCAGCGACTTTAGACGTCAGAACCGTCGCGGCGGCACCA

3718 ACAAAAGGACCACGTTCAACGCCGCCGGTTCGCTGGCGCCGCACGCCGGAGCCTCGAGT
5208 ACAAAAGGACCACGTTCAACGCCGCCGGTTCGCTGGCGCCTCACGCCCGGAGCCTCGAGT

3778 TCAGCGTGCGGCTCTTTGCCAACTAGCCTGCGTCACGGGAAATAATATGCTACGGCTTCT
5268 TCAGCGTGCGGCTCTTTGCCAACTAGCCTGCGTCACGGGAAATAATATGCTACGGCTTCT

3838 GCTTCGTCACCACTTTCACTGCCTGCTTCTGTGCGCGGTTTGGGCAACGCCCTGTCTGGC
5328 GCTTCGTCACCACTTTCACTGCCTGCTTCTGTGCGCGGTTTGGGCAACGCCCTGTCTGGC

3898 GTCTCCGTGGTCAACGCTAACGGCGAACCAGAATCCGTCCCCGCTATGGTCTAAACTGAC
5388 GTCTCCGTGGTTCACGCTAACGGCGAACCAGAATCCGTCCCCGCCATGGTCTAAACTGAC

3958 GTATTCCAAACCGCATGACGCGGCGACGTTTTACTGTCCTTTTATCTATCCCTCGCCCCC
```

Figure 7f cont.

```
5448  GTATCCCAAACCGCATGACGCGGCGACGTTTTACTGTCCTTTTCTCTATCCCTCGCCCCC

4018  ACGGTCCCCCTTGCAATTCTCGGGGTTCCAGCGGGTATTAACGGGTCCCGAGTGTCGCAA
      |||||||||||  ||||||| |||||||||||||||||||  |||||||||||||||||
5508  ACGGTCCCCCTCGCAATTCCCGGGGTTCCAGCGGGTATCAACGGGTCCCGAGTGTCGCAA

4078  CGAGACCCTGTATCTGCTGTACAACCGGGAAGGCCAGACCTTGGTGGAGAGAAGCTCCAC
      ||||||||||||||||||||||||||||||||||||||||||||||||||||||||||||
5568  CGAGACCCTGTATCTGCTGTACAACCGGGAAGGCCAGACCTTGGTGGAGAGAAGCTCCAC

4138  CTGGGTGAAAAAGGTGATCTGGTACCTGAGCGGTCGCAACCAGACCATCCTCCAACGGAT
      ||||||||||||||||||||||||  |||||||||||||||  ||||||||||||||||
5628  CTGGGTGAAAAAGGTGATCTGGTATCTGAGCGGTCGCAATCAGACCATCCTCCAACGGAT

4198  GCCCCGAACGGCTTCAAAACCGAGCGACGGAAACGTGCAGATCAGCGTGGAAGACGCCAA
      ||||||||||||| ||||||||||||||||||||||||||||||||||||||||||||||
5688  GCCCCGAACGGCTTCGAAACCGAGCGACGGAAACGTGCAGATCAGCGTGGAAGACGCCAA

4258  GATTTTTGGAGCGCACATGGTGCCCAAGCAGACCAAGCTGCTACGCTTCGTCGTCAACGA
      ||||||||||||||||||||||||||||||||||||||||||||||||||||||||||||
5748  GATTTTTGGAGCGCACATGGTGCCCAAGCAGACCAAGCTGCTACGCTTCGTCGTCAACGA

4318  TGGCACACGTTATCAGATGTGTGTGATGAAGCTGGAGAGCTGGGCTCACGTCTTCCGGGA
      ||||||  |||||||||||||||||||||||||||||||||||||  |||||||||||||
5808  TGGCACGCGTTATCAGATGTGTGTGATGAAGCTGGAGAGCTGGGCCCACGTCTTCCGGGA

4378  CTACAGCGTGTCTTTTCAGGTGCGATTGACGTTCACCGAGGCCAATAACCAGACTTACAC
      ||||||||||||||||||||||||||||||||||||||||||||||||||||||||||||
5868  CTACAGCGTGTCTTTTCAGGTGCGATTGACGTTCACCGAGGCCAATAACCAGACTTACAC

4438  GTTCTGCACCCATCCCAATCTCATCGTTTGAGCCCGTCGCGCGCGCAGGGAATTTTGAAA
      ||||||  ||||||||||||||||||||| ||||||||||||||||||||||||||||||
5928  CTTCTGTACCCATCCCAATCTCATCGTTTGAGCCCGTCGCGCGCGCAGGGAATTTTGAAA

4498  ACCGCGCGTCATGAGTCCCAAAAACCTGACGCCGTTCTTGACGGCGTTGTGGCTGTTATT
      |||||||||||||||||||||||| |||||||||||||| |||| |||||||||| ||||
5988  ACCGCGCGTCATGAGTCCCAAAGACCTGACGCCGTTCTTTGACGACGTTGTGGCTGCTATT

4558  GGATCACAGCCGCGTGCCGCGGGTACGCGCAGAAGAATGTTGCGAATTCATAAACGTCAA
      ||  ||||||||||||||||||||| |||||||||||||||||||||||||||||||||
6048  GGGTCACAGCCGCGTGCCGCGGGTGCGCGCAGAAGAATGTTGCGAATTCATAAACGTCAA

4618  CCACCCGCCGGAACGCTGTTACGATTTCAAAATGTGCAATCGCTTCACCGTCGCGTACGT
      ||||||||||||||||||||||||||||||||||||||||||||||||||||||||||||
6108  CCACCCGCCGGAACGCTGTTACGATTTCAAAATGTGCAATCGCTTCACCGTCGCGTACGT

4678  ATTTTCATGATTGTCTGCGTTCTGTGGTGCGTCTGGATCTGTCTCTCGACGTTTCTGATA
      |||||  ||||||||||||||||||||||||||||||||  ||||||||||||||||||
6168  ATTTTTATGATTGTCTGCGTTCTGTGGTGCGTCTGGATTTGTCTCTCGACGTTTCTGATA

4738  GCCATGTTCCATCGACGATCCTCGGGAATGCCAGAGTAGATTTTCATGAATACACAGGCT
      |||||||||||||||||||||||||||||||||||||||||||||||||||| |||||||
6228  GCCATGTTCCATCGACGATCCTCGGGAATGCCAGAGTAGATTTTCATGAATCCACAGGCT

4798  GCGGTGTCCGGACGGCGAAGTCTGCTACAGTCCCGAGAAAACGGCTGAGATTCGCGGGAT
      ||||||||||||||||||||||||||||||||||||||||||||||||||||||||||||
6288  GCGGTGTCCGGACGGCGAAGTCTGCTACAGTCCCGAGAAAACGGCTGAGATTCGCGGGAT

4858  CGTCACCACCATGACCCATTCATTGACACGCCAGGTCGTACACAACAAACTGACGAGCTG
      ||||||||||||||||||||||||||||||||||||||||||||||||||||||||||||
6348  CGTCACCACCATGACCCATTCATTGACACGCCAGGTCGTACACAACAAACTGACGAGCTG

4918  CAACTACAATCCGTAAGTCTCTTCCTCGAGGGCCTTACAGCCTATGGGAGAGTAAGACAG
      ||||||||||||||||||||||||||||||||||||||||||||||||||   |||||
6408  CAACTACAATCCGTAAGTCTCTTCCTCGAGGGCCTTACAGCCTATGGGAAAGTAAGAC..

4978  AGAGGGACAAAACATCATTAAAAAAAAAAAGTCTAATTTCACGTTTTGTACCC......CC
      |||||||||||||||||| |||||||||||||||||||||||||||||||||||      ||
6466  AGAGGGACAAAACATCATT.AAAAAAAAAGTCTAATTTCACGTTTTGTACCCCCCCTTCC

5032  CTTCCGTGTTGTAGGTTATACGTCGAAGCTGACGGGCGAATACGCTGCCGCAAAGTGAAC
      |  ||||||||||||||||||||||||||||||||||||||||||||||||||||||||
6525  CCTCCGTGTTGTAGGTTATACGTCGAAGCTGACGGGCGAATACGCTGCGGCAAAGTGAAC

5092  GACAAGGCGCAGTACCTGCTGGGCGCCGCTGGCAGCGTTCCCTATCGATGGATCAACCTG
      ||||||||||||||||||||||||||||||||||||||||||||||||||||||||||||
6585  GACAAGGCGCAGTACCTGCTGGGCGCCGCTGGCAGCGTTCCCTATCGATGGATCAACCTG

5152  GAATACGACAAGATAACCCGGATCGTGGGCCTGGATCAGTACCTGGAGAGCGTTAAGAAA
      ||||||||||||||||||||||||||||||||||||||||||||||||||||||||| |||
6645  GAATACGACAAGATAACCCGGATCGTGGGCCTGGATCAGTACCTGGAGAGCGTTAAAAAA

5212  CACAAACGGCTGGATGTGTGCCGCGCTAAAATGGGCTATATGCTGCAGTGAATAATAAAA
      ||||||||||||||||||||||||||||||||||||||||||||||||||||||||||||
6705  CACAAACGGCTGGATGTGTGCCGCGCTAAAATGGGCTATATGCTGCAGTGAATAATAAAA

5272  TGTGTGTTTGTCCGAAATACGCGTTTTGAGATTTCTGTCGCCGACTAAATTCATGTCGCG
      ||||||||||||||||||||||||||||||||||||||||||||||||||||||||||||
6765  TGTGTGTTTGTCCGAAATACGCGTTTTGAGATTTCTGTCGCCGACTAAATTCATGTCGCG

5332  CGATAGTGGTGTTTATCGCCGATAGAGATGGCGATATTGGAAAAATCAATATTTGAAAAT
      |||||||||||| ||||||||||||||||||||||||||||||||| |||| ||||||||
6825  CGATAGTGGTGTTTATCGCCGATAGAGATGGCGATATTGGAAAAATCGATATTTGAAAAT
```

Figure 7f cont.

```
5392 ATGGCATATTGAAAATGTCGCCGATGTGAGTTTCTGTGTAACTGATATCGCCATTTTTCC
     ||||||||||||||||||||||||||||||||||||||||||||||||||||||||||||
6885 ATGGCATATTGAAAATGTCGCCGATGTGAGTTTCTGTGTAACTGATATCGCCATTTTTCC

5452 AAAAGTGATTTTTGGGCATACGCGATATCTGGCGATAGCGCTTATATCGTTTACGGGGGA
     ||||||||||||||||||||||||||||||||||||||||||||||||||||||||||||
6945 AAAAGTGATTTTTGGGCATACGCGATATCTGGCGATAGCGCTTATATCGTTTACGGGGGA

5512 TGGCGATAGACGACTTTGGCGACTTGGGCGATTCGGTGTGTCGCAAATATCGCAGTTTCG
     ||||||||||||||| |||||||||||||| |||||||||||||||||||||||||||||
7005 TGGCGATAGACGACTTTGGTGACTTGGGCGATTCTGTGTGTCGCAAATATCGCAGTTTCG

5572 ATATAGGTGACAGACGATATGAGGCCATATCGCCGATAGAGGCGACATCGAGTTGGCACA
     |||||||||||||||||||||||| |||||||||||||||||||||||| || |||||||
7065 ATATAGGTGACAGACGATATGAGGCTATATCGCCGATAGAGGCGACATCAAGCTGGCACA

5632 TGGCCAATGGATATCGATATATACATTGCATCAATATTGGCCATTAGCCATATTAGTCAT
     |||||||| ||||||| ||||||||| |||||||||||||||||||||||||||| ||||
7125 TGGCCAATGCATATCGATCTATACATTGAATCAATATTGGCCATTAGCCATATTATTCAT

5692 TGGTTATATAGCGTAAATCAATATTGGCTAATGGCCATTGCATACGTTGCATCTATATCA
     |||||||||||| |||||||||||||||| |||||||||||||||||||| ||| |||||
7185 TGGTTATATAGCATAAATCAATATTGGCTATTGGCCATTGCATACGTTGTATCCATATCA

5752 TAATGTGTACATTTATATTGGCTCATGTCCAATATGACCGCCATGTTGACATTGATTATT
     |||| |||||||||||||||||||||||||| || |||||||||||||||||||||||||
7245 TAATATGTACATTTATATTGGCTCATGTCCAACATTACCGCCATGTTGACATTGATTATT

5812 GACTAGTTATTAATAGTAATCAATTACGGGGTCATTAGTTCATAGCCCATATATGGAGTT
     ||||||||||||||||||||||||||||||||||||||||||||||||||||||||||||
7305 GACTAGTTATTAATAGTAATCAATTACGGGGTCATTAGTTCATAGCCCATATATGGAGTT

5872 CCGCGTTACATAACTTACGGTAAATGGCCCGCCTGGCTGACCGCCCAACGACCCCCGCCC
     ||||||||||||||||||||||||||||||||||||||||||||||||||||||||||||
7365 CCGCGTTACATAACTTACGGTAAATGGCCCGCCTGGCTGACCGCCCAACGACCCCCGCCC

5932 ATTGACGTCAATAATGACGTGGGTTCCCATAGTAACGCCAATAGGGACTTTCCATTGACG
     ||||||||||||||||||| ||||||||||||||||||||||||||||||||||||||||
7425 ATTGACGTCAATAATGACGTATGTTCCCATAGTAACGCCAATAGGGACTTTCCATTGACG

5992 TCAATGGGAGGAGTATTTACGGTAAACTGCCCACTTGGCAGTACATCAAGTGTATCATAT
     |||||||| |||||||||||||||| ||||||||||||||| ||||||||||||||||||
7485 TCAATGGGTGGAGTATTTACGGTAAACTGCCCACTTGGCAGTACATCAAGTGTATCATAT

6052 GCCAAGTACGCCCCGTATTGACGTCAATGACGGTAAATGGCCCGCCTGGCATTATGCCCA
     ||||||||||||||||||||||||||||||||||||||||||||||||||||||||||||
7545 GCCAAGTACGCCCCCTATTGACGTCAATGACGGTAAATGGCCCGCCTGGCATTATGCCCA

6112 GTACATGACCTTACGGGACTTTCCTAC
     |||||||||||| ||||||||||||||
7605 GTACATGACCTTATGGGACTTTCCTAC
```

Figure 7g

Fast alignment of DNA sequences PAN1 and TB40E4

Upper line: PAN1, from 10288 to 16568
Lower line: TB40E4, from 1 to 6138

```
Seqpan1:SEQTB40E4 identity= 92%
10288 TTTAAACCTGTGTGTTGTGTGATTGATTGGTACGTGGGGGGATCCGATTTCAAAGGGAGG
      ||||||||||||||||||||||||||||||||||||||||||||||||||||||||||||
1     TTTAAACCTGTGTGTTGTGTGATTGATTGGTACGTGGGGGGATCCGATTTCAAAGGGAGG 10348 TAGTTATCGGGAATTGATGTGTCATGGACGCAGTTTTGAGTGATTTTCCGGGAATACCGG
      ||||||||||| ||||||||||||||||||| |||||||||||| |||||||||||||||
61    TAGTTATCGGGAGTTGATGTGTCATGGACGTAGTTTTGAGTGATTTTCCGGGAATACCGG 10408 ATATTACGAATTACTGTAAGTGACGTCAGAAATTAAATTATAATGCGTTTAATTTTTGGT
      |||||||||||||||| ||||||||| ||||||  ||| ||||||||||| ||  || ||
121   ATATTACGAATTACTGATAGTGACGTAGATAATAAAATTATAATGCGATTTATTTTTAGT 10468 TTATTGATCATTTTTATTGTTACAGATACA....TGTAACGGCGGTTTTGGCACTGAAGG
      | ||    |||| ||| |              || ||| |   |     | | || | ||
181   CTGTTTGGTCTTTTGATCGCGTTGTGCTATAAGGTGGAAAGTGTGGAACTACGTTGTCGG 10524 TAATGGTCGTTGTGCATGCATAGGGTATCATCGACTTTTAGGACAATTGCCTCGTGGAAC
      |  |     | |  |||    |  |||| |       |||| ||
241   TGTAGCAATGGTTCAAATCATCCCGTATTCGGCGTTTTTGGGTCGGCTATAAACCTCCA 10584 TTTCTGGTTAGGACATTTACCACCAGGCTCACATTGCCCAAAGGGACAAGTCATGATAAA
       ||       |            | |||  |    ||| ||        |  ||  | ||
301   GATCCTACATGCGACAAAACGCAACACTTTTTATTACCTCCCCGACAAACACCTGTATGT 10644 GATAGGCCAAGGACCGATCGTCTGTTTATCCGATTATCATCCTTTATCTAAGTGGATGTA
                  ||               |||
361   TTGTCTCCTGATCATTATC.........................................

10704 TGGAAATCATAAATCTGGTTCGGAAACATGGCTTCAGATAAAAATGGAAGGTCCAAGAAA

380   ............................................................

10764 TGCTACAGTAGTACAAAGATCGAATACTCGTCCATAAAGATAACGAATGTTCATAAGAAT
                                            || ||||       | |
380   .................................TATCGAAATGGGTTGATGGC

10824 TGTACTTTTATATGTATGTAAGTTTATGGATCTTTATGTTTGTCATCATATACATTAGTA
          ||    ||   || ||  |                             ||   || |  |
400   AAACGAAGTAACTGGTGGCATAAAGTGTTTATAAAGAAAAACTCTGATAATGGACCACAT

10884 GTAACATACTCAACACACTATGCGTGTACAATTTGTTTTATAGATCCGTAGTGTACAATA
       || | || || ||              |                ||   |       |  | |||  ||
460   ATAGAAGACAAAAGTGACACCAATAGACACCCGCCTTGGCGACTATAATTTTTTATAAAT

10944 AATATTACGATAAATTTTTAACGTCGGATACATTTACGATACTAAACGTACTGTATTGCA
      ||   ||||                ||    |                           ||| ||||  |  |  ||
520   TGTAAAACGAGTTGGCAATATC.......ACGTATATAGCGAAAAAGGTAATACAATGTG

11004 TTTTTTGCACGATGTTGACATC...ACATTGCTGGGCTACAAGATGGCATAACAAA...T
       ||||       || |  | ||||||||               |||                  |   |  ||| | ||| | ||||              |
573   TTTTCGACATGGTTTTGACATGGTTACACCATCCGATTCCAAATTCGCACATCAAAGTCT

11058 TATTGGTACGATACCTGTCATTGACTATATATATGTTACTGACCGTATGTCCCCTAGCCG
       || |||||||||||||||  |||||     ||||| ||||| |  ||     ||||||||||    ||
633   TATCGGTACGATACCTGTATTTGACCGCATATGTGTTATTTTCCACGTGTCCCCTATTCG

11118 TCCATCTTTTAGAATTGGAAGATTACGACAGACGCTGTCGTTGTAACAATCAAATTCTGT
      ||  |||||       |||||||||||||||||||||||  ||||||||||||||  |||||  ||||||||||||||
693   TCTATCTCTTAGAATTGGAAGATTACGACAAGCGCTGTCGTTGCAACAACCAAATTCTGT

11178 TGAATACTCTGCCAATCGGAACTGAATTGCTTAAGCCAATCGCGGCGAGCGAAAGCTGCA
      |||||||  ||||||   ||||||||| ||  ||||||||||||||||||||||  |||||||||||||||||||||||
753   TGAATACCCTGCCAGTCGGAACTCAACTGCTTAAGCCAATCGCAGCGAGCGAAAGCTGCA

11238 ATCGTCAGGAAGTGCTGGCTATTTTAAAGGACAAGGGCACCAAGTGTCTCAATCCTAACG
      ||||||||||||||||||||||||||||||||||||||||||||||||||||||||||||
813   ATCGTCAGGAAGTGCTGGCTATTTTAAAGGACAAGGGCACCAAGTGTCTCAATCCTAACG

11298 CGCAAGCCGTGCGTCGTCACATCAACCGGCTATTTTTCGGTTAATATTAGACGAGGAAC
      ||||||| |||||||||||||||||||||||||||||||||||||| ||| |||||| |||||
873   CGCAAGCTGTGCGTCGTCACATCAACCGGCTATTTTTCGGTTAATCTTAGACGAAGAAC

11358 AACGCATTTACGACGTAGTGTCTACCAATATTGAGTTCGGTGCCTGGCCAGTCCCTACGG
      |||||||||||||||||||||||||||||||||||| ||||||||||||| ||||||||
933   AACGCATTTACGACGTAGTGTCTACCAATATTGAGTTTGGTGCCTGGCCAGCCCCTACGG

11418 CCTACAAAGCCTTTCTCTGGAAATACGGCCAAGAAACTGAACTACCACCAGTTCAGATTGC
      |||||||| |||||||||||||||||| ||||||| |||||||||||||||| |||||   |||
993   CCTACAAAGCCTTTCTCTGGAAATACGCCAAGAAATTGAACTACCACCACTTCAGACTGC

11478 GCTGGTGATCATGTCCCTATTTTACCGTGCGGTAGCCCTGGGCACACTGAGCGCTCTGGT
      ||||||||||||||||||| ||||||||||||||||| |||||||||||||  |||||||||
1053  GCTGGTGATCATGTCCCTATTTTACCGTGCGGTAGCCTGGGCACACTAAGCGCTCTGGT

11538 GTGGTACAGCACTAGTATCCTGGCAGAAATTAACGAAGAATCCTGCTCCTCATCTTCTGT
      |||||||||||||||||| ||||| |||||| ||||| |||| ||||||||||||||||||||
1113  GTGGTACAGCACTAGTATCCTCGCAGAGATTAACGAAAATTCCTGCTCCTCATCTTCTGT
```

Figure 7g cont.

```
11598 GGACCACGAAGACTGCGAGGAACCGGACGAGATCGTTCGCGAAGAGCAAGACTATCGGGC
      ||||||||||| || |||||||||||||||||||||||||||||||||||||||||||||
 1173 GGACCACGAAGAGTGTGAGGAACCGGACGAGATCGTTCGCGAAGAGCAAGACTATCGGGC

11658 TCTGCTGGCCTTTTCCCTAGTGATTTGCGGTACGCTCCTCGTCACTTGTGTGATCTGAGA
      ||||||||||||||||||||||||||||'|||||||||||||||||||||||||||||||
 1233 TCTGCTGGCCTTTTCCCTAGTGATTTGCGGTACGCTCCTCGTCACTTGTGTGATCTGAGA

11718 CGTCATGCTGGTAGCGTTTATGAGTCGGGCGGTGGCCGACACGCCGCATTTCCTAACCCG
      |||||||||||||||·|||||||||||||||||||||||| |||||||||||||||||||
 1293 CGTCATGCTGGTAGTGTTTATGAGTCGGGCGGTGGCCGGCACGCCGCATTTCCTAACCCG

11778 CGCAGCATGTTGCGCTTGCTGTTCACGCTCGTCCTGCTGGCCCTCCACGGGCAGTCTGTC
      |||||||||||||||||||||||||||||||||||||||||||||||||| |||||||
 1353 CGCAGCATGTTGCGCTTGCTGTTCACGCTCGTCCTGCTGGCCCTCCACGGGCCGTCTGTC

11838 GGCGCTAGCCGCGACTATGTGCATGTTCGGCTACTGAGCTACCGAGGCGACCCCCTGGTC
      |||||||||||||||||||||||||||| |||||||||||||||||||||||||||||||
 1413 AATGCTAGCCGCGACTATGTGCATGTTCGGCTATTGAGCTACCGAGGCGACCCCCTGGTC

11898 TTCAAGCACACTTTCTCGGGTGTGCGTCGACCCTTCACCGAGCTAGGCTGGGCTGCGTGT
      ||||||||||||||| |||||||||||||||||||||||||||||||||||||||||||
 1473 TTCAAGCACACTTTTTCGGGTGTGCGTCGACCCTTCACCGAGCTAGGCTGGGCTGCGTGT

11958 CGCGACTGGGACAGTATGCATTGCACACCCTTCTGGTCTACCGATCTGGAGCAGATGACC
      |||||||||||||||||||||||||| ||||||||||||||||||| |||||||||||||
 1533 CGCGACTGGGACAGTATGCATTGCACGCCCTTCTGGTCTACCGATCCGGAGCAGATGACC

12018 GACTCGGTGCGGCGTTACAGCACGGTGAGCCCCGGTAAGGAAGTGACGCTTCAGCTTCAC
      |||||||||||||||||||||| |||||||||||||||||||||||||||||||||||||
 1593 GACTCGGTGCGGCGTTACAGCACAGTGAGCCCCGGCAAGGAAGTGACGCTTCAGCTTCAC

12078 GGGAACCAAACCGTACAGCCGTCGTTTCTAAGCTTTACGTGCCGCCTGCAGCTAGAACCC
      ||||||||||||||||||||||||||||||||||||||||||||||||||||||||||||
 1653 GGGAACCAAACCGTACAGCCGTCGTTTCTAAGCTTTACGTGCCGCCTGCAGCTAGAACCC

12138 GTGGTGGAAAATGTTGGCCTCTACGTGGCCTACGTGGTCAACGACGGTGAACGCCCACAG
      ||||||||||||||||||||||||||||||||||||||||||||||||||||||||||||
 1713 GTGGTGGAAAATGTTGGCCTCTACGTGGCCTACGTGGTCAACGACGGTGAACGCCCACAG

12198 CAGTTTTTTACACCGCAGGTAGACGTGGTACGCTTTGCTCTATATCTAGAAACGCTCTCC
      |||||||||||||||||||||||||||||||||||||||||||||||||| |||||||||
 1773 CAGTTTTTTACACCGCAGGTAGACGTGGTACGCTTTGCTCTATATCTAGAGACGCTCTCC

12258 CGGATCGTGGAACCGTTAGAATCAGGTCGCCTGGCAGTGGAATTTGATACGCCTGACCTA
      ||||||||||||||||||||||||||||||||||||||||||||||||||||||||||||
 1833 CGGATCGTGGAACCGTTAGAATCAGGTCGCCTGGCAGTGGAATTTGATACGCCTGACCTA

12318 GCTCTGGCGCCCGATTTAGTAAGCAGCCTCTTCGTGGCCGGACACGGCGAGACCGACTTT
      ||||||||||||||||||||||||||||||||||||||||||||||||||||||||||||
 1893 GCTCTGGCGCCCGATTTAGTAAGCAGCCTCTTCGTGGCCGGACACGGCGAGACCGACTTT

12378 TACATGAACTGGACGCTGCGTCGCAGTCAGACCCACTACCTGGAGGAGATGGCCTTACAG
      ||||||||||||||||||||||||||||||||||||||||||||||||||||||||||||
 1953 TACATGAACTGGACGCTGCGTCGCAGTCAGACCCACTACCTGGAGGAGATGGCCTTACAG

12438 GTGGAGATTCTAAAGCCACGCGGCGTACGTCACCGCGCTATTATCCACCATCCGAAGCTA
      ||||||||||||||| ||||||||||||||||||||||||||||||||||||||||||||
 2013 GTGGAGATTCTAAAGCCCCGCGGCGTACGTCACCGCGCTATTATCCACCATCCGAAGCTA

12498 CAGCCGGGCGTTGGCCTGTGGATAGATTTCTGCGTGTACCGCTACAACGCGCGCCTGACC
      ||||||||||||||||||||||||||||||||||||||||||||||||||||||||||||
 2073 CAGCCGGGCGTTGGCCTGTGGATAGATTTCTGCGTGTACCGCTACAACGCGCGCCTGACC

12558 CGCGGCTACGTACGATACACCCTGTCACCGAAAGCGCGCTTGCCCGCAAAAGCAGAGGGT
      ||||||||||||||||||||||||||||||||||||||||||||||||||||||||||||
 2133 CGCGGCTACGTACGATACACCCTGTCACCGAAAGCGCGCTTGCCCGCAAAAGCAGAGGGT

12618 TGGCTGGTGTCACTAGACAGATTCATCGTGCAGTACCTCAACACATTGCTGATTACAATG
      ||||||||||||||||||||||||||||||||||||||||||||||||||||||||||||
 2193 TGGCTGGTGTCACTAGACAGATTCATCGTGCAGTACCTCAACACATTGCTGATTACAATG

12678 ATGGCGGCGATATGGGCTCGCGTTTTGATAACCTACCTGGTGTCGCGGCGTCGGTAGAGG
      ||||||||||||||||||||||||||||||||||||||||||||||||||||||||||||
 2253 ATGGCGGCGATATGGGCTCGCGTTTTGATAACCTACCTGGTGTCGCGGCGTCGGTAGAGG

12738 CTTGCGGAAACCACGTCCTCGTCACACGTCGTTCGCGGACATAGCAAGAAATCCACGTCG
      ||||||||||||||||||||||||||||||||||||||||||||||||||||||||||||
 2313 CTTGCGGAAACCACGTCCTCGTCACACGTCGTTCGCGGACATAGCAAGAAATCCACGTCG

12798 CCACGTCTCGAGAATGCCGGCCCCGCGGGGTCTCCTTCGCGCAACATTCCTGGCCCTGGT
      |||||||||||||||||||||||||||||| |||||||||||||||||||||||||||||
 2373 CCACGTCTCGAGAATGCCGGCCCCGCGGGGTCCCCTTCGCGCAACATTCCTGGCCCTGGT

12858 CGCGTTCGGGTTGCTGCTTTACATGGACTTCAGCGACGCTACAAATATGACCAGCAGCAC
      |||||||||||||||| | || ||| ||||||||||| |||||| |||||||||||||||
 2433 CGCGTTCGGGTTGCTGCTTCAGATAGACCTCAGCGACGCTACGAATGTGACCAGCAGCAC

12918 AAACGTCCCTACTAGCACCAGCAGCAGAAATACCGTCGAGAGCACCACGAGTAGCGAACC
      ||| |||||||||||||||||||||||||||| |||||| |   ||||||||| |||
 2493 AAAAGTCCCTACTAGCACCAGCAGCAGAAATAGCGTCGACAATGCCACGAGTAGCGGACC

12978 TACAACCGAAACCAACATGACCACCGCCCGCGAATCTTCCGTTCACGACGCGCGCAATGA
      || |||| | ||||||||||||| ||| ||| |||||||||||||||| || |||||||
 2553 CACGACCGGGATCAACATGACCACCACCCACGAGTCTTCCGTTCACAGCGTGCGCAATGA

13038 TGAAATCATGAAAGTGCTGGCTATCCTCTTCTACATCGTGACAGGCACCTCCATTTTCAG
      ||||||||||||||||||||||||||||||||||||||||||||||||||||||||||||
 2613 CGAAATCATGAAAGTGCTGGCTATCCTCTTCTACATCGTGACAGGCACCTCCATTTTCAG
```

Figure 7g cont.

```
13098 CTTCATAGCGGTACTGATCGCGGTAGTTTACTCCTCGTGTTGCAAGCACCCGGGCCGCTT
       ||||||||||||||||||||||||||||||||||||||||||||||||||||||||||||
 2673 CTTCATAGCGGTACTGATCGCGGTAGTTTACTCCTCGTGTTGCAAGCACCCGGGCCGCTT

13158 TCGTTTCGCCGACGAAGAGGCCGTCAACCTGTTGGACGACACGGACGACAGTGGCGGTAG
       ||||||||||||||||||  ||||||||||||||||||||||||||||||||||||||| |
 2733 TCGTTTCGCCGACGAAGAAGCCGTCAACCTGTTGGACGACACGGACGACAGTGGCGGTGG

13218 CAGCCCGTTTGGCAGCGGTTCCCGACGAGGTTCTCAGATCCCCGCCGGATTTTGTTCCTC
       ||||||||||||||||||||||||||||||||||||||||||||||||||||||||||||
 2793 CAGCCCGTTTGGCAGCGGTTCCCGACGAGGTTCTCAGATCCCCGCCGGATTTTGTTCCTC

13278 GAGCCCTTATCAGCGGTTGGAAACTCGGGACTGGGACGAGGAGGAGGAGGCGTCCGCGGC
       ||||||||||||||||||||||||||||||||||||||||||||||||||||||||||||
 2853 GAGCCCTTATCAGCGGTTGGAAACTCGGGACTGGGACGAGGAGGAGGAGGCGTCCGCGGC

13338 CCGCGAGCGCATGAAACATGATCCTGAGAACGTCATCTATTTCAGAAAGGATGGCAACTT
       ||||||||||||||||||||||||||||||||||||||||||||||||||||||||||||
 2913 CCGCGAGCGCATGAAACATGATCCTGAGAACGTCATCTATTTCAGAAAGGATGGCAACTT

13398 GGACACGTCGTTCGTGAATCCCAATTATGGGAGAGGCTCACCTTTGACCATCGAATCTCA
       ||||||||||||||||||||||||||||||||||| ||||||||||||||||||||||||
 2973 GGACACGTCGTTCGTGAATCCCAATTATGGGAGAGGCTCGCCTTTGACCATCGAATCTCA

13458 CCTCTCGGACAATGAGGAGGACCCCATCAGGTACTACGTTTCGGTGTACGATGAACTGAC
       |||||||||||||||||||||| |||||||||||||||| ||||||||||||||||||||
 3033 CCTCTCGGACAATGAGGAAGACCCCATCAGGTACTACGTCTCGGTGTACGATGAACTGAC

13518 CGCCTCGGAAATGGAAGAACCTTCGAACAGCACCAGCTGGCAGATTCCCAAACTAATGAA
       ||||||||||||||||||||||||||||||||||||||||||||||||||||||||||||
 3093 CGCCTCGGAAATGGAAGAACCTTCGAACAGCACCAGCTGGCAGATTCCCAAACTAATGAA

13578 AGTTGCCATGCAACCCGTCTCGCTCAGAGATCCCGAGTACGACTAGGC..TTTTTTTTTT
       ||||||||||||||||||||||||||||||||||||||||||||||||  ||||||||||
 3153 AGTTGCCATGCAACCCGTCTCGCTCAGAGATCCCGAGTACGACTAGGCTTTTTTTTTTTT

13636 GTCTTTCAGTTCCAACTCTTTCCCCGGCCCATCACCTCGCCTATACTATGTGTATGATGT
       ||||||  ||||||||||||||||||||||||||||||||||||||||||||||||||||
 3213 ATCTTTCGGTTCCAACTCTTTCCCCGGCCCATCACCTCGCCTATACTATGTGTATGATGT

13696 CTCATAATAAAGCTTTCTTTCTCAGTCTGCAACATGCGGCTGTGTCGGGTGTGGCTGTCT
       ||||||||||||||||||||||||||||||||||||||||||||||||||||||||||||
 3273 CTCATAATAAAGCTTTCTTTCTCAGTCTGCAACATGCGGCTGTGTCGGGTGTGGCTGTCT

13756 GTTTGTCTGTGCGCCGTGGTGCTGGGTCAGTGCCAGCGGGAAACCGCGGAAAAAAACGAT
       |||||||||||||||||||||||||||||||||||||||||||  ||||| |||||||||
 3333 GTTTGTCTGTGCGCCGTGGTGCTGGGTCAGTGCCAGCGGGAGACCGCAGAAAAAAACGAT

13816 TATTACCGAGTACCGCATTACTGGGACGCGTGCTCTCGCGCGCTGCCCGACCAAACCCGT
       ||||||||||||||||||||||||||||||||||||||||||||||||||||||||||||
 3393 TATTACCGAGTACCGCATTACTGGGACGCGTGCTCTCGCGCGCTGCCCGACCAAACCCGT

13876 TACAAGTATGTGGAACAGCTCGTGGACCTCACGTTGAACTACCACTACGATGCGAGCCAC
       |||||||||||||||||||||||||||||| |||||||||||||||||||||||||||||
 3453 TACAAGTATGTGGAACAGCTCGTGGACCTCACGTTGAACTACCACTACGATGCGAGCCAC

13936 GGCTTGGACAACTTTGACGTGCTCAAGAGGTGAGGATACGCGCTAAAGGTGCATGACAAC
       |||||||||||||||||||||||||||||||||||||||||||||||||| |||||||||
 3513 GGCTTGGACAACTTTGACGTGCTCAAGAGGTGAGGATACGCGCTAAAGGTGTATGACAAC

13996 GGGAAGGTAAGGGCGAACGGGTAACGGGTAAGTAACCGCATGGGGTATGAAATGACGTTT
       ||||||||||||||||||||||||||| |||||||||||||||| || ||||||||||| 
 3573 GGGAAGGTAAGGGCGAACGGGTAACGGGCAGGTAACCGCATGGGGTGTGAAATGACGTTC

14056 GGAACCTGTGCTTGCAGAATCAACGTGACCGAGGTGTCGTTGCTCATCAGCGACTTTAGA
       ||||||||||||||||||||||||||||||||||||||||||||||||||||||||||||
 3633 GGAACCTGTGCTTGCAGAATCAACGTGACCGAGGTGTCGTTGCTCATCAGCGACTTTAGA

14116 CGTCAGAACCGTCGCGGCGGCACCAACAAAAGGACCACGTTCAACGCCGCCGGTTCGCTG
       ||||||||||||||||||||||||||||||||||||||||||||||||||||||||||||
 3693 CGTCAGAACCGTCGCGGCGGCACCAACAAAAGGACCACGTTCAACGCCGCCGGTTCGCTG

14176 GCGCCGCACGCCCGGAGCCTCGAGTTCAGCGTGCGGCTCTTTGCCAACTAGCCTGCGTCA
       ||||||||||||||||||||||||||||||||||||||||||||||||||||||||||||
 3753 GCGCCGCACGCCCGGAGCCTCGAGTTCAGCGTGCGGCTCTTTGCCAACTAGCCTGCGTCA

14236 CGGGAAATAATATGCTGCGGCTTCTGCTTCGTCACCACTTTCACTGCCTGCTTCTGTGCG
       |||||||||||||  ||||||||||||||||||||||||||||||||||||||||||||
 3813 CGGGAAATAATATGCTACGGCTTCTGCTTCGTCACCACTTTCACTGCCTGCTTCTGTGCG

14296 CGGTTTGGGCAACGCCCTGTCTGGCGTCTCCGTGGTCGACGCTAACGGCAAACCAGAATC
       |||||||||||||||||||||||||||||||||||||||  |||||||||  ||||||||
 3873 CGGTTTGGGCAACGCCCTGTCTGGCGTCTCCGTGGTCAACGCTAACGGCGAACCAGAATC

14356 CGTCCCCGCCATGGTCTAAACTGACGTATTCCAAACCGCATGACGCGGCGACGTTTTACT
       ||||||||||||||||||||||||||||||||||||||||||||||||||||||||||||
 3933 CGTCCCCGCTATGGTCTAAACTGACGTATTCCAAACCGCATGACGCGGGCGACGTTTTACT

14416 GTCCTTTTTTCTATCCCTCGCGCCCACGGTCCCCCTTGCAATTCTCGGGGTTCCAGCAGG
       |||||||| ||||||||||||||||||||||||||||||||||||||||||||||||| ||
 3993 GTCCTTTTATCTATCCCTCGCCCCCACGGTCCCCCTTGCAATTCTCGGGGTTCCAGCGGG .

14476 TATCAACGGGTCCCGAGTGTCGCAACGAGACCCTGTATCTGCTGTACAACCGGGAAGGCC
       |||  |||||||||||||||||||||||||||||||||||||||||||||||||||||||
 4053 TATTAACGGGTCCCGAGTGTCGCAACGAGACCCTGTATCTGCTGTACAACCGGGAAGGCC .

14536 AGACCTTGGTAGAGAGAAGCTCCACCTGGGTGAAAAAGGTGATCTGGTACCTGAGCGGTC
       |||||||||| |||||||||||||||||||||||||||||||||||||||||||||||||
 4113 AGACCTTGGTGGAGAGAAGCTCCACCTGGGTGAAAAAGGTGATCTGGTACCTGAGCGGTC
```

Figure 7g cont.

```
14596 GCAACCAGACCATCCTTCAACGGATGCCCCGAACGGCTTCGAAACCGAGCGACGGAAACG
      |||||||||||||||| ||||||||||||||||||||| ||||||||||||||||||||
 4173 GCAACCAGACCATCCTCCAACGGATGCCCGGAACGGCTTCAAAACCGAGCGACGGAAACG

14656 TGCAGATCAGCGTGGAAGACGCCAAGATTTTTGGAGCGCACATGGTGCCCAAGCAGACCA
      ||||||||||||||||||||||||||||||||||||||||||||||||||||||||||||
 4233 TGCAGATCAGCGTGGAAGACGCCAAGATTTTTGGAGCGCACATGGTGCCCAAGCAGACCA

14716 AGCTGCTACGCTTCGTCGTCAACGATGGCACACGTTATCAGATGTGTGTGATGAAGCTGG
      ||||||||||||||||||||||||||||||||||||||||||||||||||||||||||||
 4293 AGCTGCTACGCTTCGTCGTCAACGATGGCACACGTTATCAGATGTGTGTGATGAAGCTGG

14776 AGAGCTGAGCTCACGTCTTCCGGGACTACAGCGTGTCTTTTCAGGTGCGATTGACGTTCA
      |||||||  |||||||||||||||||||||||||||||||||||||||||||||||||||
 4353 AGAGCTGGGCTCACGTCTTCCGGGACTACAGCGTGTCTTTTCAGGTGCGATTGACGTTCA

14836 CCGAGGCCAATAACCAGACTTACACCTTCTGCACCCATCCCAATCTCATCGTTTGAGCCC
      ||||||||||||||||||||||||||||||||||||||||||||||||||||||||||||
 4413 CCGAGGCCAATAACCAGACTTACACCTTCTGCACCCATCCCAATCTCATCGTTTGAGCCC

14896 GTCGCGCGCGCAGGGAATTTTGAAAACCGCGCGTCATGAGTCCCAAAGACCTGACGCCGT
      |||||||||||||||||||||||||||||||||||||||||||||| |||||||||||||
 4473 GTCGCGCGCGCAGGGAATTTTGAAAACCGCGCGTCATGAGTCCCAAAAACCTGACGCCGT

14956 TCTTGACGGCGTTGTGGCTGCTATTGGGTCACAGCCGCGTGCCGCGGGTGCGCGCAGAAG
      |||||||||||||||||||| |||||| ||||||||||||||||||||||  ||||||||
 4533 TCTTGACGGCGTTGTGGCTGTTATTGGATCACAGCCGCGTGCCGCGGGTACGCGCAGAAG

15016 AATGTTGCGAATTCATAAACGTCAACCACCCGCCGGAACGCTGTTACGATTTCAAAATGT
      ||||||||||||||||||||||||||||||||||||||||||||||||||||||||||||
 4593 AATGTTGCGAATTCATAAACGTCAACCACCCGCCGGAACGCTGTTACGATTTCAAAATGT

15076 GCAACCGCTTCACCGTCGCGTACGTATTTTCATGATTGTCTGCGTTCTGTGGTGCGTCTG
      |||| |||||||||||||||||||||||||||||||||||||||||||||||||||||||
 4653 GCAATCGCTTCACCGTCGCGTACGTATTTTCATGATTGTCTGCGTTCTGTGGTGCGTCTG

15136 GATCTGTCTCTCGACGTTTCTGATAGCCATGTTCCATCGACGATCCTCGGGAATGCCAGA
      ||||||||||||||||||||||||||||||||||||||||||||||||||||||||||||
 4713 GATCTGTCTCTCGACGTTTCTGATAGCCATGTTCCATCGACGATCCTCGGGAATGCCAGA

15196 GTAGATTTTCATGAATCCACAGGCTGCGGTGTCCGGACGGCGAAGTCTGCTACAGTCCCG
      |||||||||||||| |||||||||||||||||||||||||||||||||||||||||||||
 4773 GTAGATTTTCATGAATACACAGGCTGCGGTGTCCGGACGGCGAAGTCTGCTACAGTCCCG

15256 AGAAAACGGCTGAGATTCGCGGGATCGTCACCACCATGACCCATTCATTGACGCGCCAGG
      |||||||||||||||||||||||||||||||||||||||||||||||||||||| |||||
 4833 AGAAAACGGCTGAGATTCGCGGGATCGTCACCACCATGACCCATTCATTGACACGCCAGG

15316 TCGTACACAACAAACTGACGAGCTGCAACTACAATCCGTAAGTCTCTTCCTCGAGGGCCT
      |||||||||||||||||||||||||||||||||||||||||||||||||||||||||||
 4893 TCGTACACAACAAACTGACGAGCTGCAACTACAATCCGTAAGTCTCTTCCTCGAGGGCCT

15376 TACAGCTTATGGGAAAGTAAGACAGAGAGGGACAAAACATCATTAAAAAAAAAAAGTCTA
      ||||||  |||||| |||||||||||||||||||||||||||| |||||||||||||||
 4953 TACAGCCTATGGGAGAGTAAGACAGAGAGGGACAAAACATCATT.AAAAAAAAAAGTCTA

15436 ATTTCACGTTTTGTACCCCCCCTTCCCCTCCGTGTTGTAGGTTATACCTCGAAGCTGACG
      |||||||||||||||||||          ||| |||||||||||||||||||||||||||
 5012 ATTTCACGTTTTGTACCC.....CCCTTCCGTGTTGTAGGTTATACCTCGAAGCTGACG

15496 GGCGAATACGCTGCGGCAAAGTGAACGACAAGGCGCAGTACCTGCTGGGCGCCGCTGGCA
      ||||||||||||||||||||||||||||||||||||||||||||||||||||||||||||
 5066 GGCGAATACGCTGCGGCAAAGTGAACGACAAGGCGCAGTACCTGCTGGGCGCCGCTGGCA

15556 GCGTTCCCTATCGATGGATCAATCTGGAATACGACAAGATAACCCGGATCGTGGGCCTGG
      |||||||||||||||||||| |||||||||||||||||||||||||||||||||||||||
 5126 GCGTTCCCTATCGATGGATCAACCTGGAATACGACAAGATAACCCGGATCGTGGGCCTGG

15616 ATCAGTACCTGGAGAGCGTTAAGAAACACAAACGGCTGGATGTGTGCCGCGCTAAAATGG
      ||||||||||||||||||||||||||||||||||||||||||||||||||||||||||||
 5186 ATCAGTACCTGGAGAGCGTTAAGAAACACAAACGGCTGGATGTGTGCCGCGCTAAAATGG

15676 GCTATATGCTGCAGTGAATAATAAAATGTGTGTTTGTCCGAAATACGCGTTTCGAGATTT
      ||||||||||||||||||||||||||||||||||||||||||||||||||||||  ||||
 5246 GCTATATGCTGCAGTGAATAATAAAATGTGTGTTTGTCCGAAATACGCGTTTTGAGATTT

15736 CTGTCGCCGACTAAATTCATGTCGCGCGATAGTGGTGTTTATCGCCGATAGAGATGGCGA
      ||||||||||||||||||||||||||||||||||||||||||||||||||||||||||||
 5306 CTGTCGCCGACTAAATTCATGTCGCGCGATAGTGGTGTTTATCGCCGATAGAGATGGCGA

15796 TATTGGAAGAATCGATATTTGAAAATATGGCATATTGAAAATGTCGCCGATGTGAGTTTC
      ||||||||| |||| ||||||||||||||||||||||||||||||||||||||||||||
 5366 TATTGGAAAAATCAATATTTGAAAATATGGCATATTGAAAATGTCGCCGATGTGAGTTTC

15856 TGTGTAACTGATATCGCCATTTTTAAAAAAGTGATTTTTGGGCATATGCGATATCTGGCG
      |||||||||||||||||||||||||    |||||||||||||||| ||||||||||||||
 5426 TGTGTAACTGATATCGCCATTTTTCAAAAGTGATTTTTGGGCATACGCGATATCTGGCG

15916 ATAACGCTTATATCGTTTACGGGGGATGGCGATAGACGACTTTGGCGACTTGGGCGATTC
      |||  |||||||||||||||||||||||||||||||||||||||||||||||||||||||
 5486 ATAGCGCTTATATCGTTTACGGGGATGGCGATAGACGACTTTGGCGACTTGGGCGATTC

15976 TGTGTGTCGCAAATATCGCAGTTTCGATATAGGTGACAGACGATATGAGGCCATATCGCC
      | ||||||||||||||||||||||||||||||||||||||||||||||||||||||||||
 5546 GGTGTGTCGCAAATATCGCAGTTTCGATATAGGTGACAGACGATATGAGGCCATATCGCC

16036 GATAGAGGCGACATCAAGTTGGCACATGGCCAATGCATATCGATATATACATTGAATCAA
      |||||||||||||||| |||||||||||||||||| ||||||||||||||||||| ||||
 5606 GATAGAGGCGACATCGAGTTGGCACATGGCCAATGGATATCGATATATACATTGCATCAA
```

Figure 7g cont.

```
16096 TATTGGCCATTAGCCACATTAGTCATTGGTTATATAGTATAAATCAATATTGGCTAATGG
      |||||||||||||| |||||||||||||||||| ||||||||||||||||||||
 5666 TATTGGCCATTAGCCATATTAGTCATTGGTTATATAGCGTAAATCAATATTGGCTAATGG

16156 CCATTGCATACGTTGTATCTATATCATAATATGTACATTTATATTGGCTCATATCCAATA
      |||||||||||||| |||||||||||| ||||||||||||||||||||| ||||||
 5726 CCATTGCATACGTTGCATCTATATCATAATGTGTACATTTATATTGGCTCATGTCCAATA

16216 TAACCGGCATGTTGACATTGATTATTGATTAGTTATTAATAGTAATCAATTACGGGGTCA
      | |||||||||||||||||||||||| |||||||||||||||||||||||||||||||
 5786 TGACCGGCATGTTGACATTGATTATTGACTAGTTATTAATAGTAATCAATTACGGGGTCA

16276 TTAGTTCATAGCCCATATATGGAGTTCCGCGTTACATAACTTACGGTAAATGGCCCGCCT
      |||||||||||||||||||||||||||||||||||||||| |||||||||||||||||
 5846 TTAGTTCATAGCCCATATATGGAGTTCCGCGTTACATAACTTACGGTAAATGGCCCGCCT

16336 GGCTGACCGCCCAACGACCCCCGCCCATTGACGTCAATAATGACGTGAGTTCCCATAGTA
      |||||||||||||||||||||||||||||||||||||||||||||| ||||||||||||
 5906 GGCTGACCGCCCAACGACCCCCGCCCATTGACGTCAATAATGACGTGGGTTCCCATAGTA

16396 ACACCAATAGGGACTTTCCATTGACGTCAATGGGAGGAGTATTTACGGTAAACTGCCCAC
       | ||||||||||||||||||||||||||||||||||||||||||||||||||||||||
 5966 ACGCCAATAGGGACTTTCCATTGACGTCAATGGGAGGAGTATTTACGGTAAACTGCCCAC

16456 TTGGCAGTACATCAAGTGTATCATATGCCAAGTACGCCCCCTATTGACGTCAATGACGGT
      ||||||||||||||||||||||||||||||||||||||||||||||||||||||||||
 6026 TTGGCAGTACATCAAGTGTATCATATGCCAAGTACGCCCCCTATTGACGTCAATGACGGT

16516 AAATGGCCCGCCTGGCATTATGCCCAGTACATGACCTTACGGGACTTTCCTAC
      ||||||||||||||||||||||||||||||||||||||||||||||||||||
 6086 AAATGGCCCGCCTGGCATTATGCCCAGTACATGACCTTACGGGACTTTCCTAC
```

Figure 7h

Fast alignment of DNA sequences PAN1 and FIX7

Upper line: PAN1, from 8800 to 16570
Lower line: FIX from 1 to 7633

```
8800  ACTGTGGCTGGAAACTGGTTACCTGTGAAGATGGCTGACTATCCTGTTCTGTCCTGGAAA
      ||||||||  |||||||||||||||||||||||||||||||||||| ||||||||||||
1     ACTGTGGCTAGAAACTGGTTACCTGTGAAGATGGCTGACTATCCTGTTGTGTCCTGGAAA

8860  AACTTTCAGCGTCGTAGGTGGACTTTGCAGTATGCGGATTAGTGAAGTTATGTCATTTAT
       ||||||||||||||||||||||||||||||||||||| ||||||||||||||||||||
61    AGCTTTCAGCGTCGTAGGTGGACTTTGCAGTATGCGGGTTAGTGAAGTTATGTCATTTAT

8920  TTACGTTTACGATCTCGTATTACAAACCGCGGAGAGGATGATACCGTTCGGCCCCATGAG
      ||||||||||||||||||||||||||||||||||||||||||||||||||||||||||||
121   TTACGTTTACGATCTCGTATTACAAACCGCGGAGAGGATGATACCGTTCGGCCCCATGAG

8980  TTATTTTTATTCTTCCGGTAGGAGGCATGAAGCCTCTGGTGATGCTCATCTGCTTCGGTG
      |||||||||||||||||||||||||||||||||||||||||||| ||  |   |  ||
181   TTATTTTTATTCTTCCGGTAGGAGGCATGAAGCCTCTGGTGATGCTTATTTTGCTGAGTA

9040  TGTTTTTACTACAGCTTGGGGGAAGCAAAATGTGTAAGCCCGATGAGGTGAAGCTGGGTA
      || | ||   |    |  ||| ||   |||| || ||||| || |  | ||   | ||
241   TGCTATTGGCATGCATAGGGAAAACTGAAATATGCAAACCCGAAGAAGTGCAATTAGGAA

9100  ACCAATGCTGCCCGCCATGCGGATCAGGACAAAAAGTTACAAAAGTGTGTACAGAGAATA
      |  ||  ||  ||||| |   ||||  |   ||| | ||||| || |||   | |||
301   ATCAGTGTTGTCCCCCATGTAAACAAGGATATCGTGTTACAGGACAATGTACGCAATATA

9160  GTGGCATAACGTGTACACTGTGCCCAAACGGCACTTATCTCACAGGGCTTTACAACTGTA
         |  ||||||| || |||   || ||||| ||| ||||||||||||||| | ||||
361   CGAGTACAACATGTACACTTTGCCCTAACGGTACGTATGTATCAGGGCTTTACAATTGTA

9220  CTAATTGTACTCAATGTAACGACACTCAGATCACGGTTCGTAACTGCACTTCCACTAATA
      | ||||| ||| | ||||| |||||| ||| ||  |||  | |||||||||||||||||
421   CCAATTGCACTGAGTGTAATGACACTGAGGTTACAATTCGTAACTGCACTTCCACTAATA

9280  ACACCATATGCGCATCTAAGAATCATACATTGTTTTCCACTCCAGGTGTCCAACATCACA
      ||||| |||||||||||||||||| ||| ||||| |||||||||||||||||||||||||
481   ACACCGTATGCGCATCAAAGAATTATACGTCGTTGTCCGTTCCAGGCGTCCAACATCATA

9340  AGCAACGACAGCAAAATCATACCGCACATGTAACCGTCAAACAAGGGAAAAGTGGTCGTC
      |||||||   ||||||||||||||||||||||||||||||||||||||||||||||||||
541   AGCAACGA...CAAAATCATACCGCACATGTAACCGTCAAACAAGGGAAAAGTGGTCGTC

9400  ATACTCTAGCCTGGTTGTCCCTCTTCATCTTTCTCGTGGGTATCATACTTTTAATTCTCT
      |||||||||||||||||||||||||||||||||||||||||||||||||||||||||||
598   ATACTCTAGCCTGGTTGTCCCTCTTCATCTTTCTCGTGGGTATCATACTTTTAATTCTCT

9460  ATCTTATAGCCGCCTATCGGAGTGAGAGATGCCAACAGTGTTGCTCAATCGGCAAAATTT
      ||||||||||||||||||||||||||||||||||||||||||||||||||||||||||||
658   ATCTTATAGCCGCCTATCGGAGTGAGAGATGCCAACAGTGTTGCTCAATCGGCAAAATTT

9520  TCTACCGCACCCTGTAAGCTTCCTGTTGTTGTTTTACATCACGGTACGATGAAGTCACA
      ||||||||||||||||||||||||||||||||||||||||||||| |||||||||||||
718   TCTACCGCACCCTGTAAGCTTCCTGTTGTTGTTTTACATCACGGTGCGATGAAGTCACA

9580  CAGATAATTACAGATGAGCTGTTCATATTTTTTATTATTTTTTCCAATTCCTGCACTAAA
      ||||||||||||||||||||||||||||||||||||||||||||||||||||||||||||
778   CAGATAATTACAGATGAGCTGTTCATATTTTTTATTATTTTTTCCAATTCCTGCACTAAA

9640  AAAAGAAGCACTTTACGGAACCGTGTCTGAATATCTGTGGGGAATTTAGGTACTTTTTGC
      |||||||||||||||||||||||||||||||||||||||||||||||||||||||||||
838   AAAAGAAGCACTTTACGGAACCGTGTCTGAATATCTGTGGGGAATTTAGGTACTTTTTGC

9700  CGACGTCAGGAAAAATAAGCTGTCGCCTACATAAGAGCCCGGTTCTATCGTGCTGTCACT
      |||||||||||||||||||||||||||||||||||||||||| |||||||||||||||||
898   CGACGTCAGGAAAAATAAGCTGTCGCCTACATAAGAGCCGGTGCTATCGTGCTGTCACT

9760  CTTTCTTGTTGCCTTCGATGTACGGCGTCCTGGCTCATTACTACTCCTTCATCAGTAGCC
      |||||||||||||||||||||||||||||||||||||||||||||||||||||||||||
958   CTTTCTTGTTGCCTTCGATGTACGGCGTCCTGGCTCATTACTACTCCTTCATCAGTAGCC

9820  CCAGCGTTATGGTTAATTTTAAGCATCATAACGCTGTACAGCTGTTGTGTGCACGGACCC
      |||||||||||||||||||||| |||||||||| || ||||||||||||||||||||||
1018  CCAGCGTTATGGTTAATTTTAAACATCATAACGCCGTGCAGCTGTTGTGTGCACGGACCC

9880  GAGACGGCACTGCCGGATGGGAACGTTTAACCCATCATGCGTCGTATCACGCGAATTATG
      ||||||||||||||||||||||||||||||||||||||||||||||||||||||| ||||
1078  GAGACGGCACTGCCGGATGGGAACGTTTAACCCATCATGCGTCGTATCACGCGAACTATG

9940  GGGCATACGCCGTGTTGATGGCTACATCGCAAAGAAAGTCCCTAGTGTTACATCGATATA
      |||||||||||||||||||||||||||||||||||||||||||||||||||||||||| |
1138  GGGCATACGCCGTGTTGATGGCTACATCGCAAAGAAAGTCCCTAGTGTTACATCGATACA

10000 GTGCCGTGACAGCCGTGGCCCTGCAGCTCATGCCTGTTGAGATGCTGCGCAAGCTAGACC
      ||||||||||||| |||||||||||||||||||||||||||||||| || |||||||| |
1198  GTGCCGTGACAGCCGTGGCCCTGCAGCTCATGCCTGTTGAGATGCTCCGTAAGCTAGATC

10060 AGTCGGACTGGGTGCGGGGTGCCTGGATCGTGTCAGAGACTTTTCCAACTAGCGACCCCA
      ||||||||||||  ||||||||||||||||||||||||||||||||||| ||||||||||
1258  AGTCGGACTGGGTACGGGGTGCCTGGATCGTGTCAGAGACTTTTCCAACCAGCGACCCCA

10120 AAGGATTTTGGAGCGACGATGACTCCTCGATGGGTGGAAGTGAAGATTGATGATGAGAAC
      |||||||||||||||||||||||||||||||||||||   ||||||||||||||||||||
```

Figure 7h cont.

```
1318   AAGGATTTTGGAGCGACGATGACTCCTCGATGGGTGGAAGTGATGATTGATGATGAGAAC

10180  CTGACAAGAAAGACGATAGAGAAATTCAGAGCTGTCATTGTAGAATTAGTCTAGATTCCT
       ||||||||||||||| ||||||||||||||||||||||||||||||||||||||||||||
1378   CTGACAAGAAAGACGAGAGAGAAATTCAGAGCTGTCATTGTAGAATTAGTCTAGATTCCT

10240  GATAATAAACGGTATCGATTTTGAAACCTAATTGACGTGTGATCGATTTTTAAACCTGTG
       ||||||||||||||||||||||||||||||||||||||||||||||||||||||||||||
1438   GATAATAAACGGTATCGATTTTGAAACCTAATTGACGTGTGATCGATTTTTAAACCTGTG

10300  TGTTGTGTGATTGATTGGTACGTGGGGGGATCCGATTTCAAAGGGAGGTAGTTATCGGGA
       |||||||||||||||||||| ||||||||||||||||||||||||||| ||||||||||
1498   TGTTGTGTGATTGATTGGTATGTGGGGGGATCCGATTTCAAAGGGGGTACTTTATCGGGA

10360  ATTGATGTGTCATGGACGCAGTTTTGAGTGATTTTCCGGGAATACCGGATATTACGAATT
       ||||||||||||||||||||||||||||||||||||||||||||||||||||||||||||
1558   ATTGATGTGTCATGGACGCAGTTTTGAGTGATTTTCCGGGAATACCGGATATTACGAATT

10420  ACTGTAAGTGACGTCAGAAATTAAATTATAATGCGTTTAATTTTTGGTTTATTGATCATT
       |||||| |||||| ||||||  |  ||||| || ||||| |||||    ||||     |
1618   GATGTAAGTTACGTCAGTAATTAAGTCAGGATGCGGTTTATTTTCGGTTTGCTGATTGGT

10480  TTTATTGTTACAGATACATGTAACGGCGGTTTTGGCACTGAAGGTAATGGTCGTTGTGCA
       ||  |     ||||  |  ||
1678   CTTGTAATCGTGTATACGTATTATTATGA............................

10540  TGCATAGGGTATCATCGACTTTTAGGACAATTGCCTCGTGGAACTTTCTGGTTAGGACAT

1707   ...............................................................

10600  TTACCACCAGGCTCACATTGCCCAAAGGGACAAGTCATGATAAAGATAGGCCAAGGACCG
                                                 || ||| | ||
1707   .........................................AGTACAAAGTACG

10660  ATCGTCTGTTTATCCGATTATCATCCTTTATCTAAGTGGATGTATGGAAATCATAAATCT
       |   |||  |        | ||  |||   |  ||  ||  | ||||| |    |||
1720   GAACTACGTTGCCCATGCACTAATGGTTTACACGATCCTTTATATGGCATATTTTATGCT

10720  GGTTCGGAAACATGGCTTCAGATAAAAATGGAAGGTC..CAAGAAATGCTACAGTAGTAC
       |||  || |   | ||                 |||     |||  |    || |   |
1780   GGTCGTGACCCTCCACGTCCTCCCGGTTGTGAAAAAGATCAATATTATTTAAAACCTCCC

10778  AAAGATCGAATACTCGTCCATAAAGATAACGAATGTTCATAAGAATTGTACTTTTATATG
       ||||  |    |    |   ||       |  | |   |  ||  | ||  |  ||||
1840   AAAGGTAAAGCTGTATGCTTAGGTCCACATCATCATTTATCAATATGGCTCAATGGTCAA

10838  TATGTAAGTTTATGGATCTTTATGTTTGTCATCATATACATTAGTAGTAACATACTCAAC
       ||  ||||||||| |    | || |       |||   ||       |||     ||
1900   AATAGTAGTTTATGGCACAAAGTGCTGGTGACGGGAAAAAACGGTAATGGACCACACGTA

10898  ACACTATGCGTGTACAATTTGTTTTATAGATCCGTAGTGTACAATAAATATTACGATAAA
       ||       ||| || |               |    |   | ||| || || ||  |
1960   ACTAAGAAAG.GTGACTTTCCTAGAGGTCGAAAAAATATAATGATTTAGCTTAATATGGA

10958  TTTTTAACGTCGGATACATTTACGATACTAAACGTACTGTATTGCATTTTTTGCACGATG
        | ||   ||  | |    | ||  ||   | |     |     |    |   | |||
2019   TATATACGATAGCTGATAAATTTTCCACGAAAAAGGATAACGCAATATGTTTTTGATATG

11018  TTGACATCA......CATTGCTGGGCTACAAGATGGCATAACAAA...TTATTGGTACGA
       || | ||        |||  |  |   | |||||| ||||       |||  |||  |
2079   GTGCTAACATGGTTACATCATTCGATTATAAACTCGCATATCAAACTTTTATCGGTACCA

11069  TACCTGTCATTGACTATATATATGTTACTGACCGTATGTCCCCTAGCCGTCCATCTTTTA
       |||||||||||| ||||||||||| |||| |||||||||||     |||||||||||||
2139   CACCTGTCATTGACCGCATATATGTTATTTACCGTGTGTTTCCCG...GTCCATCTTTTA

11129  GAATTGGAAGATTACGACAGACGCGTCGTTGTAACAATCAAATTCTGTTGAATACTCTG
       |||||||||||||||||| || |||||||||||||| ||||||||||||||||||  |||
2196   GAATTGGAAGATTACGACAGGCGTTGTCGTTGTAACAACCAAATTCTGTTGAATACCCTG

11189  CCAATCGGAACTGAATTGCTTAAGCCAATCGCGGCGAGCGAAAGCTGCAATCGTCAGGAA
       || ||||||| || ||||||||||||||||| || ||||||||||||||||||||||||
2256   CCGGTCGGAACTCAACTGCTTAAGCCAATCGCAGCGAGCGAAAGCTGCAATCGTCAGGAA

11249  GTGCTGGCTATTTTAAAGGACAAGGGCACCAAGTGTCTCAATCCTAACGCGCAAGCCGTG
       ||||||||||||||||||||||| || |||||||||||||||||||||||||||||||||
2316   GTGCTGGCTATTTTAAAGGACAAAGGAACCAAGTGTCTCAATCCTAACGCGCAAGCCGTG

11309  CGTCGTCACATCAACCGGCTATTTTTTCGGTTAATATTAGACGAGGAACAACGCATTTAC
       |||||||||||||||||||||||||||||||||| || ||||||||||||||||||||||
2376   CGTCGTCACATCAACCGGCTATTTTTTCGGTTAATCTTAGACGAGGAACAACGCATTTAC

11369  GACGTAGTGTCTACCAATATTGAGTTCGGTGCCTGGCCAGTCCCTACGGCCTACAAAGCC
       ||||||||||||||||||||||||||||||||||||||||||||||||||||||||||||
2436   GACGTAGTGTCTACCAATATTGAGTTCGGTGCCTGGCCAGTCCCTACGGCCTACAAAGCC

11429  TTTCTCTGGAAATACGCCAAGAAACTGAACTACCACCACTTCAGATTGCGCTGGTGATCA
       |||||||||||||||||||||||||||| |||||| ||| |||  ||| |||||||||||
2496   TTTCTCTGGAAATACGCCAAGAAACTTAATTACCACTACTTTAGACTGCGTTGGTGATCA

11489  TGTCCCTATTTTACCGTGCGGTAGCCCTGGGCACACTGAGCGCTCTGGTGTGGTACAGCA
       |||||||||||| ||||||||||||||||||||| ||||||||||||||||||||||||
2556   TGTCCCTATTTTACCGTGCGGTAGCCCTGGGCACGCTGAGCGCTCTGGTGTGGTATAGCA

11549  CTAGTATCCTGGCAGAAAATTAACGAAGAATCCTGCTCCTCATCTTCTGTGGACCACGAAG
       ||||||||||||||||| |||||||||||||||||||||||||||||||||||||||||||
2616   CTAGTATCCTGGCAGAGATTAACGAAGAATCCTGCTCCTCATCTTCTGTGGACCACGAAG

11609  ACTGCGAGGAACCGGACGAGATCGTTCGCGAAGAGCAAGACTATCGGGCTCTGCTGGCCT
       ||||||||||||||||||||||||||||||||||||||||||||||||||||||||||||
```

Figure 7h cont.

```
 2676 ACTGCGAGGAACCGGACGAGATCGTTCGCGAAGAGCAAGACTATCGGGCTCTGCTGGCCT

11669 TTTCCCTAGTGATTTGCGGTACGCTCCTCGTCACTTGTGTGATCTGAGACGTCATGCTGG
      ||||||||||||||||||||||||||||||||||||||||||||||||||||||||||||
 2736 TTTCCCTAGTGATTTGCGGTACGCTCCTCGTCACTTGTGTGATCTGAGACGTCATGCTGG

11729 TAGCGTTTATGAGTCGGGCGGTGGCCGACACGCCGCATTTCCTAACCGGCGCAGCATGTT
      ||||||||||||||||||||||||||||| ||||||||||||||||||||||||||||||
 2796 TAGCGTTTATGAGTCGGGCGGTGGCCGGCACGCCGCATTTCCTAACCCGCGCAGCATGTT

11789 GCGCTTGCTGTTCACGCTCGTCCTGCTGGCCCTCCACGGGCAGTCTGTCGGCGCTAGCCG
      ||||||||||||||||||||||||||| |||||||||||| ||||||| |||||||||||
 2856 GCGCTTGCTGTTCACGCTCGTCCTACTGGCCCTCCACGGGCCGTCTGTCAACGCTAGCCG

11849 CGACTATGTGCATGTTCGGCTACTGAGCTACCGAGGCGACCCCTGGTCTTCAAGCACAC
      ||||||||||||||||||||||||||||||||||||||||||||||||||||||||||
 2916 CGACTATGTGCATGTTCGGCTACTGAGCTACCGAGGCGACCCCTGGTCTTCAAGCACAC

11909 TTTCTCGGGTGTGCGTCGACCCTTCACCGAGCTAGGCTGGGCTGCGTGTCGCGACTGGGA
      ||| ||||||||||||||||||||||||||||||||||||||||| ||||||||||||||
 2976 TTTTTCGGGTGTGCGTCGACCCTTCACCGAGCTAGGCTGGGCTGTGTGTCGCGACTGGGA

11969 CAGTATGCATTGCACACCCTTCTGGTCTACCGATCTGGAGCAGATGACCGACTCGGTGCG
      ||||||||||||||||| || |||||||||||||||||||||||||||||||||||||||
 3036 CAGTATGCATTGCACGCCTTTCTGGTCTACCGATCTGGAGCAGATGACCGACTCGGTGCG

12029 GCGTTACAGCACGGTGAGCCCCGGTAAGGAAGTGACGCTTCAGCTTCACGGGAACCAAAC
       ||||||||||||||||||||||| |||||||||||||||||||||||||||||||||||
 3096 ACGTTACAGCACGGTGAGCCCCGGCAAGGAAGTGACGCTTCAGCTTCACGGGAACCAAAC

12089 CGTACAGCCGTCGTTTCTAAGCTTTACGTGCCGCCTGCAGCTAGAACCCGTGGTGGAAAA
      ||||||||||||||||||||||||||||||||||||||||||||||||||||||||||||
 3156 CGTACAGCCGTCGTTTCTAAGCTTTACGTGCCGCCTGCAGCTAGAACCCGTGGTGGAAAA

12149 TGTTGGCCTCTACGTGGCCTACGTGGTCAACGACGGTGAACGCCCACAGCAGTTTTTTAC
      ||||||||||||||||||||||||||||||||||||||||||||||||||||||||||||
 3216 TGTTGGCCTCTACGTGGCCTACGTGGTCAACGACGGTGAACGCCCACAGCAGTTTTTTAC

12209 ACCGCAGGTAGACGTGGTACGCTTTGCTCTATATCTAGAAACGCTCTCCCGGATCGTGGA
      |||||| |||||||||||||||||||||||||||||||||||||||||||||||||||||
 3276 ACCGCAAGTAGACGTGGTACGCTTTGCTCTATATCTAGAAACGCTCTCCCGGATCGTGGA

12269 ACCGTTAGAATCAGGTCGCCTGGCAGTGGAATTTGATACGCCTGACCTAGCTCTGGCGCC
      ||||||||||||||||||||||||||||||||||||||||||||||||||||||||||||
 3336 ACCGTTAGAATCAGGTCGCCTGGCAGTGGAATTTGATACGCCTGACCTAGCTCTGGCGCC

12329 CGATTTAGTAAGCAGCCTCTTCGTGGCCGGACACGGCGAGACCGACTTTTACATGAACTG
      ||||||||||||||||||||||||||||||||||||||||||||||||||||||||||||
 3396 CGATTTAGTAAGCAGCCTCTTCGTGGCCGGACACGGCGAGACCGACTTTTACATGAACTG

12389 GACGCTGCGTCGCAGTCAGACCCACTACCTGGAGGAGATGGCCTTACAGGTGGAGATTCT
       |||||||||||||||||||||||||||||||||||||||||||||||||||||||||||
 3456 GACGCTGCGTCGCAGTCAGACCCACTACCTGGAGGAGATGGCCTTACAGGTGGAGATTCT

12449 AAAGCCACGCGGCGTACGTCACCGCGCTATTATCCACCATCCGAAGCTACAGCCGGGCGT
      |||||| |||||||||||||||||||||||||||||||||| ||||||||||||||||||
 3516 AAAGCCCCGCGGCGTACGTCACCGCGCTATTATCCACCATCCTAAGCTACAGCCGGGCGT

12509 TGGCCTGTGGATAGATTTCTGCGTGTACCGCTACAACGCGCGCCTGACCCGCGGCTACGT
      ||||||||||||||||||||||||||||||||||||||||| ||||||||||||||||||
 3576 TGGCCTGTGGATAGATTTCTGCGTGTACCGCTACAACGCGCGCCTGACCCGCGGCTACGT

12569 ACGATACAGCCCTGTCACCGAAAGCGCGCTTGCCCGCAAAAGCAGAGGGTTGGCTGGTGTC
      ||||||||| ||||||||||||||||||||||||||||||||||||||||||||||||||
 3636 ACGATACACCCTGTCACCGAAAGCGCGCTTGCCCGCAAAAGCAGAGGGTTGGCTGGTGTC

12629 ACTAGACAGATTCATCGTGCAGTACCTCAACACATTGCTGATTACAATGATGGCGGCGAT
      ||||||||||||||||||||||||||||||||||||||||||||||||||||||||||||
 3696 ACTAGACAGATTCATCGTGCAGTACCTCAACACATTGCTGATTACAATGATGGCGGCGAT

12689 ATGGGCTCGCGTTTTGATAACCTACCTGGTGTCGCGGCGTCGGTAGAGGCTTGCGGAAAC
      ||||||||||||||||||||||||||||||||||||||||||||||||||||||||||||
 3756 ATGGGCTCGCGTTTTGATAACCTACCTGGTGTCGCGGCGTCGGTAGAGGCTTGCGGAAAC

12749 CACGTCCTCGTCACACGTCGTTCGCGGACATAGCAAGAAATCCACGTCGCCACGTCTCGA
      |||||||||||||||||||||||||||||||||||||||| |||||||||||||||||||
 3816 CACGTCCTCGTCACACGTCGTTCGCGGACATAGCAAGAAATTCACGTCGCCACGTCTCGA

12809 GAATGCCGGCCCCGCGGGGTCTCCTTCGCGCAACATTCCTGGCCCTGGTCGCGTTCGGGT
      ||||||||||||||||||||| |||||||||||||||||||||||||||||||||||| |
 3876 GAATGCCGGCCCCGCGGGGTCCCCTTCGCGCAACATTCCTGGCCCTGGTCGCGTTCGGAT

12869 TGCTGCTTTACATGGACTTCAGCGACGCTACAAATATGACCAGCAGCACAAACGTCCCTA
      ||||| || | || ||| |||||||||||||||||||||| |||||||||||||||||||
 3936 TGCTGTTTCAGATAGACCTCAGCGACGCTACAAATGTGACCAACAGCACAAACGTCCCTA

12929 CTAGCACCAGCAGCAGAAATACCGTCGAGAGCACCACGAGTAGCGAACCTACAACCGAAA
      |||||||||||||||||||| |||| | |||||||||| ||| || |||| |
 3996 CTAGCACCAGCAGCAGAAATAGCGTCGACAACGCCACGAGTAGCGACCCACGACGCGGGA

12989 CCAACATGACCACCGCCGCGAATCTTCCGTTCACGACGCGCGCAATGATGAAATCATGA
      ||||||||||||| ||| ||||||||||| ||||||||||||||||||||||||||||
 4056 TCAACATGACCACCCACCCACGAGTCTTCCGTTCACAACGTGCCAATGACAAAATCATGA

13049 AAGTGCTGGCTATCCTCTTCTACATCGTGACAGGCACCTCCATTTTCAGCTTCATAGCGG
      ||||||||||||||||||||||||||||||||||||||||||||||||||||||||||||
 4116 AAGTGCTGGCTATCCTCTTCTACATCGTGACAGGCACCTCCATTTTCAGCTTCATAGCGG

13109 TACTGATCGCGGTAGTTTACTCCTCGTGTTGCAAGCACCCGGGCCGCTTTCGTTTCGCCG
      |||| |||||||||||||||||||||||||||||||||||||||||||||||||||||||
```

Figure 7h cont.

```
4176  TACTCATCGCGGTAGTTTACTCCTCGTGTTGCAAGCACCCGGGCCGCTTTCGTTTCGCCG

13169 ACGAAGAGGCCGTCAACCTGTTGGACGACACGGACGACAGTGGCGGTAGCAGCCCGTTTG
      |||||||  |||||||| |||||||||||||||||||||||||| |||||||||||||||
4236  ACGAAGAAGCCGTCAATCTGTTGGACGACACGGACGACAGTGGCGGCAGCAGCCCGTTTG

13229 GCAGCGGTTCCCGACGAGGTTCTCAGATCCCCGCCGGATTTTGTTCCTCGAGCCCTTATC
      ||||||||||||||||||||||||||||||||||||||||||||||||||||||||||||
4296  GCAGCGGTTCCCGACGAGGTTCTCAGATCCCCGCCGGATTTTGTTCCTCGAGCCCTTATC

13289 AGCGGTTGGAAACTCGGGACTGGGACGAGGAGGAGGAGGCGTCCGCGGCCCGCGAGCGCA
      ||||||||||||||||||||||||||||||||||||||||||||||||||||||||||||
4356  AGCGGTTGGAAACTCGGGACTGGGACGAGGAGGAGGAGGCGTCCGCGGCCCGCGAGCGCA

13349 TGAAACATGATCCTGAGAACGTCATCTATTTCAGAAAGGATGGCAACTTGGACACGTCGT
      |||||||||||||||||||||||||||||||||||||||||||||||||||||||||||
4416  TGAAACATGATCCTGAGAACGTCATCTATTTCAGAAAGGATGGCAACTTGGACACGTCGT

13409 TCGTGAATCCCAATTATGGGAGAGGCTCACCTTTGACCATCGAATCTCACCTCTCGGACA
      |||||||||||||||||||||||||| ||||||||||||||||||||||||||||||||
4476  TCGTGAATCCCAATTATGGGAGAGGCTCGCCTTTGACCATCGAATCTCACCTCTCGGACA

13469 ATGAGGAGGACCCCATCAGGTACTACGTTTCGGTGTACGATGAACTGACCGCCTCGGAAA
      ||||||||||||||||||||||||||  |||||||||||||||||||||||||||||||
4536  ATGAGGAGGACCCCATCAGGTACTACGTCTCGGTGTACGATGAACTGACCGCCTCGGAAA

13529 TGGAAGAACCTTCGAACAGCACCAGCTGGCAGATTCCCAAACTAATGAAAGTTGCCATGC
      |||||||||||  |||||||||||||||||||||||||||||||||||||||||| | ||
4596  TGGAAGAACCTTCCAACAGCACCAGCTGGCAGATTCCCAAACTAATGAAAGTTGCTACGC

13589 AACCCGTCTCGCTCAGAGATCCCGAGTACGACTAGGCTTTTTTTTTGTCTTTCAGTTCC
      |||||||||||||||||||||||||||||||||||| ||||||||||||||||  |||
4656  AACCCGTCTCGCTCAGAGATCCCGAGTACGACTAGGCTTTTTTTTTGTCTTTCGGTTCC

13649 AACTCTTTCCCCGCCCCATCACCTCGCCTATACTATGTGTATGATGTCTCATAATAAAGC
      ||||||||||||||||||||||||||||||||||||||||||||||||||||||||||||
4716  AACTCTTTCCCCGCCCCATCACCTCGCCTATACTATGTGTATGATGTCTCATAATAAAGC

13709 TTTCTTTCTCAGTCTGCAACATGCGGCTGTGTCGGGTGTGGCTGTCTGTTTGTCTGTGCG
      |  ||||||||||||||||||||||||||||||||||||||||||||||||||||||||
4776  TCTCTTTCTCAGTCTGCAACATGCGGCTGTGTCGGGTGTGGCTGTCTGTTTGTCTGTGCG

13769 CCGTGGTGCTGGGTCAGTGCCAGCGGGAAACCGCGGAAAAAAACGATTATTACCGAGTAC
      |||||||||||||||||||||||||||||  ||||| ||||||||||||||||||||||
4836  CCGTGGTGCTGGGTCAGTGCCAGCGGGAGACCGCAGAAAAAAACGATTATTACCGAGTAC

13829 CGCATTACTGGGACGCGTGCTCTCGCGCGCTGCCCGACCAAACCCGTTACAAGTATGTGG
      ||||||||||||||||||||||||||||||||||  |||||||||||||||||||||||
4896  CGCATTACTGGGACGCGTGCTCTCGCGCGCTGCCCTGACCAAACCCGTTACAAGTATGTGG

13889 AACAGCTCGTGGACCTCACGTTGAACTACCACTACGATGCGAGCCACGGCTTGGACAACT
      |||||||||||||||||||||||||||||||||||||||||||||||||||||||||||
4956  AACAGCTCGTGGACCTCACGTTGAACTACCACTACGATGCGAGCCACGGCTTGGACAACT

13949 TTGACGTGCTCAAGAGGTGAGGATACGCGCTAAAGGTGCATGACAACGGGAAGGTAAGGG
      ||||||||||||||||||||||  ||||||||||||||   |||||||||||||||||||
5016  TTGACGTGCTCAAGAGGTGAGGGTACGCGCTAAAGGTGTATGACAACGGGAAGGTAAGGG

14009 CGAACGGGTAACGGGTAAGTAACCGCATGGGGTATGAAATGACGTTTGGAACCTGTGCTT
      |||||||||||||||||| |||||||||||||||| |||||||||||| ||||||||||
5076  CGAACGGGTAACGGGTAGGTAACCGCATGGGGTGTGAAATGACGTTCGGAACCTGTGCTT

14069 GCAGAATCAACGTGACCGAGGTGTCGTTGCTCATCAGCGACTTTAGACGTCAGAACCGTC
      ||||||||||||||||||||||||||||||||||||||||||||||||||||||||||||
5136  GCAGAATCAACGTGACCGAGGTGTCGTTGCTCATCAGCGACTTTAGACGTCAGAACCGTC

14129 GCGGCGGCACCAACAAAAGGACCACGTTCAACGCCGCCGGTTCGCTGGCGCCGCACGCCC
      |||||||||||||||||||||||||||||||||||||||||| |||||||||| |||||
5196  GCGGCGGCACCAACAAAAGGACCACGTTCAACGCCGCCGGTTCGCTGGCGCCTCAGGCCC

14189 GGAGCCTCGAGTTCAGCGTGCGGCTCTTTGCCAACTAGCCTGCGTCACGGGAAATAATAT
      ||||||||||||||||||||||||||||||||||||||||||||||||||||||||||||
5256  GGAGCCTCGAGTTCAGCGTGCGGCTCTTTGCCAACTAGCCTGCGTCACGGGAAATAATAT

14249 GCTGCGGCTTCTGCTTCGTCACCACTTTCACTGCCTGCTTCTGTGCGCGGTTTGGGCAAC
      |||  ||||||||||||||||||||||||||||||||||||||||||||||||||||||
5316  GCTACGGCTTCTGCTTCGTCACCACTTTCACTGCCTGCTTCTGTGCGCGGTTTGGGCAAC

14309 GCCCTGTCTGGCGTCTCCGTGGTCGACGCTAACGGCAAACCAGAATCCGTCCCCGCCATG
      ||||||||||||||||||||  ||||||||||||  ||||||||||||||||||||||||
5376  GCCCTGTCTGGCGTCTCCGTGGTTCACGCTAACGGCGAACCAGAATCCGTCCCCGCCATG

14369 GTCTAAACTGACGTATTCCAAACCGCATGACGCGGCGACGTTTTACTGTCCTTTTTTCTA
      ||||||||||||||  |||||||||||||||||||||||||||||||||||||||  ||||
5436  GTCTAAACTGACGTATCCCAAACCGCATGACGCGGCGACGTTTTACTGTCCTTTTCTCTA

14429 TCCCTCGCCCCCACGGTCCCCCTTGCAATTCTCGGGGTTCCAGCAGGTATCAACGGGTCC
      ||||||||||||||||||||||||  |||||| |||||| ||| |||||||||||||||
5496  TCCCTCGCCCCCACGGTCCCCCTCGCAATTCCCGGGGTTCCAGCGGGTATCAACGGGTCC

14489 CGAGTGTCGCAACGAGACCCTGTATCTGCTGTACAACCGGGAAGGCCAGACCTTGGTAGA
      ||||||||||||||||||||||||||||||||||||||||||||||||||||||||  ||
5556  CGAGTGTCGCAACGAGACCCTGTATCTGCTGTACAACCGGGAAGGCCAGACCTTGGTGGA

14549 GAGAAGCTCCACCTGGGTGAAAAAGGTGATCTGGTACCTGAGCGGTCGCAACCAGACCAT
      ||||||||||||  ||||||||||||||||||  |||||  ||||||||||||||||||
5616  GAGAAGCTCCACCCGGGTGAAAAAGGTGATCTGGTATCTGAGCGGTCGCAATCAGACCAT

14609 CCTTCAACGGATGCCCCGAACGGCTTCGAAACCGAGCGACGGAAACGTGCAGATCAGCGT
      |||  |||||||||||||||||||||||||||||||||||||||||||||||||||||||
```

Figure 7h cont.

```
 5676 CCTCCAACGGATGCCCCGAACGGCTTCGAAACCGAGCGACGGAAACGTGCAGATCAGCGT

14669 GGAAGACGCCAAGATTTTTGGAGCGGCACATGGTGCCCAAGCAGACCAAGCTGCTACGCTT
      ||||||||||||||||||||||||||||||||||||||||||||||||||||||||||||
 5736 GGAAGACGCCAAGATTTTTGGAGCGCACATGGTGCCCAAGCAGACCAAGCTGCTACGCTT

14729 CGTCGTCAACGATGGCACACGTTATCAGATGTGTGTGATGAAGCTGGAGAGCTGAGCTCA
      ||||||||||||||||||||| |||||||||||||||||||||||||||||||| || ||
 5796 CGTCGTCAACGATGGCACGCGTTATCAGATGTGTGTGATGAAGCTGGAGAGCTGGGCCCA

14789 CGTCTTCCGGGACTACAGCGTGTCTTTTCAGGTGCGATTGACGTTCACCGAGGCCAATAA
      ||||||||||||||||||||||||||||||||||||||||||||||||||||||||||||
 5856 CGTCTTCCGGGACTACAGCGTGTCTTTTCAGGTGCGATTGACGTTCACCGAGGCCAATAA

14849 CCAGACTTACACCTTCTGCACCCATCCCAATCTCATCGTTTGAGCCCGTCGCGCGCGCAG
      ||||||||||||||| ||||||||||||||||||||||||||||||||||||||||||||
 5916 CCAGACTTACACCTTCTGTACCCATCCCAATCTCATCGTTTGAGCCCGTCGCGCGCGCAG

14909 GGAATTTTGAAAACCGCGCGTCATGAGTCCCAAAGACCTGACGCCGTTCTTGACGGCGTT
      ||||||||||||||||||||||||||||||||||||||||||||||||||||||||| |||
 5976 GGAATTTTGAAAACCGCGCGTCATGAGTCCCAAAGACCTGACGCCGTTCTTGACGACGTT

14969 GTGGCTGCTATTGGGTCACAGCCGCGTGCCGCGGGTGCGCGCAGAAGAATGTTGCGAATT
      ||||||||||||||||||||||||||||||||||||||||||||||||||||||||||||
 6036 GTGGCTGCTATTGGGTCACAGCCGCGTGCCGCGGGTGCGCGCAGAAGAATGTTGCGAATT

15029 CATAAACGTCAACCACCCGCCGGAACGCTGTTACGATTTCAAAATGTGCAACCGCTTCAC
      ||||||||||||||||||||||||||||||||||||||||||||||||| ||||||||||
 6096 CATAAACGTCAACCACCCGCCGGAACGCTGTTACGATTTCAAAATGTGCAATCGCTTCAC

15089 CGTCGCGTACGTATTTTCATGATTGTCTGCGTTCTGTGGTGCGTCTGGATCTGTCTCTCG
      |||||||||||||||||| |||||||||||||||||||||||||||||||| ||||||||
 6156 CGTCGCGTACGTATTTTTATGATTGTCTGCGTTCTGTGGTGCGTCTGGATTTGTCTCTCG

15149 ACGTTTCTGATAGCCATGTTCCATCGACGATCCTCGGGAATGCCAGAGTAGATTTTCATG
      ||||||||||||||||||||||||||||||||||||||||||||||||||||||||||||
 6216 ACGTTTCTGATAGCCATGTTCCATCGACGATCCTCGGGAATGCCAGAGTAGATTTTCATG

15209 AATCCACAGGCTGCGGTGTCCGGACGGCGAAGTCTGCTACAGTCCCGAGAAAACGGCTGA
      ||||||||||||||||||||||||||||||||||||||||||||||||||||||||||||
 6276 AATCCACAGGCTGCGGTGTCCGGACGGCGAAGTCTGCTACAGTCCCGAGAAAACGGCTGA

15269 GATTCGCGGGATCGTCACCACCATGACCCATTCATTGACGCGCCAGGTCGTACACAACAA
      |||||||||||||||||||||||||||||||||||||||| |||||||||||||||||||
 6336 GATTCGCGGGATCGTCACCACCATGACCCATTCATTGACACGCCAGGTCGTACACAACAA

15329 ACTGACGAGCTGCAACTACAATCCGTAAGTCTCTTCCTCGAGGGCCTTACAGCGTTATGGG
      |||||||||||||||||||||||||||||||||||||||||||||||||||||||| ||||
 6396 ACTGACGAGCTGCAACTACAATCCGTAAGTCTCTTCCTCGAGGGCCTTACAGCGTATGGG

15389 AAAGTAAGACAGAGAGGGACAAAACATCATTAAAAAAAAAAAGTCTAATTTCACGTTTTG
      ||||||||   ||||||||||||||||||  |||||||||||||||||||||||||||||
 6456 AAAGTAAGAC..AGAGGGACAAAACATCATT..AAAAAAAAGTCTAATTTCACGTTTTG

15449 TACCCCCCCTTCCCCTCCGTGTTGTAGGTTATACCTCGAAGCTGACGGGCGAATACGCTG
      |||||||| ||||||||||||||||||||||||||||||||||||||||||||||||||||
 6512 TACCCCCCCTTCCCCTCCGTGTTGTAGGTTATACCTCGAAGCTGACGGGCGAATACGCTG

15509 CGGCAAAGTGAACGACAAGGCGCAGTACCTGCTGGGCGCCGCTGGCAGCGTTCCCTATCG
      ||||||||||||||||||||||||||||||||||||||||||||||||||||||||||||
 6572 CGGCAAAGTGAACGACAAGGCGCAGTACCTGCTGGGCGCCGCTGGCAGCGTTCCCTATCG

15569 ATGGATCAATCTGGAATACGACAAGATAACCCGGATCGTGGGCCTGGATCAGTACCTGGA
      |||||||| |||||||||||||||||||||||||||||||||||||||||||||||||||
 6632 ATGGATCAACCTGGAATACGACAAGATAACCCGGATCGTGGGCCTGGATCAGTACCTGGA

15629 GAGCGTTAAGAAACACAAACGGCTGGATGTGTGCCGCGCTAAAATGGGCTATATGCTGCA
      ||||||||| ||||||||||||||||||||||||||||||||||||||||||||||||||
 6692 GAGCGTTAAAAAACACAAACGGCTGGATGTGTGCCGCGCTAAAATGGGCTATATGCTGCA

15689 GTGAATAATAAAATGTGTGTTTGTCCGAAATACGCGTTTCGAGATTTCTGTCGCCGACTA
      ||||||||||||||||||||||||||||||||||||||| ||||||||||||||||||||
 6752 GTGAATAATAAAATGTGTGTTTGTCCGAAATACGCGTTTTGAGATTTCTGTCGCCGACTA

15749 AATTCATGTCGCGCGATAGTGGTGTTTATCGCCGATAGAGATGGCGATATTGGAAGAATC
      |||||||||||||||||||||||||||||||||||||||||||||||||||||||| ||||
 6812 AATTCATGTCGCGCGATAGTGGTGTTTATCGCCGATAGAGATGGCGATATTGGAAAAATC

15809 GATATTTGAAAATATGGCATATTGAAAATGTCGCCGATGTGAGTTTCTGTGTAACTGATA
      ||||||||||||||||||||||||||||||||||||||||||||||||||||||||||||
 6872 GATATTTGAAAATATGGCATATTGAAAATGTCGCCGATGTGAGTTTCTGTGTAACTGATA

15869 TCGCCATTTTTAAAAAAGTGATTTTTGGGCATATGCGATATCTGGCGATAACGCTTATAT
      ||||||||||   |||||||||||||||||||| ||||||||||||||||| ||||||||
 6932 TCGCCATTTTTCCAAAAGTGATTTTTGGGCATACGCGATATCTGGCGATAGCGCTTATAT

15929 CGTTTACGGGGGATGGCGATAGACGACTTTGGCGACTTGGGCGATTCTGTGTGTCGCAAA
      ||||||||||||||||||||||||||||||||| ||||||||||||||||||||||||||
 6992 CGTTTACGGGGGATGGCGATAGACGACTTTGGTGACTTGGGCGATTCTGTGTGTCGCAAA

15989 TATCGCAGTTTCGATATAGGTGACAGACGATATGAGGCCATATCGCCGATAGAGGCGACA
      |||||||||||||||||||||||||||||||||||| |||||||| ||||||||||||||
 7052 TATCGCAGTTTCGATATAGGTGACAGACGATATGAGGCTATATCGCCGATAGAGGCGACA

16049 TCAAGTTGGCACATGGCCAATGCATATCGATATATACATTGAATCAATATTGGCCATTAG
      |||||  ||||||||||||||||||||||||||||||||| |||||||||||||||||||
 7112 TCAAGCTGGCACATGGCCAATGCATATCGATCTATACATTGAATCAATATTGGCCATTAG

16109 CCACATTAGTCATTGGTTATATAGTATAAATCAATATTGGCTAATGGCCATTGCATACGT
      ||| |||| |||||||||||||||||||| |||||||||||||| |||||||||||||||
```

Figure 7h cont.

```
7172  CCATATTATTCATTGGTTATATAGCATAAATCAATATTGGCTATTGGCCATTGCATACGT

16169 TGTATCTATATCATAATATGTACATTTATATTGGCTCATATCCAATATAACCGCCATGTT
      ||||||  ||||||||||||||||||||||||||||||  |||||  |  |||||||||||
7232  TGTATCCATATCATAATATGTACATTTATATTGGCTCATGTCCAACATTACCGCCATGTT

16229 GACATTGATTATTGATTAGTTATTAATAGTAATCAATTACGGGGTCATTAGTTCATAGCC
      ||||||||||||||  |||||||||||||||||||||||||||||||||||||||||||
7292  GACATTGATTATTGACTAGTTATTAATAGTAATCAATTACGGGGTCATTAGTTCATAGCC

16289 CATATATGGAGTTCCGCGTTACATAACTTACGGTAAATGGCCCGCCTGGCTGACCGCCCA
      ||||||||||||||||||||||||||||||||||||||||||||||||||||||||||||
7352  CATATATGGAGTTCCGCGTTACATAACTTACGGTAAATGGCCCGCCTGGCTGACCGCCCA

16349 ACGACCCCCGCCCATTGACGTCAATAATGACGTGAGTTCCCATAGTAACACCAATAGGGA
      |||||||||||||||||||||||||||||||||| ||||||||||||| |||||||||||
7412  ACGACCCCCGCCCATTGACGTCAATAATGACGTATGTTCCCATAGTAACGCCAATAGGGA

16409 CTTTCCATTGACGTCAATGGGAGGAGTATTTACGGTAAACTGCCCACTTGGCAGTACATC
      |||||||||||||||||||||  |||||||||||||||||||||||||||||||||||||
7472  CTTTCCATTGACGTCAATGGGTGGAGTATTTACGGTAAACTGCCCACTTGGCAGTACATC

16469 AAGTGTATCATATGCCAAGTACGCCCCCTATTGACGTCAATGACGGTAAATGGCCCGCCT
      |||||||||||||||||||||||||||||||||||||||||||||||||||||||||||
7532  AAGTGTATCATATGCCAAGTACGCCCCCTATTGACGTCAATGACGGTAAATGGCCCGCCT

16529 GGCATTATGCCCAGTACATGACCTTACGGGACTTTCCTACTT
      ||||||||||||||||||||||||| ||||||||||||||||
7592  GGCATTATGCCCAGTACATGACCTTATGGGACTTTCCTACTG
```

RECOMBINANT VECTOR CONTAINING INFECTIOUS HUMAN CYTOMEGALOVIRUS GENOME WITH PRESERVED WILD-TYPE CHARACTERISTICS OF CLINICAL ISOLATES

This application is a continuation of U.S. application Ser. No. 10/275,287 filed Nov. 13, 2002, which is a 371 of International Application No: PCT/EP02/01867 filed Feb. 21, 2002. The disclosure of the prior applications is hereby incorporated by reference in its entirety.

The present invention is concerned with recombinant vectors containing infectious genome sequences of human cytomegalovirus (HCMV) and being useful for the production of reconstituted HCMV virus retaining phenotypic characteristics of a clinical virus isolate including the ability to grow on endothelial cells and to induce microfusion events. Further, the invention concerns the use of such recombinant vectors for the production of reconstituted HCMV virus with the mentioned characteristics as well as the use of reconstituted infectious HCMV virus for the production of vaccines and/or antibodies against the virus. Further embodiments of the invention are the use of reconstituted virus for the screening of drugs, the use of the recombinant vector and/or the reconstituted virus for studying genes and function of genes, as well as other uses. A further subject of the present invention are HCMV virus mutants, in which the region UL130 to UL132 is either deleted or mutated in such a way that the ability to induce microfusion events is lost or in which the region UL128 to UL132 is deleted or mutated in such a way that PMNL (polymorphonuclear leukocytes) and/or HUVEC (human umbilical vein endothelial cells) tropism is reduced or lost. Further embodiments are uses of such virus mutants or transfer of the genetic region UL132-128 of FIX-Bac into fibroblast adapted laboratory strains of HCMV (for example AD169) to regain PMNL and HUVEC tropism.

HCMV is a leading cause of birth defects when infection is acquired by HCMV-seronegative women during pregnancy (refs 1, 2, 3). In addition, HCMV represents one of the major opportunistic pathogens in immunocompromised individuals, such as bone marrow and solid organs transplant recipients and patients with primary or acquired (AIDS) immune deficiency. However, the pathogenesis of HCMV infection is not well understood. The main factor affecting research on this topic is recognized in the lack of the possibility of reproducing in vitro aspects of HCMV infection which are thought to be crucial in vivo. In particular, HCMV has been demonstrated to be able to infect in vivo several tissues and a number of cell types (refs 1, 4), providing a wide spectrum of symptomatic diseases and organ localizations in immunocompromised individuals (refs 5, 6) or inducing defects in multiple organs during embryogenesis which can be summarized as "congenital HCMV syndrome". In addition, a striking in vivo characteristic of primary HCMV infection in immunocompetent individuals (ref 7) and of active HCMV infection in immunocompromised patients (ref 8), is the presence of infectious virus and viral materials in circulating polymorphonuclear leukocytes (PMNL) (refs 9, 10). The latter is a major prognostic marker, which is highly predictive of disease progression in immunocompromised patients. Provided that the virus does not appear to fully replicate in PMNL, rather it can actively promote transfer of preformed viral particles to PMNL from productively infected cells by virus-induced microfusion events (ref 11), HCMV-positive PMNL are a powerful vehicle for viral dissemination.

In contrast, currently available HCMV laboratory-adapted reference strains (AD169, Towne, Davis and Toledo) (refs 12, 13) lost phenotypic characteristics thought to be important for pathogenicity "in vivo". Examples of pathogenic characteristics of clinical isolates are: i) preferential cell-to-cell spread, ii) tropism for a broad spectrum of tissues, iii) ability to transfer infectious virus to PMNL. Laboratory-adapted strains lost these biologic characteristics during propagation in standard cell culture (human embryonic fibroblasts, HEF). In addition, reference strains show a different genome organization with respect to clinical strains. In fact, clinical strains have 13.5 kb of additional genome sequence which present a particular orientation in clinical strains. Moreover, due to the intrinsic slow HCMV replication in cell culture, the generation of mutants for studying different phenotypic characteristics is extremely cumbersome and time consuming.

Consequently, it was the object of the present invention to provide a possibility to in vitro produce HCMV virus that still retains the pathogenic characteristics of clinical isolates. Further objects of the invention are to provide vectors containing the viral genome that allow to mutagenize the viral genome for e.g. studying the function of specific regions of the genome or to provide for mutated virus that can be used e.g. for vaccine production.

These objects are solved by the present invention as described in the following:

A first subject of the present invention is a recombinant vector containing DNA sequences of human cytomegalovirus (HCMV) and being useful for the production of reconstituted HCMV virus retaining phenotypic characteristics of a clinical virus isolate including the ability to grow on endothelial cells and to induce microfusion events, such recombinant vector being characterized in that it is obtainable by inserting the infectious genome from a clinical isolate of HCMV virus into a bacterial cloning vehicle.

Within the context of the present invention it has been observed that low passage clinical isolates retained both the broad cell tropism observed in vivo and the capability to transfer virus via microfusion to PMNL (ref 11). The invention is based on the surprising finding that cloning clinical isolates of HCMV virus in the so-called BAC system (WO99/06582) provides for the first time the possibility to in vitro produce HCMV virus that shows at least the most important characteristics of HCMV virus. These are above all the ability to grow on endothelial cells and to induce microfusion events to promote transfer of viral particles between cells. From the standpoint of the present knowledge about HCMV infection, these two characteristics seem to be most important for the infectivity of wild-type virus. Especially the use of the BAC system opens the possibility of propagation of stable HCMV genetic material in a heterologous biological system as e.g. *E. coli*. In particular, the accumulation of mutations during the HEF adaption procedure, which is ultimately responsible for the loss of broad tissue tropism by presently available reference laboratory adapted strains, is avoided. Thus, a recombinant vector according to the present invention provides the possibility to in vitro produce a new reference strain for genetic analysis of HCMV strains circulating in vivo. The vector according to the present invention provides a genetic background encoding phenotypic characteristics crucial for HCMV pathogenesis in vivo.

The recombinant vector according to the invention, apart from providing the possibility to produce infectious virus in vitro, also represents a unique reagent for identifying viral genes and viral gene functions, which are crucial for HCMV pathogenesis. In fact, it retains the complete gene structure of HCMV strains present in vivo and virus produced therefrom retains key known pathogenetic characteristics, namely endothelial cell tropism and microfusion phenotype and most likely others like Nk-cell resistance and infection of bronchoepithelial cells and chondrocytes as well as dendritic cells, monocytes and/or macrophages. Maintainance and replication of the recombinant vector including the viral genome is dissociated from replication of the virus in cell culture, but is preserved by replication of the viral DNA in the bacterial system. This provides a solution to obtaining standard genetic material for biological studies.

In a preferred embodiment of the present invention the recombinant vector contains the complete infectious genome of HCMV and lacks only genes US2-US6 which are not required for virus replication nor for HUVEC or PMNL tropism. However, it is also possible to produce mutants that lack at least part of the DNA or contain substitutions in the DNA. In this way, virus mutants can be produced specifically by deleting or substituting parts of the DNA. This allows to study and map the gene functions of HCMV easily. In principle any bacterial cloning system can be used to insert HCMV DNA, as long as it retains the ability for DNA replication in suitable host cells and is able to coreplicate the viral DNA. It is preferred to use cloning vehicles that are present with a low copy number in the host cell to achieve better stability of the viral sequences in the recombinant vector.

In a further preferred embodiment the recombinant vector according to the invention is produced using a bacterial cloning vehicle that contains DNA sequences which are homologous to the HCMV DNA and insertion is effected by homologous recombination. In an especially preferred embodiment the bacterial cloning vehicle is a BAC system vector, as described in WO99/06582, which is already mentioned above. The disclosure of WO99/06582, especially as far as it relates to the preparation of vectors and insertion of viral genome, is herewith incorporated by reference.

An especially preferred recombinant vector is designated FIX-Bac-7 and has been deposited as described in the following. This recombinant vector is especially useful for studying functions of HCMV virus or producing HCMV virus, since it contains an infectious HCMV virus genome with preserved wildtype characteristics stably integrated into a BAC system vector. FIX-Bac-7-vector can be propagated like a normal recombinant vector and does not lose the viral DNA or functions.

A further subject of the present invention is a bacterial culture which contains a recombinant vector according to the invention. Such bacterial culture is able to reproduce recombinant vector and preferably such a bacterial culture is an *E. coli* cell line, especially *E. coli* DH10B. In a most preferred embodiment such bacterial culture according to the invention contains at least one copy of FIX-Bac-7, and is designated FIX-Bac-7-*E. coli* DH10B. This cell line has been deposited with the Deutsche Sammiung von Mikroorganismen und Zelikulturen GmbH-DSZM as DSM 13958 on Dec. 14, 2000.

Further subjects of the present invention are uses of the recombinant vector according to the invention. One preferred use is the production of reconstituted HCMV virus retaining the phenotypic characteristics of a parental clinical isolate including the ability to grow on endothelial cells and to induce microfusion.

As described above, these two characteristics are considered as being most important for retaining the infectivity of wild-type HCMV. However, it is to be understood that within the context of the present invention also other characteristics of wild-type virus may be conserved during the production as described in claim. Especially features like HUVEC- and/or PMNL-tropism are also considered important and are preferably retained by the HCMV virus which is reconstituted according to the present invention.

For the production of reconstituted HCMV virus it is preferred to transfect the recombinant vector into a suitable eukaryotic host cell and collect the reconstituted infectious virus after culturing of the cells.

A suitable eukaryotic host cell is a permissive cell which allows the virus to replicate and virus particles being formed. The reconstituted infectious HCMV virus obtained according to the present invention can e.g. be used for the production of vaccines and/or antibodies. It can also be used for the screening of drugs for their antiviral activity as well as generally for other potential uses of virus. Such uses are further subjects of the present invention. It has been observed that in some cases the packaging of the virus particles is impaired, obviously due to the presence of vector sequences in addition to virus genome. In such a case it is preferred to remove the sequences of the cloning vehicle from the recombinant vector prior to replication and packaging. In such embodiment it is further preferred to use a cloning vehicle that contains flanking sequences which are homologous to sequences of the virus to allow the removal of at least part of the cloning vehicle by homologous recombination or to flank the Bac vector with loxP sites for removal with cre recombinase. For virus production from the recombinant vector it is again referred to WO99/06582 describing such methods in principle.

Still further subjects of the present invention are the use of recombinant vectors according to the present invention for vaccine development and/or for the development and/or screening of substances which inhibit viral gene production on transcriptional and/or translational level.

The concept of prophylactic vaccination using live attenuated viral strains led in the early 70ies to the generation of the Towne strain, after extensive passaging (>135 passages) of a clinical isolate of fibroblast culture. This live vaccine, when administered to humans, proved to be ineffective at protecting individuals from HCMV infections (refs 14-20). Strikingly, infection with vaccinal strain could raise antibody titers as well as cellular response. However, these responses were not protective. Today it is known that the Towne strain lost large genomic regions during fibroblast adaption. Other approaches include subunit vaccines again targeting gene products identified and characterized in attenuated strains. Finally, the generation of chimeric viruses using the Towne strain and a low passage isolate (Toledo) has been proposed (refs 12, 13), however, both Towne and Toledo lack key characteristics associated with HCMV pathogenesis in vivo. In particular, they lack both endothelial cell tropism and the microfusion phenotype. Thus, using such a vaccine it was not possible to raise an efficient immunologic response against these important viral encoded functions.

The identification of genetic determinants for tissue tropism and body dissemination will lead to the design of better prophylactic and therapeutic vaccines. In this respect, the identification of the genetic determinants for endothelial cell tropism and for transfer of virus from productively infected cells to PMNL appear of particular importance. In fact, it is known that during active HCMV infection in immunocompromised patients endothelial cells are productively infected, while it is thought that endothelium might be the major reservoir for latent HCMV infection (refs 1, 21-28). Finally, the importance of HCMV infected PMNL in viral dissemination is highlighted by (i) the possibility to detect such cells in immunocompetent persons only during primary infection, (ii) relation to viral transmission of HCMV to the fetus in pregnant women (refs 2, 3, 7, 29) and (iii) the tight correlation between the number of HCMV infected PMNL and the severity of clinical symptoms (ref 30). It is therefore evident that production of vaccines by using either the recombinant vector according to the invention or reconstituted infectious HCMV virus that is produced according to the invention opens the possibility to raise vaccines that not only raise antibodies but also protect the patient against HCMV infections and its consequences.

For drug discovery as well as for vaccine production, determinants for viral pathogenicity will be obvious targets for chemotherapeutic intervention. The generation of target specific antiviral drugs can be achieved in different ways:
1. The identification of gene products responsible for crucial biological functions (tropism for particular cell types, microfusion) might lead to the reconstruction of biochemical systems for screening of large collections of compounds; helpful will also be a random transposon mutagenesis of FIX-Bac-7 and reconstitution of mutants from transposon libraries.
2. Peptides or small molecules interfering with protein-protein interactions can be synthesized by available computer-assisted chemical modelling;
3. Inhibition of viral gene product synthesis can be achieved by interference at transcriptional or translational level using established gene therapy approaches.

Therefore also the use of a recombinant vector or a reconstituted HCMV virus for the development and/or screening of substances which inhibit viral gene production on transcriptional and/or translational level are preferred embodiments of the present invention.

Within the investigational work of the present invention it has further been established that the region UL130 to UL132 of HCMV virus is responsible for the ability of the virus to induce microfusion events in PMNL and HUVEC tropism. Hence, a virus mutant which is deleted or mutated in this region of the viral genome in such a way that the ability to induce microfusion or HUVEC tropism is lost, is a further subject of the present invention. Such virus can easily be produced using the recombinant vector according to the present invention and deleting or mutating the mentioned region by methods that are known to the man in the art (see also Example 5). It is especially preferred to completely delete this region, however, partially deleting or mutating the region is also possible as long as the resulting mutant does not show microfusion induction or HUVEC tropism. Using the recombinant vector according to the present invention, it will be easily possible for the man in the art to track down the minimal mutation or deletion that is necessary to prevent induction of microfusion events or HUVEC tropism of a respective HCMV mutant.

It has further been established that the region UL128 to UL132 of HCMV virus is responsible for PMNL and/or HUVEC tropism. The genetic region spanning UL131 to UL128 seems to confer PMNL tropism, whereas HUVEC tropism is encoded within the genetic region of UL132 to UL128 genes. Mutants that contain deletions or mutations within this UL128 to UL132 region of HCMV virus are therefore another preferred embodiment of the present invention. Also for these mutants it is either possible to delete the complete region or to just partially delete or mutate the region and thereby reduce or prevent PMNL and/or HUVEC tropism.

Such HCMV virus mutants in comparison with RV-FIX-7 can advantageously be used for studying pathogenicity and its genetic basis. Especially studying interaction of adherent cells with wild-type virus in comparison with mutant virus will reveal further mechanisms of infection by HCMV virus. Such use of the mutants and RV-FIX-7 therefore are a further preferred embodiment of the present invention. The HCMV virus mutants which affect the genetic region UL132-128 of the invention, lacking the ability to induce microfusion, also have lost the ability to grow on endothelial cells. The cell tropism of this mutant is also changed. The virus mutant seems to indicate a potentially novel mechanism of HCMV infection by a cell to cell infection pathway not through the natural receptor but through cell fusion events. Thus, avoiding the need to exit the cell for reinfection, but rather spreading genetic material from cell to cell through a plasma bridge. Also these mutants and RV-FIX-7 are targets for the development of vaccines and/or antibodies or the design of small molecules and peptides. Such vaccines and antibodies will provide at least some protection against HCMV virus infection.

Further possible uses of the HCMV virus mutants and RV-FIX-7 according to the invention are use in diagnostics, for drug screening, as attenuation marker, for the development of modified vectors, for the development of peptides or antisense genes or antisense RNA, which block the activity of the microfusion gene and wild-type virus and/or for the screening for such peptides, antisense genes or antisense RNA. A still further use is the studying of innate as well as adapted immune surveillance and immune counterstrategies as e.g. NK-cell resistance of virally infected target cells, cytotoxic and helper T-cell recognition, impact of tissue tropism on HCMV latency and reactivation. Also studying the impact on classic (HLA-A,B,C) and non classic (HLA-E, HLA-G, MIC A/B) MHC regulation on infected target cells (fibroblasts, endothelial cells, dendritic cells, trophoblasts, bronchoepithelial cells, smooth muscle cells) as well as induction or prevention of apoptosis and cell suicide.

Such applications and uses will be well aware to the man in the art upon reading the disclosure of the present invention. Providing a stable system for in vitro production of infectious HCMV virus, tracking down the microfusion gene in the viral region UL131 to UL128 and the HUVEC cell tropism region between UL128 and UL132 as well as the provision of the possibility to easily produce virus mutants allow for the first time to study infectious HCMV virus activities and properties with a standardized virus strain, and the thus provided possibility to mutate in vitro a virus that corresponds to a clinical isolate opens tremendous possiblities for studying functions and ways of infections and their consequences for the infected person.

The possibility to produce infectious virus as well as mutants of infectious virus or antigens contained in the genome of the infectious virus opens new outlooks for vaccine development and drug design as well as drug screening.

The examples of the present invention contain disclosure on several different mutants and transcriptional analyses that were used to track down the genetic regions responsible for microfusion as well as cell tropism. These mutants are especially preferred mutants according to the present invention and are further subjects of the present invention.

The present invention will be further explained by the following example and figures:

FIGS. 1A-E:

HUVECs were infected with low MOI (1A-B) or high MOI (1C-D) with either clinical wild-type isolate VR1814 (1A-C) or bac-cloned and reconstituted virus RV-FIX-7 (1B-D). Staining was done with an ie 1/2 mab as primary antibody and an anti-mouse peroxidase labelled mab as secondary antibody (1A-D). VR1814 (1E) or RV-FIX-7 (1F) infected HUVECs were cocultivated with peripheral blood polymorphonuclear leukocytes (PMNL) and the lower matrix phosphoprotein (pp65) was detected in the nuclei of PMNL by indirect immunofluorescence.

FIGS. 1E-F demonstrate that RV-FIX-7 (1F) retained the capability to infect HUVECs and induce microfusion as compared to WT virus VR1814 (1E).

The pp65 staining was performed as described in Journal of Microbiology 36, 3585-3589, 1998.

FIG. 2

DNA derived from individually grown FIX-Bac clones (lanes 1-5 and lanes 7-11) or wild-type VR1814 (lanes 6 and 12) was digested with either EcoRI (lanes 1-6 or BglII (lanes 7-12) and separated on a 0.5% agarose gel. The restriction cut and subsequent Southern Blot analyses confirmed the correct integration of the gpt-bac cassette between US1 and US7. In the EcoRI restriction cut a 5.9 kb band arises due to the integration of the gpt-Bac cassette. An "a" sequence polymorphism could also be confirmed which arises due to a shuffling of "a" sequences at the internal and terminal repeats during the replication of HCMV.

M: molecular weight marker 1 kb ladder.

Analyses were performed as previously described (Journal of Virology, 8320-8329, 1999).

FIG. 3

DNA derived from individually grown FIX-Bac-7 clones (lane 1 and 6) or FIX-Bac-7 mutant clones Δ-ULB' (lanes 2-3 and lanes 7-8) or ΔULB 130-132 (lanes 4-5 and lanes 9-10) was digested with either HindIII (lanes 1-5) or BglII (6-10), respectively, and run on a 0.5% agarose gel. A novel band at around 6.5 kb arises in both mutant clones in the HindIII restriction cut. An additional band at around 4.7 kb arises in the Δ-ULB' clones in the HindIII cut as compared to the parallel clone FIX-Bac-7. The generation and testing of the mutants is described in the text.

M: molecular weight marker 1 kb ladder.

FIG. 4:

DNA derived from individually grown Towne-long-Bac (TowneL), Towne-short-Bac (TowneS), Phoebe-Bac, Powers-Bac and TB40E-Bac clones was digested with either EcoRI (lanes 1-2 and 4-6) or BglII (lanes 8-9 and 11-13) and separated on a 0.5% agarose gel. The restriction cut and subsequent Southern Blot analyses confirmed the correct integration of the gpt-bac cassette between US1 and US6/7. In the EcoRI restriction cut a 5.9 kb band arises due to the integration of the gpt-Bac cassette. An "a" sequence polymorphism could also be confirmed which arises due to a shuffling of "a" sequences at the internal and terminal repeats during the replication of HCMV.

M: molecular weight marker 1 kb ladder.

Analyses were performed as previously described (Journal of Virology, 8320-8329, 1999).

Figure 5A:
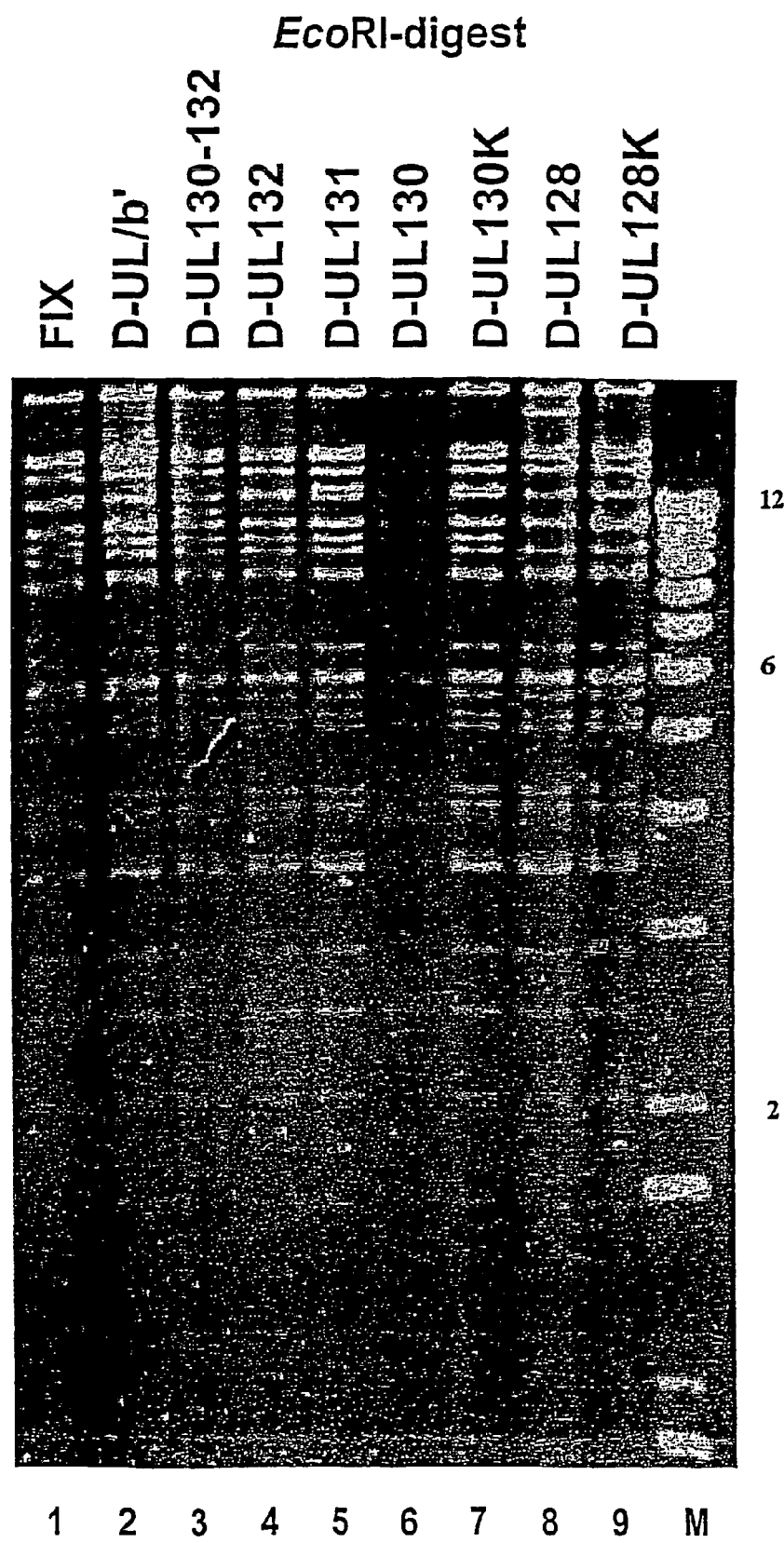
Figure 5B:
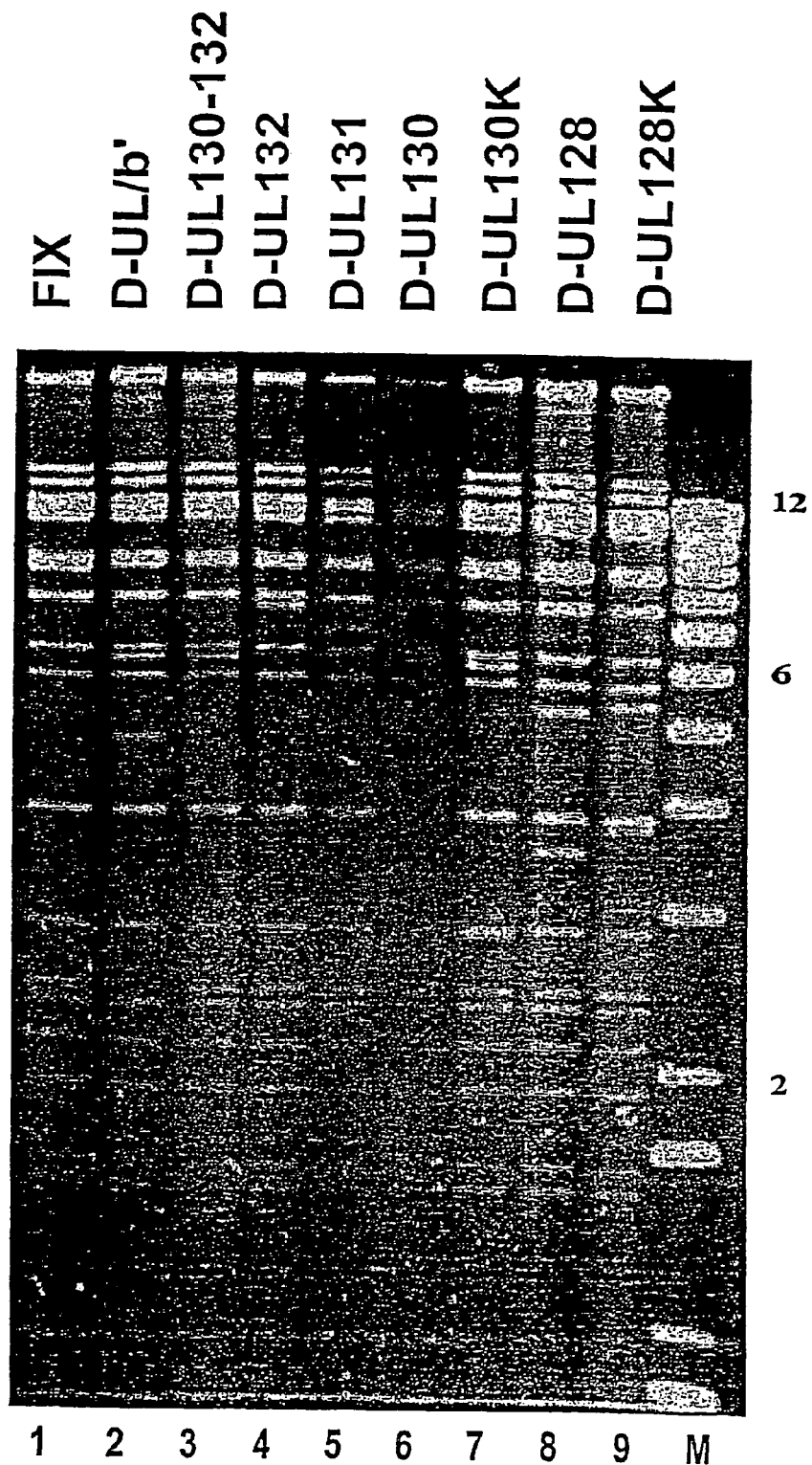

FIGS. 5a and 5b:

DNA derived from individually grown FIX-bac-7 bacmid clones (lane 1) or FIX-bac-7 mutant bacmid clones Δ-UL/b' (lane 2), Δ-UL130-132 (lane 3), Δ-UL132 (lane 4), Δ-UL131 (lane 5), Δ-UL130 (lane 6), Δ-UL130K (lane 7), Δ-UL128 (lane 8), Δ-UL128K (lane 9) was digested with either EcoRI (FIG. 5a) or HindIII (FIG. 5b), respectively, and run on a 0.5% agarose gel. By probing with the pAcyc177 probe (for detection of the correct integration of the kanamycin resistance gene) the predicted bands can be detected by Southern Blot hybridization in the HindIII digest (FIG. 5b): a 6.5 kb and 4.7 kb band in Δ-UL/' (lane 2), a 6.5 kb and 1.3 kb band in Δ-UL130-132 (lane 3), a 7.5 kb and 1.3 kb band in Δ-UL132 (lane 4), a 7.0 kb and 2.2 kb band in Δ-UL131 (lane 5), a 6.0 kb and 2.8 kb band in Δ-UL130 (lane 6), a 6.0 kb and 2.8 kb band in Δ-UL130K (lane 7), a 5.2 kb and 3.6 kb band in Δ-UL128 (lane 8) and a 5.3 kb band in Δ-UL128K (lane 9).

M: molecular weight marker 1 kb ladder. Analyses were performed as previously described (Journal of Virology, 8320-8239, 1999).

FIG. 6: shows the following sequence comparisons:
a) Comparison RACE clone1 (Bases 2 . . . 1754 of SEQ ID NO:15) to FIX genomic sequence (Bases 4803 . . . 6782 of SEQ ID NO:1);
b) Race clone 3-10 (Bases 2 . . . 1882 of SEQ ID NO:7) to FIX genomic sequence (Bases 4793 . . . 6793 of SEQ ID NO:1);
c) Race clone 1 (Bases 1 . . . 1777 of SEQ ID NO:15) to RACE clone 3-10(Bases 11 . . . 1895 of SEQ ID NO:7);
d) RACE clone 1, (SEQ ID NO:15), 3-10(Bases 12 . . . 1940 of SEQ ID NO:7), 75-3 (Bases 12 . . . 1411 of SEQ ID NO:16), 72-2-4 (Bases 12 . . . 756 of SEQ ID NO:13) to FIX genomic sequence (designated VR7) (Bases 4501 . . . 7646 of SEQ ID NO:1);
e) RACE clone 1(SEQ ID NO:15), 3-4(SEQ ID NO:6), 3-10 (Bases 12 . . . 1940 of SEQ ID NO:7), 75-3(Bases 12 . . . 1411 of SEQ ID NO:16), 57-5-2(SEQ ID NO:52), 57-5 (Bases 12 . . . 651 of SEQ ID NO:8), 57-6(SEQ ID NO:53), 72-8(Bases 1 . . . 888 of SEQ ID NO:27), 73-8(SEQ ID NO:54), 74-5(Bases 12 . . . 686 of SEQ ID NO:18), 75-5 (SEQ ID NO:55) to Fix genomic sequence (designated VR7) (Bases 4701 . . . 6890 of SEQ ID NO: 1).

FIG. 7: shows fast sequence alignment of
a) FIX7(SEQ ID NO:1)-HCU 33331 (SEQ ID NO:56);
b) TB40E4(SEQ ID NO:4)-HCU 33331 (SEQ ID NO:57);
c) PAN1(SEQ ID NO:2)- HCU 33331 (SEQ ID NO:58);
d) TB40E4(SEQ ID NO:13)-FIX7 (SEQ ID NO:1);
e) TB40E1(SEQ ID NO:3)-TB4OE4 (SEQ ID NO:4);
f) TB40E1(SEQ ID NO:4)-FIX7 (SEQ ID NO:1);
g) PAN1(SEQ ID NO:2)-TB40E4 (SEQ ID NO:4);
h) PAN1(SEQ ID NO:2)-FIX7 (SEQ ID NO:1).

The sequence listing contains the following sequences:
SEQ ID NO:1 FIX7,
SEQ ID NO:2 PAN1,
SEQ ID NO:3 TB40E1,
SEQ ID NO:4 TB40E4 and the RACE sequences:
SEQ ID NO:5 Seq57-5-2-,
SEQ ID NO:6 Seq3'-4-,
SEQ ID NO:7 Seq3-10-,
SEQ ID NO:8 Seq57-5-,
SEQ ID NO:9 Seq57-6-,
SEQ ID NO:10 Seq57-7-,
SEQ ID NO:11 Seq72-1-10-,
SEQ ID NO:12 Seq72-2-17-,
SEQ ID NO:13 Seq72-2-4-,
SEQ ID NO:14 Seq72-5-,
SEQ ID NO:15 Seqrace(1)-,
SEQ ID NO:16 Seq75-3-,
SEQ ID NO:17 Seq74-4-,
SEQ ID NO:18 Seq74-5-,
SEQ ID NO:19 Seq74-8,
SEQ ID NO:20 Seq75-1-,
SEQ ID NO:21 Seq75-4-,
SEQ ID NO:22 Seq76-7-,
SEQ ID NO:23 Seq75-5-,
SEQ ID NO:24 Seq77-14-
SEQ ID NO:25 Seq73-8-,
SEQ ID NO:26 Seq75-17-,
SEQ ID NO:27 Seq72-8,
SEQ ID NO:28 Seq74-3-.

EXAMPLE 1

Characterization of VR1814

HCMV virus strain VR1814 was isolated from cervical secretions and passaged in HEF 43 times. Before BAC cloning, VR 1814 was cultured in HUVEC for 2 months. HUVEC (human umbelical vein endothelial cell)-tropism and PMNL-tropism of VR1814 were determined by: i) propagating VR1814 in primary HUVEC cultures (Revello et al., J. Gen. Virol., submitted) and ii) coculturing purified PMNL with HUVEC infected with VR1814, following by immunologic staining of positive PMNL (Revello, J. Clin. Invest. 1998; Gerna et al.)(FIG. 1A-E).

EXAMPLE 2

Cloning of the Clinical HCMV Isolate VR1814 as FIX (Fusion Inducing Factor X)-Bac (Bacterial Artificial Chromosome) in E. coli. Generation of the FIX Recombinant Containing the Bac Vector The HCMV recombinant virus was generated by homologous recombination in cell culture. The plasmid pEB 1997 (Borst et al., J. Virol 73, 8320-8329, 1999) was linearized with the restriction enzyme Xcml. pEB1997 contains a tk-gpt-bac-cassette flanked with HCMV homologous sequences of US1-US2 (nt 192648 to 193360) on the right side and US6-US7. (nt 195705-197398) on the left side of the cassette. HFF cells (human forescin fibroblasts) ($1\times10^7$ cells) were transfected with 35 µg of linearized plasmid pEB1997 using a Gene Pulser II (Biorad). Conditions of transfection were 960 µF, 220V. Cells were seeded in a T25 tissue culture flask and cultured overnight in DMEM supplemented with 5% FCS. After 24 h the monolayer was washed once with PBS and infected with an MOI 5 (moiety of infection) using the HUVEC grown clinical isolate VR1814 from Example 1 for 6 h. Cells were washed after infection and DMEM 5% FCS was added. Cells were cultured for 2 weeks until 100% CPE (cytopathogenic effect) was reached. Infected cells and supernatant were used to infect a new flask of a confluent monolayer of HF cells for 6 hours. Cells were washed carefully with PBS and selection medium was applied containing (100 µM xanthine and 25 µM mycophenolic acid). After 3 weeks when 100% CPE was reached, cells and supernatant were used for two successive rounds of infection and selection in tissue culture.

EXAMPLE 3

Generation of the FIX-Bac in E. coli

After three rounds of selection in tissue culture the cell monolayer was washed with ice cold PBS and cells were lysed in 1 ml TES-buffer (10 mM Tris Cl pH 7.4, 10 mM EDTA pH 8.0, 0.6% SDS). To obtain circular viral intermediates a modified HIRT extraction was applied. The sticky lysate was poured into a 2 ml eppendorf vial and 0.3 ml 5 M NaCl was added and carefully mixed. After 24 h of incubation at 4° C. cellular DNA and proteins was pelleted out by centrifugation at 14.000 rpm for 30 min. The supernatant containing the circular intermediates was phenol/chloroform extracted once and subsequently precipitated in 2½ volumes of 95% ethanol and 0.1×3 M Na-acetate (pH 5.2) for 24 h at −20° C. DNA was pelleted at 14000 rpm at 4° C. for 30 min and washed with 70% ethanol. The dry DNA pellet was resuspended in 100 µl destilled water and allowed to dissolve for 24 h. Twenty-five µl of viral DNA was electroporated into E. coli DH10B using a Gene Pulser II (Biorad). Conditions were 200 Ohm, 25 µF, 2.3 kV. After incubation in LB for 2 hours at 37° C., bacteria were spun for 30 sec at 6000 rpm, resuspended in 100 µl of LB medium and plated onto agar plates containing chloramphenicol. After 48 h colonies were picked and grown in liquid culture for bacmid preparation as previously described (ref 31). FIG. 1 shows the EcoRI and Bgl II restriction pattern of 5 representative clones of FIX-Bac compared to WT-virus. Since the unit long (UL) and unit short (US) region of HCMV can flip relatively to each other, two isomeric forms can be observed in E. coli. Additional polymorphism is added by the number of "a" sequence repeats in the terminal and internal repeat region which vary in individual clones.

EXAMPLE 4A

Reconstitution of Infectious Virus from FIX-Bac

To recover infectious virus from FIX-Bac clones, DNA was prepared using Nucleobond columns as previously described (ref 31). 1 µg of DNA was added to 10 µl Superfect (Gibco) and 80 µl of RPMI and incubated for 30 min to allow DNA complexes to form. A subconfluent layer of MRC-5 fibroblast in a 6 well dish seeded for 24 h was serum starved for 30 min in RPMI. Medium was completely removed after 30 min and replaced with 1 ml DMEM 5%. FCS over 6 well. The DNA transfection mix was diluted with 100 µl of DMEM 5% FCS and added to the cells of a 6 well. After 4 h the transfection mix was removed and 2 ml of fresh DMEM 5% FCS was added per well. After 1 week cells were split into a new flask (T25) and cultured until 100% CPE is achieved.

EXAMPLE 4B

Phenotypic Characterization of Reconstitued RV-FIX-Bac-Viruses

Figure 2:
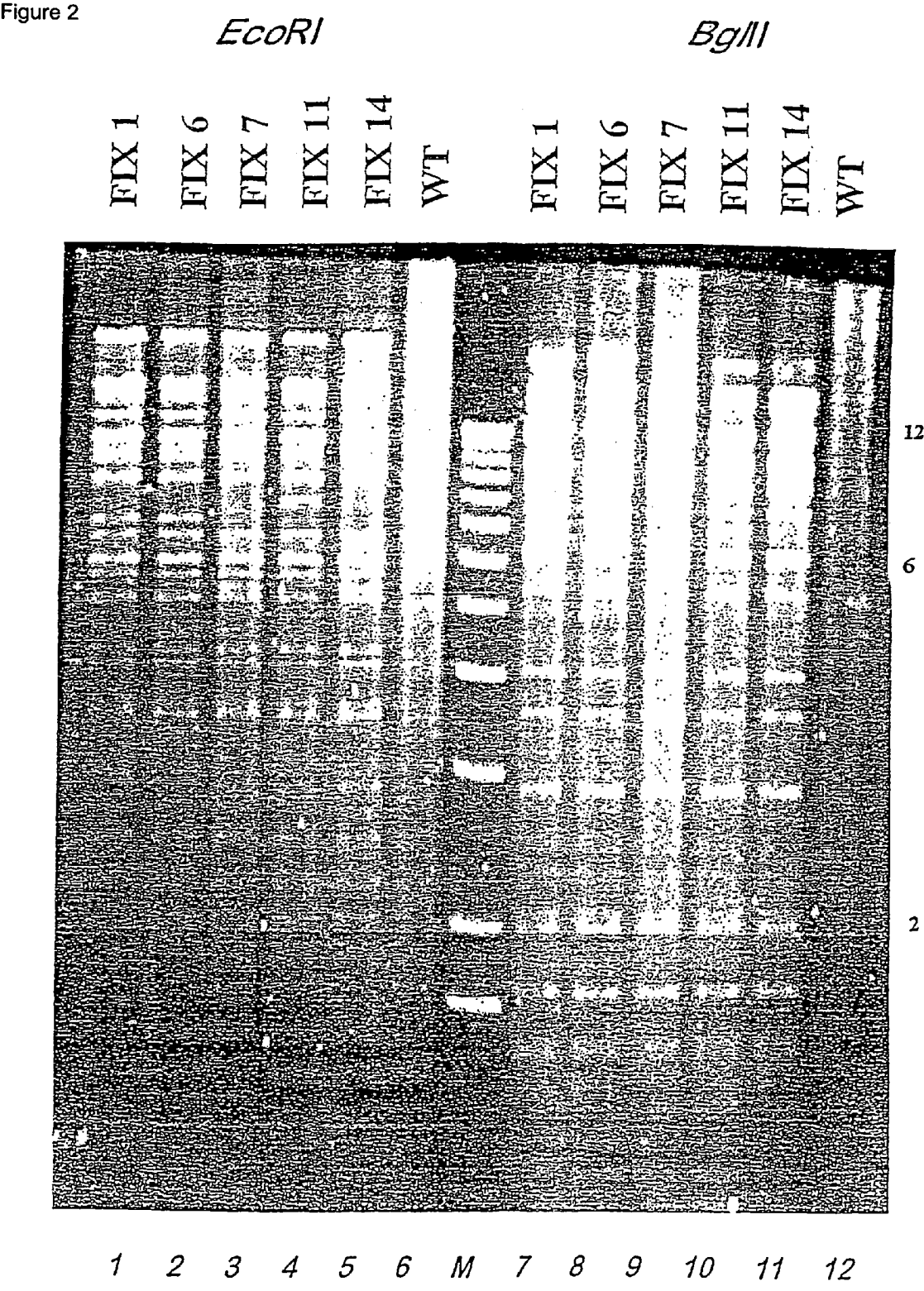

Infectious viruses were reconstitued from transfection of FIX-Bac clones #1, #6, #7, #11 and #14 (referred to as RV-FIX-1, RV-FIX-6, RV-FIX-7, RV-FIX-11 and RV-FIX-14, respectively) in HEF cells. Reconstituted viruses (RV) were then assayed for HUVEC-tropism and PMNL-tropism as reported. All RV-FIX-Bac derived viruses retained the phenotype observed in the parental VR1814 isolate (FIG. 2).

EXAMPLE 5

Mutation

To identify the region in the FIX-Bac-7 genome responsible for microfusion induction and endothelial cell tropism, 13.8 kB of the ULb' region were removed (mutant referred to as Delta-ULb'; primers P-ULb' and P-132) using homologous recombination with a linear PCR fragment in a recombination proficient E. coli strain. A second mutant was generated which specifically deleted the beginning of ULb' region namely UL130-132 (referred to as Delta-UL130-13; primers P-132 and P-130) which is inverted in orientation in the clinical isolates as compared to the low passage isolate Toledo. The primers used for generation of the linear PCR fragments with plasmid pAcyc177 (New England Biolabs) as a template were as follows:

```
P-ULb':                                    (SEQ ID NO:29)
5'-CGC TGT AGG GAT AAA TAG TGC GAT GGC GTT TGT GGG
AGA ACG CAG TAG CGA TGG GTT GCG ACG TGC ACC GAT
TTA TTC AAC AAA GCC ACG-3'

P-130:                                     (SEQ ID NO:30)
5'-AAC GGC GTC AGG TCT TTG GGA CTC ATG ACG CGC GGT
TTT CAA AAT TCC CTG CGC GCG CGA CGG GCG CCA GTG
TTA CAA CCA ATT AAC C-3'

P-132:                                     (SEQ ID NO:31)
5'AAA CCA CGT CCT CGT CAC ACG TCG TTC GCG GAG ATA
GCA AGA AAT CCA CGT CGC CAC ATC TCG AGA CGA TTT
ATT CAA CAA AGC CAC G-3'
```

The mutant viruses were reconstituted in MRC-5 cells as described under Example 4a. Testing of the Delta-ULb' and Delta-UL130-132 mutants for capacity to induce microfusion or efficiently infect endothelial cells reveiled a loss of both phenotypes. Thus, the genetic region UL130-132 is inducing both microfusion and endothelial cell tropism and the deletion of the region in the clinical isolate leads to the loss of phenotype described.

A control mutant deleting the region UL45 in the genome of FIX-Bac-7 generated according to the same method (and referred to as Delta-UL45) retained the ability to induce microfusion and grow in endothelial cells. PCR primers used for generation of this mutant were:

```
P-45.1:                                    (SEQ ID NO:32)
5'-GCC AGT GGT ACC ACT TGA GCA TCC TGG CCA GAA GCA
CGT CGG GCG TCA TCC CCG AGT CAT AGT AGC GAT TTA
TTC AAG AAA GCC ACG-3'

P-45.2:                                    (SEQ ID NO:33)
5'-ACA CAT CGC ACA CAG ACT TTA TAA ACC GTA GTT GTC
GGC GCC ATC TAG ACT CAC TTT ATT GAA AGC CAG TGT
TAC AAC CAA TTA ACC-3'
```

Thus, the capacity to induce microfusion may reflect a novel mechanism of HCMV to spread its genome from cell to cell and infect cells which do not express the as yet elusive natural receptor of HCMV. Consequently, the genetic region UL130-132 is a crucial determinant for tissue tropism and pathogenesis of HCMV.

Figure 3:
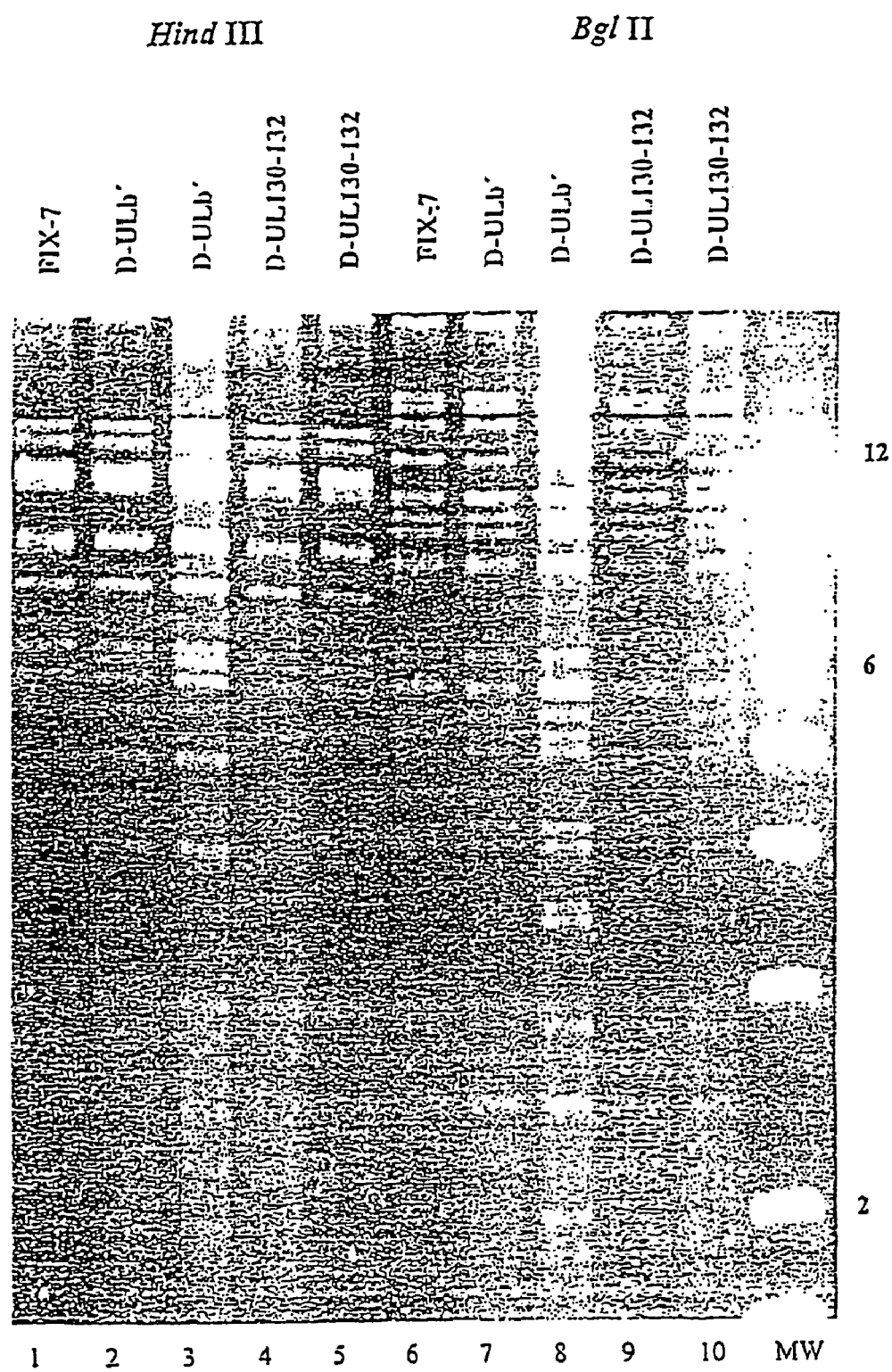

FIG. 3 shows HindIII and BglII restriction patterns of the FIX-Bac mutant clones in comparison to the parental clone (FIX-7).

EXAMPLE 6

As further examples for feasibility of the cloning of clinical isolates of HCMV as bacterial artificial chromosomes in *E. coli*, the clinical isolates Phoebe, Powers and TB40E were cloned as bacmids according to the method described above. Additionally the vaccine strains Towne-long and Towne-short were cloned as bacmids to prove that the method of bac cloning is also feasible for cloning of vaccine strains fo HCMV. Phoebe-Bac, Powers-Bac and TB40E-Bac were deposited with the Deutsche Sammiung für Mikroorganismen und Zelikulturen (DSZM), under DSM 14358 (Phoebe-Bac), DSM 14359 (Powers-Bac) and DSM 14360 (TB40E-Bac).

Figure 4:
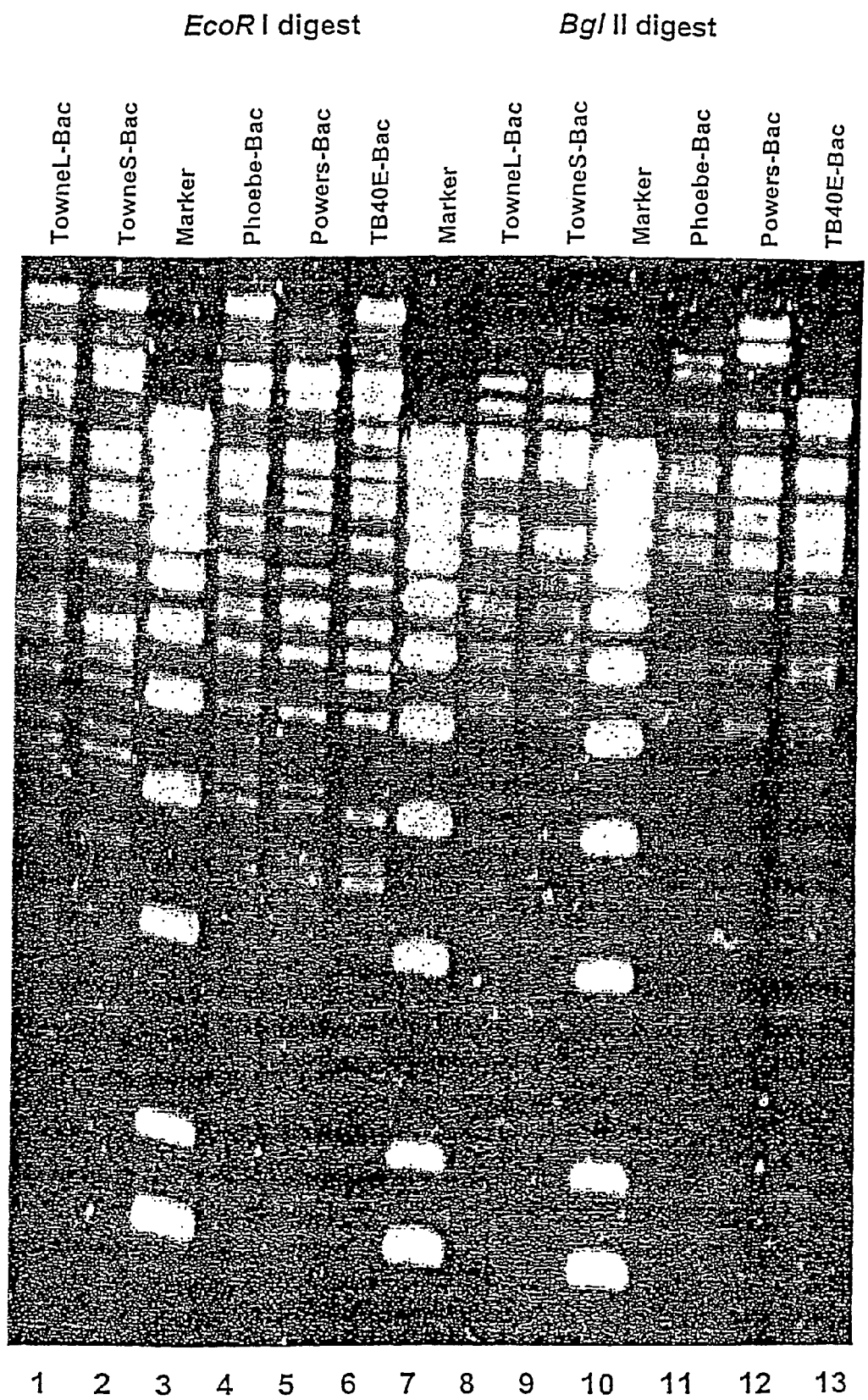

Analyses of the bacmids are shown in FIG. 4.

EXAMPLE 7

Generation of FIX-bac-7 Mutants

A linear PCR fragment was generated using the kanamycin resistance gene from plasmid pAcyc177 (New England Biolabs) as a template. The primers used for generation of the linear PCR fragments have about 60 bp HCMV homolgous sequence on the 5' and 3' ends, respectively, and were designed as follows:

```
Mutant D-UL130
                                           (SEQ ID NO:34)
P-130-for: 5'-GCG CCA CAC GCC CGG AGC CTC GAG TTC
AGC GTG CGG CTC TTT GCC AAC TAG CCT GCG TCA CGG
CGA TTT ATT CAA CAA AGC-3'

(SEQ ID NO:30)
P-130-rev: 5'-AAC GGC GTC AGG TCT TTG GGA CTC ATG
ACG CGC GGT TTT CAA AAT TCC CTG CGC GCG CGA CGG
GCG CCA GTG TTA CAA CCA ATT AAC C-3'

Mutant D-UL130K
                                           (SEQ ID NO:35)
P-130-for-kons: 5'-CCC GGA GCC TCG AGT TCA GCG TGC
GGC TCT TTG CCA ACT AGC CTG CGT CAC GGG AAA TAA
TCG ATT TAT TCA ACA AGC CA CG-3'

(SEQ ID NO:30)
P-130-rev: 5'-AAC GGC GTC AGG TCT TTG GGA CTC ATG
ACG CGC GGT TTT CAA AAT TCC CTG CGC GCG CGA CGG
GCG CCA GTG TTA CAA CCA ATT AAC C-3'

Mutant D-UL131:
                                           (SEQ ID NO:36)
P-131-for: 5'-TGT CTT TCG GTT CCA ACT CTT TCC CCG
CCC CAT CAC CTC GCC TGT ACT ATG TGT CGA TTT ATT
CAA CAA AGC CAC G-3'

(SEQ ID NO:37)
P-131-rev: 5'-GCT AGT TGG CAA AGA GCC GCA CGC TGA
ACT CGA GGC TCC GGG CGT GTG GCG GCC AGT GTT ACA
ACC AAT TAA CC-3'

Mutant D-132
                                           (SEQ ID NO:31)
P-132-for: 5'-AAA CCA CGT CCT CGT CAC ACG TCG TTC
GCG GAC ATA GCA AGA AAT CCA CGT CGC CAC ATC TCG
AGA CGA TTT ATT CAA CAA AGC CAC G-3'

(SEQ ID NO:38)
P-132-rev: 5'-ATG AGA CAT CAT ACA CAT AGT ACA GGC
GAG GTG ATG GGG CGG GGA AAG AGT TGG AAC CGA AAG
GCC AGT GTT ACA ACC-3'

Mutant D-128
                                           (SEQ ID NO:39)
P-128-for: 5'-GCA CCC ATC CCA ATC TCA TCG TTT GAG
CCC GTC GCG CGC GCA GGG AAT TTT GAA AAC CGC GCG
TCC GAT TTA TTC AAC AAA GCC ACG-3'

(SEQ ID NO:40)
P-128-rev: 5'-TCG CGC GAC ATG AAT TTA GTC GGC GAC
AGA AAT CTC GAA ACG CGT ATT TCG GAC AAA CAC ACA
TGC CAG TGT TAC AAC CAA TTA ACC-3'

Mutant D-128K
                                           (SEQ ID NO:41)
P-128-for-kons: 5'-TGC GTT CTG TGG TGC GTC TGG ATC
TGT CTC TCG ACG TTT CTG ATA GCC ATG TTC CAT CGA
CGA TTT ATT CAA CAA AGC CAC G-3'

(SEQ ID NO:42)
P-128-kons2: 5'-CGG CAC ACA TCC AGC CGT TTG TGT
TTC TTA ACG CTC TCC AGG TAC TGA TCC AGG CCC ACG
GCC AGT GTT ACA ACC AAT TAA-3'
```

PCR was performed using the plasmid pAcyc177 as a template. FIX-bac-7 mutants were generated in a recombinant proficient E. coli strain by transformation of the respective purified PCR product into the FIX-bac-7 containing E. coli strain. The mutant clones were selected on chloramphenicol (12.5 µg/ml) and kanamycin (50 µg/ml) containing agarose plates. Subsequently, individual clones were picked and grown in Luria Bertani medium supplemented with chloramphenicol (12.5 µg/ml) and kanamycin (50 µg/ml). DNA of the resulting bacmid clones was analysed by restriction enzyme analyses and Southern Blot hybridization.

EXAMPLE 8

Determination of the PMN- and HUVEC Phenotype of the RV-FIX Mutants

All RV-FIX (reconstituted virus-FIX) mutant viruses were reconstituted from FIX-bab-7 mutant clones as previously described. Phenotypical testing for PMNL tropism and HUVEC tropism was also performed as previously described. Table 1 provides a summary of the virus mutant phenotypes. As a conclusion of phenotypical testing the mutant viruses we confer that PMNL tropism and induction of microfuesion events is encoded within the genetic region spanning UL131-UL128 genes and HUVEC tropism is encoded within the genetic region of UL-132-128 genes. Disruption of the genes UL131-128 abrogates both HUVEC and PMN tropism phenotype and consequently the genetic region between UL131 and UL128 is essentially required for PMNL tropism and induction of microfusion events of clinical HCMV isolates. Additionally UL132 gene is contributing to the HUVEC phenotype of clinical isolates of HCMV. Taken together we have identified a genetic region (UL132-128) within clinical isolates of HCMV which encodes important pathogenicity features of clinical isolates. The same region may also provide important pathogenicity factors for growth of clinical isolates in other cell types like dendritic cells, monocytes, macrophages, stem cells and may confer the resistance of clinical isolates of HCMV to NK cell recognition by coding for chemokine-like or cytokine-like factors. The genetic region of UL132-128 identified in FIX-bac-7 is therefore an important target for drug design, gene therapy and vaccine development against HCMV. We expect that the transfer of the UL132-128 genetic region of FIX-bac into the laboratory strain AD169 will confer HUVEC tropism, PMNL tropism and microfusion phenotype characteristics to the fibroblast adapted AD169 laboratory strain or any other virus strain.

TABLE 1

Testing of PMNL- and HUVEC-tropism of RV-FIX mutant viruses

| | experiment 1[a] PMNL-tropism | experiment 2 HUVEC-tropism |
| --- | --- | --- |
| RV-FIX WT | positive | growth on HUVEC |
| RV-FIX D-UL/b' | negative | no growth at passage 4 |
| RV-FIX D-UL130 | negative | no growth at passage 4 |
| RV-FIX D-UL131 | negative | no growth at passage 4 |
| RV-FIX D-UL132 | positive | no growth at passage 4 |
| RV-FIX D-UL130-132 | negative | no growth at passage 4 |
| RV-FIX D-UL130K | negative | no growth at passage 4 |
| RV-FIX D-UL128 | negative | no growth at passage 4 |
| RV-FIX D-UL128K | negative | no growth at passage 4 |
| RV-FIX D-UL45 | positive | growth on HUVEC |

[a]Two independent experiments are shown.

EXAMPLE 9

Transcript Mapping and Sequencing of the FIX-bac UL/b' Region

For mapping of the transcripts spanning the UL132-128 region 5' RACE (rapid amplification of cDNA ends) and 3' RACE procedures were performed using the Clontech SMART™ RACE cDNA Amplification kit according to the manufacturers' instructions. RNA was generated from RV-FIX infected fibroblasts (MOI 0.1) at day 7 p.i. using the Qiagen RNA extraction and mRNA purification kits.

Gene Specific RACE Primers were as follows:

For rapid amplification of cDNA ends (RACE) from the 5' RACE cDNA sample the following primers were used:

```
                                       (SEQ ID NO:43)
Primer 57-GSP1: 5'-CGG CAC ACA TCC AGC CGT TTG
TGT TTC TTA 3'

(SEQ ID NO:44)
Primer 72-GSP2-5'RACE-1: 5'-TAA CGC TCT CCA GGT
ACT GAT CCA GGC CCA -3'

(SEQ ID NO:45)
Primer 73-GSP-5'RACE-2: 5'TCG TCA GTT TGT TGT GTA
CGA CCT GGC GTG-3'

(SEQ ID NO:46)
Primer 74-GSP2-5'RACE-3: 5'TAT TGG CCT CGG TGA
ACG TCA ATC GCA CCT-3'
```

For rapid amplification of cDNA ends (RACE) from the 3' RACE cDNA sample the following primers were used:

```
                                       (SEQ ID NO:47)
Primer 56-GSP2: 5'-TGT GTC GGG TGT GGC TGT CTG TTT
GTC TGT-3'

(SEQ ID NO:48)
Primer 75-GSP2-3'RACE-1: 5'-TCT GCT TCG TCA CCA
CTT TCA CTG CCT GCT-3'

(SEQ ID NO:49)
Primer 76-GSP2-3'RACE-2: 5'-CGC AGA AGA ATG TTG
CGA ATT CAT AAA CGT-3'

(SEQ ID NO:50)
Primer 77-GSP2-3'RACE-3: 5'-GCT GCG GTG TCC GGA
CGG CGA AGT CTG CTA-3'

(SEQ ID NO:51)
Primer 78GSP2-3'RACE-4 5'-CCA GCT GGC AGA TTC
CCA AAC TAA TGA AAG-3'.
```

PCR products were subsequently cloned into pT-Adv vector using the AdvanTAge™PCR Cloning Kit (Clontech)

according to the manufacturers' guidance. Individual clones were screened for cDNA inserts by DNA preparation and EcoRI restriction cut. Insert containing clones were sequenced using M13 sequencing primers. The respective sequences of the 3'RACE and 5'RACE clones are attached as individual sequencing files: Clones RACE1, 3-4,3-10, 57-5-2, 57-5, 57-6, 57-7, 72-1-10, 72-2-4, 72-2-17, 72-5, 72-8, 73-8, 74-3, 74-4, 74-5, 74-8, 75-1, 75-3, 75-4, 75-5, 75-17, 76-7, 77-14.

A comparison of the FIX-Bac genomic sequence (designated VR) and individual RACE clones is depicted in FIG. 6:
a) Comparison RACE clone1 to FIX genomic sequence;
b) RACE clone 3-10 to FIX genomic sequence;
c) RACE clone 1 to RACE clone 3-10;
d) RACE clone 1, 3-10, 75-3, 72-2-4 to FIX genomic sequence (designated VR7);
e) RACE clone 1, 3-4,3-10, 75-3, 57-5-2, 57-5, 57-6, 72-8, 73-8, 74-5, 75-5 to FIX genomic sequence (designated VR7)

The genomic sequence of the UL/b' region of a clinical bacmid clone PAN1 is attached as sequence file (Seq Id No.2). Parts of the genomic sequence of the UL/b' region of FIX7-Bac (Seq Id No. 1), TB40E1-Bac (Seq Id No.3) and TB40-E4-Bac (Seq Id No.4) were also determined and are attached as sequencing files. In FIG. 7 the genomic sequences of PAN-Bac, FIX-Bac and TB40E-Bac were compared in a sequence alignment to the published genomic sequence of Toledo (gb:HCU 33331) and to each other using DNAman software:
Fast sequence alignment of
a) FIX7-HCU 33331;
b) TB40E4-HCU 33331;
c) PAN1-HCU 33331;
d) TB40E4-FIX7;
e) TB40E1-TB40E4;
f) TB40E1-FIX7;
g) PAN1-TB40E4;
h) PAN1-FIX7.

In summary, our RACE PCR analyses have identified several novel transcripts within the UL132 to UL128 region of FIX-bac. Two transcripts (RACE clone 3-10, RACE clone1 and RACE clone 3'-4) are of particular interest. They show that one major transcript of about 2.0 kb is covering the whole UL131-128 region (see FIG. 6*a-c*). RACE clone1, RACE clone 3'-4 and RACE clone 3-10 have a ployA tail and are spliced at the 3' end (position 1721 nt to 1845 nt referred to FIG. 6*e*). Both, RACE clone 1 and RACE clone 3'-4 have an additional splice at the 5' end (position 331 nt to 440 nt referred to FIG. 6*e*). The ATG start codon of these transcripts is at position nt 96 to nt 98 referred to FIG. 6*e*). The predicted 5' end of these three transcripts is presumably 10-50 bp upstream of the sequenced end of the clones (nt 50 to nt 100 referred to FIG. 6*e*). 5' ends of other transcripts in the UL131-128 region are shown in FIG. 6*d-e*) and could be mapped to nt 641 in clone 75-5; nt 717 in clone 57-5-2; nt 783 in clone 57-5; nt 438 in clone 74-5; nt 970 in clone 73-8 and nt 1150 in clone 72-8.

Since it was shown that the genetic region of UL132 to UL128 is the genetic determinant for induction of microfusion, HUVEC and PMN tropism, the identified transcripts running through this region are candidates for therapeutic intervention, drug design, vaccine development, attenuation of virus virulence, spread and antigenicity of the virus, latency and reactivation as well as immunological control of HCMV by immune cells (NK cells, T-cells, B-cells, dendritic cells, endothelial cells and monocytes, macrophages, hematopoietic precursors and stem cells). Ectopic transfer of the genetic region UL132-128 of FIX-Bac-7 or the respective identified cDNAs into a fibroblast adapted HCMV virus (for example AD169) will confer microfusion characteristics, cell to cell spread of virus material, HUVEC and PMNL tropism and possibly other pathogenicity features to the respective virus.

The invention claimed is:

1. A recombinant vector containing the infectious genome of human cytomegalovirus (HCMV) retaining phenotypic characteristics of a clinical virus isolate including the ability to grow on endothelial cells, to induce microfusion and to spread viral material from human umbilical vein endothelial cells (HUVEC) to polymorphonuclear leukocytes (PMNL), obtainable by inserting DNA from a clinical isolate of HCMV virus into a bacterial cloning vehicle wherein the recombinant vector is FIX-Bac-7.

2. A bacterial cell line containing a recombinant vector containing an infectious genome of human cytomegalovirus (HCMV) retaining phenotypic characteristics of a clinical virus isolate including the ability to grow on endothelial cells, to induce microfusion and to spread viral material from human umbilical vein endothelial cells (HUVEC) to polymorphonuclear leukocytes (PMNL), obtainable by inserting DNA from a clinical isolate of HCMV virus into a bacterial cloning vehicle;

wherein said bacterial cell line is designated FIX-Bac-7-*E.coli* DH 10B and deposited as DSM 13958 containing at least one copy of FIX-Bac-7.

* * * * *

UNITED STATES PATENT AND TRADEMARK OFFICE
CERTIFICATE OF CORRECTION

| | |
|---|---|
| PATENT NO. | : 7,700,350 B2 |
| APPLICATION NO. | : 11/180000 |
| DATED | : April 20, 2010 |
| INVENTOR(S) | : Gabriele Hahn |

Page 1 of 1

It is certified that error appears in the above-identified patent and that said Letters Patent is hereby corrected as shown below:

On the Title Page of the patent, please correct the Assignee as follows:

(73) Assignee: Delete "Vical Incorporated, San Diego, CA" and insert --The Wistar Institute of Anatomy & Biology, Philadelphia, PA--

Signed and Sealed this

Fourteenth Day of September, 2010

David J. Kappos
*Director of the United States Patent and Trademark Office*

SEQUENCE LISTING

<160> NUMBER OF SEQ ID NOS: 58

<210> SEQ ID NO 1
<211> LENGTH: 7646
<212> TYPE: DNA
<213> ORGANISM: Human cytomegalovirus

<400> SEQUENCE: 1

```
actgtggcta gaaactggtt acctgtgaag atggctgact atcctgttgt gtcctggaaa      60
agctttcagc gtcgtaggtg gactttgcag tatgcgggtt agtgaagtta tgtcatttat     120
ttacgtttac gatctcgtat tacaaaccgc ggagaggatg ataccgttcg gccccatgag     180 ttattttat tcttccggta ggaggcatga agcctctggt gatgcttatt ttgctgagta     240
tgctattggc atgcataggg aaaactgaaa tatgcaaacc cgaagaagtg caattaggaa     300
atcagtgttg tcccccatgt aaacaaggat atcgtgttac aggacaatgt acgcaatata     360
cgagtacaac atgtacactt tgccctaacg gtacgtatgt atcagggctt tacaattgta     420
ccaattgcac tgagtgtaat gacactgagg ttacaattcg taactgcact tccactaata     480
acaccgtatg cgcatctaag aattatacgt cgttgtccgt tccaggcgtc caacatcata     540
agcaacgaca aaatcatacc gcacatgtaa ccgtcaaaca agggaaaagt ggtcgtcata     600
```

```
ctctagcctg gttgtccctc ttcatctttc tcgtgggtat catacttttta attctctatc    660 ttatagccgc ctatcggagt gagagatgcc aacagtgttg ctcaatcggc aaaattttct    720
accgcaccct gtaagcttcc tgttgttgtt tttacatcac ggtgcgatga agtcacacag    780
ataattacag atgagctgtt catatttttt attattttt ccaattcctg cactaaaaaa    840
agaagcactt tacggaaccg tgtctgaata tctgtgggga atttaggtac tttttgccga    900
cgtcaggaaa aataagctgt cgcctacata agagcccggt gctatcgtgc tgtcactctt    960
tcttgttgcc ttcgatgtac ggcgtcctgg ctcattacta ctccttcatc agtagcccca   1020
gcgttatggt taattttaaa catcataacg ccgtgcagct gttgtgtgca cggacccgag   1080
acggcactgc cggatgggaa cgtttaaccc atcatgcgtc gtatcacgcg aactatgggg   1140
catacgccgt gttgatggct acatcgcaaa gaaagtccct agtgttacat cgatacagtg   1200
ccgtgacagc cgtggccctg cagctcatgc ctgttgagat gctccgtaag ctagatcagt   1260
cggactgggt acggggtgcc tggatcgtgt cagagacttt tccaaccagc gaccccaaag   1320
gattttggag cgacgatgac tcctcgatgg gtggaagtga tgattgatga tgagaacctg   1380
acaagaaaga cgagagagaa attcagagct gtcattgtag aattagtcta gattcctgat   1440
aataaacggt atcgattttg aaacctaatt gacgtgtgat cgatttttaa acctgtgtgt   1500
tgtgtgattg attggtatgt gggggatcc gatttcaaag gggggtactt atcgggaatt   1560
gatgtgtcat ggacgcagtt ttgagtgatt ttccgggaat accggatatt acgaattgat   1620
gtaagttacg tcagtaatta agtcaggatg cggtttattt tcggtttgct gattggtctt   1680
gtaatcgtgt atacgtatta ttatgaagta caaagtacgg aactacgttg cccatgcact   1740
aatggtttac acgatccttt atatggcata ttttatgctg gtcgtgaccc tccacgtcct   1800
cccggttgtg aaaaagatca atattattta aaacctccca aaggtaaagc tgtatgctta   1860
ggtccacatc atcatttatc aatatggctc aatggtcaaa atagtagttt atggcacaaa   1920
gtgctggtga cgggaaaaaa cggtaatgga ccacacgtaa ctaagaaagg tgactttcct   1980
agaggtcgaa aaaatataat gatttagctt aatatggata tatacgatag ctgataaatt   2040
ttccacgaaa aaggataacg caatatgttt ttgatatggt gctaacatgg ttacatcatt   2100
cgattataaa ctcgcatatc aaactttat cggtaccaca cctgtcattg accgcatata   2160
tgttatttac cgtgtgtttc ccggtccatc ttttagaatt ggaagattac gacaggcgtt   2220
gtcgttgtaa caaccaaatt ctgttgaata ccctgccggt cggaactcaa ctgcttaagc   2280
caatcgcagc gagcgaaagc tgcaatcgtc aggaagtgct ggctatttta aaggacaaag   2340
gaaccaagtg tctcaatcct aacgcgcaag ccgtgcgtcg tcacatcaac cggctatttt   2400
ttcggttaat cttagacgag gaacaacgca tttacgacgt agtgtctacc aatattgagt   2460
tcggtgcctg gccagtccct acggcctaca aagcctttct ctggaaatac gccaagaaac   2520
ttaattacca ctactttaga ctgcgttggt gatcatgtcc ctattttacc gtgcggtagc   2580
cctgggcacg ctgagcgctc tggtgtggta tagcactagt atcctggcag agattaacga   2640
agaatcctgc tcctcatctt ctgtggacca cgaagactgc gaggaaccgg acgagatcgt   2700
tcgcgaagag caagactatc gggctctgct ggccttttcc ctagtgattt gcggtacgct   2760
cctcgtcact tgtgtgatct gagacgtcat gctggtagcg tttatgagtc gggcggtggc   2820
cggcacgccg catttcctaa cccgcgcagc atgttgcgct tgctgttcac gctcgtccta   2880
ctggccctcc acgggccgtc tgtcaacgct agccgcgact atgtgcatgt tcggctactg   2940
agctaccgag gcgacccct ggtcttcaag cacacttttt cgggtgtgcg tcgacccttc   3000
```

```
accgagctag gctgggctgt gtgtcgcgac tgggacagta tgcattgcac gcctttctgg    3060
tctaccgatc tggagcagat gaccgactcg gtgcgacgtt acagcacggt gagccccggc    3120
aaggaagtga cgcttcagct tcacgggaac caaaccgtac agccgtcgtt tctaagcttt    3180
acgtgccgcc tgcagctaga acccgtggtg gaaaatgttg gcctctacgt ggcctacgtg    3240
gtcaacgacg gtgaacgccc acagcagttt tttacaccgc aagtagacgt ggtacgcttt    3300
gctctatatc tagaaacgct ctcccggatc gtggaaccgt tagaatcagg tcgcctggca    3360
gtggaatttg atacgcctga cctagctctg gcgcccgatt tagtaagcag cctcttcgtg    3420
gccggacacg gcgagaccga cttttacatg aactggacgc tgcgtcgcag tcagacccac    3480
tacctggagg agatggcctt acaggtggag attctaaagc cccgcggcgt acgtcaccgc    3540
gctattatcc accatcctaa gctacagccg ggcgttggcc tgtggataga tttctgcgtg    3600
taccgctaca cgcgcgcct gacccgcggc tacgtacgat acaccctgtc accgaaagcg    3660
cgcttgcccg caaaagcaga gggttggctg gtgtcactag acagattcat cgtgcagtac    3720
ctcaacacat tgctgattac aatgatggcg gcgatatggg ctcgcgtttt gataacctac    3780
ctggtgtcgc ggcgtcggta gaggcttgcg gaaaccacgt cctcgtcaca cgtcgttcgc    3840
ggacatagca agaaattcac gtcgccacgt ctcgagaatg ccggcccgc ggggtcccct    3900 tcgcgcaaca ttcctggccc tggtcgcgtt cggattgctg tttcagatag acctcagcga    3960
cgctacaaat gtgaccaaca gcacaaacgt ccctactagc accagcagca gaaatagcgt    4020
cgacaacgcc acgagtagcg gacccacgac cgggatcaac atgaccacca cccacgagtc    4080
ttccgttcac aacgtgcgca atgacaaaat catgaaagtg ctggctatcc tcttctacat    4140
cgtgacaggc acctccattt tcagcttcat agcggtactc atcgcggtag tttactcctc    4200
gtgttgcaag cacccgggcc gctttcgttt cgccgacgaa gaagccgtca atctgttgga    4260
cgacacggac gacagtggcg gcagcagccc gtttggcagc ggttcccgac gaggttctca    4320
gatccccgcc ggattttgtt cctcgagccc ttatcagcgg ttggaaactc gggactggga    4380
cgaggaggag gaggcgtccg cggcccgcga gcgcatgaaa catgatcctg agaacgtcat    4440
ctatttcaga aaggatggca acttggacac gtcgttcgtg aatcccaatt atgggagagg    4500
ctcgcctttg accatcgaat ctcacctctc ggacaatgag gaggacccca tcaggtacta    4560
cgtctcggtg tacgatgaac tgaccgcctc ggaaatggaa gaaccttcca acagcaccag    4620
ctggcagatt cccaaactaa tgaaagttgc tacgcaaccc gtctcgctca gagatcccga    4680
gtacgactag gcttttttt ttgtctttcg gttccaactc tttccccgcc ccatcacctc    4740
gcctatacta tgtgtatgat gtctcataat aaagctctct ttctcagtct gcaacatgcg    4800
gctgtgtcgg gtgtggctgt ctgtttgtct gtgcgccgtg gtgctgggtc agtgccagcg    4860
ggagaccgca gaaaaaaacg attattaccg agtaccgcat tactgggacg cgtgctctcg    4920
cgcgctgcct gaccaaaccc gttacaagta tgtggaacag ctcgtggacc tcacgttgaa    4980
ctaccactac gatgcgagcc acggcttgga caactttgac gtgctcaaga ggtgagggta    5040
cgcgctaaag gtgtatgaca acgggaaggt aagggcgaac gggtaacggg taggtaaccg    5100
catggggtgt gaaatgacgt tcggaacctg tgcttgcaga atcaacgtga ccgaggtgtc    5160
gttgctcatc agcgacttta gacgtcagaa ccgtcgcggc ggcaccaaca aaaggaccac    5220
gttcaacgcc gccggttcgc tggcgcctca cgcccggagc ctcgagttca gcgtgcggct    5280 cttttgccaac tagcctgcgt cacgggaaat aatatgctac ggcttctgct tcgtcaccac    5340
```

```
tttcactgcc tgcttctgtg cgcggtttgg gcaacgccct gtctggcgtc tccgtggttc    5400
acgctaacgg cgaaccagaa tccgtccccg ccatggtcta aactgacgta tcccaaaccg    5460
catgacgcgg cgacgtttta ctgtcctttt ctctatccct cgcccccacg gtccccctcg    5520
caattcccgg ggttccagcg ggtatcaacg ggtcccgagt gtcgcaacga gaccctgtat    5580
ctgctgtaca accgggaagg ccagaccttg gtggagagaa gctccacctg ggtgaaaaag    5640
gtgatctggt atctgagcgg tcgcaatcag accatcctcc aacggatgcc ccgaacggct    5700
tcgaaaccga gcgacggaaa cgtgcagatc agcgtggaag acgccaagat ttttggagcg    5760
cacatggtgc ccaagcagac caagctgcta cgcttcgtcg tcaacgatgg cacgcgttat    5820
cagatgtgtg tgatgaagct ggagagctgg gcccacgtct tccgggacta cagcgtgtct    5880
tttcaggtgc gattgacgtt caccgaggcc aataaccaga cttacacctt ctgtacccat    5940
cccaatctca tcgtttgagc ccgtcgcgcg cgcagggaat tttgaaaacc gcgcgtcatg    6000
agtcccaaag acctgacgcc gttcttgacg acgttgtggc tgctattggg tcacagccgc    6060
gtgccgcggg tgcgcgcaga agaatgttgc gaattcataa acgtcaacca cccgccggaa    6120
cgctgttacg atttcaaaat gtgcaatcgc ttcaccgtcg cgtacgtatt tttatgattg    6180
tctgcgttct gtggtgcgtc tggatttgtc tctcgacgtt tctgatagcc atgttccatc    6240
gacgatcctc gggaatgcca gagtagattt tcatgaatcc acaggctgcg gtgtccggac    6300
ggcgaagtct gctacagtcc cgagaaaacg gctgagattc gcgggatcgt caccaccatg    6360
acccattcat tgacacgcca ggtcgtacac aacaaactga cgagctgcaa ctacaatccg    6420
taagtctctt cctcgagggc cttacagcct atgggaaagt aagacagagg gacaaaacat    6480
cattaaaaaa aaagtctaat ttcacgttTT gtaccccccc ttcccctccg tgttgtaggt    6540
tatacctcga agctgacggg cgaatacgct gcggcaaagt gaacgacaag gcgcagtacc    6600
tgctgggcgc cgctggcagc gttccctatc gatggatcaa cctggaatac gacaagataa    6660
cccggatcgt gggcctggat cagtacctgg agagcgttaa aaaacacaaa cggctggatg    6720
tgtgccgcgc taaatgggc tatatgctgc agtgaataat aaaatgtgtg tttgtccgaa    6780
atacgcgttt tgagatttct gtcgccgact aaattcatgt cgcgcgatag tggtgtttat    6840
cgccgataga gatggcgata ttggaaaaat cgatatttga aaatatggca tattgaaaat    6900
gtcgccgatg tgagtttctg tgtaactgat atcgccattt ttccaaaagt gattttgggg    6960
catacgcgat atctggcgat agcgcttata tcgtttacgg gggatggcga tagacgactt    7020
tggtgacttg ggcgattctg tgtgtcgcaa atatcgcagt ttcgatatag gtgacagacg    7080
atatgaggct atatcgccga tagaggcgac atcaagctgg cacatggcca atgcatatcg    7140
atctatacat tgaatcaata ttggccatta gccatattat tcattggtta tatagcataa    7200
atcaatattg gctattggcc attgcatacg ttgtatccat atcataatat gtacatttat    7260
attggctcat gtccaacatt accgccatgt tgacattgat tattgactag ttattaatag    7320
taatcaatta cggggtcatt agttcatagc ccatatatgg agttccgcgt tacataactt    7380
acggtaaatg gcccgcctgg ctgaccgccc aacgaccccc gcccattgac gtcaataatg    7440
acgtatgttc ccatagtaac gccaataggg actttccatt gacgtcaatg ggtggagtat    7500
ttacggtaaa ctgcccactt ggcagtacat caagtgtatc atatgccaag tacgccccct    7560
attgacgtca atgacggtaa atggcccgcc tggcattatg cccagtacat gaccttatgg    7620
gactttccta ctggcagtac atctac                                         7646
```

<210> SEQ ID NO 2
<211> LENGTH: 16570
<212> TYPE: DNA
<213> ORGANISM: Human cytomegalovirus

<400> SEQUENCE: 2

| | | | | | |
|---|---|---|---|---|---|
| ttttcgggac | ggtcggttaa | cgtgggtttc | aggggaaagc | tgtaagcacg | ggaaaggagc | 60 |
| gctgataggc | gaggcaacgc | acgaaggtcc | aagcggcggc | ggcgccgact | tccaccatca | 120 |
| ggccaacgac | cagcatccgc | agcagcagcg | cccaggcgat | ctcgcgctcg | acgacggcta | 180 |
| cggcgacgag | gcagaacatc | tcaacccaga | cgacaagcgc | caggaggtag | agcacggccg | 240 |
| gaaagaccgc | gggcgttaac | atctagtcgc | ggagaaggaa | acaaaaacgg | ttgaaaacgg | 300 |
| ggactgcgga | gttgctttgt | tcaggagacg | acgacgggag | cgaacgggat | ggcgctggat | 360 |
| acgctagcgg | ggctggctat | ctgcgtgggt | ctagtcatgg | gtgtcaccgt | gatcgcgtcg | 420 |
| tgcgcgctgc | tggtgtttta | ttattgcgat | gagagagggg | atggccgtcc | gtcgaagctg | 480 |
| ttgcaacgta | gcattcgacg | ttggcgacac | ggccttagca | ccgaatcctt | aaccgctatc | 540 |
| ctgccggacg | gttcgtccac | ggagcagaag | atctaccaca | cgcgacttta | agtcgcggag | 600 |
| gaagttacgt | gggtaggagg | gcaccgtgcc | ccgaggcggc | gacgggctag | cgtataacaa | 660 |
| gccgcgcgac | atcgggcgag | cggcggtgag | acagacgcgg | gcacgtcggt | ggcgatagcc | 720 |
| atgagttcca | gcaacaatct | cgatccctgg | attcccgtgt | gcgtcgtggt | agtcatgacc | 780 |
| tccgtagtcc | tgttcgcagg | tctgcacgtg | tacctgtggt | acgttcggcg | gcagctggtg | 840 |
| gcgttctgcc | tggagaaggt | gtgcgtccgc | tgctgcggta | aagatgagac | gacgccgctg | 900 |
| gtggaggatg | ccaaccgccg | gccgagctgg | agatggtgga | agtgtcagac | gagcgttact | 960 |
| aggagatcgc | cgcggccgat | gggcgccggc | ggacgtgact | cggcagccgc | tgtagggata | 1020 |
| aatagtgcga | tggcgtttgt | gggagaacgc | agtagcgatg | ggttgcgacg | tgcacgatcc | 1080 |
| ttcgtggcaa | tgccaatggg | gcgttcccac | gattattgtg | gcctggatag | catgcgcggc | 1140 |
| cctgggaatt | tggtgtttgg | cgggatggtc | gtcgaatttg | tcttctggag | ccggcattgc | 1200 |
| agccgtggtc | ggctgttctg | ttttcatgat | tttccttttgc | gcgtacctca | tccgttaccg | 1260 |
| ggaattcttt | aaagactccg | taatcgacct | cctcacctgc | cgatgggttc | gctactgcag | 1320 |
| ctgcagctgc | aagtgcagct | gcaaatgcat | ctcgggcccc | tgcagccgct | gctgttcagc | 1380 |
| gtgttacaaa | gagacgatga | tttacgacat | ggtccaatac | ggtcatcgac | ggcgtcccgg | 1440 |
| acacggcgac | gatcccgaca | gggtgatctg | cgagatagtg | gaaagtcccc | cggtttcggc | 1500 |
| gccgacggtg | tccgtccccc | cgccgtcgga | ggagtcccac | cagcccgtca | tcccaccgca | 1560 |
| gccgccagca | ccgacatcgg | aacccaaacc | gaagaaaggt | agggcgaaag | ataaaccgaa | 1620 |
| gggtagaccg | aaggacaaac | ctccgtgtga | accgacggtg | agtccacaac | caccgtcgca | 1680 |
| gccgacggca | atgcccggcg | gtccgcccga | cacgcctccc | cccgccatgc | cgcagatgcc | 1740 |
| acccggcgta | gccgaggcgg | tacaagctgc | cgtgcaggcg | gccgtggccg | cgactctaca | 1800 |
| acaacaacag | cagcagcatc | agaccggaac | gtaacccgcc | cccggtgtga | tgaggaattt | 1860 |
| tccgacttgg | cccacatctc | cttcctcagt | gttttggacaa | taaacacatt | ccttgccaaa | 1920 |
| aaatgacgtt | tccagaaatc | caaggcataa | atgtccgtac | accggccctt | cccgacacgg | 1980 |
| agtttgagat | tccaagcagg | agagaagatc | atggtgtgga | tatggctcgg | cgtcgggctc | 2040 |
| ctcggcggta | ccggactggc | ttccctggtc | ctggccattt | ccttatttac | ccagcgccga | 2100 |
| ggccgcaagc | gatccgacga | gacttcgtcg | cgaggccggc | tcccgggtgc | tgcttctgat | 2160 |

```
aagcgtggtg cctgcgcgtg ctgctatcga aatccgaaag aagacgtcgt cgagccgctg   2220
gatctggaac tggggctcat gcgggtggcc acccacccgc cgacgccgca ggtgccgcgg   2280
tgtacgtcgc tctacatagg agaggatggt ctgccgatag ataaacccga gtttcctccg   2340
gcgcggttcg aaatcccega cgtatccacg ccgggaacgc cgaccagcat cggccgatct   2400
ccgtcgcatt gctcctcgtt gagctctttg tcgtcttcga ccagcgtcga cacggtgctg   2460
catcagccgc cgccatcctg gaagccacct ccgccgcccg agcgcaagaa gcggccgcct   2520
acgccgccgg tccgggcccc caccacgcgg ctgtcgtcgc acaggccccc gacgccgata   2580
cccgcgccgc gtaagaacct gagcacgccg cccatcaaga aaacaccgcc gcccacgaaa   2640
cccaagccgg tcggctggac accgccggtg acacccaggc ccttcccgaa aacgccgacg   2700
ccacaaaagc cgccgcggaa tccgagacta ccacgcaccg tcggtctgga gaatctctcg   2760
aaagtgggac tctcgtgtcc ctgtccccga ccccgcacgc cgacggagcc gaccacgctg   2820
cctatcgtgt cggtttccga gttagccccg cctcctcgat ggtcggacat cgaggaactc   2880
ttggaaaagg cggtgcagag cgtcatgaag gacgctgagt ctatgcagat gacctgagac   2940
cgaaggagcg agcgcgtccg ttgtacagtt gtatagcagc acacgccttc cctcttttc    3000 accgcagcta agagagagaa agagagtatg tcagtcaagg gcgtggagat gccagaaatg   3060
acgtgggact tggacgttgg aaataaatgg cggcgtcgaa aggccctgag tcgcattcac   3120
cggttctggg aatgtcggct acgggtgtgg tggctgagtg acgccggcgt aagagaaacc   3180
gacccaccgc gtccccgacg ccgcccgact tggatgaccg cggtgtttca cgttatctgt   3240
gccgttttgc ttacgcttat gattatggcc atcggcgcgc tcatcgcgta cttaagatat   3300
tatcaccagg acagttggcg agacatgctc cacgatctat tttgcggctg tcattatccc   3360
gagaagtgcc gtcggcacca cgagcggcag agaaggagac ggcgagccat ggatgtgccc   3420
gacccggaac tcgcgacccc ggcccgccgg ccgttgaacg aagctatgta ctacggcagc   3480
ggctgtcgct tcgacacggt ggaaatggtg gacgagacga gacccgcgcc gccggcgctg   3540
tcgtcgcccg aaaccggcga cgatagcaac gacgacgcgg ttgccggcgg aggtgctggc   3600
ggggtaacat caccegegac tcgtacgacg tcgccgaacg cgctgctgcc ggaatggatg   3660
gatgcggtgc atgtggcggt ccaagccgcc gttcaagcga ccgtgcaagt aagtggcccg   3720
cgggagaacg ccgtatctcc cgctacgtaa gagggttgag ggggccgttc ccgcgcgagt   3780
gctgtacaaa agagagagac tgggacgtag atccggacag aggacggtca ccatggacga   3840
tctgccgctg aatgtcgggt tacccatcat cggcgtgatg ctcgtgctga tcgtggccat   3900
cctctgctat ctggcttacc actggcacga caccttcaaa ctagtgcgca tgtttctgag   3960
ctaccgctgg ctgatccgct gttgcagct gtacggggag tacgagcgcc ggttcgcgga   4020
cctgtcgtct ctgggcctcg gcgccgtacg gcgggagtcg dacagacgat accgtttctc   4080
cgaacggccc gacgagatct tggtccgttg ggaggaagtg tcttcccagt gcagctacgc   4140
gtcgtcgcgg ataacagacc gccgcgcggg ttcatcgtct tcgtcgtcgg tccacgtcgc   4200
tagccagaga aacagcgtgc ctccgccgga catggcggtg acggcgccgc tgaccgacgt   4260
cgatctgttg aaaccgtga cgggatccgc gacgcagttc accaccgtag ccatggtaca    4320
ttatcatcaa gagtacacgt gaatgagaaa agaaaaaag aggggagcgg atcgcgataa    4380
tgtcgctttg acattctctg ctcgatctac tcagcgtctg cacgaaacgg cgtccgcacg   4440
gaggcgagcc caagcgtatc tgcagcaagc ggttctttct ctcggtgatg gtggcagcat   4500
cggtggcggg agcttgttcg gacgatggac ggtgaggagt ccctggcgat caggcggctc   4560
```

```
ccgggtgtgg agttcaacgg gtggtaatgg tggcggtgat cggtgttaga aaacggtggc    4620
cctggcaaac atatatctac tgtaaatcct ctgctctgtt aataaaaagc cacttttca    4680
catgagttcg taattttatt gtgtagtgga aattttacg tcattgggaa accccagaat    4740
gaaagagtat aatgtgcaca tcaccgggag ttccctgtca gtacgaatgt acacaacgcg    4800
ggttacatta cgataaactt tccggtaaaa caatgccgat acagcgtgta taacgctgat    4860
tgttacgaca aacgggttcg tatatcaatt atatagtaac ggacatgctg tggatactag    4920
ctttacttgc gcttaccgcg acagcgagtg agactactac aggcaccagt tctaattcca    4980
gtacttccac caatagcagc aacagtactg tagcaccaac cacgccatca gtagcatgcg    5040
ttcaagcttt tggcggcagt aattggacat ttccacagct cgcgctgctt gccgctagcg    5100
gctggacatt atctggactc cttctcttat ttacctgctg cttttgctgc ttttggctag    5160
tacgtaaaat ctgcagctgc tgcggcaact cctccgagtc agagagcaaa acaacccacg    5220
cgtacaccaa tgccgcattc acttcttccg acgcgacgct acccatgggc actacagggt    5280
cgtacactcc cccacaggac ggctcatttc cacctccgcc tcggtgacac agggtaaacc    5340
gaaaccaacg ttgaatctga cgcggtttcg gaaagcctga gacgtcactt tcacaatgac    5400
gttcgtagac acgttgatca taaaacaccg tagaggctaa ggcttcggta gggagacacc    5460
tcaactgttc ctgatgagca cccgcgctct catctcttca gacttgtcat gaccccccgct   5520
cagactaacg ccactaccac cgtgcacccg cacgacgcaa aaaacggcag cggcggtagt    5580
gccctgccga ccctcgtcgt tttcggcttc atcgttacgc tacttttctt tctctttatg    5640
ctctactttt ggaacaacga cgtgttccgt aagctgctcc gctgcgcttg gatccagcgc    5700
tgctgcgacc gcttcgacgc gtggcaagac gaggtcatct accgtcgtcc atcacgtcgt    5760
tcccaaagcg acgacgagag tcgtactaac agcgtgtcat cgtacgttct tttatcaccc    5820
gcgtccgatg gcagttttga caacccggca ctgacagaag ccgtcgacag cgtggacgac    5880
tgggcgacca cctcggtttt ttacgccacg tccgacgaaa cggcggacac cgagcgccga    5940
gattcgcagc aactgctcat cgagcttccg ccggagccgc tcccgcccga tgtggtagcg    6000
gccatgcaga aagcggtgaa acgcgctgta cagaacgcgc tgcgccacag ccacgactct    6060
tggcagcttc atcagaccct gtgacgcaga tgaacgttcc ttcttaaaca tccgaggtag    6120
caatgagaca ggtcgcgtac cgccggcgac gcgagagttc ctgcgcggtg ctggtccacc    6180
acgtcggccg cgacggcgac ggcgaggagg aggcagcaaa aaagacctgc aaaaaaaccg    6240
gacgctcagt tgcgggcatc ccgggcgaga agctgcgtcg cacggtggtc accaccacgc    6300
cggcccgacg tttgagcggc cgacacacgg agcaggagca ggcgggcagc gtctctgtga    6360
aaagggaag aaaagaatca tcatgtgccg cggggagtcg ctccgaactc tgccgtggct    6420
gttctgggcg ctgttgagct gccgcgcgact cctcgaatat tcttcctctt cgttcccctt    6480
cgccaccgct gacatcgccg aaaagatgtg gccgagaac tatgagacca cgtcgccggc    6540
gccggtgttg tcgccgagg gagagcaagt taccatcccc tgcacggtca tgacacactc    6600
ctggcccatg gtttccattc gcgcacgttt ctgtcgttcc cacgacggta gcgacgagct    6660
catcctggac gccgtcaaag gccatcggct gatgaacgga ctccagtacc gcctgccgta    6720
cgccacttgg aatttctcgc agttgcatct cggccaaata ttctcgctta cttttaacgt    6780
atcgatggac acggcgggca tgtacgagtg cgtgctgcgc aattacagcc acggcctcat    6840
catgcaacgc tttgtaattc tcacgcagct ggagacgctc agccggcccg atgaaccttg    6900
```

```
ttgcacaccg gcgttaggtc gctactcgtt gggagaccag atctggtcgc cgacgccctg   6960
gcgtctacgg aatcacgact gcggaacgta ccgcggcttt caacgcaact acttctatat   7020
cggccgcgcc gacgccgagg attgctggaa acccgcatgt ccggacgagg aacccgaccg   7080
ctgttggaca gtgatacagc gttaccggct ccccggcgac tgctaccgtt cgcagccaca   7140
cccgccgaaa tttttaccgg tgacgccagc accgccggcc gacatagaca ccgggatgtc   7200
tccctgggcc actcggggaa tcgcggcgtt tttaggattt tggagtattt ttaccgtatg   7260
tttcctatgc tacctgtgtt acctgcagtg ttgtggacgc tggtgtccca cgccgggaag   7320
gggacgacga ggcggtgagg gctatcgacg cctaccgact tacgatagtt accccggtgt   7380
tagaaagatg aagaggtgag aacacgcata aataaaaaa atgagatatt aaaaaatgta   7440
gtgtgtgaag tgtgaatagt atgattaaaa tatgcggatt gaatgggcgt gtttgttatt   7500
cggatacttt gtgtcatccg ttgggagcga acggtcatta tcctatcgtt accacctgga   7560
atctaattca tctaccaacg tggtttgcaa cggaaacatt tccgtgtttg taaacggcac   7620
cctgggtgtt cggtatgacg ttacaatagg aatcggtagt ccatatccac tagtaggaca   7680
cctcacaatc ataagtcttg aatcttggtt taaaccttgg atttttaaaca caacttacaa   7740
taaatatcca ttaaatacaa ctgaaacgtt ttataatgta gacgcggaaa atttacgtcg   7800
cgtatcccaa tatttctaca aactaggtg ggtaaaaacg agtttacaag aaaatcacac   7860
ctgtaacctc acaaacaata tacctaccta tgaatatcag gtaaacgtaa acaacgga   7920
ttacctaaca ctaatatcct cgggatggca agaccatcta aactcacca ccataaatag   7980
tacacacttt aacctcacaa aatcgaacat aaccagcatt caaaaatatc tcaacactac   8040
ctgcatagaa agactccgta actcacctt ggagcccgta tacaccacaa ctatgcctca   8100
aaacgtaaca acacctcaac acataacaac cactctgtac acaacacctc caaatgcaat   8160
aacaattcaa gatacaactc aaagccatac tgtacagacg ccgtcttta acgacacaca   8220
taacgtgacg gaacacacgt taaacataag ctacgtttta tcacaaaaaa cgaataacac   8280
aacatcaccg tgggtatatg ccataccctat gggcgccaca gccacaatag gcgccagttt   8340
atatatcggg aaacacttta cgccggttag gtccgtatac gaagtatggc gcggtcagta   8400
aagatgattc tgattcaaca catatacccc ccacgatcct cgaacacctt acagcatatg   8460
agcaaaaaac aagaaagtat aaccacaatc acatttgggc gaataacacg ctgtcatcca   8520
ctaacgtcta ttaatctaat gtttaacggg agctgtactg tcgccgttaa aatgtccatg   8580
ggagtcaatg tacctgggta accgctgtca gccttggtga caggtgtaat cacagctgcc   8640
acataactca cgaagcctcc aatcacagca gcacacacaa tcctaacgcc attggcgtgt   8700
ataaaagttc ggaaaactcg acggttgtac ggcacgacaa atcgatgtag tggtatgtgt   8760
ttccagcggg gaccgtgtgc ggtctcttag gttcgctata ctgtggctgg aaactggtta   8820
cctgtgaaga tggctgacta tcctgttctg tcctggaaaa actttcagcg tcgtaggtgg   8880
actttgcagt atgcggatta gtgaagttat gtcatttatt tacgtttacg atctcgtatt   8940
acaaaccgcg gagaggatga taccgttcgg ccccatgagt tatttttatt cttccggtag   9000
gaggcatgaa gcctctggtg atgctcatct gcttcggtgt gttttttacta cagcttgggg   9060
gaagcaaaat gtgtaagccc gatgaggtga agctgggtaa ccaatgctgc ccgccatgcg   9120
gatcaggaca aaaagttaca aaagtgtgta cagagaatag tggcataacg tgtacactgt   9180
gcccaaacgg cacttatctc acagggcttt acaactgtac taattgtact caatgtaacg   9240
acactcagat cacggttcgt aactgcactt ccactaataa caccatatgc gcatctaaga   9300
```

-continued

| | | | | | |
|---|---|---|---|---|---|
| atcatacatt | gttttccact | ccaggtgtcc | aacatcacaa | gcaacgacag | caaaatcata | 9360 |
| ccgcacatgt | aaccgtcaaa | caagggaaaa | gtggtcgtca | tactctagcc | tggttgtccc | 9420 |
| tcttcatctt | tctcgtgggt | atcatacttt | taattctcta | tcttatagcc | gcctatcgga | 9480 |
| gtgagagatg | ccaacagtgt | tgctcaatcg | gcaaaatttt | ctaccgcacc | ctgtaagctt | 9540 |
| cctgttgttg | tttttacatc | acggtacgat | gaagtcacac | agataattac | agatgagctg | 9600 |
| ttcatatttt | ttattatttt | ttccaattcc | tgcactaaaa | aaagaagcac | tttacggaac | 9660 |
| cgtgtctgaa | tatctgtggg | gaatttaggt | acttttgcc | gacgtcagga | aaaataagct | 9720 |
| gtcgcctaca | taagagcccg | gttctatcgt | gctgtcactc | tttcttgttg | ccttcgatgt | 9780 |
| acggcgtcct | ggctcattac | tactccttca | tcagtagccc | cagcgttatg | gttaatttta | 9840 |
| agcatcataa | cgctgtacag | ctgttgtgtg | cacggacccg | agacggcact | gccggatggg | 9900 |
| aacgtttaac | ccatcatgcg | tcgtatcacg | cgaattatgg | ggcatacgcc | gtgttgatgg | 9960 |
| ctacatcgca | aagaaagtcc | ctagtgttac | atcgatatag | tgccgtgaca | gccgtggccc | 10020 |
| tgcagctcat | gcctgttgag | atgctgcgca | agctagacca | gtcggactgg | gtgcggggtg | 10080 |
| cctggatcgt | gtcagagact | tttccaacta | gcgaccccaa | aggattttgg | agcgacgatg | 10140 |
| actcctcgat | gggtggaagt | gaagattgat | gatgagaacc | tgacaagaaa | gacgatagag | 10200 |
| aaattcagag | ctgtcattgt | agaattagtc | tagattcctg | ataataaacg | gtatcgattt | 10260 |
| tgaaacctaa | ttgacgtgtg | atcgattttt | aaacctgtgt | gttgtgtgat | tgattggtac | 10320 |
| gtgggggat | ccgatttcaa | agggaggtag | ttatcgggaa | ttgatgtgtc | atggacgcag | 10380 |
| ttttgagtga | ttttccggga | ataccggata | ttacgaatta | ctgtaagtga | cgtcagaaat | 10440 |
| taaattataa | tgcgtttaat | ttttggttta | ttgatcattt | ttattgttac | agatacatgt | 10500 |
| aacggcggtt | ttggcactga | aggtaatggt | cgttgtgcat | gcatagggta | tcatcgactt | 10560 |
| ttaggacaat | tgcctcgtgg | aactttctgg | ttaggacatt | taccaccagg | ctcacattgc | 10620 |
| ccaaagggac | aagtcatgat | aaagataggc | caaggaccga | tcgtctgttt | atccgattat | 10680 |
| catcctttat | ctaagtggat | gtatggaaat | cataaatctg | gttcggaaac | atggcttcag | 10740 |
| ataaaaatgg | aaggtccaag | aaatgctaca | gtagtacaaa | gatcgaatac | tcgtccataa | 10800 |
| agataacgaa | tgttcataag | aattgtactt | ttatatgtat | gtaagtttat | ggatctttat | 10860 |
| gtttgtcatc | atatacatta | gtagtaacat | actcaacaca | ctatgcgtgt | acaatttgtt | 10920 |
| ttatagatcc | gtagtgtaca | ataaatatta | cgataaattt | ttaacgtcgg | atacatttac | 10980 |
| gatactaaac | gtactgtatt | gcattttttg | cacgatgttg | acatcacatt | gctgggctac | 11040 |
| aagatggcat | aacaaattat | tggtacgata | cctgtcattg | actatatata | tgttactgac | 11100 |
| cgtatgtccc | ctagccgtcc | atcttttaga | attggaagat | tacgacagac | gctgtcgttg | 11160 |
| taacaatcaa | attctgttga | atactctgcc | aatcggaact | gaattgctta | agccaatcgc | 11220 |
| ggcgagcgaa | agctgcaatc | gtcaggaagt | gctggctatt | ttaaaggaca | agggcaccaa | 11280 |
| gtgtctcaat | cctaacgcgc | aagccgtgcg | tcgtcacatc | aaccggctat | tttttcggtt | 11340 |
| aatattagac | gaggaacaac | gcatttacga | cgtagtgtct | accaatattg | agttcggtgc | 11400 |
| ctggccagtc | cctacggcct | acaaagcctt | tctctggaaa | tacgccaaga | aactgaacta | 11460 |
| ccaccacttc | agattgcgct | ggtgatcatg | tccctatttt | accgtgcggt | agccctgggc | 11520 |
| acactgagcg | ctctggtgtg | gtacagcact | agtatcctgg | cagaaattaa | cgaagaatcc | 11580 |
| tgctcctcat | cttctgtgga | ccacgaagac | tgcgaggaac | cggacgagat | cgttcgcgaa | 11640 |

```
gagcaagact atcgggctct gctggccttt tccctagtga tttgcggtac gctcctcgtc  11700
acttgtgtga tctgagacgt catgctggta gcgtttatga gtcgggcggt ggccgacacg  11760
ccgcatttcc taacccgcgc agcatgttgc gcttgctgtt cacgctcgtc ctgctggccc  11820
tccacgggca gtctgtcggc gctagccgcg actatgtgca tgttcggcta ctgagctacc  11880
gaggcgaccc cctggtcttc aagcacactt tctcgggtgt gcgtcgaccc ttcaccgagc  11940
taggctgggc tgcgtgtcgc gactgggaca gtatgcattg cacacccttc tggtctaccg  12000
atctggagca gatgaccgac tcggtgcggc gttacagcac ggtgagcccc ggtaaggaag  12060
tgacgcttca gcttcacggg aaccaaaccg tacagccgtc gtttctaagc tttacgtgcc  12120
gcctgcagct agaacccgtg gtggaaaatg ttggcctcta cgtggcctac gtggtcaacg  12180
acggtgaacg cccacagcag tttttacac cgcaggtaga cgtggtacgc tttgctctat   12240
atctagaaac gctctcccgg atcgtggaac cgttagaatc aggtcgcctg gcagtggaat  12300
ttgatacgcc tgacctagct ctggcgcccg atttagtaag cagcctcttc gtggccggac  12360
acggcgagac cgacttttac atgaactgga cgctgcgtcg cagtcagacc cactacctgg  12420
aggagatggc cttacaggtg gagattctaa agccacgcgg cgtacgtcac cgcgctatta  12480
tccaccatcc gaagctacag ccgggcgttg gcctgtggat agatttctgc gtgtaccgct  12540
acaacgcgcg cctgacccgc ggctacgtac gatacaccct gtcaccgaaa gcgcgcttgc  12600
ccgcaaaagc agagggttgg ctggtgtcac tagacagatt catcgtgcag tacctcaaca  12660
cattgctgat tacaatgatg gcggcgatat gggctcgcgt tttgataacc tacctggtgt  12720
cgcggcgtcg gtagaggctt gcggaaacca cgtcctcgtc acacgtcgtt cgcggacata  12780
gcaagaaatc cacgtcgcca cgtctcgaga atgccggccc cgcggggtct ccttcgcgca  12840
acattcctgg ccctggtcgc gttcgggttg ctgctttaca tggacttcag cgacgctaca  12900
aatatgacca gcagcacaaa cgtccctact agcaccagca gcagaaatac cgtcgagagc  12960
accacgagta gcgaacctac aaccgaaacc aacatgacca ccgcccgcga atcttccgtt  13020
cacgacgcgc gcaatgatga aatcatgaaa gtgctggcta tcctcttcta catcgtgaca  13080
ggcacctcca tttttcagctt catagcggta ctgatcgcgg tagtttactc ctcgtgttgc  13140
aagcacccgg gccgctttcg tttcgccgac gaagaggccg tcaacctgtt ggacgacacg  13200
gacgacagtg gcggtagcag cccgtttggc agcggttccc gacgaggttc tcagatcccc  13260
gccggatttt gttcctcgag cccttatcag cggttggaaa ctcgggactg ggacgaggag  13320
gaggaggcgt ccgcggcccg cgagcgcatg aaacatgatc ctgagaacgt catctatttc  13380
agaaaggatg gcaacttgga cacgtcgttc gtgaatccca attatgggag aggctcacct  13440
ttgaccatcg aatctcacct ctcggacaat gaggaggacc ccatcaggta ctacgtttcg  13500
gtgtacgatg aactgaccgc ctcggaaatg aagaaccttc gaacagcac cagctggcag   13560 attcccaaac taatgaaagt tgccatgcaa cccgtctcgc tcagagatcc cgagtacgac  13620
taggcttttt tttttgtctt tcagttccaa ctctttcccc gccccatcac ctcgcctata  13680
ctatgtgtat gatgtctcat aataaagctt tctttctcag tctgcaacat gcggctgtgt  13740
cgggtgtggc tgtctgtttg tctgtgcgcc gtggtgctgg gtcagtgcca gcgggaaacc  13800
gcggaaaaaa acgattatta ccgagtaccg cattactggg acgcgtgctc tcgcgcgctg  13860
cccgaccaaa cccgttacaa gtatgtggaa cagctcgtgg acctcacgtt gaactaccac  13920
tacgatgcga gccacggctt ggacaacttt gacgtgctca agaggtgagg atacgcgcta  13980
aaggtgcatg acaacgggaa ggtaagggcg aacgggtaac gggtaagtaa ccgcatgggg  14040
```

```
tatgaaatga cgtttggaac ctgtgcttgc agaatcaacg tgaccgaggt gtcgttgctc   14100
atcagcgact ttagacgtca gaaccgtcgc ggcggcacca acaaaaggac cacgttcaac   14160
gccgccggtt cgctggcgcc gcacgcccgg agcctcgagt tcagcgtgcg gctctttgcc   14220
aactagcctg cgtcacggga ataatatgc tgcggcttct gcttcgtcac cactttcact    14280
gcctgcttct gtgcgcggtt tgggcaacgc cctgtctggc gtctccgtgg tcgacgctaa   14340
cggcaaacca gaatccgtcc ccgccatggt ctaaactgac gtattccaaa ccgcatgacg   14400
cggcgacgtt ttactgtcct tttttctatc cctcgccccc acggtccccc ttgcaattct   14460
cggggttcca gcaggtatca acgggtcccg agtgtcgcaa cgagaccctg tatctgctgt   14520
acaaccggga aggccagacc ttggtagaga aagctccac ctgggtgaaa aaggtgatct    14580
ggtacctgag cggtcgcaac cagaccatcc ttcaacggat gccccgaacg gcttcgaaac   14640
cgagcgacgg aaacgtgcag atcagcgtgg aagacgccaa gattttttgga gcgcacatgg  14700 tgcccaagca gaccaagctg ctacgcttcg tcgtcaacga tggcacacgt tatcagatgt   14760
gtgtgatgaa gctggagagc tgagctcacg tcttccggga ctacagcgtg tcttttcagg   14820
tgcgattgac gttcaccgag gccaataacc agacttacac cttctgcacc catcccaatc   14880
tcatcgtttg agcccgtcgc gcgcgcaggg aattttgaaa accgcgcgtc atgagtccca   14940
aagacctgac gccgttcttg acggcgttgt ggctgctatt gggtcacagc cgcgtgccgc   15000
gggtgcgcgc agaagaatgt tgcgaattca taaacgtcaa ccacccgccg gaacgctgtt   15060
acgatttcaa aatgtgcaac cgcttcaccg tcgcgtacgt attttcatga ttgtctgcgt   15120
tctgtggtgc gtctggatct gtctctcgac gtttctgata gccatgttcc atcgacgatc   15180
ctcgggaatg ccagagtaga ttttcatgaa tccacaggct gcggtgtccg gacggcgaag   15240
tctgctacag tcccgagaaa acggctgaga ttcgcgggat cgtcaccacc atgacccatt   15300
cattgacgcg ccaggtcgta cacaacaaac tgacgagctg caactacaat ccgtaagtct   15360
cttcctcgag ggccttacag cttatgggaa agtaagacag agagggacaa aacatcatta   15420
aaaaaaaaaa gtctaatttc acgttttgta cccccccttc ccctccgtgt tgtaggttat   15480
acctcgaagc tgacgggcga atacgctgcg gcaaagtgaa cgacaaggcg cagtacctgc   15540
tgggcgccgc tggcagcgtt ccctatcgat ggatcaatct ggaatacgac aagataaccc   15600
ggatcgtggg cctggatcag tacctggaga gcgttaagaa acacaaacgg ctggatgtgt   15660
gccgcgctaa aatgggctat atgctgcagt gaataataaa atgtgtgttt gtccgaaata   15720
cgcgtttcga gatttctgtc gccgactaaa ttcatgtcgc gcgatagtgg tgtttatcgc   15780
cgatagagat ggcgatattg gaagaatcga tatttgaaaa tatggcatat tgaaaatgtc   15840
gccgatgtga gtttctgtgt aactgatatc gccatttta  aaaagtgat ttttgggcat   15900 atgcgatatc tggcgataac gcttatatcg tttacggggg atggcgatag acgactttgg   15960
cgacttgggc gattctgtgt gtcgcaaata tcgcagtttc gatataggtg acagacgata   16020
tgaggccata tcgccgatag aggcgacatc aagttggcac atggccaatg catatcgata   16080
tatacattga atcaatattg gccattagcc acattagtca ttggttatat agtataaatc   16140
aatattggct aatggccatt gcatacgttg tatctatatc ataatatgta catttatatt   16200
ggctcatatc caatataacc gccatgttga cattgattat tgattagtta ttaatagtaa   16260
tcaattacgg ggtcattagt tcatagccca tatgtggagt tccgcgttac ataacttacg   16320
gtaaatggcc cgcctggctg accgcccaac gacccccgcc cattgacgtc aataatgacg   16380
```

-continued

```
tgagttccca tagtaacacc aatagggact ttccattgac gtcaatggga ggagtattta    16440
cggtaaactg cccacttggc agtacatcaa gtgtatcata tgccaagtac gcccccctatt   16500 gacgtcaatg acggtaaatg gcccgcctgg cattatgccc agtacatgac cttacgggac    16560
tttcctactt                                                           16570
```

<210> SEQ ID NO 3
<211> LENGTH: 6141
<212> TYPE: DNA
<213> ORGANISM: Human cytomegalovirus

<400> SEQUENCE: 3

```
tttaaacctg tgtgttgtgt gattgattgg tacgtggggg gatccgattt caaagggagg      60
tagttatcgg gagttgatgt gtcatggacg tagttttgag tgattttccg ggaataccgg     120
atattacgaa ttactaatag tgacgtagat aataaaatta taatgcgatt tattttagt     180 ctgtttggtc ttttgatcgc gttgtgctat aaggtggaaa gtgtggaact acgttgtcgg    240
tgtagcaatg gttcaaatca tcccgtattc ggcgttttt gggtcggcta taaacctcca     300
gatcctacat gcgacaaaac gcaacacttt ttattacctc cccgacaaac acctgtatgt    360
ttgtctcctg atcattatct atcgaaatgg gttgatggca aacgaagtaa ctggtggcat    420
aaagtgttta taagaaaaaa ctctgataat ggaccacata tagaagacaa aagtgacacc    480
aatagacacc cgccttggcg actataattt tttataaatt gtaaaacgag ttggcaatat    540
cacgtatata gcgaaaaagg taatacaatg tgttttcgac atggttttga catggttaca    600
ccatccgatt ccaaattcgc acatcaaagt cttatcggta cgatacctgt atttgaccgc    660
atatgtgtta ttttccacgt gtcccctatt cgtctatctc ttagaattgg aagattacga    720
caagcgctgt cgttgcaaca accaaattct gttgaatacc ctgccagtcg gaactcaact    780
gcttaagcca atcgcagcga gcgaaagctg caatcgtcag gaagtgctgg ctattttaaa    840
ggacaagggc accaagtgtc tcaatcctaa cgcgcaagct gtgcgtcgtc acatcaaccg    900 gctattttt cggttaatct tagacgaaga acaacgcatt tacgacgtag tgtctaccaa    960
tattgagttt ggtgcctggc agccccctac ggcctacaaa gcctttctct ggaaatacgc   1020
caagaaattg aactaccacc acttcagact gcgctggtga tcatgtccct attttaccgt   1080
gcggtagctc tgggcacact aagcgctctg gtgtggtaca gcactagtat cctcgcagag   1140
attaacgaaa attcctgctc ctcatcttct gtggaccacg aagagtgtga ggaaccggac   1200
gagatcgttc gcgaagagca agactatcgg gctctgctgg ccttttccct agtgatttgc   1260
ggtacgctcc tcgtcacttg tgtgatctga gacgtcatgc tggtagtgtt tatgagtcgg   1320
gcggtggccg gcacgccgca tttcctaacc cgcgcagcat gttgcgcttg ctgttcacgc   1380
tcgtcctgct ggcccctccac gggccgtctg tcaatgctag ccgcgactat gtgcatgttc   1440
ggctattgag ctaccgaggc gaccccctgg tcttcaagca cacttttttcg ggtgtgcgtc   1500 gacccttcac cgagctaggc tgggctgcgt gtcgcgactg ggacagtatg cattgcacgc   1560
ccttctggtc taccgatccg gagcagatga ccgactcggt gcggcgttac agcacagtga   1620
gccccggcaa ggaagtgacg cttcagcttc acgggaacca aaccgtacag ccgtcgtttc   1680
taagctttac gtgccgcctg cagctagaac ccgtggtgga aaatgttggc ctctacgtgg   1740
cctacgtggt caacgacggt gaacgcccac agcagttttt tacaccgcag gtagacgtgg   1800
tacgctttgc tctatatcta gagacgcgtct cccggatcgt ggaaccgtta gaatcaggtc   1860
gcctggcagt ggaatttgat acgcctgacc tagctctggc gcccgattta gtaagcagcc   1920
```

```
tcttcgtggc cggacacggc gagaccgact tttacatgaa ctggacgctg cgtcgcagtc    1980
agacccacta cctggaggag atggccttac aggtggagat tctaaagccc cgcggcgtac    2040
gtcaccgcgc tattatccac catccgaagc tacagccggg cgttggcctg tggatagatt    2100
tctgcgtgta ccgctacaac gcgcgcctga cccgcggcta cgtacgatac accctgtcac    2160
cgaaagcgcg cttgcccgca aaagcagagg gttggctggt gtcactagac agattcatcg    2220
tgcagtacct caacacattg ctgattacaa tgatggcggc gatatgggct cgcgttttga    2280
taacctacct ggtgtcgcgg cgtcggtaga ggcttgcgga aaccacgtcc tcgtcacacg    2340
tcgttcgcgg acatagcaag aaatccacgt cgccacgtct cgagaatgcc ggccccgcgg    2400
ggtccccttc gcgcaacatt cctggccctg gtcgcgttcg ggttgctgct tcagatagac    2460
ctcagcgacg ctacgaatgt gaccagcagc acaaaagtcc ctactagcac cagcagcaga    2520
aatagcgtcg acaatgccac gagtagcgga cccacgaccg ggatcaacat gaccaccacc    2580
cacgagtctt ccgttcacag cgtgcgcaat gacgaaatca tgaaagtgct ggctatcctc    2640
ttctacatcg tgacaggcac ctccattttc agcttcatag cggtactgat cgcggtagtt    2700
tactcctcgt gttgcaagca cccgggccgc tttcgtttcg ccgacgaaga agccgtcaac    2760
ctgttggacg acacggacga cagtggcggt ggcagcccgt ttggcagcgg ttcccgacga    2820
ggttctcaga tccccgccgg attttgttcc tcgagcccct atcagcggtt ggaaactcgg    2880
gactgggacg aggaggagga ggcgtccgcg gcccgcgagc gcatgaaaca tgatcctgag    2940
aacgtcatct atttcagaaa ggatggcaac ttggacacgc cgttcgtgaa tcccaattat    3000
gggagaggct cgcctttgac catcgaatct cacctctcgg acaatgagga agaccccatc    3060
aggtactacg tctcggtgta cgatgaactg accgcctcgg aaatggaaga accttcgaac    3120
agcaccagct ggcagattcc caaactaatg aaagttgcca tgcaacccgt ctcgctcaga    3180
gatcccgagt acgactaggc tttttttttt ttatctttcg gttccaactc tttccccgcc    3240
ccatcacctc gcctatacta tgtgtatgat gtctcataat aaagctttct ttctcagtct    3300
gcaacatgcg gctgtgtcgg gtgtggctgt ctgtttgtct gtgcgccgtg gtgctgggtc    3360
agtgccagcg ggagaccgca gaaaaaaacg attattaccg agtaccgcat tactgggacg    3420
cgtgctctcg cgcgctgccc gaccaaaccc gttacaagta tgtggaacag ctcgtggacc    3480
tcacgttgaa ctaccactac gatgcgagcc acggcttgga caactttgac gtgctcaaga    3540
ggtgaggata cgcgctaaag gtgtatgaca acgggaaggt aagggcgaac gggtaacggg    3600
caggtaaccg catgggtgtg aaatgacgt tcggaacctg tgcttgcaga atcaacgtga    3660
ccgaggtgtc gttgctcatc agcgacttta gacgtcagaa ccgtcgcggc ggcaccaaca    3720
aaaggaccac gttcaacgcc gccggttcgc tggcgccgca cgcccggagc ctcgagttca    3780
gcgtgcggct ctttgccaac tagcctgcgt cacgggaaat aatatgctac ggcttctgct    3840
tcgtcaccac tttcactgcc tgcttctgtg cgcggtttgg gcaacgccct gtctggcgtc    3900
tccgtggtca acgctaacgg cgaaccagaa tccgtcccg ctatggtcta aactgacgta    3960
ttccaaaccg catgacgcgg cgacgtttta ctgtcctttt atctatccct cgcccccacg    4020
gtcccccttg caattctcgg ggttccagcg ggtattaacg ggtccgagt gtcgcaacga    4080 gaccctgtat ctgctgtaca accgggaagg ccagaccttg gtggagagaa gctccacctg    4140
ggtgaaaaag gtgatctggt acctgagcgg tcgcaaccag accatcctcc aacggatgcc    4200
ccgaacggct tcaaaaccga gcgacggaaa cgtgcagatc agcgtggaag acgccaagat    4260
```

| | | | | | |
|---|---|---|---|---|---|
| ttttggagcg | cacatggtgc | ccaagcagac | caagctgcta | cgcttcgtcg | tcaacgatgg | 4320 |
| cacacgttat | cagatgtgtg | tgatgaagct | ggagagctgg | gctcacgtct | tccgggacta | 4380 |
| cagcgtgtct | tttcaggtgc | gattgacgtt | caccgaggcc | aataaccaga | cttacacctt | 4440 |
| ctgcacccat | cccaatctca | tcgtttgagc | ccgtcgcgcg | cgcagggaat | tttgaaaacc | 4500 |
| gcgcgtcatg | agtcccaaaa | acctgacgcc | gttcttgacg | gcgttgtggc | tgttattgga | 4560 |
| tcacagccgc | gtgccgcggg | tacgcgcaga | agaatgttgc | gaattcataa | acgtcaacca | 4620 |
| cccgccggaa | cgctgttacg | atttcaaaat | gtgcaatcgc | ttcaccgtcg | cgtacgtatt | 4680 |
| ttcatgattg | tctgcgttct | gtggtgcgtc | tggatctgtc | tctcgacgtt | tctgatagcc | 4740 |
| atgttccatc | gacgatcctc | gggaatgcca | gagtagattt | tcatgaatcc | acaggctgcg | 4800 |
| gtgtccggac | ggcgaagtct | gctacagtcc | cgagaaaaac | ggctgagatt | cgcgggatcg | 4860 |
| tcaccaccat | gacccattca | ttgacacgcc | aggtcgtaca | caacaaactg | acgagctgca | 4920 |
| actacaatcc | gtaagtctct | tcctcgaggg | ccttacagcc | tatgggagag | taagacagag | 4980 |
| agggacaaaa | catcattaaa | aaaaaaagtc | taatttcacg | ttttgtaccc | ccttccgtg | 5040 |
| ttgtaggtta | tacctcgaag | ctgacgggcg | aatacgctgc | ggcaaagtga | acgacaaggc | 5100 |
| gcagtacctg | ctgggcgccg | ctggcagcgt | tccctatcga | tggatcaacc | tggaatacga | 5160 |
| caagataacc | cggatcgtgg | gcctggatca | gtacctggag | agcgttaaga | aacacaaacg | 5220 |
| gctggatgtg | tgccgcgcta | aaatgggcta | tatgctgcag | tgaataataa | aatgtgtgtt | 5280 |
| tgtccgaaat | acgcgttttg | agatttctgt | cgccgactaa | attcatgtcg | cgcgatagtg | 5340 |
| gtgtttatcg | ccgatagaga | tggcgatatt | ggaaaaatca | atatttgaaa | atatggcata | 5400 |
| ttgaaaatgt | cgccgatgtg | agtttctgtg | taactgatat | cgccatttt | ccaaaagtga | 5460 |
| tttttgggca | tacgcgatat | ctggcgatag | cgcttatatc | gtttacgggg | gatggcgata | 5520 |
| gacgactttg | gcgacttggg | cgattcggtg | tgtcgcaaat | atcgcagttt | cgatataggt | 5580 |
| gacagacgat | atgaggccat | atcgccgata | gaggcgacat | cgagttggca | catggccaat | 5640 |
| ggatatcgat | atatacattg | catcaatatt | ggccattagc | catattagtc | attggttata | 5700 |
| tagcgtaaat | caatattggc | taatggccat | tgcatacgtt | gcatctatat | cataatgtgt | 5760 |
| acatttatat | tggctcatgt | ccaatatgac | cgccatgttg | acattgatta | ttgactagtt | 5820 |
| attaatagta | atcaattacg | gggtcattag | ttcatagccc | atatatggag | ttccgcgtta | 5880 |
| cataacttac | ggtaaatggc | ccgcctggct | gaccgcccaa | cgaccccgc | ccattgacgt | 5940 |
| caataatgac | gtgggttccc | atagtaacgc | caatagggac | tttccattga | cgtcaatggg | 6000 |
| aggagtattt | acggtaaact | gcccacttgg | cagtacatca | agtgtatcat | atgccaagta | 6060 |
| cgccccctat | tgacgtcaat | gacggtaaat | ggcccgcctg | gcattatgcc | cagtacatga | 6120 |
| ccttacggga | ctttcctact | t | | | | 6141 |

<210> SEQ ID NO 4
<211> LENGTH: 6138
<212> TYPE: DNA
<213> ORGANISM: Human cytomegalovirus

<400> SEQUENCE: 4

| | | | | | |
|---|---|---|---|---|---|
| tttaaacctg | tgtgttgtgt | gattgattgg | tacgtggggg | gatccgattt | caaagggagg | 60 |
| tagttatcgg | gagttgatgt | gtcatggacg | tagttttgag | tgattttccg | ggaataccgg | 120 |
| atattacgaa | ttactgatag | tgacgtagat | aataaaatta | taatgcgatt | tatttttagt | 180 |
| ctgtttggtc | ttttgatcgc | gttgtgctat | aaggtggaaa | gtgtggaact | acgttgtcgg | 240 |

-continued

```
tgtagcaatg gttcaaatca tcccgtattc ggcgttttt gggtcggcta taaacctcca   300
gatcctacat gcgacaaaac gcaacacttt ttattacctc cccgacaaac acctgtatgt   360
ttgtctcctg atcattatct atcgaaatgg gttgatggca aacgaagtaa ctggtggcat   420
aaagtgttta taagaaaaa ctctgataat ggaccacata tagaagacaa aagtgacacc    480
aatagacacc cgccttggcg actataattt tttataaatt gtaaaacgag ttggcaatat   540
cacgtatata gcgaaaaagg taatacaatg tgttttcgac atggttttga catggttaca   600
ccatccgatt ccaaattcgc acatcaaagt cttatcggta cgatacctgt atttgaccgc   660
atatgtgtta ttttccacgt gtcccctatt cgtctatctc ttagaattgg aagattacga   720
caagcgctgt cgttgcaaca accaaattct gttgaatacc ctgccagtcg gaactcaact   780
gcttaagcca atcgcagcga gcgaaagctg caatcgtcag gaagtgctgg ctattttaaa   840
ggacaagggc accaagtgtc tcaatcctaa cgcgcaagct gtgcgtcgtc acatcaaccg   900
gctatttttt cggttaatct tagacgaaga acaacgcatt tacgacgtag tgtctaccaa   960
tattgagttt ggtgcctggc cagccccctac ggcctacaaa gcctttctct ggaaatacgc  1020
caagaaattg aactaccacc acttcagact gcgctggtga tcatgtccct attttaccgt  1080
gcggtagctc tgggcacact aagcgctctg gtgtggtaca gcactagtat cctcgcagag  1140
attaacgaaa attcctgctc ctcatcttct gtggaccacg aagagtgtga ggaaccggac  1200
gagatcgttc gcgaagagca agactatcgg gctctgctgg cctttccct agtgatttgc   1260
ggtacgctcc tcgtcacttg tgtgatctga gacgtcatgc tggtagtgtt tatgagtcgg  1320
gcggtggccg gcacgccgca tttcctaacc cgcgcagcat gttgcgcttg ctgttcacgc  1380
tcgtcctgct ggccctccac gggccgtctg tcaatgctag ccgcgactat gtgcatgttc  1440
ggctattgag ctaccgaggc gacccctgg tcttcaagca cacttttcg ggtgtgcgtc    1500
gacccttcac cgagctaggc tgggctgcgt gtcgcgactg ggacagtatg cattgcacgc  1560
ccttctggtc taccgatccg gagcagatga ccgactcggt gcggcgttac agcacagtga  1620
gccccggcaa ggaagtgacg cttcagcttc acgggaacca aaccgtacag ccgtcgtttc  1680
taagctttac gtgccgcctg cagctagaac ccgtggtgga aaatgttggc ctctacgtgg  1740
cctacgtggt caacgacggt gaacgcccac agcagttttt tacaccgcag gtagacgtgg  1800
tacgctttgc tctatatcta gagacgctct cccggatcgt ggaaccgtta gaatcaggtc  1860
gcctggcagt ggaatttgat acgcctgacc tagctctggc gcccgattta gtaagcagcc  1920
tcttcgtggc cggacacggc gagaccgact tttacatgaa ctggacgctg cgtcgcagtc  1980
agacccacta cctggaggag atggccttac aggtggagat tctaaagccc cgcggcgtac  2040
gtcaccgcgc tattatccac catccgaagc tacagccggg cgttggcctg tggatagatt  2100
tctgcgtgta ccgctacaac gcgcgcctga cccgcggcta cgtacgatac accctgtcac  2160
cgaaagcgcg cttgcccgca aaagcagagg gttggctggt gtcactagac agattcatcg  2220
tgcagtacct caacacattg ctgattacaa tgatggcggc gatatgggct cgcgttttga  2280
taacctacct ggtgtcgcgg cgtcggtaga ggcttgcgga aaccacgtcc tcgtcacacg  2340
tcgttcgcgg acatagcaag aaatccacgt cgccacgtct cgagaatgcc ggccccgcgg  2400
ggtcccttc gcgcaacatt cctggccctg gtcgcgttcg ggttgctgct tcagatagac   2460
ctcagcgacg ctacgaatgt gaccagcagc acaaaagtcc ctactagcac cagcagaga   2520
aatagcgtcg acaatgccac gagtagcgga cccacgaccg ggatcaacat gaccaccacc  2580
```

```
cacgagtcttccgttcacagcgtgcgcaatgacgaaatcatgaaagtgctggctatcctc    2640 ttctacatcgtgacaggcacctccatttcagcttcatagcggtactgatcgcggtagtt    2700 tactcctcgtgttgcaagcacccgggccgctttcgtttcgccgacgaagaagccgtcaac    2760 ctgttggacgacacggacgacagtggcggtggcagcccgtttggcagcggttcccgacga    2820 ggttctcagatccccgccggattttgttcctcgagcccttatcagcggttggaaactcgg    2880 gactgggacgaggaggaggaggcgtccgcgcccgcgagcgcatgaaacatgatcctgag    2940 aacgtcatctatttcagaaaggatggcaacttggacacgtcgttcgtgaatcccaattat    3000 gggagaggctcgcctttgacatcgaatctcacctctcggacaatgaggaagaccccatc    3060 aggtactacgtctcggtgtacgatgaactgaccgcctcggaaatggaagaaccttcgaac    3120 agcaccagctggcagattcccaaactaatgaaagttgccatgcaacccgtctcgctcaga    3180 gatcccgagtacgactaggcttttttttttttatctttcggttccaactctttccccgcc    3240 ccatcacctcgcctatactatgtgtatgatgtctcataataaagctttcttctcagtct    3300 gcaacatgcggctgtgtcggtgtggctgtctgtttgtctgtgcgccgtggtgctgggtc    3360 agtgccagcgggagaccgcagaaaaaaacgattattaccgagtaccgcattactgggacg    3420 cgtgctctcgcgcgctgcccgaccaaacccgttacaagtatgtggaacagctcgtggacc    3480 tcacgttgaactaccactacgatgcgagccacggcttggacaactttgacgtgctcaaga    3540 ggtgaggatacgcgctaaagtgtatgacaacgggaaggtaagggcgaacgggtaacggg    3600 caggtaaccgcatggggtgtgaaatgacgttcggaacctgtgcttgcagaatcaacgtga    3660 ccgaggtgtcgttgctcatcagcgactttagacgtcagaaccgtcgcggcggcaccaaca    3720 aaaggaccacgttcaacgccgccggttcgctggcgccgcacgcccggagcctcgagttca    3780 gcgtgcggcttttgccaactagcctgcgtcacgggaataatatgctacggcttctgct    3840 tcgtcaccactttcactgcctgcttctgtgcgcggtttggcaacgccctgtctggcgtc    3900 tccgtggtcaacgctaacggcgaaccagaatccgtccccgctatggtctaaactgacgta    3960 ttccaaaccgcatgacgcggcgacgttttactgtccttttatctatccctcgcccccacg    4020 gtcccccttgcaattctcggggttccagcgggtattaacgggtcccgagtgtcgcaacga    4080 gaccctgtatctgctgtacaaccgggaaggccagaccttggtggagagaagctccacctg    4140 ggtgaaaaagtgatctggtacctgagcggtcgcaaccagaccatcctccaacgatgcc    4200 ccgaacggcttcaaaaccgagcgacggaaacgtgcagatcagcgtggaagacgccaagat    4260 ttttggagcgcacatggtgccccaagcagaccaagctgctacgcttcgtcgtcaacgatgg    4320 cacacgttatcagatgtgtgtgatgaagctggagagctgggctcacgtctccgggacta    4380 cagcgtgtctttcaggtgcgattgacgttcaccgaggccaataaccagacttacacctt    4440 ctgcacccatcccaatctcatcgtttgagccgtcgcgcgcgcagggaatttgaaaacc    4500 gcgcgtcatgagtcccaaaaacctgacgccgttcttgacgcgttgtggctgttattgga    4560 tcacagccgcgtgccgcgggtacgcgcagaagaatgttgcgaattcataacgtcaacca    4620 cccgccggaacgctgttacgatttcaaaatgtgcaatcgcttcaccgtcgcgtacgtatt    4680 ttcatgattgtctgcgttctgtggtgcgtctggatctgtctctcgacgttctgatagcc    4740 atgttccatcgacgatcctcgggaatgccagagtagatttcatgaatacacaggctgcg    4800 gtgtccggacggcgaagtctgctacagtcccgagaaaacgctgagattcgcgggatcgt    4860 caccaccatgacccattcattgacacgccaggtcgtacacaacaaactgacgagctgcaa    4920 ctacaatccgtaagtctcttcctcgagggccttacagcctatgggagagtaagacagaga    4980
```

-continued

| | |
|---|---|
| gggacaaaac atcattaaaa aaaaaagtct aatttcacgt tttgtacccc ccttccgtgt | 5040 |
| tgtaggttat acctcgaagc tgacgggcga atacgctgcg gcaaagtgaa cgacaaggcg | 5100 |
| cagtacctgc tgggcgccgc tggcagcgtt ccctatcgat ggatcaacct ggaatacgac | 5160 |
| aagataaccc ggatcgtggg cctggatcag tacctggaga gcgttaagaa cacaaacgg | 5220 |
| ctggatgtgt gccgcgctaa aatgggctat atgctgcagt gaataataaa atgtgtgttt | 5280 |
| gtccgaaata cgcgttttga gatttctgtc gccgactaaa ttcatgtcgc gcgatagtgg | 5340 |
| tgtttatcgc cgatagagat ggcgatattg gaaaaatcaa tatttgaaaa tatggcatat | 5400 |
| tgaaaatgtc gccgatgtga gtttctgtgt aactgatatc gccattttc caaaagtgat | 5460 |
| ttttgggcat acgcgatatc tggcgatagc gcttatatcg tttacggggg atggcgatag | 5520 |
| acgactttgg cgacttgggc gattcggtgt gtcgcaaata tcgcagtttc gatataggtg | 5580 |
| acagacgata tgaggccata tcgccgatag aggcgacatc gagttggcac atggccaatg | 5640 |
| gatatcgata tatacattgc atcaatattg gccattagcc atattagtca ttggttatat | 5700 |
| agcgtaaatc aatattggct aatgccatt gcatacgttg catctatatc ataatgtgta | 5760 |
| catttatatt ggctcatgtc caatatgacc gccatgttga cattgattat tgactagtta | 5820 |
| ttaatagtaa tcaattacgg ggtcattagt tcatagccca tatatggagt tccgcgttac | 5880 |
| ataacttacg gtaaatggcc cgcctggctg accgcccaac gacccccgcc cattgacgtc | 5940 |
| aataatgacg tgggttccca tagtaacgcc aatagggact ttccattgac gtcaatggga | 6000 |
| ggagtattta cggtaaactg cccacttggc agtacatcaa gtgtatcata tgccaagtac | 6060 |
| gcccctatt gacgtcaatg acggtaaatg gcccgcctgg cattatgccc agtacatgac | 6120 |
| cttacgggac tttcctac | 6138 |

<210> SEQ ID NO 5
<211> LENGTH: 1245
<212> TYPE: DNA
<213> ORGANISM: Human cytomegalovirus

<400> SEQUENCE: 5

| | |
|---|---|
| cggcacacat ccagccgttt gtgtttctta acgctctcca ggtactgatc caggcccacg | 60 |
| atccgggtta tcttgtcgta ttccaggttg atccatcgat agggaacgct gccagcggcg | 120 |
| cccagcaggt actgcgcctt gtcgttcact ttgccgcagc gtattcgccc gtcagcttcg | 180 |
| aggtataacg gattgtagtt gcagctcgtc agtttgttgt gtacgacctg gggtgtcaat | 240 |
| gaatgggtca tggtggtgac gatcccgcga atctcagccg ttttctcggg actgtagcag | 300 |
| acttcgccgt ccggacaccg cagcctgtgg attcatgaaa atctactctg cattcccga | 360 |
| ggatcgtcga tggaacatgg ctatcagaaa cgtcgagaga cagatccaga cgcaccacag | 420 |
| aacgcagaca atcatgaaaa tacgtacgcg acggtgaagc gattgcacat tttgaaatcg | 480 |
| taacagcgtt ccggcgggtg gttgacgttt atgaattcgc aacattcttc tgcgcgtacc | 540 |
| cgcggcacgc ggctgtgacc caatagcagc acaacgccg tcaagaacgg cgtcaggttt | 600 |
| ttgggactca tgacgcgcgg ttttcaaaat tccctgcgcg cgcgacgggc tcaaacgatg | 660 |
| agattgggat gggtgcagaa ggtgtaagtc tggttattgg cctcggtgaa cgtcaatcgc | 720 |
| acctgaaaag acacgctgta gtcccggaag acgtgggccc agctctccag tttcatcaca | 780 |
| cacatctgat aacgtgtgcc gtcgttgacg acgaaacgta gcagcttggt ctgcttgggc | 840 |
| accatgtgcg ctccaaaaat cttggcgtct tccacgctga tctgcacgtt tccgtcgctc | 900 |

```
ggtttcgaag ccgttcgggg catccgttgg aggatggtct gattgcgacc gctcagatac    960
cagatcacct ttttcaccca ggtggagctt ctctccacca aggtctggcc ttcccggttg   1020
tacagcagat acagggtctc gttgcgacac tcgggacccg ttgatacccg ctggaacccc   1080
gggaattgcg aggggaccg tgggggcgag ggatagagaa aaggacagta aaacgtcgcc   1140
gcgtcatgcg gtttgggata cgtcagttta gaccatggcg gggacggatt ctccccgcgt   1200
actctgcgtt gttaccactg cttgccctat agtgagtcgt attag                   1245

<210> SEQ ID NO 6
<211> LENGTH: 1814
<212> TYPE: DNA
<213> ORGANISM: Human cytomegalovirus

<400> SEQUENCE: 6
tgtgtcgggt gtggctgtct gtttgtctgt gcgccgtggt gctgggtcag tgccagcggg     60
agaccgcaga aaaaaacgat tattaccgag taccgcatta ctgggacgcg tgctctcgcg    120
cgctgcctga ccaaacccgt tacaagtatg tggaacagct cgtggacctc acgttgaact    180
accactacga tgcgagccac ggcttggaca actttgacgt gctcaagaga atcaacgtga    240
ccgaggtgtc gttgctcatc agcgacttta gacgtcagaa ccgtcgcggc ggcaccaaca    300
aaaggaccac gttcaacgcc gccggttcgc tggcgcctca cgcccggagc ctcgagttca    360
gcgtgcggct ctttgccaac tagcctgcgt cacgggaaat aatatgctac ggcttctgct    420
tcgtcaccac tttcactgcc tgcttctgtg cgcggtttgg gcaacgccct gtctggcgtc    480
tccgtggttc acgctaacgg cgaaccagaa tccgtccccg ccatggtcta aactgacgta    540
tcccaaaccg catgacgcgg cgacgtttta ctgtcctttt ctctatccct cgcccccacg    600
gtccccctcg caattcccgg ggttccagcg ggtatcaacg ggtcccgagt gtcgcaacga    660
gaccctgtat ctgctgtaca accgggaagg ccagaccttg gtggagagaa gctccacctg    720
ggtgaaaaag gtgatctggt atctgagcgg tcgcaatcag accatcctcc aacggatgcc    780
ccgaacggct tcgaaaccga gcgacggaaa cgtgcagatc agcgtggaag acgccaagat    840
ttttggagcg cacatggtgc ccaagcagac caagctgcta cgtttcgtcg tcaacgatgg    900
cacacgttat cagatgtgtg tgatgaaact ggagagctgg gcccacgtct ccgggacta    960 cagcgtgtct tttcaggtgc gattgacgtt caccgaggcc aataaccaga cttacacctt   1020
ctgcacccat cccaatctca tcgtttgagc ccgtcgcgcg cgcagggaat tttgaaaacc   1080
gcgcgtcatg agtcccaaaa acctgacgcc gttcttgacg cgttgtggc tgctattggg   1140 tcacagccgc gtgccgcggg tacgcgcaga agaatgttgc gaattcataa acgtcaacca   1200
cccgccggaa cgctgttacg atttcaaaat gtgcaatcgc ttcaccgtcg cgtacgtatt   1260
ttcatgattg tctgcgttct gtggtgcgtc tggatctgtc tctcgacgtt tctgatagcc   1320
atgttccatc gacgatcctc gggaatgcca gagtagattt tcatgaatcc acaggctgcg   1380
gtgtccggac ggcgaagtct gctacagtcc cgagaaaacg gctgagattc gcgggatcgt   1440
caccaccatg acccattcat tgacacgcca ggtcgtacac aacaaactga cgagctgcaa   1500
ctacaatccg ttataccctcg aagctgacgg gcgaatacgc tgcggcaaag tgaacgacaa   1560
ggcgcagtac ctgctgggcg ccgctggcag cgttccctat cgatggatca acctggaata   1620
cgacaagata acccggatcg tgggcctgga tcagtacctg gagagcgtta agaaacacaa   1680
acggctggat gtgtgccgcg ctaaaatggg ctatatgctg cagtgaataa taaaatgtgt   1740
gtttgtcaaa aaaaaaaaaa aaaaaaagta ctctgcgttg ttaccactgc ttgccctata   1800
```

<210> SEQ ID NO 7
<211> LENGTH: 1951
<212> TYPE: DNA
<213> ORGANISM: Human cytomegalovirus

<400> SEQUENCE: 7

```
gaattcggct ttgtgtcggg taaggctgtc tgtttgtctg tgcgccgtgg tgctgggtca     60
gtgccagcgg gagaccgcag aaaaaaacga ttattaccga gtaccgcatt actgggacgc    120
gtgctctcgc gcgctgcctg accaaacccg ttacaagtat gtggaacagc tcgtggacct    180
cacgttgaac taccactacg atgcgagcca cggcttggac aactttgacg tgctcaagag    240
gtgagggtac gcgctaaagg tgtatgacaa cgggaaggta agggcgaacg ggtaacgggt    300
aggtaaccgc atggggtgtg aaatgacgtt cggaacctgt gcttgcagaa tcaacgtgac    360
cgaggtgtcg ttgctcatca gcgactttag acgtcagaac cgtcgcggcg caccaacaa     420
aaggaccacg ttcaacgccg ccggttcgct ggcgcctcac gcccggagcc tcgagttcag    480
cgtgcggctc tttgccaact agcctgcgtc acgggaaata atatgctacg gcttctgctt    540
cgtcacactt tcactgcctg cttctgtgcg cggtttgggc aacgccctgt ctggcgtctc    600
cgtggttcac gctaacggcg aaccagaatc cgtccccgcc atggtctaaa ctgacgtatc    660
ccaaaccgca tgacgcggcg acgttttact gtccttttct ctatccctcg ccccacggt     720
cccctcgca attcccgggg ttccagcggg tatcaacggg tcccgagtgt cgcaacgaga    780
ccctgtatct gctgtacaac cgggaaggcc agaccttggt ggagagaagc tccacctggg    840
tgaaaaggc gatctggtat ctgagcggtc gcaatcagac catcctccaa cggatgcccc    900
gaacggcttc gaaaccgagc gacggaaacg tgcagatcag cgtggaagac gccaagattt    960
ttggagcgca catggtgccc aagcagacca agctgctacg tttcgtcgtc aacgatggca   1020
cacgttatca gatgtgtgtg atgaaactgg agagctgggc ccacgtcttc cgggactaca   1080
gcgtgtcttt tcaggtgcga ttgacgttca ccgaggccaa taaccagact tacaccttct   1140
gcacccatcc caatctcatt gtttgagccc gtcgcgcgcg cagggaattt tgaaaaccgc   1200
gcgtcatgag tcccaaaaac ctgacgccgt tcttgacggc gttgtggctg ctattgggtc   1260
acagccgcgt gccgcgggta cgcgcagaag aatgttgcga attcataaac gtcaaccacc   1320
cgccggaacg ctgttacgat ttcaaaatgt gcaatcgctt caccgtcgcg tacgtatttt   1380
catgattgtc tgcgttctgt ggtgcgtctg gatctgtctc tcgacgtttc tgatagccat   1440
gttccatcga cgatcctcgg gaatgccaga gtagatttc atgaatccac aggctgcggt    1500
gtccggacgg cgaagtctgc tacagtcccg agaaaacggc tgagattcgc gggatcgtca   1560
ccaccatgac ccattcattg acacgccagg tcgtacacaa caaactgacg agctgcaact   1620
acaatccgtt ataccctcgaa gctgacgggc gaatacgctg cggcaaagtg aacgacaagg   1680
cgcagtacct gctgggcgcc gctggcagcg ttccctatcg atggatcaac ctggaatacg   1740
acaagataac ccggatcgtg ggcctggatc agtacctgga gagcgttaag aaacacaaac   1800
ggctggatgt gtgccgcgct aaaatgggct atatgctgca gtgaataata aaatgtgtgt   1860
ttgtccggaa aaaaaaaaaa aaagaaaaaa aaagtactct gcgttgttac cactgcttgc   1920
cctatagtga gtcgtattag aagccgaatt c                                  1951
```

<210> SEQ ID NO 8

<211> LENGTH: 651
<212> TYPE: DNA
<213> ORGANISM: Human cytomegalovirus

<400> SEQUENCE: 8

```
gaattcggct tctaatacga ctcactatag ggcaagcagt ggtaacaacg cagagtacgc    60
gggggtcctt ttctctatcc ctcgccccca cggtccccct cgcaattccc ggggttccag   120
cgggtatcaa cgggtcccga gtgtcgcaac gagaccctgt atctgctgta caaccgggaa   180
ggccagacct tggtggagag aagctccacc tgggtgaaaa aggtgatctg gtatctgagc   240
ggtcgcaatc agaccatcct ccaacggatg ccccgaacgg cttcgaaacc gagcgacgga   300
aacgtgcaga tcagcgtgga agacgccaag atttttggag cgcacatggt gcccaagcag   360
accaagctgc tacgtttcgt cgtcaacgat ggcacacgtt atcagatgtg tgtgatgaaa   420
ctggagagct gggcccacgt cttccgggac tacagcgtgt cttttcaggt gcgattgacg   480
ttcaccgagg ccaataacca gacttacacc ttctgcaccc atcccaatct catcgtttga   540
gcccgtcgcg cgcgcaggga attttgaaaa ccgcgcgtca tgagtcccaa aaacctgacg   600
ccgttcttga cggcgttgtg gctgctattg ggtcacagcc gcgtgccgcg g            651
```

<210> SEQ ID NO 9
<211> LENGTH: 581
<212> TYPE: DNA
<213> ORGANISM: Human cytomegalovirus

<400> SEQUENCE: 9

```
gaattcggct tcggcacaca tccagccgtt tgtgtttctt aacgctctcc aggtactgat    60
ccaggcccac gatccgggtt atcttgtcgt attccaggtt gatccatcga tagggaacgc   120
tgccagcggc gcccagcagg tactgcgcct tgtcgttcac tttgccgcag cgtattcgcc   180
cgtcagcttc gaggtataac ggattgtagt tgcagctcgt cagtttgttg tgtacgacct   240
ggcgtgtcaa tgaatgggtc atggtggtga cgatcccgcg aatctcagcc gttttctcgg   300
gactgtagca gacttcgccg tccggacacc gcagcctgtg gattcatgaa aatctactct   360
ggcattcccg gggatcgtcg atggaacatg gctatcagaa acgtcgagag acagatccag   420
acgcaccaca gaacgcagac gatcatgaaa atacgtacgc gacggtgaag cgattgcaca   480
ttttgaaatc gtaacagcgt tccggcgggt gtttgacgtt tatgaattcg caacattctt   540
ctgcgcgtac ccgcggcacg cggctgtgac ccaatagcag c                       581
```

<210> SEQ ID NO 10
<211> LENGTH: 547
<212> TYPE: DNA
<213> ORGANISM: Human cytomegalovirus

<400> SEQUENCE: 10

```
gaattcggct tcggcacaca tccagccgtt tgtgtttctt aacgctctcc aggtactgat    60
ccaggcccac gatccgggtt atcttgtcgt attccaggtt gatccatcga tagggaacgc   120
tgccagcggc gcccagcagg tactgcgcct tgtcgttcac tttgccgcag cgtattcgcc   180
cgtcagcttc gaggtataac ggattgtagt tgcagctcgt cagtttgttg tgtacgacct   240
ggcgtgtcaa tgaatgggtc atggtggtga cgatcccgcg aatctcagcc gttttctcgg   300
gactgtagca gacttcgccg tccggacacc gcagcctgtg gattcatgaa aatctactct   360
ggcattcccg aggatcgtcg atggaacatg gctatcagaa acgtcgagag acagatccag   420
acgcaccaca gaacgcagac aatcatgaaa ataccccgg tactctgcgt tgttaccact   480
```

```
gcttcccgcg tactctgcgt tgttaccact gcttgcccta tagtgagtcg tattagaagc    540
cgaattc                                                              547

<210> SEQ ID NO 11
<211> LENGTH: 253
<212> TYPE: DNA
<213> ORGANISM: Human cytomegalovirus

<400> SEQUENCE: 11
gaattcggct tctaatacga ctcactatag ggcctggatc agtacctgga gagcgttagt     60
gggcctggat cagtacctgg agagcgttag tgggcctgga tcagtacctg gagagcgtta   120
gtgggcctgg atcagtacct ggagagcgtt agtgggcctg gatcagtacc tggagagcgt   180
tagtgggcct ggatcagtac ctggagagcg ttagtgggcc tggaagtacc tggagagcgt   240
taaagccgaa ttc                                                      253

<210> SEQ ID NO 12
<211> LENGTH: 614
<212> TYPE: DNA
<213> ORGANISM: Human cytomegalovirus

<400> SEQUENCE: 12
gaattcggct taacctctcc aggtactgat ccaggcccac gatccgggtt atcttgtcgt     60
attccaggtt gatccatcga tagggaacgc tgccagcggc gcccagcagg tactgcgcct   120
tgtcgttcac tttgccgcag cgtattgccc gtcagcttc gaggtataac ggattgtagt   180
tgcagctcgt cagtttgttg tgtacgacct ggcgtgtcaa tgaatgggtc atggtggtga   240
cgatcccgcg aatctcagcc gttttctcgg gactgtagca gacttcgccg tccggacacc   300
gcagcctgtg gattcatgaa atctactct ggcattcccg aggatcgtcg atggaacatg   360
gctatcagaa acgtcgagag acagatccag acgcaccaca gaacgcagac aatcatgaaa   420
atacgtacgc gacggtgaag cgattgcaca ttttgaaatc gtaacagcgt tccggcgggt   480
ggttgacgtt tatgaattcg caacattctt ctgcgcgtac ccgcggcacg cggctgtgac   540
ccaatagcag ccacaacgcc gtcaagaacg gcgtcaggtt tttgggactc atgacgcgcg   600
gttttcaaaa ttcc                                                     614

<210> SEQ ID NO 13
<211> LENGTH: 767
<212> TYPE: DNA
<213> ORGANISM: Human cytomegalovirus

<400> SEQUENCE: 13
gaattcggct ttaacgctct ccaggtactg atccaggccc acgtcttccg ggactacagc     60 gtgtctttc aggtgcgatt gacgttcacc gaggccaata accagactta caccttctgc   120
acccatccca atctcatcgt ttgagcccgt cgcgcgcgca tgaaaaccgc gcgtcatgag   180
tcccaaaaac ctgacgccgt tcttgacggc gttgtggctg ctattgggtc acagccgcgt   240
gccgcgggta cgcgcagaag aatgttgcga attcataaac gtcaaccacc gccggaacg   300 ctgttacgat ttcaaaatgt gcaatcgctt caccgtcgcg tacgtatttt catgattgtc   360
tgcgttctgt ggtgcgtctg gatctgtctc tcgacgtttc tgatagccat gttccatcga   420
cgatcctcgg gaatgccaga gtagattttc atgaatccac aggctgcggt gtccggacgg   480
cgaagtctgc tacagtcccg agaaaacggc tgagattcgc gggatcgtca ccaccatgac   540
```

| | |
|---|---|
| ccattcattg acacgccagg tcgtacacaa caaactgacg agctgcaact acaatccgtt | 600 |
| atacctcgaa gctgacgggc gaatacgctg cggcaaagtg aacgacaagg cgcagtacct | 660 |
| gctgggcgcc gctggcagcg ttccctagat ggatcaacct ggaatacgac aagataaccc | 720 |
| ggatcgtggg cctggatcag tacctggaga gcgttaaagc cgaattc | 767 |

<210> SEQ ID NO 14
<211> LENGTH: 577
<212> TYPE: DNA
<213> ORGANISM: Human cytomegalovirus

<400> SEQUENCE: 14

| | |
|---|---|
| gaattcggct taatacgact cactataggg caagcagtgg taacaacgca gagtacgcgg | 60 |
| ggcagaagaa tgttgcgaat tcataaacgt caaccacccg ccggaacgct gttacgattt | 120 |
| caaaatgtgc aatcgcttca ccgtcgcgta cgtattttca tgattgtctg cgttctgtgg | 180 |
| tcgtctgga tctgtctctc gacgtttctg atagccatgt tccatcgacg atcctcggga | 240 |
| atgccagagt agattttcat gaatccacag gctgcggtgt ccggacggcg aagtctgcta | 300 |
| cagtcccgag aaaacggctg agattcgcgg gatcgtcacc accatgaccc attcattgac | 360 |
| acgccaggcc gtacacaaca aactgacgag ctgcaactac aatccgttat acctcgaagc | 420 |
| tgacgggcga atacgctgcg gcaaagtgaa cgacaaggcg cagtacctgc tgggcgccgc | 480 |
| tggcagcgtt ccctatcgat ggatcaacct ggaatacgac aagataaccc ggatcgtggg | 540 |
| cctggatcag tacctggaga gcgttaaagc cgaattc | 577 |

<210> SEQ ID NO 15
<211> LENGTH: 1778
<212> TYPE: DNA
<213> ORGANISM: Human cytomegalovirus

<400> SEQUENCE: 15

| | |
|---|---|
| ttgtgtcggg tgtggctgtc tgtttgtctg tgcgccgtgg tgctgggtca gtgccagcgg | 60 |
| gagaccgcag aaaaaaacga ttattaccga gtaccgcatt actgggacgc gtgctctcgc | 120 |
| gcgctgcctg accaaacccg ttacaagtat gtggaacagc tcgtggacct cacgttgaac | 180 |
| taccactacg atgcgagcca cggcttggac aactttgacg tgctcaagag aatcaacgtg | 240 |
| accgaggtgt cgttgctcat cagcgacttt agacgtcaga accgtcgcgg cggcaccaac | 300 |
| aaaaggacca cgttcaacgc cgccggttcg ctggcgcctc acgcccggag cctcgagttc | 360 |
| agcgtgcggc tctttgccaa ctagcctgcg tcacgggaaa taatatgcta cggcttctgc | 420 |
| ttcgtcacca ctttcactgc ctgcttctgt gcgcggtttg ggcaacgccc tgtctggcgt | 480 |
| ctccgtggtt cacgctaacg gcgaaccaga atccgtcccc gccatggtct aaactgacgt | 540 |
| atcccaaacc gcatgacgcg gcgacgtttt actgtccttt tctctatccc tcgccccac | 600 |
| ggtccccctc gcaattcccg gggttccagc gggtatcaac gggtcccgag tgtcgcaacg | 660 |
| agaccctgta tctgctgtac aaccgggaag ccagaccttt ggtggagaga agctccacct | 720 |
| gggtgaaaaa ggtgatctgg tatctgagcg gtcgcaatca gaccatcctc caacggatgc | 780 |
| cccgaacggc ttcgaaaccg agcgacggaa acgtgcagat cagcgtggaa gacgccaaga | 840 |
| tttttggagc gcacatggtg cccaagcaga ccaagctgct acgtttcgtc gtcaacgatg | 900 |
| gcacacgtta tcagatgtgt gtgatgaaac tggagagctg ggcccacgtc ttccgggact | 960 |
| acagcgtgtc tttcaggtg cgattgacgt tcaccgaggc caataaccag acttacacct | 1020 |
| tctgcaccca tcccaatctc atcgtttgag cccgtcgcgc gcgcagggaa ttttgaaaac | 1080 |

```
cgcgcgtcat gagtcccaaa aacctgacgc cgttcttgac ggcgttgtgg ctgctattgg    1140
gtcacagccg cgtgccgcgg gtacgcgcag aagaatgttg cgaattcata acgtcaacc    1200 acccgccgga acgctgttac gatttcaaaa tgtgcaatcg cttcaccgtc gcgtacgtat    1260
tttcatgatt gtctgcgttc tgtggtgcgt ctggatctgt ctctcgacgt ttctgatagc    1320
catgttccat cgacgatcct cgggaatgcc agagtagatt tcatgaatc cacaggctgc    1380 ggtgtccgga cggcgaagtc tgctacagtc ccgagaaaac ggctgagatt cgcgggatcg    1440
tcaccaccat gacccattca ttgacacgcc aggtcgtaca caacaaactg acgagctgca    1500
actacaatcc gttatacctc gaagctgacg gcgaatacg ctgcggcaaa gtgaacgaca    1560
aggcgcagta cctgctgggc gccgctgca gcgttcccta tcgatggatc aacctggaat    1620
acgacaagat aacccggatc gtgggcctgg atcagtacct ggagagcgtt aagaaacaca    1680
aacggctgga tgtgtgccgc gctaaaatgg gctatatgct gcagtgaata ataaaatgtg    1740
tgtttgtccg aaaaaaaaaa aaaaaaaaaa aaaaaaaa                             1778

<210> SEQ ID NO 16
<211> LENGTH: 1422
<212> TYPE: DNA
<213> ORGANISM: Human cytomegalovirus

<400> SEQUENCE: 16
gaattcggct ttctgcttcg tcaccacttt cactgcctgc ttctgtgcgc ggtttgggca     60
acgccctgtc tggcgtctcc gtggttcacg ctaacggcga accagaatcc gtccccgcca    120
tggtctaaac tgacgtatcc caaaccgcat gacgcggcga cgttttactg tccttttctc    180
tatccctcgc ccccacggtc ccctcgcaa ttcccggggt tccagcgggt atcaacgggt    240
cccgagtgtc gcaacgagac cctgtatctg ctgtacaacc gggaaggcca gaccttggtg    300
gagagaagct ccacctgggt gaaaaaggtg atctggtatc tgagcggtcg caatcagacc    360
atcctccaac ggatgccccg aacggcttcg aaaccgagcg acggaaacgt gcagatcagc    420
gtggaagacg ccaagatttt tggagcgcac atggtgccca agcagaccaa gctgctacgt    480 tcgtcgtca acgatggcac acgttatgtg tgatgaaact ggagagctgg gcccacgtct    540
tccgggacta cagcgtgtct tttcaggtgc gattgacgtt caccgaggcc aataaccaga    600
cttacacctt ctgcacccat cccaatctca tcgtttgagc ccgtcgcgcg cgcagggaat    660
tttgaaaacc gcgcgtcatg agtcccaaaa acctgacgcc gttcttgacg gcgttgtggc    720
tgctattggg tcacagccgc gtgccgcggg tacgcgcaga agaatgttgc gaattcataa    780
cgtcaaccca cccgccggaa cgctgttacg atttcaaaat gtgcaatcgc ttcaccgtcg    840
cgtacgtatt ttcatgattg tctgcgttct gtggtgcgtc tggatctgtc tctcgacgtt    900
tctgatagcc atgttccatc gacgatcctc gggaatgcca gagtagattt catgaatcc    960 acaggctgcg gtgtccggac ggcgaagtct gctacagtcc cgagaaaacg gctgagattc   1020
gcgggatcgt caccaccatg acccattcat tgacacgcca ggtcgtacac aacaaactga   1080
cgagctgcaa ctacaatccg ttatacctcg aagctgacgg gcgaatacgc tgcggcaaag   1140
tgaacgacaa ggcgcagtac ctgctgggcg ccgctggcag cgttccctat cgatggatca   1200
acctggaata cgacaagata acccggatcg tgggcctgga tcagtacctg gagagcgtta   1260
agaaacacaa acggctggat gtgtgccgcg ctaaatggg ctatatgctg cagtgaataa   1320
taaaatgtgt gtttgtccaa aaaaaaaaaa aaaaaaaaa aaaagtactc tgcgttgtta   1380
```

```
ccactgcttg ccctatagtg agtcgtatta gaagccgaat tc                      1422

<210> SEQ ID NO 17
<211> LENGTH: 510
<212> TYPE: DNA
<213> ORGANISM: Human cytomegalovirus

<400> SEQUENCE: 17
gaattcggct tctaatacga ctcactatag ggcaagcagt ggtaacaacg cagagtacgc    60
ggggactgtc cttttctcta tccctcgccc ccacggtccc cctcgcaatt cccggggttc   120
cagcgggtat caacgggtcc cgagtgtcgc aacgagaccc tgtatctgct gtacaaccgg   180
gaaggccaga ccttggtgga gagaagctcc acctgggtga aaaggtgat  ctggtatctg   240 agcggtcgca atcagaccat cctccaacgg atgccccgaa cggcttcgaa accgagcgac   300
ggaaacgtgc agatcagcgt ggaagacgcc aagattttg  agcgcacat ggtgcccaag   360 cagaccaagc tgctacgttt cgtcgtcaac gatggcacac gttatcagat gtgtgtgatg   420
aaactggaga gctgggccca cgtcttccgg gactacagcg tgtcttttca ggtgcgattg   480
acgttcaccg aggccaataa agccgaattc                                    510

<210> SEQ ID NO 18
<211> LENGTH: 686
<212> TYPE: DNA
<213> ORGANISM: Human cytomegalovirus

<400> SEQUENCE: 18
gaattcggct tctaatacga ctcactatag ggcaagcagt ggtaacaacg cagagtacgc    60
ggggcactac gatgcgagcc acggcttgga caactttgac gtgctcaaga gaatcaacgt   120
gaccgaggtg tcgttgctca tcagcgactt tagacgtcag aaccatcgcg gcggcaccaa   180
caaaaggacc acgttcaacg ccgccggttc gctggcgcct cacgcccgga gcctcgagtt   240
cagcgtgcgg ctccttgcca actagcctgc gtcacgggaa ataatatgct acggcttctg   300
cttcgtcacc actttcactg cctgcttctg tgcgcggttt gggcaacgcc ctgtctggcg   360
tctccgtggt tcacgctaac ggcgaaccag aatccgtccc cgccatggtc taaactgacg   420
tatcccaaac cgcatgacgc ggcgacgttt tgctgtcctt ttctctatcc ctcgccccca   480
cggtccccct cgcaattccc ggggttccag cgggtatcaa cgggtcccga gtgtcgcaac   540
gagaccctgt atctgctgta caaccgggaa ggccagacct tggtggagag aagctccacc   600
tgggtgaaaa aggtgatctg gtatctgagc ggtcgcaatc agaccatcct ccaacggatg   660
ccccgaacgg cttcgaaacc gagcga                                        686

<210> SEQ ID NO 19
<211> LENGTH: 670
<212> TYPE: DNA
<213> ORGANISM: Human cytomegalovirus

<400> SEQUENCE: 19
gaattcggct tctaatacga ctcactatag ggcaagcagt ggtaacaacg cagagtacgc    60
ggggagaacc gtcgcggcgg caccaacaaa aggaccacgt tcaacgccgc cggttcgctg   120
gcgcctcacg cccggagcct cgagttcagc gtgcggctct tgccaactag cctgcgtca   180 cgggaaataa tatgctacgg cttctgcttc gtcaccactt tcactgcctg cttctgtgcg   240
cggtttgggc aacgccctgt ctggcgtctc cgtggttcac gctaacgcg aaccagaatc   300 cgtccccgcc atggtctaaa ctgacgtatc ccaaaccgca tgacgcggcg acgttttact   360
```

```
gtccttttct ctatccctcg ccccacggt ccccctcgca attccgggg ttccagcggg    420 tatcaacggg tcccgagtgt cgcaacgaga ccctgtatct gctgtacaac cgggaaggcc    480
agaccttggt ggagagaagc tccacctggg tgaaaaaggt gatctggtat ctgagcggtc    540
gcaatcagac catcctccaa cggatgcccc gaacggcttc gaaaccgagc gacggaaacg    600
tgcagatcag cgtggaagac gccaagattt ttggagcgca catggtgccc aagcagacca    660
agctgctacg                                                            670
```

```
<210> SEQ ID NO 20
<211> LENGTH: 226
<212> TYPE: DNA
<213> ORGANISM: Human cytomegalovirus

<400> SEQUENCE: 20
gaattcggct tctaatacga ctcactatag ggcaagcagt ggtaacaacg cagagtactt     60
tttttttttt tttttttttt ttttttggga tacgtcagtt tagaccatgg cggggacgga    120
ttctggttcg ccgttagcgt gaaccacgga gacgccagac agggcgttgc ccaaaccgcg    180
cacagaagca ggcagtgaag tggtgacgaa gcagaaagcc gaattc                   226
```

```
<210> SEQ ID NO 21
<211> LENGTH: 653
<212> TYPE: DNA
<213> ORGANISM: Human cytomegalovirus

<400> SEQUENCE: 21
gaattcggct ttctgcttcg tcaccacttc actgcctgct tctgtgcgcg gtttgggcaa     60
cgccctgtct ggcgtctccg tggttcacgc taacggcgaa ccagaatccg tccccgccat    120 ggtctaaaact gacgtatccc aaaccgcatg acgcggcgac gttttactgt ccttttctct    180
atccctcgcc cccacggtcc ccctcgcaat tcccgggggtt ccagcgggta tcaacgggtc    240
ccgagtgtcg caacgagacc ctgtatctgc tgtacaaccg ggaaggccag accttggtgg    300
agagaagctc cacctgggtg aaaaaggtga tctggtatct gagcggtcac aatcagacca    360
tcctccaacg gatgcccga acggcttcga accgagcga cggaaacgtg cagatcagcg      420
tggaagacgc caagattttt ggagcgcaca tggtgcccaa gcagaccaag ctgctacgtt    480
tcgtcgtcaa cgatggcaca cgttatcaga tgtgtgtgat gaaactggag agctgggccc    540
acgtcttccg ggactacgac aagataaccc ggatcgtggg cctggatcag tacctggaga    600
gcgttaagaa acacaaacgg ctggatgtgt gccgcgctaa aatgggctat atg           653
```

```
<210> SEQ ID NO 22
<211> LENGTH: 607
<212> TYPE: DNA
<213> ORGANISM: Human cytomegalovirus

<400> SEQUENCE: 22
gaattcggct tcgcagaaga atgttgcgaa ttcataaacg tcaaccaccc gccggaacgc     60
tgttacgatt tcaaaatgtg caatcgcttc accgtcgcgt acgtattttc atgattgtct    120
gcgttctgtg gtgcgtctgg atctgtctct cgacgtttct gatagccatg ttccatcgac    180
gatcctcggg aatgccagag tagattttca tgaatccaca ggctgcggtg tccggacggc    240
gaagtctgct acagtcccga gaaaacggct gagattcgcg ggatcgtcac caccatgacc    300
cattcattga cacgccaggt cgtacacaac aaactgacga gctgcaacta caatccgtta    360
```

-continued

| | |
|---|---|
| tacctcgaag ctgacgggcg aatacgctgc ggcaaagtga acgacaaggc gcagtacctg | 420 |
| ctgggcgccg ctggcagcgt tccctatcga tggatcaacc tggaatacga caagataacc | 480 |
| cggatcgtgg gcctggatca gtacctggag agcgttaaga aacacaaacg gctggatgtg | 540 |
| tgccgcgcta aaatgggcta tatgctgcag tgaataataa aatgtgtgtt tgtccggaaa | 600 |
| aaaaaaa | 607 |

<210> SEQ ID NO 23
<211> LENGTH: 658
<212> TYPE: DNA
<213> ORGANISM: Human cytomegalovirus

<400> SEQUENCE: 23

| | |
|---|---|
| gaattgtctg cttcgtcacc atttcactgc ctgcttctgt gcgcggtttg ggcaacgccc | 60 |
| tgtctggcgt ctccgtggtt cacgctaacg gcgaaccaga atccgtcccc gccatggtct | 120 |
| aaactgacgt atcccaaacc gcatgacgcg gcgacgtttt actgtccttt tctctatccc | 180 |
| tcgcccccac ggtcccccctc gcaattcccg gggttccagc gggtatcaac gggtcccgag | 240 |
| tgtcgcaacg agaccctgta tctgctgtac aaccgggaag gccagacctt ggtggagaga | 300 |
| agctccacct gggtgaaaaa ggtgatctgg tatctgagcg gtcgcaatca gaccatcctc | 360 |
| caacggatgc cccgaacggc ttcgaaaccg agcgacggaa acgtgcagat cagcgtggaa | 420 |
| gacgccaaga ttttggagc gcacatggtg cccaagcaga ccaagctgct acgtttcgtc | 480 |
| gtcaacgatg gcacacgtta tcagatgtgt gtgatgaaac tggagagctg ggcccacgtc | 540 |
| ttccgggact acagcgtgtc ttttcaggtg cgattgacgt tcaccgaggc caataaccag | 600 |
| acttacacct tctgcaccca tcccaatctc atcgtttgag cccgtcgcgc gcgcaggg | 658 |

<210> SEQ ID NO 24
<211> LENGTH: 503
<212> TYPE: DNA
<213> ORGANISM: Human cytomegalovirus

<400> SEQUENCE: 24

| | |
|---|---|
| gaattcggct tctaatacga ctcactatag ggcaagcagc ggtaacaacg cagagtactt | 60 |
| tttttttttt tttttttttt tttttttgga caaacacaca gtttattatt cactgcagca | 120 |
| tatagcccat tttagcgcgg cacacatcca gccgtttgtg tttcttaacg ctctccaggt | 180 |
| actgatccag gcccacgatc cgggttatct tgtcgtattc caggttgatc catcgatagg | 240 |
| gaacgctgcc agcggcgccc agcaggtact gcgccttgtc gttcactttg ccgcagcgta | 300 |
| ttcgcccgtc agcttcgagg tataacggat tgtagttgca gctcgtcagt ttgttgtgta | 360 |
| cgacctggcg tgtcaatgaa tgggtcatgg tggtgacgat cccgcgaatc tcagccgttt | 420 |
| tctcgggact gtagcagact cgccgtccg gacaccgcag caagccgaat tccagcacac | 480 |
| tggcggccgt tactagtgga tcc | 503 |

<210> SEQ ID NO 25
<211> LENGTH: 636
<212> TYPE: DNA
<213> ORGANISM: Human cytomegalovirus

<400> SEQUENCE: 25

| | |
|---|---|
| gaattcggct tctaatacga ctcactatag ggcaagcagt ggtaacaacg cagagtacgc | 60 |
| gggggaccat cctccaacgg atgccccgaa cggcttcgaa accgagcgac ggaaacgtgc | 120 |
| agatcagcgt ggaagacgcc aagatttttg gagcgcacat ggtgcccaag cagaccaagc | 180 |

-continued

```
tgctacgttt cgtcgtcaac gatggcacac gttatcagat gtgtgtgatg aaactggaga    240
gctgggccca cgtcttccgg gactacagcg tgtctttca ggtgcgattg acgttcaccg      300
aggccaataa ccagacttac accttctgca cccatcccaa tctcatcgtt tgagcccgtc    360
gcgcgcgcag ggaattttga aaaccgcgcg tcatgagtcc caaaaacctg acgccgttct    420
tgacggcgtt gtggctgcta ttgggtcaca gccgcgtgcc gcgggtacgc gcagaagaat    480
gttgcgaatt cataaacgtc aaccacccgc cggaacgctg ttacgatttc aaaatgtgca    540
atcgcttcac cgtcgcgtac gtattttcat gattgtctgc gttctgtggt gcgtctggat    600
ctgtctctcg acgtttctga tagccatgtt ccatcg                               636
```

<210> SEQ ID NO 26
<211> LENGTH: 1432
<212> TYPE: DNA
<213> ORGANISM: Human cytomegalovirus

<400> SEQUENCE: 26

```
gaattcggct ttctgcttcg tcaccacttt cactgcctgc ttctgtgcgc ggtttgggca     60
acgccctgtc tggcgtctcc gtggttcacg ctaacggcga accagaatcc gtccccgcca   120
tggtctaaac tgacgtatcc caaaccgcat gacgcggcga cgtttactg tccttttctc    180 tatccctcgc ccccacggtc ccctcgcaa ttcccggggt tccagcgggt atcaacgggt    240
cccgagtgtc gcaacgagac cctgtatctg ctgtacaacc gggaaggcca gaccttggtg   300
gagagaagct ccacctaggt gaaaaaggtg atctggtatc tgagcggtcg caatcagacc   360
atcctccaac ggatgccccg aacggcttcg aaaccgagcg acggaaacgt gcagatcagc   420
gtggaagacg ccaagatttt tggagcgcac atggtgccca agcagaccaa gctgctacgt   480
ttcgtcgtca acgatggcac acgttatcag atgtgtgtga tgaaactgga gagctgggcc   540
cacgtcttcc gggactacag cgtgtctttt caggtgcgat tgacgttcac cgaggccaat   600
aaccagactt acaccttctg cacccatccc aatctcatcg tttgagcccg tcgcgcgcgc   660
agggaatttt gaaaaccgcg cgtcatgagt cccaaaaacc tgacgccgtt cttgacggcg   720
ttgtggctgc tattgggtca gccgcgtg ccgcgggtac gcgcagaaga atgttgcgaa   780
ttcataaacg tcaaccaccc gccggaacgc tgttacgatt tcaaaatgtg caatcgcttc    840
accgtcgcgt acgtattttc atgattgtct gcgttctgtg gtgcgtctgg atctgtctct    900
cgacgtttct gatagccatg ttccatcgac gatcctcggg aatgccagag tagattttca    960
tgaatccaca ggctgcggtg tccggacggc gaagtctgct acagtcccga gaaaacggct   1020
gagattcgcg ggatcgtcac caccatgacc cattcattga cacgccaggt cgtacacaac    1080
aaactgacga gctgcaacta caatccgtta tacctcgaag ctgacgggcg aatacgctgc   1140
ggcaaagtga cgacaaggc gcagtacctg ctgggcgccg ctgcagcgt tccctatcga    1200 tggatcaacc tggaatacga caagataacc cggatcgtgg gcctggatca gtacctggag   1260
agcgttaaga aacacaaacg gctggatgtg tgccgcgcta aatgggcta tatgctgcag   1320 tgaataataa aatgtgtgtt tgtccaaaaa aaaaaaaaaa aaaaaaaaa aaaagtactc    1380 tgcgttgtta ccactgcttg ccctatagtg agtcgtatta aagccgaat tc              1432
```

<210> SEQ ID NO 27
<211> LENGTH: 880
<212> TYPE: DNA
<213> ORGANISM: Human cytomegalovirus

<400> SEQUENCE: 27

```
taacgctctc caggtactga tccaggccca cgatccgggt tatcttgtcg tattccaggt    60
tgatccatcg atagggaacg ctgccagcgg cgcccagcag gtactgcgcc ttgtcgttca   120
ctttgccgca gcgtattcgc ccgtcagctt cggggtataa cctacaacac ggaggggaag   180
ggggtacaa aacgtgaaat tagactttt ttttttaat gatgttttgt ccctctctgt    240
cttactctcc cataggctgt aaggcccag aggaagagac ttacgattg tagttgcagc    300
tcgtcagttt gttgtgtacg acctggcgtg tcaatgaatg ggtcatggtg gtgacgatcc   360
cgcgaatctc agccgttttc tcgggactgt agcagcttc gccgtccgga caccgcagcc   420
tgtggattca tgaaaatcta ctctggcatt cccgaggatc gtcgatggaa catggctatc   480
agaaacgtcg agagacagat ccagacgcac acagaacgc agacaatcat gaaaatacgt   540
acgcgacggt gaagcgattg cacattttga aatcgtaaca gcgttccggc gggtggttga   600
cgtttatgaa ttcgcaacat tcttctgcgc gtacccgcgg cacgcggctg tgacccaata   660
gcagccacaa cgccgtcaag aacggcgtca ggttttggg actcatgacg cgcggttttc    720
aaaattccct gcgcgcgcga cgggctcaaa cgatgagatt gggatgggtg cagaaggtgt   780
aagtctggtt attggcctcg gtgaacgtca atcgcacctg aaaagacgcg ctgtagtccc   840
ggaagacgtg ggcctggatc agtacctgga gagcgttaga                        880
```

<210> SEQ ID NO 28
<211> LENGTH: 417
<212> TYPE: DNA
<213> ORGANISM: Human cytomegalovirus

<400> SEQUENCE: 28

```
gaattcggct tctaatacga ctcactatag gcaagcagt ggtaacaacg cagagtacgc     60
ggggaccctg tatctgctgt acaaccggga aggccagacc ttggtggaga gaagctccac   120
ctgggtgaaa aaggtgatct ggtatctgag cggtcgcaat cagaccatcc tccaacggat   180
gccccgaacg gcttcgaaac cgagcgacg aaacgtgcag atcagcgtgg aagacgccaa   240
gattttgga gcgcacgtgg tgcccaagca gaccaagctg ctacgtttcg tcgtcaacga   300
tggcacacgt tatcagatgt gtgtgatgaa actggagagc tgggcccacg tcttccggga   360
ctacagcgtg tcttttcagg tgcgattacg ttcaccgagg ccaataaagc cgaattc     417
```

<210> SEQ ID NO 29
<211> LENGTH: 90
<212> TYPE: DNA
<213> ORGANISM: Artificial Sequence
<220> FEATURE:
<223> OTHER INFORMATION: primer

<400> SEQUENCE: 29

```
cgctgtaggg ataaatagtg cgatggcgtt tgtgggagaa cgcagtagcg atgggttgcg    60
acgtgcaccg atttattcaa caaagccacg                                   90
```

<210> SEQ ID NO 30
<211> LENGTH: 87
<212> TYPE: DNA
<213> ORGANISM: Artificial Sequence
<220> FEATURE:
<223> OTHER INFORMATION: primer

<400> SEQUENCE: 30

```
aacggcgtca ggtctttggg actcatgacg cgcggttttc aaaattccct gcgcgcgcga    60
```

```
cgggcgccag tgttacaacc aattaac                                               87

<210> SEQ ID NO 31
<211> LENGTH: 88
<212> TYPE: DNA
<213> ORGANISM: Artificial Sequence
<220> FEATURE:
<223> OTHER INFORMATION: primer

<400> SEQUENCE: 31
aaaccacgtc ctcgtcacac gtcgttcgcg dacatagcaa gaaatccacg tcgccacatc           60
tcgagacgat ttattcaaca aagccacg                                              88

<210> SEQ ID NO 32
<211> LENGTH: 87
<212> TYPE: DNA
<213> ORGANISM: Artificial Sequence
<220> FEATURE:
<223> OTHER INFORMATION: primer

<400> SEQUENCE: 32
gccagtggta ccacttgagc atcctggcca gaagcacgtc gggcgtcatc cccgagtcat           60
agtagcgatt tattcaacaa agccacg                                               87

<210> SEQ ID NO 33
<211> LENGTH: 87
<212> TYPE: DNA
<213> ORGANISM: Artificial Sequence
<220> FEATURE:
<223> OTHER INFORMATION: primer

<400> SEQUENCE: 33
acacatcgca cacagacttt ataaaccgta gttgtcggcg ccatctagac tcactttatt           60
gaaagccagt gttacaacca attaacc                                               87

<210> SEQ ID NO 34
<211> LENGTH: 81
<212> TYPE: DNA
<213> ORGANISM: Artificial Sequence
<220> FEATURE:
<223> OTHER INFORMATION: primer

<400> SEQUENCE: 34
gcgccacacg cccggagcct cgagttcagc gtgcggctct tgccaacta gcctgcgtca           60 cggcgattta ttcaacaaag c                                                     81

<210> SEQ ID NO 35
<211> LENGTH: 83
<212> TYPE: DNA
<213> ORGANISM: Artificial Sequence
<220> FEATURE:
<223> OTHER INFORMATION: primer

<400> SEQUENCE: 35
cccggagcct cgagttcagc gtgcggctct tgccaacta gcctgcgtca cgggaaataa           60
tcgatttatt caacaaagcc acg                                                   83

<210> SEQ ID NO 36
<211> LENGTH: 76
<212> TYPE: DNA
<213> ORGANISM: Artificial Sequence
<220> FEATURE:
```

```
<223> OTHER INFORMATION: primer

<400> SEQUENCE: 36
tgtctttcgg ttccaactct ttccccgccc catcacctcg cctgtactat gtgtcgattt    60
attcaacaaa gccacg                                                    76

<210> SEQ ID NO 37
<211> LENGTH: 74
<212> TYPE: DNA
<213> ORGANISM: Artificial Sequence
<220> FEATURE:
<223> OTHER INFORMATION: primer

<400> SEQUENCE: 37
gctagttggc aaagagccgc acgctgaact cgaggctccg ggcgtgtggc ggccagtgtt    60
acaaccaatt aacc                                                      74

<210> SEQ ID NO 38
<211> LENGTH: 78
<212> TYPE: DNA
<213> ORGANISM: Artificial Sequence
<220> FEATURE:
<223> OTHER INFORMATION: primer

<400> SEQUENCE: 38
atgagacatc atacacatag tacaggcgag gtgatggggc ggggaaagag ttggaaccga    60
aaggccagtg ttacaacc                                                  78

<210> SEQ ID NO 39
<211> LENGTH: 87
<212> TYPE: DNA
<213> ORGANISM: Artificial Sequence
<220> FEATURE:
<223> OTHER INFORMATION: primer

<400> SEQUENCE: 39
gcacccatcc caatctcatc gtttgagccc gtcgcgcgcg cagggaattt tgaaaaccgc    60
gcgtccgatt tattcaacaa agccacg                                        87

<210> SEQ ID NO 40
<211> LENGTH: 87
<212> TYPE: DNA
<213> ORGANISM: Artificial Sequence
<220> FEATURE:
<223> OTHER INFORMATION: primer

<400> SEQUENCE: 40
tcgcgcgaca tgaatttagt cggcgacaga aatctcgaaa cgcgtatttc ggacaaacac    60
acatgccagt gttacaacca attaacc                                        87

<210> SEQ ID NO 41
<211> LENGTH: 82
<212> TYPE: DNA
<213> ORGANISM: Artificial Sequence
<220> FEATURE:
<223> OTHER INFORMATION: primer

<400> SEQUENCE: 41
tgcgttctgt ggtgcgtctg gatctgtctc tcgacgtttc tgatagccat gttccatcga    60
cgatttattc aacaaagcca cg                                             82
```

```
<210> SEQ ID NO 42
<211> LENGTH: 81
<212> TYPE: DNA
<213> ORGANISM: Artificial Sequence
<220> FEATURE:
<223> OTHER INFORMATION: primer

<400> SEQUENCE: 42
cggcacacat ccagccgttt gtgtttctta acgctctcca ggtactgatc caggcccacg      60
gccagtgtta caaccaatta a                                                81

<210> SEQ ID NO 43
<211> LENGTH: 30
<212> TYPE: DNA
<213> ORGANISM: Artificial Sequence
<220> FEATURE:
<223> OTHER INFORMATION: primer

<400> SEQUENCE: 43
cggcacacat ccagccgttt gtgtttctta                                       30

<210> SEQ ID NO 44
<211> LENGTH: 30
<212> TYPE: DNA
<213> ORGANISM: Artificial Sequence
<220> FEATURE:
<223> OTHER INFORMATION: primer

<400> SEQUENCE: 44
taacgctctc caggtactga tccaggccca                                       30

<210> SEQ ID NO 45
<211> LENGTH: 30
<212> TYPE: DNA
<213> ORGANISM: Artificial Sequence
<220> FEATURE:
<223> OTHER INFORMATION: primer

<400> SEQUENCE: 45
tcgtcagttt gttgtgtacg acctggcgtg                                       30

<210> SEQ ID NO 46
<211> LENGTH: 30
<212> TYPE: DNA
<213> ORGANISM: Artificial Sequence
<220> FEATURE:
<223> OTHER INFORMATION: primer

<400> SEQUENCE: 46
tattggcctc ggtgaacgtc aatcgcacct                                       30

<210> SEQ ID NO 47
<211> LENGTH: 30
<212> TYPE: DNA
<213> ORGANISM: Artificial Sequence
<220> FEATURE:
<223> OTHER INFORMATION: primer

<400> SEQUENCE: 47
tgtgtcgggt gtggctgtct gtttgtctgt                                       30

<210> SEQ ID NO 48
<211> LENGTH: 31
<212> TYPE: DNA
<213> ORGANISM: Artificial Sequence
<220> FEATURE:
```

```
<223> OTHER INFORMATION: primer

<400> SEQUENCE: 48
tctgcttcgt caccactttt cactgcctgc t                                            31

<210> SEQ ID NO 49
<211> LENGTH: 30
<212> TYPE: DNA
<213> ORGANISM: Artificial Sequence
<220> FEATURE:
<223> OTHER INFORMATION: primer

<400> SEQUENCE: 49
cgcagaagaa tgttgcgaat tcataaacgt                                              30

<210> SEQ ID NO 50
<211> LENGTH: 30
<212> TYPE: DNA
<213> ORGANISM: Artificial Sequence
<220> FEATURE:
<223> OTHER INFORMATION: primer

<400> SEQUENCE: 50
gctgcggtgt ccggacggcg aagtctgcta                                              30

<210> SEQ ID NO 51
<211> LENGTH: 30
<212> TYPE: DNA
<213> ORGANISM: Artificial Sequence
<220> FEATURE:
<223> OTHER INFORMATION: primer

<400> SEQUENCE: 51
ccagctggca gattcccaaa ctaatgaaag                                              30

<210> SEQ ID NO 52
<211> LENGTH: 1245
<212> TYPE: DNA
<213> ORGANISM: Human cytomegalovirus

<400> SEQUENCE: 52
ctaatacgac tcactatagg gcaagcagtg gtaacaacgc agagtacgcg gggagaatcc             60
gtccccgcca tggtctaaac tgacgtatcc caaaccgcat gacgcggcga cgttttactg            120
tccttttctc tatccctcgc ccccacggtc cccctcgcaa ttcccggggt tccagcgggt            180
atcaacgggt cccgagtgtc gcaacgagac cctgtatctg ctgtacaacc gggaaggcca            240
gaccttggtg gagagaagct ccacctgggt gaaaaaggtg atctggtatc tgagcggtcg            300
caatcagacc atcctccaac ggatgccccg aacggcttcg aaaccgagcg acggaaacgt            360
gcagatcagc gtggaagacg ccaagatttt tggagcgcac atggtgccca gcagaccaa            420 gctgctacgt ttcgtcgtca cgacggcac acgttatcga atgtgtgtga tgaaactgga             480
gagctgggcc cacgtcttcc gggactacag cgtgtctttt caggtgcgat tgacgttcac            540
cgaggccaat aaccagactt acaccttctg cacccatccc aatctcatcg tttgagcccg            600
tcgcgcgcgc agggaattt gaaaaccgcg cgtcatgagt cccaaaaaacc tgacgccgtt            660 cttgacggcg ttgtggctgc tattgggtca cagccgcgtg ccgcgggtac gcgcagaaga            720
atgttgcgaa ttcataaacg tcaaccaccc gccggaacgc tgttacgatt tcaaaatgtg            780
caatcgcttc accgtcgcgt acgtattttc atgattgtct gcgttctgtg gtgcgtctgg            840
atctgtctct cgacgtttct gatagccatg ttccatcgac gatcctcggg aatgccagag            900
```

```
tagatttca tgaatccaca ggctgcggtg tccggacggc gaagtctgct acagtcccga    960
gaaaacggct gagattcgcg ggatcgtcac caccatgacc cattcattga cacccaggt   1020 cgtacacaac aaactgacga gctgcaacta caatccgtta tacctcgaag ctgacgggcg   1080
aatacgctgc ggcaaagtga acgacaaggc gcagtacctg ctgggcgccg ctggcagcgt   1140
tccctatcga tggatcaacc tggaatacga caagataacc cggatcgtgg gcctggatca   1200
gtacctggag agcgttaaga aacacaaacg gctggatgtg tgccg                  1245

<210> SEQ ID NO 53
<211> LENGTH: 568
<212> TYPE: DNA
<213> ORGANISM: Human cytomegalovirus

<400> SEQUENCE: 53
gctgctattg ggtcacagcc gcgtgccgcg ggtacgcgca aagaatgtt gcgaattcat      60 aaacgtcaaa cacccgccgg aacgctgtta cgatttcaaa atgtgcaatc gcttaccgtc    120
gcgtacgtat tttcatgatc gtctgcgttc tgtggtgcgt ctggatctgt ctctcgacgt    180
ttctgatagc catgttccat cgacgatccc cgggaatgcc agagtagatt ttcatgaatc    240
cacaggctgc ggtgtccgga cggcgaagtc tgctacagtc ccgagaaaac ggctgagatt    300
cgcgggatcg tcaccaccat acccattcat gacacgcca ggtcgtacac aacaaactga    360
cgagctgcaa ctacaatccg ttatacctcg aagctcacgg gcgaatacgc tgcggcaaag    420
tgaacgacaa ggcgcagtac ctgctgggcg ccgctgcag cgttccctat cgatggatca    480
acctggaata cgacaagata acccggatcg tgggcctgga tcagtacctg gagagcgtta    540
agaaacacaa acggctggat gtgtgccg                                       568

<210> SEQ ID NO 54
<211> LENGTH: 787
<212> TYPE: DNA
<213> ORGANISM: Human cytomegalovirus

<400> SEQUENCE: 54
ctaatacgac tcactatagg gcaagcagtg gtaacaacgc agagtacgcg ggggaccatc     60
ctccaacgga tgccccgaac ggcttcgaaa ccgagcgacg gaaacgtgca gatcagcgtg    120
gaagacgcca agattttgg agcgcacatg gtgcccaagc agaccaagct gctacgttc    180 gtcgtcaacg atggcacacg ttatcagatg tgtgtgatga actggagag ctgggcccac    240 gtcttccggg actacagcgt gtcttttcag gtgcgattga cgttcaccga ggccaataac    300
cagacttaca ccttctgcac ccatcccaat ctcatcgttt gagcccgtcg cgcgcgcagg    360
gaattttgaa aaccgcgcgt catgagtccc aaaaacctga cgccgttctt gacggcgttg    420
tggctgctat tgggtcacag ccgcgtgccg cgggtacgcg caagaatg ttgcgaattc    480 ataaacgtca accacccgcc ggaacgctgt tacgatttca aaatgtgcaa tcgcttcacc    540
gtcgcgtacg tatttttcatg attgtctgcg ttctgtggtg cgtctggatc tgtctctcga    600
cgtttctgat agccatgttc catcgacgat cctcgggat gccagagtag attttcatga    660
atccacaggc tgcggtgtcc ggacggcgaa gtctgctaca gtcccgagaa acggctgag    720 attcgcggga tcgtcaccac catgacccat tcattgacac gccaggtcgt acacaacaaa    780
ctgacga                                                               787

<210> SEQ ID NO 55
```

<211> LENGTH: 1292
<212> TYPE: DNA
<213> ORGANISM: Human cytomegalovirus

<400> SEQUENCE: 55

```
tctgcttcgt caccatttca ctgcctgctt ctgtgcgcgg tttgggcaac gccctgtctg    60
gcgtctccgt ggttcacgct aacggcgaac cagaatccgt ccccgccatg gtctaaactg   120
acgtatccca aaccgcatga cgcggcgacg ttttactgtc cttttctcta tccctcgccc   180
ccacggtccc cctcgcaatt cccggggttc cagcgggtat caacgggtcc cgagtgtcgc   240
aacgagaccc tgtatctgct gtacaaccgg aaggccaga ccttggtgga gagaagctcc   300
acctgggtga aaaaggtgat ctggtatctg agcggtcgca atcagaccat cctccaacgg   360
atgccccgaa cggcttcgaa accgagcgac ggaaacgtgc agatcagcgt ggaagacgcc   420
aagattttg gagcgcacat ggtgcccaag cagaccaagc tgctacgttt cgtcgtcaac   480
gatggcacac gttatcagat gtgtgtgatg aaactggaga gctgggccca cgtcttccgg   540
gactacagcg tgtcttttca ggtgcgattg acgttcaccg aggccaataa ccagacttac   600
accttctgca cccatcccaa tctcatcgtt tgagcccgtc gcgcgcgcag ggaattttga   660
aaaccgcgcg tcatgagtcc caaaaacctg acgccgttct tgacggcgtt gtggctgcta   720
ttgggtcaca gccgcgtgcc gcgggtacgc gcagaagaat gttgcgaatt cataaacgtc   780
aaccacccgc cggaacgctg ttacgatttc aaaatgtgca atcgcttcac cgtcgcgctg   840
cggtgtccgg acggcgaagt ctgctacagt cccgagaaaa cggctgagat cgcgggatc   900
gtcaccacca tgacccattc attgacacgc caggtcgtac acaacaaact gacgagctgc   960
aactacaatc cgttataccct cgaagctgac gggcgaatac gctgcggcaa agtgaacgac  1020
aaggcgcaac aaggcgcagt acctgctggg cgccgctggc agcgttccct atcgatggat  1080
caacctggaa tacgacaaga taacccggat cgtgggcctg atcagtacc tggagagcgt  1140
taagaaacac aaacggctgg atgtgtgccg cgctaaaatg ggctatatgc tgcagtgaat  1200
aataaaatgt gtgtttgtac aaaaaaaaaa aaaaaaaaa aaaagtact ctgcgttgtt   1260
accactgctt gccctatagt gagtcgtatt ag                                1292
```

<210> SEQ ID NO 56
<211> LENGTH: 7650
<212> TYPE: DNA
<213> ORGANISM: Human cytomegalovirus

<400> SEQUENCE: 56

```
actgtggctg gaaactggtt acctgtgaag atggctaact atcctgttct gtcctggaaa    60
aacttttggc gtcgtaggtg gactttgcag tatgcgggtt agtgaagtta tgtcatttat   120
ttacgtttac gatctcgtat tacaaaccgc ggagaggatg ataccgttcg gccccatgag   180
ttattttat tcttccggta ggaggcatga agcctctgat aatgctcatc tgctttgctg   240
tgatattatt gcagcttgga gtgactaaag tgtgtcagca aatgaagtg caactgggca   300
atgagtgctg ccctccgtgt ggttcgggac aaagagttac taaagtatgc acggattata   360
ccagtgtaac gtgtaccccct tgccccaacg gcacgtatgt atcgggactt acaactgta   420
ccgattgcac tcaatgtaac gtcactcagg tcatgattcg taactgcact tccaccaata   480
ataccgtatg cgcacctaag aaccatacgt acttttccac tccaggcgtc caacatcaca   540
aacaacgaca gcaaaatcat accgcacata taaccgtcaa acaaggaaaa agcggtcgtc   600
atactctagc ctggttgtct ctctttatct ttcttgtggg tatcatactt ttaattctct   660
```

```
atcttatagc cgcctatcgg agtgagagat gccaacagtg ttgctcaatc ggcaaaattt    720
tctaccgcac cctgtaagct tcctgttgtt gtttttacat cacggtacga tgaagtcaca    780
cagataatta cagatgagct gttcatattt tttattattt tttccaattc ctgcactaaa    840
aaaagaagca ctttacggaa ccgtgtctga gtatctgtgg ggaatttagg tactttttgc    900
cgacgtcagg aaaaataagt gtcgcctaca taagagcccg gtgctatcgt gctgtcactc    960
tttcttgttg ccttcgatgt acggcgtcct ggctcattac tactccttca tcagtagccc   1020
cagcgttatg gttaatttta agcatcataa cgccgtgcag ctgttatgtg cacggacccg   1080
agacgcactg ccggatggga acgtttaacc catcatgcgt cgtatcacgc gaactacggg   1140
gcatacgccg tgttgatggc tacatcgcaa agaaagtccc tagtgttaca tcgatacagt   1200
gccgtgacag ccgtggccct gcagctcatg cctgttgaga tcgtccgcaa gctagatcag   1260
tcggactggg tgcggggtgc ctggatcgtg tcagagactt ttccaactag cgaccccaaa   1320
ggagtttgga gcgacgatga ctcctcgatg ggtggaagtg atgattgatg atgagaacct   1380
gacaagaaag acgagagaga aatttagagc tgtcattgta gaattagtct agattcctga   1440
taataaacag tatcgatttt gaaacctaat tgacgtgtga tcgatttta aacctctgtg    1500 ttgtgtgatt gattggtatg tgggggggatc cgatttcaaa gggggggtact tatcgggaat   1560 tgatgtgtca tggacgcagt tttgagcgat tttccgggaa taccggatat tacgaattac   1620
tggtagtgac gtagataata aaattataat gcgattaatt tttggtgcgt tgattatttt   1680
tttagcatat gtgtatcatt atgaggtgaa tggaacagaa ttacgctgca gatgtcttca   1740
tagaaaatgg ccgcctaata aaattatatt gggtaattat tggcttcatc gcgatcccag   1800
agggcccgga tgcgataaaa atgaacattt attgtatcca gacggaagga aaccgcctgg   1860
acctggagta tgtttatcgc ccgatcacct cttctcaaaa tggttagaca aacacaacga   1920
taataggtgg tataatgtta acataacgaa atcaccagga ccgagacgaa taaatataac   1980
cttgataggt gttagaggat aatatttaat gtatgttttc aaacagacaa gttcgttaaa   2040 acaaatatt acagtatgtg tttaatatgg tgctaacatg gttgcaccat ccggtttcaa   2100
actcgcatat caatctgtta tcggtacgac acctgtcatt aatcgcatat atgttactta   2160
ccatatgtcc cctagccgtc catgttttag aactagaaga ttacgacagg cgctgccgtt   2220
gcaacaacca aattctgttg aatacccctgc cggtcggaac cgaattgctt aagccaatcg   2280
cagcgagcga aagctgcaat cgtcaggaag tgctggctat tttaaaggac aagggaacca   2340
agtgtctcaa tcctaacgcg caagccgtgc gtcgtcacat caaccggcta ttttttcggt   2400
taatcttaga cgaggaacaa cgcatttacg acgtagtgtc taccaatatt gagttcggtg   2460
cctggccagt ccctacggcc tacaaagcct ttctttggaa atacgccaag agactgaact   2520
accaccactt cagactgcgc tgtgatcat gtccctattt taccgtgcgg tagctctggg   2580
cacgctaagc gctttggtgt ggtacagcac tagcatcctc gcagagatta acgaaaattc   2640
ctgctcctca tcttctgcgg atcacgaaga ctgcgaggaa ccggacgaga tcgttcgcga   2700
agagcaagac tatcgggctc tgctggcctt ttccctagtg atttgcggta cgctcctcgt   2760
cacttgtgtg atctgagacg tcatgctggt agcgtttatg agtcgggcgg tggccgacac   2820
gccgcatttc ctaacccgcg cagcatgttg cgcttgctgt tcacgctcgt cctgctggcc   2880
ctccacgggc agtctgtcgg cgctagccgc gactatgtgc atgttcggct actgagctac   2940
cgaggcgacc ccctggtctt caagcacact ttctcggggtg tgcgtcgacc cttcaccgag   3000
```

```
ctaggctggg ctgcgtgtcg cgactgggac agtatgcatt gcacaccctt ctggtctacc    3060
gatctggagc agatgaccga ctcggtgcgg cgttacagca cggtgagccc cggcaaggaa    3120
gtgacgcttc agcttcacgg gaaccaaacc gtacagccgt cgtttctaag ctttacgtgc    3180
cgcctgcagc tagaacccgt ggtggaaaat gttggcctct acgtggccta cgtggtcaac    3240
gacggcgaac gcccacaaca gttttttaca ccgcaggtag acgtggtacg ctttgctcta    3300
tatctagaaa cactctcccg gatcgtggaa ccgttagaat caggtcgcct ggcagtggaa    3360
tttgatacgc ctgacctagc tctggcgccc gatttagtaa gcagcctctt cgtggccgga    3420
cacggcgaga ccgactttta catgaactgg acgctgcgtc gcagtcagac ccactacctg    3480
gaggagatgg ccttacaggt ggagattcta aaaccccgcg gcgtacgtca ccgcgctatt    3540
atccaccatc cgaagctaca gccgggcgtt ggcctgtgga tagatttctg cgtgtaccgc    3600
tacaacgcgc gcctgacccg cggctacgta cgatacaccc tgtcaccgaa agcgcgcttg    3660
cccgcaaaag cagagggttg gctggtgtca ctagacagat tcatcgtgca gtacctcaac    3720
acattgctga ttacaatgat ggcggcgata tgggctcgcg ttttgataac ctacctggtg    3780
tcgcggcgtc ggtagaggct tgcggaaacc acgtcctcgt cacacgtcgt tcgcggacat    3840
agcaagaaat ccacgtcgcc acatctcgag aatgccggcc ttgcggggtc ccttcgcgc    3900
aacattcctg gccctggtcg cgttcgggtt gctgcttcag atagacctca gcgacgctac    3960
gaatgtgacc agcagcacaa aagtccctac tagcaccagc aacagaaata acgtcgacaa    4020
cgccacgagt agcggaccca caaccgggat caacatgacc accacccacg agtcttccgt    4080
tcacaacgtg cgcaataacg agatcatgaa agtgctggct atcctcttct acatcgtgac    4140
aggcacctcc attttcagct tcatagcggt actgatcgcg gtagtttact cctcgtgttg    4200
caagcacccg ggccgctttc gtttcgccga cgaagaggcc gtcaacctgt ggacgacac    4260
ggacgacagt ggcggcagca gcccgtttgg cagcggttcc cgacgaggtt ctcagatccc    4320
cgccggattt tgttcctcga gcccttatca gcggttggaa actcgggact gggacgagga    4380
ggaggaggcg tccgcggccc gcgagcgcat gaaacatgat cctgagaacg tcatctattt    4440
cagaaaggat ggcaacttgg acacgtcgtt cgtgaatccc aattatggga gaggctcgcc    4500
tttgaccatc gaatctcacc tctcggacaa tgaggaggac cccatcaggt actacgtttc    4560
ggtgtacgat gaactgaccg cctcggaaat ggaagaacct tcgaacagca ccagctggca    4620
gattcccaaa ctaatgaaag ttgccatgca acccgtctcg ctcagagatc ccgagtacga    4680
ctaggctttt tttttttgtct ttcggttcca actctttccc cgcccatca cctcgcctgt    4740
actatgtgta tgatgtctca taataaagct ttctttctca gtctgcaaca tgcagctgtg    4800
tcgggtgtgg ctgtctgttt gtctgtgcgc cgtggtgctg ggtcagtgcc agcgggaaac    4860
cgcggaaaaa aacgattatt accgagtacc gcattactgg gacgcgtgct ctcgcgcgct    4920
gcccgaccaa acccgttaca agtatgtgga acagctcgtg gacctcacgt tgaactacca    4980
ctacgatgcg agccacggct tggacaactt tgacgtgctc aagaggtgag ggtacgcgct    5040
aaaggtgcat gacaacggga aggtaaggc gaacgggtaa cggctaagta accgcatggg    5100
gtatgaaatg acgtttggaa cctgtgcttg cagaatcaac gtgaccgagg tgtcgttgct    5160
catcagcgac tttagacgtc agaaccgtcg cggcggcacc aacaaaagga ccacgttcaa    5220
cgccgccggt tcgctggcgc cacacgcccg gagcctcgag ttcagcgtgc ggctcttgc    5280
caactagcct gcgtcacggg aaataatatg ctgcggcttc tgcttcgtca ccactttcac    5340
tgcctgcttc tgtgcgcggt ttgggcaacg ccctgtctgg cgtctccgtg gtcgacgcta    5400
```

-continued

```
acggcaaacc agaatccgtc cccgccatgg tctaaactga cgtattccaa accgcatgac    5460
gcggcgacgt tttactgtcc tttctctat ccctcgcccc cacggtcccc cttgcaattc      5520
tcggggttcc agcaggtatc aacgggtccc gagtgtcgca acgagaccct gtatctgctg    5580
tacaaccggg aaggccagac cttggtggag agaagctcca cctgggtgaa aaaggtgatc    5640
tggtatctga gcggtcgcaa ccagaccatc ctccaacgga tgccccaaac ggcttcgaaa    5700
ccgagcgacg gaaacgtgca gatcagcgtg aagacgcca agattttggg agcgcacatg     5760
gtgcccaagc agaccaagct gctacgcttc gtcgtcaacg atggcacgcg ttatcagatg    5820
tgtgtgatga agctggagag ctgggcccac gtcttccggg actacagcgt gtcttttcag    5880
gtgcgattga cgttcaccga ggccaataac cagacttaca ccttctgtac ccatcccaat    5940
ctcatcattt gagcccgtcg cgcgcgcagg gaattttgaa aaccgcgcgt catgagtccc    6000
aaagacctga cgccgttctt gacgacgttg tggctgctat tgggtcacag ccgcgtgccg    6060
cgggtgcgcg cagaagaatg ttgcgaattc ataaacgtca accaccccgcc ggaacgctgt    6120 tacgatttca aaatgtgcaa tcgcttcacc gtcgcgtacg tattttcatg attgtctgcg    6180
ttctgtggtg cgtctggatt tgtctctcga cgtttctgat agccatgttc catcgacgat    6240
cctcgggaat gccagagtag attttcatga atccacaggc tgcggtgtcc ggacggcgaa    6300
gtctgctaca gtcccgagaa aacggctgag attcgcggga tcgtcaccac catgacccat    6360
tcattgacac gccaggtcgt acacaacaaa ctgacgagct gcaactacaa tccgtaagtc    6420
tcttcctcga gggccttaca gcctatggga gagtaagaca gagagggaca aaacatcatt    6480
aaaaaaaaaa gtctaatttc acgtttttgta ccccccttcc cctccgtgtt gtagcccatc    6540
ggccgcggcg atcctagt aacactcgtc cgacacttcc accatctcca gctcggccgg      6600
cggttcggca tcctctacca gcggcgtcgt ctcatctttg ccgcagcagc ggacgcacac    6660
cttctccagg cagaacgcca ccagctgccg ccgaacgtac cacaggtaca cgtgcagacc    6720
tgcgaacagg actacggagg tcatgaccac cacgacgcac acgggaatcc agggatcgag    6780
attgttgctg gaactcgcta tcgccaccga cgtgcccgcg tctgtctcac cgccgctcgc    6840
ccgatgtcgc gcggcttgtt atacgctagc ccgtcgccgc ctcggggcac ggtgccctcc    6900
tacccacgta acttcctccg tgacttaaag tcgcgtgtgg tagatctcct gctccgtgga    6960
cgaaccgtcc ggcaggatag cggttaagga ttcggtgcta aggccgtgtc gccaacgtcg    7020
aatgctacgt tgcaacagct tcgacggacg gccatcccct ctctcatcgc aataataaaa    7080
caccagcagc gcgcacgacg cgatcacggt gacacccatg attagaccca cgcagatagc    7140
cagccccgct agcgtatcta gcgccatccc gttcgctccc gttgtctcct gagcgaagca    7200
acttctcggt ccccgttttc aacagttttt gtttccttct ccgcgactag atgttaacgc    7260
ccgcggtctt tccggccgtg ctctacctcc tggcgcttgt cgtctgggtt gagatgttct    7320
gcctcgtcgc cgtagccgtc gtcgagcgcg agatcgcctg ggcgctgctg ctgcggatgc    7380
tggtcgttgg cctgatggtg gaagtcgcg ccgccgccgc ttggaccttc gtgcgttgtc     7440
ttgcctatca gcgctccttc cccgtgctta cggccttccc ctgaaaccca cgttaaccga    7500
ccgtcccaaa aacgcggtg ttaacacagg aaaaaagaa accacgcagg aaccgcgcag      7560
gaaccacgcg gaacatggga cactatctgg aaatcctgtt caacgtcatc gtcttcactc    7620
tgctgctcgg cgtcatggtc agtatcgtcg                                     7650
```

<210> SEQ ID NO 57

<211> LENGTH: 6136
<212> TYPE: DNA
<213> ORGANISM: Human cytomegalovirus

<400> SEQUENCE: 57

```
tttaaacctc tgtgttgtgt gattgattgg tatgtggggg gatccgattt caaaggggggg      60
tacttatcgg gaattgatgt gtcatggacg cagttttgag cgattttccg ggaataccgg     120
atattacgaa ttactggtag tgacgtagat aataaaatta taatgcgatt aattttttggt    180
gcgttgatta tttttttagc atatgtgtat cattatgagg tgaatggaac agaattacgc     240
tgcagatgtc ttcatagaaa atggccgcct aataaaatta tattgggtaa ttattggctt     300
catcgcgatc ccagagggcc cggatgcgat aaaaatgaac atttattgta tccagacgga     360
aggaaaccgc ctggacctgg agtatgttta tcgcccgatc acctcttctc aaaatggtta     420
gacaaacaca cgataatag gtggtataat gttaacataa cgaaatcacc aggaccgaga      480
cgaataaata taaccttgat aggtgttaga ggataatatt taatgtatgt tttcaaacag     540
acaagttcgt taaaacaaaa tattacagta tgtgtttaat atggtgctaa catggttgca     600
ccatccggtt tcaaactcgc atatcaatct gttatcggta cgacacctgt cattaatcgc     660
atatatgtta cttaccatat gtcccctagc cgtccatgtt ttagaactag aagattacga     720
caggcgctgc cgttgcaaca accaaattct gttgaatacc ctgccggtcg gaaccgaatt     780
gcttaagcca atcgcagcga gcgaaagctg caatcgtcag gaagtgctgg ctattttaaa     840
ggacaaggga accaagtgtc tcaatcctaa cgcgcaagcc gtgcgtcgtc acatcaaccg     900
gctatttttt cggttaatct tagacgagga acaacgcatt tacgacgtag tgtctaccaa     960
tattgagttc ggtgcctggc cagtccctac ggcctacaaa gccttctttt ggaaatacgc    1020
caagagactg aactaccacc acttcagact gcgctggtga tcatgtccct atttaccgt     1080
gcggtagctc tgggcacgct aagcgctttg gtgtggtaca gcactagcat cctcgcagag    1140
attaacgaaa attcctgctc ctcatcttct gcggatcacg aagactgcga ggaaccggac    1200
gagatcgttc gcgaagagca agactatcgg gctctgctgg ccttttccct agtgatttgc    1260
ggtacgctcc tcgtcacttg tgtgatctga gacgtcatgc tggtagcgtt tatgagtcgg    1320
gcggtggccg acacgccgca tttcctaacc cgcgcagcat gttgcgcttg ctgttcacgc    1380
tcgtcctgct ggccctccac gggcagtctg tcggcgctag ccgcgactat gtgcatgttc    1440
ggctactgag ctaccgaggc gacccccctgg tcttcaagca cactttctcg ggtgtgcgtc    1500
gaccccttcac cgagctaggc tgggctgcgt gtcgcgactg ggacagtatg cattgcacac    1560
ccttctggtc taccgatctg gagcagatga ccgactcggt gcggcgttac agcacggtga    1620
gccccggcaa ggaagtgacg cttcagcttc acgggaacca aaccgtacag ccgtcgtttc    1680
taagctttac gtgccgcctg cagctagaac ccgtggtgga aaatgttggc ctctacgtgg    1740
cctacgtggt caacgacggc gaacgcccac aacagttttt tacaccgcag gtagacgtgg    1800
tacgctttgc tctatatcta gaaacactct cccggatcgt ggaaccgtta gaatcaggtc    1860
gcctggcagt ggaatttgat acgcctgacc tagctctggc gcccgattta gtaagcagcc    1920
tcttcgtggc cggacacggc gagaccgact tttacatgaa ctggacgctg cgtcgcagtc    1980
agacccacta cctggaggag atggcctttac aggtggagat tctaaaaccc gcggcgtac     2040
gtcaccgcgc tattatccac catccgaagc tacagccggg cgttggcctg tggatagatt    2100
tctgcgtgta ccgctacaac gcgcgcctga cccgcggcta cgtacgatac accctgtcac    2160
cgaaagcgcg cttgcccgca aaagcagagg gttggctggt gtcactagac agattcatcg    2220
```

-continued

```
tgcagtacct caacacattg ctgattacaa tgatggcggc gatatgggct cgcgttttga   2280
taacctacct ggtgtcgcgg cgtcggtaga ggcttgcgga aaccacgtcc tcgtcacacg   2340
tcgttcgcgg acatagcaag aaatccacgt cgccacatct cgagaatgcc ggccttgcgg   2400
ggtccccttc gcgcaacatt cctggccctg gtcgcgttcg ggttgctgct tcagatagac   2460
ctcagcgacg ctacgaatgt gaccagcagc acaaaagtcc ctactagcac cagcaacaga   2520
aataacgtcg acaacgccac gagtagcgga cccacaaccg ggatcaacat gaccaccacc   2580
cacgagtctt ccgttcacaa cgtgcgcaat aacgagatca tgaaagtgct ggctatcctc   2640
ttctacatcg tgacaggcac ctccattttc agcttcatag cggtactgat cgcggtagtt   2700
tactcctcgt gttgcaagca cccgggccgc tttcgtttcg ccgacgaaga ggccgtcaac   2760
ctgttggacg acacggacga cagtggcggc agcagcccgt ttggcagcgg ttcccgacga   2820
ggttctcaga tccccgccgg attttgttcc tcgagccctt atcagcggtt ggaaactcgg   2880
gactgggacg aggaggagga ggcgtccgcg gcccgcgagc gcatgaaaca tgatcctgag   2940
aacgtcatct atttcagaaa ggatggcaac ttggacacgt cgttcgtgaa tcccaattat   3000
gggagaggct cgccttttgac catcgaatct cacctctcgg acaatgagga ggaccccatc   3060
aggtactacg tttcggtgta cgatgaactg accgcctcgg aaatggaaga accttcgaac   3120
agcaccagct ggcagattcc caaactaatg aaagttgcca tgcaacccgt ctcgctcaga   3180
gatcccgagt acgactaggc ttttttttttt gtctttcggt tccaactctt tcccgcccc   3240
atcacctcgc ctgtactatg tgtatgatgt ctcataataa agctttcttt ctcagtctgc   3300
aacatgcagc tgtgtcgggt gtggctgtct gtttgtctgt gcgccgtggt gctgggtcag   3360
tgccagcggg aaaccgcgga aaaaaacgat tattaccgag taccgcatta ctgggacgcg   3420
tgctctcgcg cgctgcccga ccaaacccgt tacaagtatg tggaacagct cgtggacctc   3480
acgttgaact accactacga tgcgagccac ggccttggaca actttgacgt gctcaagagg   3540
tgagggtacg cgctaaaggt gcatgacaac gggaaggtaa gggcgaacgg gtaacggcta   3600
agtaaccgca tggggtatga aatgacgttt ggaacctgtg cttgcagaat caacgtgacc   3660
gaggtgtcgt tgctcatcag cgactttaga cgtcagaacc gtcgcggcgg caccaacaaa   3720
aggaccacgt tcaacgccgc cggttcgctg gcgccacacg cccggagcct cgagttcagc   3780
gtgcggctct ttgccaacta gcctgcgtca cgggaaataa tatgctgcgg cttctgcttc   3840
gtcaccactt tcactgcctg cttctgtgcg cggtttgggc aacgccctgt ctggcgtctc   3900
cgtggtcgac gctaacggca aaccagaatc cgtccccgcc atggtctaaa ctgacgtatt   3960
ccaaaccgca tgacgcggcg acgttttact gtccttttct ctatccctcg cccccacggt   4020
ccccccttgca attctcgggg ttccagcagg tatcaacggg tcccgagtgt cgcaacgaga   4080
ccctgtatct gctgtacaac cgggaaggcc agaccttggt ggagagaagc tccacctggg   4140
tgaaaaaggt gatctggtat ctgagcggtc gcaaccagac catcctccaa cggatgcccc   4200
aaacggcttc gaaaccgagc gacggaaacg tgcagatcag cgtggaagac gccaagattt   4260
ttggagcgca catggtgccc aagcagacca agctgctacg cttcgtcgtc aacgatggca   4320
cgcgttatca gatgtgtgtg atgaagctgg agagctgggc ccacgtcttc cgggactaca   4380
gcgtgtcttt tcaggtgcga ttgacgttca ccgaggccaa taaccagact tacaccttct   4440
gtacccatcc caatctcatc atttgagccc gtcgcgcgcg cagggaattt tgaaaaccgc   4500
gcgtcatgag tcccaaagac ctgacgccgt tcttgacgac gttgtggctg ctattgggtc   4560
```

-continued

```
acagccgcgt gccgcgggtg cgcgcagaag aatgttgcga attcataaac gtcaaccacc    4620
cgccggaacg ctgttacgat ttcaaaatgt gcaatcgctt caccgtcgcg tacgtatttt    4680
catgattgtc tgcgttctgt ggtgcgtctg gatttgtctc tcgacgtttc tgatagccat    4740
gttccatcga cgatcctcgg gaatgccaga gtagattttc atgaatccac aggctgcggt    4800
gtccggacgg cgaagtctgc tacagtcccg agaaaacggc tgagattcgc gggatcgtca    4860
ccaccatgac ccattcattg acacgccagg tcgtacacaa caaactgacg agctgcaact    4920
acaatccgta agtctcttcc tcgagggcct tacagcctat gggagagtaa gacagagagg    4980
gacaaaacat cattaaaaaa aaaagtctaa tttcacgttt tgtaccccc ttcccctccg      5040
tgttgtagcc catcggccgc ggcgatctcc tagtaacact cgtccgacac ttccaccatc    5100
tccagctcgg ccggcggttc ggcatcctct accagcggcg tcgtctcatc tttgccgcag    5160
cagcggacgc acaccttctc caggcagaac gccaccagct gccgccgaac gtaccacagg    5220
tacacgtgca gacctgcgaa caggactacg gaggtcatga ccaccacgac gcacacggga    5280
atccagggat cgagattgtt gctggaactc gctatcgcca ccgacgtgcc cgcgtctgtc    5340
tcaccgccgc tcgcccgatg tcgcgcggct tgttatacgc tagcccgtcg ccgcctcggg    5400
gcacggtgcc ctcctaccca cgtaacttcc tccgtgactt aaagtcgcgt gtggtagatc    5460
tcctgctccg tggacgaacc gtccggcagg atagcggtta aggattcggt gctaaggccg    5520
tgtcgccaac gtcgaatgct acgttgcaac agcttcgacg gacggccatc ccctctctca    5580
tcgcaataat aaaacaccag cagcgcgcac gacgcgatca cggtgacacc catgattaga    5640
cccacgcaga tagccagccc cgctagcgta tctagcgcca tcccgttcgc tcccgttgtc    5700
tcctgagcga agcaacttct cggtccccgt tttcaacagt ttttgtttcc ttctccgcga    5760
ctagatgtta acgcccgcgg tctttccggc cgtgctctac ctcctggcgc ttgtcgtctg    5820
ggttgagatg ttctgcctcg tcgccgtagc cgtcgtcgag cgcgagatcg cctgggcgct    5880
gctgctgcgg atgctggtcg ttggcctgat ggtggaagtc ggcgccgccg ccgcttggac    5940
cttcgtgcgt tgtcttgcct atcagcgctc cttccccgtg cttacggcct tcccctgaaa    6000
cccacgttaa ccgaccgtcc caaaaacgcc ggtgttaaca caggaaaaaa agaaaccacg    6060
caggaaccgc gcaggaacca cgcggaacat gggacactat ctggaaatcc tgttcaacgt    6120
catcgtcttc actctg                                                    6136
```

<210> SEQ ID NO 58
<211> LENGTH: 15549
<212> TYPE: DNA
<213> ORGANISM: Human cytomegalovirus

<400> SEQUENCE: 58

```
cgctgtaggg ataaatagtg cgatggcgtt tgtgggagaa cgcagtagcg atgggttgcg      60
acgtgcacga tccttcgtgg caatgccaat ggggcgttcc cacgattatc gtggcctgga     120
taacatgcgc ggctttagga atttggtgtt tggcgggatc gtcggcggat gtctcttcgg     180
gacccggcat cgcagccgta gtcggctgtt ctgttttcat gatttcctc tgcgcgtatc      240
tcatccgtta ccgggaattc ttcaaagact ccgtaatcga cctccttacc tgccgatggg     300
ttcgctactg cagctgcagc tgtaagtgca gctgcaaatg catctcgggc ccctgtagcc     360
gctgctgttc agcgtgttac aaggagacga tgatttacga catggtccaa tacggtcatc     420
gacgcgtcc cggacacggc gacgatcccg acagggtgat ctgcgagata gtcgagagtc      480
ccccggtttc ggcgccgacg gtgtccgtcc ccccgccgtc ggaggagtcc caccagcccg     540
```

-continued

```
tcatcccacc gcagccgcca gcaccgacat cggaacccaa accgaagaaa ggtagggcga      600
aagataaacc gaagggtaga ccgaaagaca aacctccgtg cgaaccgacg gtgagttcac      660
aaccaccgtc gcagccgacg gcaatgcccg gcggtccgcc cgacgcgcct ccccccgcca      720
tgccgcagat gccacccggc gtggccgagg cggtacaagc tgccgtgcag gcggccgtgg      780
ccgcggctct acaacaacag cagcagcatc agaccggaac gtaacccgcc cccggtgcga      840
taaggaattt tccgacttgg cgcacatctc cttcctcaat gtttggacaa taaacacatt      900
ccttgccaaa aaatgacgtt tccagaaatc caaggcataa atgtccgtac accgcccttt      960
cccaacacgg agtttgagat ccaagcagg agagaagatc atggtgtgga tatggctcgg     1020
catcgggctc ctcggcggta ccggactggc ttccctggtc ctggccattt ccttatttac     1080
ccagcgccga ggccgcaagc gatccgacga gacttcgtcg cgaggccggc tcccgggtgc     1140
tgcttctgat aagcgtggtg cctgcgcgtg ctgctatcga aatccgaaag aagacgtcgt     1200
cgagccgctg gatctggaac tggggctcat gcgggtggac acccaccccgc cgacgccgca     1260 ggtgccgcgc tgtacgtcgc tctacatagg agaggatggt ctgccgatag ataaacccga     1320
gtttcctccg gcgcggttcg agatcccga cgtatccacg ccgggaacgc cgaccagcat     1380
cggccgatct ccgtcgcatt gctcctcgtc gagctctttg tcgtcctcga ccagcgtcga     1440
cacggtgctg tatcagccgc cgccatcctg gaagccacct ccgccgcccg ggcgcaagaa     1500
gcggccgcct acgccgccgg tccgggcccc caccacgcgg ctgtcgtcgc acagaccccc     1560
gacgccgata cccgcgccgc gtaagaacct gagcacgccg cccaccaaga aaacgccgcc     1620
gcccacgaaa cccaagccgg tcggctggac accgccggtg acaccaggc ccttcccgaa      1680 aacgccgacg ccacaaaagc cgccgcggaa tccgagacta ccgcgcaccg tcggtctgga     1740
gaatctctcg aaggtgggac tctcgtgtcc ctgtccccga ccccgcacgc cgacggagcc     1800
gaccacgctg cctatcgtgt cggtttccga gctagcccg cctcctcgat ggtcggacat      1860
cgaggaactc ttggaacagg cggtgcagag cgtcatgaag gacgccgagt cgatgcagat     1920
gacctgagac cgaaagagcg agcgcgtccg ttgtacagtt gtatagcagc acacgccttc     1980
cctctttttc accgcagcta agagagagaa agagagtatg tcagtcaagg gcgtggagat     2040
gccagaaatg acgtgggact tggacgttag aaataaatgg cggcgtcgaa aggccctgag     2100
tcgcattcac cggttctggg aatgtcggct acgggtgtgg tggctgagtg acgccggcgt     2160
aagagaaacc gacccaccgc gtccccgacg ccgcccgact tggatgaccg cggtgtttca     2220
cgttatctgt gccgttttgc ttacgcttat gattatggcc atcggcgcgc tcatcgcgta     2280
cttaagatat taccaccagg acagttggcg agacatgctc cacgatctat tttgcggctg     2340
tcattatccc gagaagtgcc gtcggcacca cgagcggcag agaaggagac ggcaagccat     2400
ggatgtgccc gacccggaac tcggcgaccc ggccgccgg ccgttgaacg gagctatgta      2460
ctacggcagc ggctgtcgct tcgacacggt ggaaatggtg gacgagacga gacccgcgcc     2520
gccggcgctg tcatcgcccg aaaccggcga cgatagcaac gacgacgcgg ttgcggcgg     2580 aggtgctggc ggggtaacat caccccgcgac tcgtacgacg tcgccgaacg cactgctgcc     2640
agaatggatg gatgcggtgc atgtggcggt ccaagccgcc gttcaagcga ccgtgcaagt     2700
aagtggcccg cgggagaacg ccgtatctcc cgctacgtaa gagggttgag ggggccgttc     2760
ccgcgcgagt gctgtacaaa agagagagac tgggacgtag atccggacag aggacggtca     2820
ccatggacga tctgccgctg aatgtcgggt tacccatcat cggcgtgatg ctcgtgctga     2880
```

```
tcgtggccat cctctgctat ctggcttacc actggcacga caccttcaaa ctggtgcgca    2940
tgtttctgag ctaccgctgg ctgatccgct gttgcgagct gtacggggag tacgagcgcc    3000
ggttcgcgga cctgtcgtct ctgggcctcg gcgccgtacg gcgggagtcg acagacgat     3060 accgtttctc cgaacggccc gacgagatct tggtccgttg ggaggaagtg tcttcccagt    3120
gcagctacgc gtcgtcgcgg ataacagacc gccgtgtggg ttcatcgtct tcgtcgtcgg    3180
tccacgtcgc tagccagaga aacagcgtgc ctccgccgga catggcggtg acggcgccgc    3240
tgaccgacgt cgatctgttg aaacccgtga cgggatccgc gacgcagttc accaccgtag    3300
ccatggtaca ttatcatcaa gagtacacgt gaatgagaaa agaaaaaag aggggagcgg     3360 atcgcgataa tgtcgctttg acattctctg ctcgatctac tcagcgtctg cacgaaacgg    3420
catccgcacg gaggcgagcc caagcgtatc tgcagcaagc ggttctttcc ctcggtgatg    3480
gtggcagcat cggtggcggg agcttgttcg gacgatggac ggtgaggagt ccctggcgat    3540
caggcggctc ccgggtgtgg agttcaacgg gtggtaatgg tggcggtgat cggtgttaga    3600
aaacggtggc cctggcaaac atatatctac tgtaaaccct ctgctctgtt aataaaaagc    3660
acacttttca catgagttcg taattttatt gtgtagtgga aattttacg tcattgggaa      3720 accccagaat gaaagagtat aatgtgcata tcaccggggg ttccctgtca gtacgaatgt    3780
acacaacgcg ggttacatta cgataaactt tccggtaaaa cgatgccgat acagcgtgta    3840
taacgctgat tgttacgaca acgagttgg tatatccatt atatagtaac gaacatgctg     3900
tggatattag ttttatttgc actcgccgca tcggcgagtg aaaccactac aggtaccagc    3960
tctaattcca gtcaatctac tagtgctacc gccaacacga ccgtatcgac atgtattaat    4020
gcctctaacg gcagtagctg gacagtacca cagctcgcgc tgcttgccgc tagcggctgg    4080
acattatctg gactccttct cttatttacc tgctgctttt gctgcttttg gctagtacgt    4140
aaaatctgca gctgctgcgg caactcctcc gagtcagaga gcaaaacaac ccacgcgtac    4200
accaatgccg cattcacttc ttccgacgca acgttaccca tgggcactac agggtcgtac    4260
actcccccac aggacggctc atttccacct ccgcctcggt gacgtaggct aaaccgaaac    4320
ccacgttgaa cctaacgcgg tttcggaagg cctgagacgt cactttcaca atgacgtccg    4380
tatacacgtt catcataaaa caccgtagag gctaaggctt cggtagggag agacctcaac    4440
tgttcctgat gagcacccgt gctctcatct cttcagactt gtcatgaccc ccgctcagac    4500
taacgcgact accaccgtgc acccgcacga cgcaaaaaac ggcagcggcg gtagtgccct    4560
gccgaccctc gtcgttttcg gctttatcgt tacgctactt ttctttctct ttatgctcta    4620
cttttggaac aacgacgtgt tccgtaagct gctccgtgcg cttggatcca gcgctgttgc    4680
gaccgcttcg acgcgtggca agacgaggtc atctaccgtc gtccatcacg tcgttcccag    4740
agcgacgacg agagtcgtac taacagcgtg tcatcgtacg ttcttttatc acccgcgtcc    4800 gatgcggtt ttgacaaccc ggcactgaca gaggccgtcg acagcgtgga cgactgggcg      4860
accacctcgg ttttctacgc cacgtccgac gaaacggcgg acgccgagcg ccgagactcg    4920
cagcaactgc tcatcgagct tccgccggag ccgctcccgc cgacgtggt ggcggccatg      4980 cagaaagcag tgaaacgcgc tgtacagaac gcactacgac acagccacga ctcttggcag    5040
cttcatcaga ccctgtgacg ccagatgaac gttccttctt aaacatccga ggtagcaatg    5100
agacaggtcg cgtaccgccg gcgacgcgag agttcctgcg cggtgctggt ccaccacgtc    5160
ggccgcgacg cgacggcga gggggaggca gcaaaaaaga cctgcaaaaa aaccggacgc      5220
tcagttgcgg gcatcccggg cgagaagctg cgtcgcacgg tggtcaccac cacgccggcc    5280
```

```
cgacgtttga gcggccgaca cacggagcag gagcaggcgg gcatgcgtct ctgtgaaaaa    5340
gggaagaaaa gaatcatcat gtgccgccgg gagtcgctcc gaactctgcc gtggctgttc    5400
tgggtgctgt tgagctgccc gcgactcctc gaatattctt cctcttcgtt ccccttcgcc    5460
accgctgaca ttgccgaaaa gatgtgggcc gagaattatg agaccacgtc gccggcgccg    5520
gtgttggtcg ccgagggaga gcaagttacc atcccctgca cggtcatgac acactcctgg    5580
cccatggtct ccattcgcgc acgtttctgt cgttcccacg acggcagcga cgagctcatc    5640
ctggacgccg tcaaaggcca tcggctgatg aacggactcc agtaccgcct gccgtacgcc    5700
acttggaatt tctcgcaatt gcatctcggc caaatattct cgcttacttt taacgtatcg    5760
atggacacag ccggcatgta cgaatgcgtg ctacgcaact acagccacgg cctcatcatg    5820
caacgcttcg taattctcac gcagctggag acgctcagcc ggcccgacga accttgctgc    5880
acaccggcgt taggtcgcta ctcgctggga gaccagatct ggtcgccgac gccctggcgt    5940
ctacggaatc acgactgcgg aacgtaccgc ggctttcaac gcaactactt ctatatcggc    6000
cgcgccgacg ccgaggattg ctggaaaccc gcatgtccgg acgaggaacc cgaccgctgt    6060
tggacagtga tacagcgtta ccggctcccc ggcgactgct accgttcgca gccacacccg    6120
ccgaaatttt taccggtgac gccagcaccg ccggccgaca tagacaccgg gatgtctccc    6180
tgggccactc ggggaatcgc ggcgttttg gggttttgga gtattttac cgtatgtttc     6240 ctatgctacc tgtgttatct gcagtgttgt ggacgctggt gtcccacgcc gggaagggga    6300
cgacgaggcg gtgagggcta tcgacgccta ccgacttacg atagttaccc cggtgttaga    6360
aagatgaaga ggtgagaaca cgtataaaat aaaaaaataa tatgttaaaa aatgcagtgt    6420
gtgaagtgtg aatagtgtga ttaaaatatg cggattgaat gggtgtggtg gttattcgga    6480
tactttgtgt catccgttgg gagcgaacgg tcattatcct atcgttacca cttggaatct    6540
aattcatcta ccaacgtggt ttgcaacgga acatttccg tgtttgtaaa cggcacccta     6600
ggtgtgcggt ataacattac ggtaggaatc agttcgtctt tattaatagg acaccttact    6660
atacaagtat tggaatcatg gttcacaccc tgggtccaaa ataaaagtta caacaaacaa    6720
cccctaggtg acactgaaac gctttataat atagatagcg aaaacattca tcgcgtatct    6780
caatattttc acacaagatg gataaaatct ctgcaagaga atcacacttg cgacctcaca    6840
aacagtacac ctacctatac atatcaagta aacgtgaaca cacgaatta cctaacacta     6900 acatcctcgg gatggcaaga ccgtctaaat tacaccgtca taaatagtac acactttaac    6960
ctcacagaat cgaacataac cagcattcaa aaatatctca acactacctg catagaaaga    7020
ctccgtaact acaccttgga gtccgtatac accacaactg tgcctcaaaa cataacaaca    7080
tctcaacacg caacaaccac tatgcacaca atacctccaa atacaataac aattcaaaat    7140
acaactcaaa gccatactgt acagacgccg tcttttaacg acacacataa cgtgacgaaa    7200
cacacgttaa acataagcta cgtttttatca caaaaaacga ataacacaac atcaccgtgg    7260
atatatgcca tacctatggg cgctacagcc acaataggcg ccggtttata tatcgggaaa    7320
cactttacgc cggttaagtt cgtatacgag gtatggcgcg gtcagtaaag acgattcgga    7380
ttcaacacat atactcccca cgatcctcga cacccttaca gcatatgagc aaaaaacaag    7440
aaagtatagc cacaatcaca tttgggcgaa taacatgctg tcatccacta gcgtctatta    7500
atctaatgtt taacgggagc tgtactgtca ccgttaaaat atccatggga atcaacgggt    7560
caaccaacgt ccatcagctt gtgattgtgc tccatctggg taaccgctgt cagccttggc    7620
```

```
gacaggtgta atcacagctg tcacataact cacgaagcct ccaatcacag cagcacacat  7680
agtcctaacg ccattggcgt gtataaaagt tcggaaaact tgacggttgt acggcacgac  7740
aaatcgatgt agtggtatgt ttttccagca gagaccgtgt gcggtctctt aggttcgcta  7800
tactgtggct ggaaactggt tacctgtgaa gatggctaac tatcctgttc tgtcctggaa  7860
aaacttttgg cgtcgtaggt ggactttgca gtatgcgggt tagtgaagtt atgtcattta  7920
tttacgttta cgatctcgta ttacaaaccg cggagaggat gataccgttc ggccccatga  7980
gttattttta ttcttccggt aggaggcatg aagcctctga taatgctcat ctgctttgct  8040
gtgatattat tgcagcttgg agtgactaaa gtgtgtcagc ataatgaagt gcaactgggc  8100
aatgagtgct gccctccgtg tggttcggga caaagagtta ctaaagtatg cacggattat  8160
accagtgtaa cgtgtacccc ttgccccaac ggcacgtatg tatcgggact ttacaactgt  8220
accgattgca ctcaatgtaa cgtcactcag gtcatgattc gtaactgcac ttccaccaat  8280
aataccgtat gcgcacctaa gaaccatacg tactttccca ctccaggcgt ccaacatcac  8340
aaacaacgac agcaaaatca taccgcacat ataaccgtca aacaaggaaa aagcggtcgt  8400
catactctag cctggttgtc tctctttatc tttcttgtgg gtatcatact tttaattctc  8460
tatcttatag ccgcctatcg gagtgagaga tgccaacagt gttgctcaat cggcaaaatt  8520
ttctaccgca ccctgtaagc ttcctgttgt tgttttttaca tcacggtacg atgaagtcac  8580
acagataatt acagatgagc tgttcatatt ttttattatt ttttccaatt cctgcactaa  8640
aaaaagaagc actttacgga accgtgtctg agtatctgtg gggaatttag gtacttttg  8700
ccgacgtcag gaaaaataag tgtcgcctac ataagagccc ggtgctatcg tgctgtcact  8760
ctttcttgtt gccttcgatg tacggcgtcc tggctcatta ctactccttc atcagtagcc  8820
ccagcgttat ggttaatttt aagcatcata acgccgtgca gctgttatgt gcacggaccc  8880
gagacgcact gccggatggg aacgtttaac ccatcatgcg tcgtatcacg cgaactacgg  8940
ggcatacgcc gtgttgatgg ctacatcgca aagaaagtcc ctagtgttac atcgatacag  9000
tgccgtgaca gccgtggccc tgcagctcat gcctgttgag atcgtccgca agctagatca  9060
gtcggactgg gtgcggggtg cctggatcgt gtcagagact tttccaacta gcgaccccaa  9120
aggagtttgg agcgacgatg actcctcgat gggtggaagt gatgattgat gatgagaacc  9180
tgacaagaaa gacgagagag aaatttagag ctgtcattgt agaattagtc tagattcctg  9240
ataataaaca gtatcgattt tgaaacctaa ttgacgtgtg atcgattttt aaacctctgt  9300
gttgtgtgat tgattggtat gtgggggggat ccgatttcaa aggggggtac ttatcgggaa  9360
ttgatgtgtc atggacgcag ttttgagcga ttttccggga ataccggata ttacgaatta  9420
ctggtagtga cgtagataat aaaattataa tgcgattaat ttttggtgcg ttgattattt  9480
ttttagcata tgtgtatcat tatgaggtga atggaacaga attacgctgc agatgtcttc  9540
atagaaaatg gccgcctaat aaaattatat tgggtaatta ttggcttcat cgcgatccca  9600
gagggcccgg atgcgataaa aatgaacatt tattgtatcc agacggaagg aaaccgcctg  9660
gacctggagt atgtttatcg cccgatcacc tcttctcaaa atggttagac aaacacaacg  9720
ataataggtg gtataatgtt aacataacga aatcaccagg accgagacga ataaatataa  9780
ccttgatagg tgttagagga taatatttaa tgtatgtttt caaacagaca agttcgttaa  9840
aacaaaatat tacagtatgt gtttaatatg gtgctaacat ggttgcacca tccggtttca  9900
aactcgcata tcaatctgtt atcggtacga cacctgtcat taatcgcata tatgttactt  9960
accatatgtc ccctagccgt ccatgtttta gaactagaag attacgacag gcgctgccgt 10020
```

```
tgcaacaacc aaattctgtt gaatacoctg ccggtcggaa ccgaattgct taagccaatc   10080
gcagcgagcg aaagctgcaa tcgtcaggaa gtgctggcta ttttaaagga caagggaacc   10140
aagtgtctca atcctaacgc gcaagccgtg cgtcgtcaca tcaaccggct attttttcgg   10200
ttaatcttag acgaggaaca acgcatttac gacgtagtgt ctaccaatat tgagttcggt   10260
gcctggccag tccctacggc ctacaaagcc tttctttgga aatacgccaa gagactgaac   10320
taccaccact tcagactgcg ctggtgatca tgtccctatt ttaccgtgcg gtagctctgg   10380
gcacgctaag cgctttggtg tggtacagca ctagcatcct cgcagagatt aacgaaaatt   10440
cctgctcctc atcttctgcg gatcacgaag actgcgagga accggacgag atcgttcgcg   10500
aagagcaaga ctatcgggct ctgctggcct tttccctagt gatttgcggt acgctcctcg   10560
tcacttgtgt gatctgagac gtcatgctgg tagcgtttat gagtcgggcg gtggccgaca   10620
cgccgcattt cctaacccgc gcagcatgtt gcgcttgctg ttcacgctcg tcctgctggc   10680
cctccacggg cagtctgtcg gcgctagccg cgactatgtg catgttcggc tactgagcta   10740
ccgaggcgac cccctggtct tcaagcacac tttctcgggt gtgcgtcgac ccttcaccga   10800
gctaggctgg gctgcgtgtc gcgactggga cagtatgcat tgcacaccct tctggtctac   10860
cgatctggag cagatgaccg actcggtgcg gcgttacagc acggtgagcc ccggcaagga   10920
agtgacgctt cagcttcacg ggaaccaaac cgtacagccg tcgtttctaa gctttacgtg   10980
ccgcctgcag ctagaacccg tggtggaaaa tgttggcctc tacgtggcct acgtggtcaa   11040
cgacggcgaa cgcccacaac agttttttac accgcaggta gacgtggtac gctttgctct   11100
atatctagaa acactctccc ggatcgtgga accgttagaa tcaggtcgcc tggcagtgga   11160
atttgatacg cctgacctag ctctggcgcc cgatttagta agcagcctct tcgtggccgg   11220
acacggcgag accgactttt acatgaactg gacgctgcgt cgcagtcaga cccactacct   11280
ggaggagatg gccttacagg tggagattct aaaaccccgc ggcgtacgtc accgcgctat   11340
tatccaccat ccgaagctac agccgggcgt tggcctgtgg atagatttct gcgtgtaccg   11400
ctacaacgcg cgcctgaccc gcggctacgt acgatacacc ctgtcaccga aagcgcgctt   11460
gcccgcaaaa gcagagggtt ggctggtgtc actagacaga ttcatcgtgc agtacctcaa   11520
cacattgctg attacaatga tggcggcgat atgggctcgc gttttgataa cctacctggt   11580
gtcgcggcgt cggtagaggc ttgcggaaac cacgtcctcg tcacacgtcg ttcgcggaca   11640
tagcaagaaa tccacgtcgc cacatctcga gaatgccggc cttgcggggt ccccttcgcg   11700
caacattcct ggccctggtc gcgttcgggt tgctgcttca gatagacctc agcgacgcta   11760
cgaatgtgac cagcagcaca aaagtcccta ctagcaccag caacagaaat aacgtcgaca   11820
acgccacgag tagcggaccc acaaccggga tcaacatgac caccacccac gagtcttccg   11880
ttcacaacgt gcgcaataac gagatcatga aagtgctggc tatcctcttc tacatcgtga   11940
caggcacctc cattttcagc ttcatagcgg tactgatcgc ggtagtttac tcctcgtgtt   12000
gcaagcaccc gggccgcttt cgtttcgccg acgaagaggc cgtcaacctg ttggacgaca   12060
cggacgacag tggcggcagc agcccgtttg gcagcggttc ccgacgaggt tctcagatcc   12120
ccgccggatt ttgttcctcg agcccttatc agcggttgga aactcgggac tgggacgagg   12180
aggaggaggc gtccgcggcc cgcgagcgca tgaaacatga tcctgagaac gtcatctatt   12240
tcagaaagga tggcaacttg gacacgtcgt tcgtgaatcc caattatggg agaggctcgc   12300 cttttgaccat cgaatctcac ctctcggaca atgaggagga ccccatcagg tactacgttt   12360
```

```
cggtgtacga tgaactgacc gcctcggaaa tggaagaacc ttcgaacagc accagctggc   12420
agattcccaa actaatgaaa gttgccatgc aacccgtctc gctcagagat cccgagtacg   12480
actaggcttt ttttttttgtc tttcggttcc aactctttcc ccgccccatc acctcgcctg   12540
tactatgtgt atgatgtctc ataataaagc tttctttctc agtctgcaac atgcagctgt   12600
gtcgggtgtg gctgtctgtt tgtctgtgcg ccgtggtgct gggtcagtgc cagcgggaaa   12660
ccgcggaaaa aaacgattat taccgagtac cgcattactg ggacgcgtgc tctcgcgcgc   12720
tgcccgacca aacccgttac aagtatgtgg aacagctcgt ggacctcacg ttgaactacc   12780
actacgatgc gagccacggc ttggacaact ttgacgtgct caagaggtga gggtacgcgc   12840
taaaggtgca tgacaacggg aaggtaaggg cgaacgggta acggctaagt aaccgcatgg   12900
ggtatgaaat gacgtttgga acctgtgctt gcagaatcaa cgtgaccgag gtgtcgttgc   12960
tcatcagcga ctttagacgt cagaaccgtc gcggcggcac caacaaaagg accacgttca   13020
acgccgccgt ttcgctggcg ccacacgccc ggagcctcga gttcagcgtg cggctctttg   13080
ccaactagcc tgcgtcacgg gaaataatat gctgcggctt ctgcttcgtc accactttca   13140
ctgcctgctt ctgtgcgcgg tttgggcaac gccctgtctg gcgtctccgt ggtcgacgct   13200
aacggcaaac cagaatccgt ccccgccatg gtctaaactg acgtattcca aaccgcatga   13260
cgcggcgacg ttttactgtc cttttctcta tccctcgccc ccacggtccc ccttgcaatt   13320
ctcggggttc cagcaggtat caacgggtcc cgagtgtcgc aacgagaccc tgtatctgct   13380
gtacaaccgg gaaggccaga ccttggtgga gagaagctcc acctgggtga aaaaggtgat   13440
ctggtatctg agcggtcgca accagaccat cctccaacgg atgccccaaa cggcttcgaa   13500
accgagcgac ggaaacgtgc agatcagcgt ggaagacgcc aagattttg gagcgcacat   13560 ggtgcccaag cagaccaagc tgctacgctt cgtcgtcaac gatggcacgc gttatcagat   13620
gtgtgtgatg aagctggaga gctgggccca cgtcttccgg gactacagcg tgtcttttca   13680
ggtgcgattg acgttcaccg aggccaataa ccagacttac accttctgta cccatcccaa   13740
tctcatcatt tgagcccgtc gcgcgcgcag ggaattttga aaaccgcgcg tcatgagtcc   13800
caaagacctg acgccgttct tgacgacgtt gtggctgcta ttgggtcaca gccgcgtgcc   13860
gcgggtgcgc gcagaagaat gttgcgaatt cataaacgtc aaccaccgc cggaacgctg   13920 ttacgatttc aaaatgtgca atcgcttcac cgtcgcgtac gtattttcat gattgtctgc   13980
gttctgtggt gcgtctggat ttgtctctcg acgtttctga tagccatgtt ccatcgacga   14040
tcctcgggaa tgccagagta gattttcatg aatccacagg ctgcggtgtc cggacggcga   14100
agtctgctac agtcccgaga aaacggctga gattcgcggg atcgtcacca ccatgaccca   14160
ttcattgaca cgccaggtcg tacacaacaa actgacgagc tgcaactaca atccgtaagt   14220
ctcttcctcg agggccttac agcctatggg agagtaagac agagagggac aaaacatcat   14280
taaaaaaaaa agtctaattt cacgttttgt acccccttc ccctccgtgt tgtagcccat   14340
cggccgcggc gatctcctag taacactcgt ccgacacttc caccatctcc agctcggccg   14400
gcggttcggc atcctctacc agcggcgtcg tctcatcttt gccgcagcag cggacgcaca   14460
ccttctccag gcagaacgcc accagctgcc gccgaacgta ccacaggtac acgtgcagac   14520
ctgcgaacag gactacggag gtcatgacca ccacgacgca cacgggaatc cagggatcga   14580
gattgttgct ggaactcgct atcgccaccg acgtgcccgc gtctgtctca ccgccgctcg   14640
cccgatgtcg cgcggcttgt tatacgctag cccgtcgccg cctcggggca cggtgccctc   14700
ctacccacgt aacttcctcc gtgacttaaa gtcgcgtgtg gtagatctcc tgctccgtgg   14760
```

-continued

```
acgaaccgtc cggcaggata gcggttaagg attcggtgct aaggccgtgt cgccaacgtc  14820
gaatgctacg ttgcaacagc ttcgacggac ggccatcccc tctctcatcg caataataaa  14880
acaccagcag cgcgcacgac gcgatcacgg tgacacccat gattagaccc acgcagatag  14940
ccagccccgc tagcgtatct agcgccatcc cgttcgctcc cgttgtctcc tgagcgaagc  15000
aacttctcgg tccccgtttt caacagtttt tgtttccttc tccgcgacta gatgttaacg  15060
cccgcggtct ttccggccgt gctctacctc ctggcgcttg tcgtctgggt tgagatgttc  15120
tgcctcgtcg ccgtagccgt cgtcgagcgc gagatcgcct gggcgctgct gctgcggatg  15180
ctggtcgttg gcctgatggt ggaagtcggc gccgccgccg cttggacctt cgtgcgttgt  15240
cttgcctatc agcgctcctt ccccgtgctt acggccttcc cctgaaaccc acgttaaccg  15300
accgtcccaa aaacgccggt gttaacacag gaaaaaaaga aaccacgcag gaaccgcgca  15360
ggaaccacgc ggaacatggg acactatctg gaaatcctgt tcaacgtcat cgtcttcact  15420
ctgctgctcg gcgtcatggt cagtatcgtc gcttggtact tcacgtgaac caccgtcgtc  15480
ccggtttaaa aaccatcatc gacggccgtt ataaagccac ccggacacgc gccgcggcac  15540
ttgcctacg                                                          15549
```